(12) United States Patent
Clackson et al.

(10) Patent No.: US 6,649,595 B2
(45) Date of Patent: Nov. 18, 2003

(54) REGULATION OF BIOLOGICAL EVENTS USING NOVEL COMPOUNDS

(75) Inventors: Timothy P. Clackson, Arlington, MA (US); Michael Z. Gilman, Newton, MA (US); Dennis A. Holt, Royersford, PA (US); Terence P. Keenan, Cambridge, MA (US); Leonard Rozamus, Bedford, MA (US); Wu Yang, Princeton, NJ (US)

(73) Assignee: ARIAD Gene Therapeutics, Inc., Cambridge, MA (US)

( * ) Notice: Subject to any disclaimer, the term of this patent is extended or adjusted under 35 U.S.C. 154(b) by 0 days.

(21) Appl. No.: 09/781,804

(22) Filed: Feb. 12, 2001

(65) Prior Publication Data

US 2002/0107189 A1 Aug. 8, 2002

Related U.S. Application Data

(60) Division of application No. 09/012,097, filed on Jan. 22, 1998, now Pat. No. 6,187,757, which is a continuation-in-part of application No. 08/791,044, filed on Jan. 28, 1997, now abandoned, which is a continuation-in-part of application No. 08/481,941, filed on Jun. 7, 1995, now abandoned, which is a continuation-in-part of application No. PCT/US96/09948, filed on Jun. 7, 1996.
(60) Provisional application No. 60/015,502, filed on Feb. 9, 1996.

(51) Int. Cl.⁷ .............................. C12N 5/10; A61K 31/70
(52) U.S. Cl. ...................... 514/31; 435/325; 435/355; 435/372; 435/372.3; 435/375; 536/6.5
(58) Field of Search ................... 514/31, 44; 435/325, 435/355, 372, 372.3, 375; 536/6.5

(56) References Cited

U.S. PATENT DOCUMENTS

| | | | |
|---|---|---|---|
| 4,797,368 A | 1/1989 | Carter | 435/320.1 |
| 5,091,389 A | 2/1992 | Ondeyka | 514/291 |
| 5,093,338 A | 3/1992 | Byrne | 514/291 |

(List continued on next page.)

FOREIGN PATENT DOCUMENTS

| | | |
|---|---|---|
| WO | WO91/13889 | 9/1991 |
| WO | WO92/05179 | 4/1992 |
| WO | WO92/14737 | 9/1992 |
| WO | WO92/19595 | 11/1992 |
| WO | WO93/04680 | 3/1993 |
| WO | WO93/10122 | 5/1993 |
| WO | WO93/11130 | 6/1993 |
| WO | WO93/13663 | 7/1993 |
| WO | WO93/18043 | 9/1993 |
| WO | WO93/24641 | 12/1993 |
| WO | WO93/25533 | 12/1993 |
| WO | WO94/02136 | 2/1994 |
| WO | WO94/02137 | 2/1994 |
| WO | WO94/04540 | 3/1994 |
| WO | WO94/09010 | 4/1994 |
| WO | WO94/10843 | 5/1994 |
| WO | WO94/18207 | 8/1994 |
| WO | WO94/21644 | 9/1994 |
| WO | WO94/25022 | 11/1994 |
| WO | WO95/02684 | 1/1995 |
| WO | WO95/04060 | 2/1995 |
| WO | WO95/04521 | 2/1995 |
| WO | WO95/04738 | 2/1995 |
| WO | WO95/07468 | 3/1995 |
| WO | WO95/15328 | 6/1995 |
| WO | WO95/16691 | 6/1995 |
| WO | WO96/20951 | 7/1996 |
| WO | WO96/26285 | 8/1996 |
| WO | WO96/39530 | 12/1996 |
| WO | WO96/41865 | 12/1996 |
| WO | WO97/10502 | 3/1997 |
| WO | WO98/02441 | 1/1998 |

OTHER PUBLICATIONS

Ao et al., (1995) Transplanation Proc., vol. 27(6): 3349–3350.
Belshaw, et al., (1996) PNAS USA, vol. 93: 4604–4607.
Borrelli, et al., (1988) Proc. Natl. Acad. Sci. USA, vol. 85: 7572–7576.
Breitman, et al., (1987) Science, vol. 238: 1563–1565.
Breitman et al., (1990) Mol. Cell. Biol., vol. 10: 474–479.
Brown, et al., (1994) Nature, vol. 369: 756–758.
Chen, et al., (1995) PNAS USA, vol. 92: 4947–4951.
Chiu et al., (1994) PNAS USA, vol. 91: 12574–12578.
Cunningham et al., (1989) Science, vol. 244: 1081–1085.
Das et al., (1995) Nature, vol. 374: 657–660.
Dennis et al, (1994) J. Biol. Chem, vol. 269: 22129–22136.
Ferry et al., (1991) PNAS USA, vol. 88: 8377–8381.
Fields et al., (1989) Nature, vol. 340: 245–246.
Flotte et al., (1993) J. Biol. Chem, vol. 268: 3781–3790.
Graef et al., (1997) EMBO J. 16: 5618–5628.
Grinfeld, et al., (1994) Tetrahedron Letters, vol. 35: 6835–6838.
Helliwell et al., (1994) Mol Biol Cell 5: 105–118.
Heyman et al., (1989) PNAS USA, vol. 86: 2698–2702.
Hiebert et al., (1989) Proc. Natl. Acad. Sci, USA, vol. 86: 3594–3598.
Ho, et al., (1996) Nature, vol. 382: 822–826.
Holsinger, et al., (1995) PNAS USA, vol. 92: 9810–9814.
Hu, (1995) Structure, vol. 3: 431–433.
Hu et al., (1990) Science, vol. 250: 1400–1403.
Kaneda et al., (1989) Science, vol. 243: 375–378.
Kay, (1996) Biochem. J., vol. 314: 361–385.
Kordower et al., (1994) PNAS USA, vol 91(23):10898–902.
Kunz et al., (1993) Cell, vol. 73: 585–596.

(List continued on next page.)

*Primary Examiner*—David Guzo
*Assistant Examiner*—David A. Lambertson
(74) *Attorney, Agent, or Firm*—David L. Berstein

(57) ABSTRACT

Materials and methods are disclosed for regulation of biological events such as target gene transcription and growth, proliferation or differentiation of engineered cells.

36 Claims, 4 Drawing Sheets

U.S. PATENT DOCUMENTS

| | | | |
|---|---|---|---|
| 5,109,112 A | 4/1992 | Siekierka | 530/350 |
| 5,116,756 A | 5/1992 | Dumont | 435/253.5 |
| 5,139,941 A | 8/1992 | Muzyczka | 435/456 |
| 5,140,018 A | 8/1992 | Klein | 514/63 |
| 5,147,877 A | 9/1992 | Goulet | 514/291 |
| 5,173,414 A | 12/1992 | Lebkowski | 435/91.4 |
| 5,198,421 A | 3/1993 | Chen | 514/11 |
| 5,200,411 A | 4/1993 | Edmunds | 514/291 |
| 5,208,241 A | 5/1993 | Ok | 514/291 |
| 5,210,030 A | 5/1993 | Petuch | 435/119 |
| 5,221,625 A | 6/1993 | Chen | 435/253.5 |
| 5,225,403 A | 7/1993 | Treiber | 514/63 |
| 5,247,076 A | 9/1993 | Goulet | 540/456 |
| 5,252,479 A | 10/1993 | Srivastava | 435/235.1 |
| 5,252,732 A | 10/1993 | Sinclair | 540/456 |
| 5,258,389 A | 11/1993 | Goulet | 514/291 |
| 5,310,901 A | 5/1994 | Parsons | 540/456 |
| 5,310,903 A | 5/1994 | Goulet | 540/456 |
| 5,318,895 A | 6/1994 | Kahn | 435/32 |
| 5,324,644 A | 6/1994 | Ruby | 435/119 |
| 5,354,678 A | 10/1994 | Lebkowski | 435/463 |
| 5,362,718 A | 11/1994 | Skotnicki | 514/63 |
| 5,362,735 A | 11/1994 | Luengo | 514/291 |
| 5,373,014 A | 12/1994 | Failli | 514/291 |
| 5,378,836 A | 1/1995 | Kao | 540/456 |
| 5,387,680 A | 2/1995 | Nelson | 540/456 |
| 5,436,146 A | 7/1995 | Shenk | 435/457 |
| 5,457,182 A | 10/1995 | Wiederrecht | 530/402 |
| 5,457,194 A | 10/1995 | Luly | 540/456 |
| 5,484,799 A | 1/1996 | Hochlowski | 514/345 |
| 5,525,610 A | 6/1996 | Caufield | 514/291 |
| 5,527,907 A | 6/1996 | Or | 540/456 |
| 5,534,632 A | 7/1996 | Or | 540/456 |
| 5,541,189 A | 7/1996 | Luly | 514/291 |
| 5,541,193 A | 7/1996 | Kawai | 514/291 |
| 5,561,137 A | 10/1996 | Or | 514/291 |
| 5,561,228 A | 10/1996 | Or | 540/456 |
| 5,563,172 A | 10/1996 | Wagner | 514/456 |
| 5,583,139 A | 12/1996 | Or | 514/291 |
| 5,597,715 A | 1/1997 | Ford | 435/118 |
| 5,604,234 A | 2/1997 | Or | 514/291 |
| 5,622,866 A | 4/1997 | Motamedi | 435/486 |
| 5,648,361 A | 7/1997 | Holt | 514/291 |
| 5,658,776 A | 8/1997 | Flotte | 435/457 |
| 5,834,266 A | 11/1998 | Crabtree | 435/456 |
| 5,869,337 A | 2/1999 | Crabtree | 435/372.3 |
| 5,871,982 A | 2/1999 | Wllson | 435/457 |
| 5,985,890 A | 11/1999 | Cottens | 514/291 |
| 5,985,906 A | 11/1999 | Meingassner | 514/383 |
| 6,001,557 A | 12/1999 | Wilson | 435/5 |
| 6,013,627 A | 1/2000 | Dreyfuss | 514/9 |
| 6,066,721 A | 5/2000 | Khosla | 536/23.1 |
| 6,150,137 A | 11/2000 | Berlin | 435/69.7 |
| 6,187,757 B1 * | 2/2001 | Clackson et al. | 514/31 |

OTHER PUBLICATIONS

Lakey et al., (1995) Transplantation Proc., vol. 27(6): 3266.
Liberles et al, (1997) PNAS USA, vol. 94: 7825–7830.
Luengo et al., (1995) J. Org. Chem., 59, 6512.
Luengo et al., (1995) Current Biology, 2: 471–481.
Luengo et al., (1995) Chem & Biol, vol. 2(7): 471–481.
Luo, et al., (1996) Nature, vol. 383: 181–185.
Muller et al., (1991) MCB, vol. 11: 1785–1792.
Palmiter, et al., (1987) Cell, vol. 50: 435–443.
Pomeranz, et al., (1995) Science, vol. 267: 93–96.
Pruschy et al., (1994) Chemistry & Biology, vol. 1: 163–172.
Rajotte et al., (1995) Transplantation Proc. Vol 27: 3389.
Riddell, et al., (1996) Nature Med., vol. 2: 216–223.
Rivera, et al., (1996) Nature Medicine, vol. 2: 1028–1032.
Sabatini et al., (1994) Cell, 78; 35–43.
Siekieka et al., (1989) Nature, vol. 341: 755–757.
Smith et al., (1997) J. Am. Chem. Soc., vol. 119: 962–973.
Spencer et al., (1995) PNAS USA, vol. 92: 9805–9809.
Spencer, et al., (1993) Science, 262:1019–1024.
Spencer, et al., (1996) Current Biology, vol. 6: 839–847.
Staendart, et al., (1990) Nature, vol. 346: 671–674.
Stemmer, (1994) Nature, vol. 370: 389–391.
Thomas et al, (1987) Cell, vol. 51: 503–512.
Uchiyama, et al., (1993) Peptide Chemistry vol. 31(1):89–92.
Van Duyne et al., (1991) J. Amer. Chem. Soc., vol. 113: 7433–7434.
Winn et al., (1994) PNAS USA, vol. 91(6): 2324–2328.
Liberles et al. PNAS USA 94:7825–7830 1997.*

* cited by examiner

REGULATION OF BIOLOGICAL EVENTS USING NOVEL COMPOUNDS

This application is a divisional application of and incorporates by reference the full contents of, U.S. Ser. No. 09/012,097 now U.S. Pat. No. 6,187,757 (filed Jan. 22, 1998 as a continuation in part of U.S. Ser. No. 08/791,044, filed Jan. 28, 1997, now abandoned which itself is a continuation in part of U.S. Ser. No. 08/481,941 (filed Jun. 7, 1995, now abandoned) and of U.S. Ser. No. 60/015,502 (filed Feb. 9, 1996) and is C-I-P of International Application No. PCT/US96/09948 (filed internationally Jun. 7, 1996)

BACKGROUND OF THE INVENTION

Rapamycin is a macrolide antibiotic produced by *Streptomyces hygroscopicus* which binds to a FK506-binding protein, FKBP, with high affinity to form a rapamycin:FKBP complex. Reported Kd values for that interaction are as low as 200 pM. The rapamycin:FKBP complex binds with high affinity to the large cellular protein, FRAP, to form a tripartite, [FKBP:rapamycin]:[FRAP], complex. In that complex rapamycin acts as a dimerizer or adapter to join FKBP to FRAP.

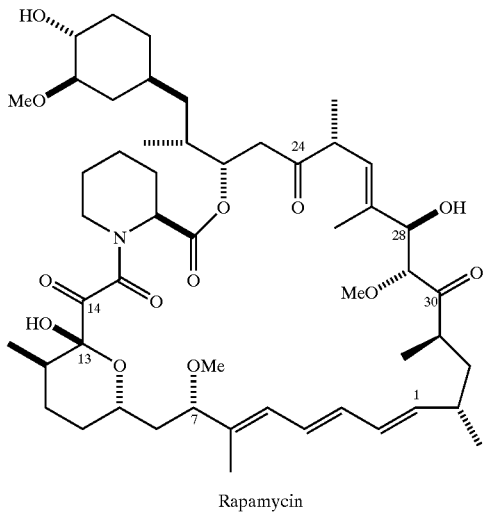

Rapamycin

A number of naturally occurring FK506 binding proteins (FKBPs) are known. See e.g. Kay, 1996, Biochem. J. 314:361–385 (review). FKBP-derived domains have been incorporated in the design of chimeric proteins for use in biological switches in genetically engineered cells. Such switches rely upon ligand-mediated multimerization of the protein components to trigger a desired biological event. See e.g. Spencer et al, 1993, Science 262:1019–1024 and PCT/US94/01617. While the potent immunosuppressive activity of FK506 would limit its utility as a multimerizing agent, especially in animals, dimers of FK506 (and related compounds) can be made which lack such immunosuppressive activity. Such dimers have been shown to be effective for multimerizing chimeric proteins containing FKBP-derived ligand binding domains.

Rapamycin, like FK506, is also capable of multimerizing appropriately designed chimeric proteins. We have previously designed biological switches using rapamycin and various derivatives or analogs thereof ("rapalogs") as multimerizing agents (see WO96/41865). In the case of rapamycin itself, its significant biological activities, including potent immunosuppressive activity, rather severely limit its use in biological switches in certain applications, especially those in animals or animal cells which are sensitive to rapamycin. Improved rapalogs for such applications, especially rapalogs with reduced immunosuppressive activity, would be very desirable.

A large number of structural variants of rapamycin have been reported, typically arising as alternative fermentation products or from synthetic efforts to improve the compound's therapeutic index as an immunosuppressive agent. For example, the extensive literature on analogs, homologs, derivatives and other compounds related structurally to rapamycin ("rapalogs") include, among others, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and alternative substitution on the cyclohexyl ring or replacement of the cyclohexyl ring with a substituted cyclopentyl ring. Additional historical information is presented in the background sections of U.S. Pat. Nos. 5,525,610; 5,310,903 and 5,362,718.

U.S. Pat. No. 5,527,907 is illustrative of the patent literature. That document discloses a series of compounds which were synthesized in an effort to make immunosuppressive rapalogs with reduced side effects. The compounds are disclosed via seven generic structural formulas, each followed by extensive lists (two to five or more columns of text each) setting forth possible substituents at various positions on the rapamycin ring. The document includes over 180 synthetic examples. The many structural variants of that invention were reported to be potent immunosuppressive agents.

SUMMARY OF THE INVENTION

This invention provides methods and materials for multimerizing chimeric proteins in genetically engineered cells using improved rapalogs, preferably while avoiding the immunosuppressive effects of rapamycin.

The genetically engineered cells contain one or more recombinant nucleic acid constructs encoding specialized chimeric proteins as described herein. Typically a first chimeric protein contains one or more FKBP domains which are capable of binding to an improved rapalog of this invention. This first chimeric protein is also referred to herein as an "FKBP fusion protein" and further comprises at least one protein domain heterologous to at least one of its FKBP domains. The complex formed by the binding of the FKBP fusion protein to the rapalog is capable of binding to a second chimeric protein which contains one or more FRB domains (the "FRB fusion protein"). The FRB fusion protein further comprises at least one protein domain heterologous to at least one of its FRB domains. In some embodiments, the FKBP fusion protein and the FRB fusion protein are different from one another. In other embodiments, however, the FKBP fusion protein is also an FRB fusion protein. In those embodiments, the chimeric protein comprises one or more FKBP domains as well as one or more FRB domains. In such cases, the first and second chimeric proteins may be the same protein, may be referred to as FKBP-FRB fusion proteins and contain at least one domain heterologous to the FKBP and/or FRB domains.

The chimeric proteins may be readily designed, based on incorporation of appropriately chosen heterologous domains, such that their multimerization triggers one-or more of a wide variety of desired biological responses. The nature of the biological response triggered by rapalog-mediated complexation is determined by the choice of heterologous domains in the fusion proteins. The heterologous domains are therefore referred to as "action" or "effector" domains. The genetically engineered cells for use in practicing this invention will contain one or more recombinant nucleic acid constructs encoding the chimeric proteins, and in certain applications, will further contain one or more accessory nucleic acid constructs, such as one or more target gene constructs. Illustrative biological responses, applications of the system and types of accessory nucleic acid constructs are discussed in detail below.

A system involving related materials and methods is disclosed in WO 96/41865 (Clackson et al) and is expected to be useful in a variety of applications including, among others, research uses and therapeutic applications. That system involves the use of a multimerizing agent comprising rapamycin or a rapalog of the generic formula:

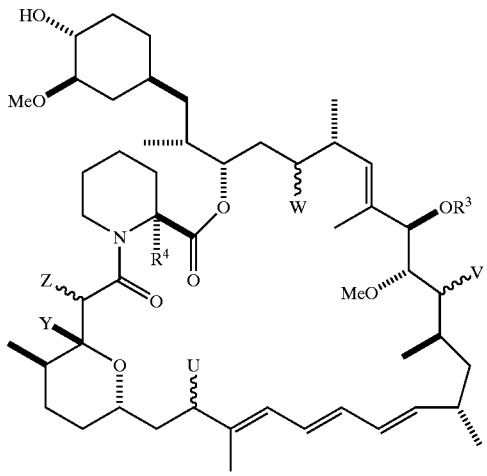

wherein U is —H, —OR¹, —SR¹, —OC(O)R¹, —OC(O)NHR¹, —NHR¹, —NHC(O)R¹, —NHSO₂—R¹ or —R²; R² is a substituted aryl or allyl or alkylaryl (e.g. benzyl or substituted benzyl); V is —R³ or (═O); W is ═O, ═NR⁴═NOR⁴, ═NNHR⁴, —NHOR⁴, —NHNHR⁴, —OR⁴, —OC(O)R⁴, —OC(O)NR⁴ or —H; Y is —OR⁵, —OC(O)R⁵ or —OC(O)NHR⁵; Z is ═O, —OR⁶, —NR⁶, —H, —NC(O)R⁶, —OC(O)R⁶ or —OC(O)NR⁶; R³ is H, —R⁷, —C(O)R⁷, —C(O)NHR⁷ or C-28/C-30 cyclic carbonate; and R⁴ is H or alkyl; where R¹, R⁴, R⁵, R⁶ and R⁷ are independently selected from H, alkyl, alkylaryl or aryl, as those terms are defined in WO 96/41865. A number of rapalogs are specifically disclosed in that document.

The subject invention is based upon a system similar to that disclosed in WO 96/41865, but involves the use of improved rapalogs as the multimerizing agents. The subject invention thus provides a method for multimerizing chimeric proteins in cells which comprises (a) providing appropriately engineered cells containing nucleic acid constructs for directing the expression of the desired chimeric protein (s) and any desired accessory recombinant constructs, and (b) contacting the cells with an improved rapalog or a pharmaceutically acceptable derivative thereof as described herein. The rapalog forms a complex containing itself and at least two molecules of the chimeric protein(s). Improved rapalogs for use in this invention include the following.

One class of improved rapalogs for use in this invention consists of those compounds which comprise the substructure shown in Formula I:

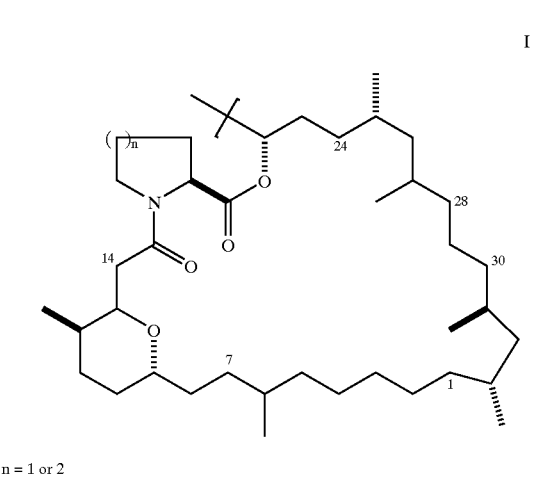

n = 1 or 2 bearing any number of a variety of substituents, and optionally unsaturated at one or more carbon—carbon bonds unless specified to the contrary herein, which have a substantially reduced immunosuppressive effect as compared with rapamycin. By a "substantially reduced immunosuppressive effect" we mean that the rapalog has less than 0.1, preferably less than 0.01, and even more preferably, less than 0.005 times the immunosuppressive effect observed or expected with an equimolar amount of rapamycin, as measured either clinically or in an appropriate in vitro or in vivo surrogate of human immunosuppressive activity, preferably carried out on tissues of lymphoid origin, or alternatively, that the rapalog yields an EC50 value in such an in vitro assay which is at least ten times, preferably at least 100 times and more preferably at least 250 times larger than the EC50 value observed for rapamycin in the same assay.

One appropriate in vitro surrogate of immunosuppression in a human patient is inhibition of human T cell proliferation in vitro. This is a conventional assay approach that may be conducted in a number of well known variations using various human T cells or cells lines, including among others human PBLs and Jurkat cells. A rapalog may thus be assayed for human immunosuppressive activity and compared with rapamycin. A decrease in immunosuppressive activity relative to rapamycin measured in an appropriate in vitro assay is predictive of a decrease in immunosuppressive activity in humans, relative to rapamycin. Such in vitro assays may be used to evaluate the rapalog's relative immunosuppressive activity.

A variety of illustrative examples of such rapalogs are disclosed herein. This class of improved rapalogs includes, among others, those which bind to human FKBP12, or inhibit its rotamase activity, within an order of magnitude of results obtained with rapamycin in any conventional FKBP binding or rotamase assay.

Other classes of improved rapalogs for use in this invention are defined with reference to the structure shown in Formula II:

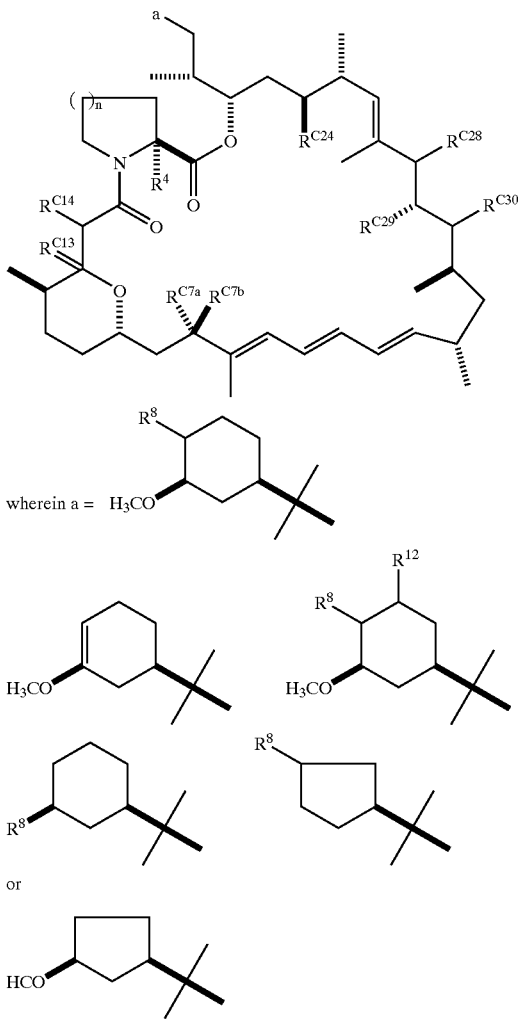

and,
one of $R^{C7a}$ and $R^{C7b}$ is H and the other is —H, halo, —$R^2$, —$OR^1$, —$SR^1$, —$OC(O)R^1$ or —$OC(O)NHR^1$, —$NHR^1$, —$NR^1R^2$, —$NHC(O)R^1$, or —$NH$—$SO_2$—$R^1$ where $R^2$=aliphatic, heteroaliphatic, aryl, heteroaryl or alkylaryl (e.g. benzyl or substituted benzyl);

$R^{C30}$ is halo, —$OR^3$ or (=O);

$R^{C24}$ is =O, =$NR^4$, =$NOR^4$, =$NNHR^4$, =$NHOR^4$, =$NHNHR^4$, =$OR^4$, —$OC(O)R^4$ or —$OC(O)NR^4$, halo or —H;

$R^{C13}$ and $R^{C28}$ are independently H, halo, —$OR^3$, —$OR^5$, —$OC(O)R^5$, —$OC(O)NHR^5$, —$SR^5$, —$SC(O)R^5$, —$SC(O)NHR^5$, —$NR^5R^{5'}$ or —$N(R^5)(CO)R^{5'}$;

$R^{C14}$ is =O, —$OR^6$, —$NR^6$, —H, —$NC(O)R^6$, —$OC(O)R^6$ or —$OC(O)NR^6$;

$R^3$ is H, —$R^7$, —$C(O)R^7$ or —$C(O)NHR^7$ or a cyclic moiety (e.g., carbonate) bridging C28 and C30; and, $R^{C29}$ is H or $OR^{11}$ (e.g., OH or OMe);

where each substituent may be present in either stereochemical orientation unless otherwise indicated, and where wach occurence of $R^1$, $R^4$, $R^5$, $R^6$, $R^7$, $R^9$, $R^{10}$ and $R^{11}$ is independently selected from H, aliphatic, heteroaliphatic, aryl, and heteroaryl; and $R^8$ is H, halo, —CN, =O, —OH, —$NR^9R^{10}$, $OSO_2CF_3$, $OSO_2F$, $OSO_2R^{4'}$, $OCOR^{4'}$, $OCONR^{4'}R^{5'}$, or $OCON(OR^{4'})R^{5'}$.

Improved rapalogs useful in praticing this invention, including rapalogs of Formula II, may contain substituents in any of the possible stereoisomeric orientations, and may comprise one stereoisomer subtantially free of other stereoisomers (>90%, and preferable >95%, free from other stereoisomers on a molar basis) or may comprise a mixture of stereoisomers.

One class of improved rapalogs for use in this invention which are of particular interest are rapalogs of Formula II wherein one or both of $R^{C13}$ and $R^{C28}$ is independently H, halo, —$OR^3$, —$OR^5$, —$OC(O)R^5$, —$OC(O)NHR^5$, —$SR^5$, —$SC(O)R^5$, —$SC(O)NHR^5$, —$NR^5R^{5'}$ or —$N(R^5)(CO)R^{5'}$, where each halo moiety is independently selected form F, Cl, Br and I. One subset of such compounds differs in structure from rapamycin only at one or both of $R^{C13}$ and $R^{C28}$. Another subset of such compounds differs in structure from rapamycin at one or more additional positions, as set forth above in connection with Formula II or in connection with any of the other classes of improved rapalogs noted herein. Compounds of both subsets which are of particular note are those in which one or both of $R^{C13}$ and $R^{C28}$ is a helo substituent, independently selected from F, Cl, Br and I, or a substituted or unsubstituted amino moiety or acylated derivative thereof. These compounds include the 13-halo rapamycins, 28-halo rapamycins, 13, 28-dihalo rapamycins and related compounds in which one or more other moities (e.g. one or both substituents at C7, for instance), in addition to the C13 and C28 substituents, differ from the corresponding moiety(ies) in rapamycin.

Another class of improved rapalogs for use in this invention which are of particular interest are rapalogs of Formula II wherein both $R^{C24}$ and $R^{C30}$ are other than =O. This class includes 24, 30-tetrahydro rapamycin and mono and diethers thereof and the 24,30-dihalo rapamycins. One subset of such compounds differs in structure from rapamycin only at $R^{C24}$ and $R^{C30}$. Another subset of such compounds differs in structure from rapamycin at one or more additional positions (e.g. one or both substituents at C7, for instance), as set forth above in connection with Formula II or in connection with any of the other classes of improved rapalogs noted herein.

Another class of improved rapalogs for use in this invention which are of particular interest are rapalogs of Formula II wherein $R^{C7a}$ and $R^{C7b}$ are moieties other than a substituted or unsubstituted allyl group or a methoxy moiety. This class includes rapalogs in which one of $R^{C7a}$ and $R^{C7b}$ is H and the other is phenyl, di- or tri-substituted phenyl or a mono- or di-substituted heterocyclic moiety. Illustrative examples include among others, o,p-dialkoxyphenyl substituents (e.g., o,p-dimethoxyphenyl, o-methoxy-p-ethoxyphenyl, o-ethoxy-p-methoxyphenyl, o,p-diethoxyphenyl, o,p-di (n- or iso-)propoxyphenyl, etc.), trialkoxyphenyl substituents, monosubstituted heterocycles such as methylthiophene, etc. One subset of such compounds differs in structure from rapamycin only at $R^{C24}$ and $R^{C30}$. Another subset of such compounds differs in structure from rapamycin at one or more additional position, as set forth above in connection with Formula II or in connection with any of the other classes of improved rapalogs noted herein.

Another class of improved rapalogs for use in this invention which are of particular interest are rapalogs of Formula II wherein n is 1. This class of rapalogs includes rapalogs comprising a prolyl ring system in place of a pipicolate ring system. One subset of such compounds differs in structure from rapamycin only with respect to the pipicolate ring system. Another subset of such compounds differs in structure from rapamycin with respect to one or more additional structural features (e.g. one or both substituents at C7, for instance), as set forth above in connection with Formula II or in connection with any of the other classes of improved rapalogs noted herein.

Another class of improved rapalogs for use in this invention which are of particular interest are rapalogs of Formula II wherein moiety "a" is other than

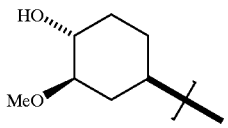

One subset of such compounds differs in structure from rapamycin only with respect to the ring system, "a". Another subset of such compounds differs in structure from rapamycin with respect to one or more additional structural features (e.g. one or both substituents at C7, for instance), as set forth above in connection with Formula II or in connection with any of the other classes of improved rapalogs noted herein. This class of rapalogs include the class of 43-epi-rapalogs in which the hydroxyl moiety at position 43 has the opposite stereochemical orientation with that shown immediately above, is a mixture of stereoisomers of the 43-hydroxyl group or contains derivatives of any of the foregoing, including ethers, esters, carbamates, halides and other derivatives of any of the foregoing position 43 rapalogs. This class further includes rapalogs in which the cyclohexyl ring is otherwise substituted and/or contains 5 ring atoms in place of the characteristic substituted cyclohexyl ring of rapamycin.

Again, the improved rapalogs as described herein are used in a method for multimerizing chimeric proteins in genetically engineered cells. The method involves (a) providing appropriately engineered cells containing nucleic acid constructs for directing the expression of the desired chimeric proteins (and any desired accessory recombinant constructs), and (b) contacting the cells with an improved rapalog or a pharmaceutically acceptable derivative thereof.

In one embodiment, at least one of the chimeric proteins contains at least one FKBP domain whose peptide sequence differs from a naturally occurring FKBP peptide sequence, e.g. the peptide sequence of human FKBP12, at up to ten amino acid residues in the peptide sequence. Preferably the number of changes in peptide sequence is limited to five, and more preferably to 1, 2, or 3. In embodiments in which the rapalog comprises a structural modification relative to rapamycin at $R^{C28}$, at $R^{C24}$ and $R^{C30}$, and/or at $R^{C7a}$ and/or $R^{C7b}$, it is also of special interest that at least one of the chimeric proteins contains at least one FKBP domain comprising at least one amino acid replacement relative to the sequence of a naturally occurring FKBP, especially a mammalian FKBP such as human FKBP12. Mutations of particular interest include replacement of either or both of Phe36 and Phe99 of human FKBP12 sequence with independently selected replacement amino acids, e.g. valine, methionine, alanine or serine.

In another embodiment, at least one of the chimeric proteins contains at least one FRB domain whose peptide sequence differs from a naturally occurring FRB peptide sequence, e.g. the FRB domain of human FRAP, at up to ten amino acid residues in the peptide sequence. Preferably the number of changes in peptide sequence is limited to five, and more preferably to 1, 2, or 3. in many cases it will be preferred that the FRB domain contains a single amino acid replacement relative to the peptide sequence of the corresponding FRB domain of human FRAP or some other mammalian FRAP/TOR species. Mutations of particular interest include replacement of one or more of T2098, D2102, Y2038, F2039, K2095 of an FRB domain derived from human FRAP with independently selected replacement amino acids, e.g. A, N, H, L, or S. Also of interest are the replacement of one or more of F1975, F1976, D2039 and N2035 of an FRB domain derived from yeast TOR1, or the replacement of one or more of F1978, F1979, D2042 and N2038 of an FRB domain derived from yeast TOR2, with independently selected replacement amino acids, e.g. H, L, S, A or V.

In certain embodiments the chimeric protein(s) contain at least one modification in peptide sequence, preferably up to three modifications, relative to naturally occurring sequences, in both one or more FKBP domains and one or more FRB domains.

As mentioned previously, in the various embodiments of this invention, the chimeric protein(s) contain one or more "action" or "effector" domains which are heterologous with respect to the FKBP and/or FRB domains. Effector domains may be selected from a wide variety of protein domains including DNA binding domains, transcription activation domains, cellular localization domains and signaling domains (i.e., domains which are capable upon clustering or multimerization, of triggering cell growth, proliferation, differentiation, apoptosis, gene transcription, etc.). A variety of illustrative effector domains which may be used in practising this invention are disclosed in the various scientific and patent documents cited herein.

For example, in certain embodiments, one fusion protein contains at least one DNA binding domain (e.g., a GAL4 or ZFHD1 DNA-binding domain) and another fusion protein contains at least one transcription activation domain (e.g., a VP16 or p65 transcription activation domain). Ligand-mediated association of the fusion proteins represents the formation of a transcription factor complex and leads to initiation of transcription of a target gene linked to a DNA sequence recognized by (i.e., capable of binding with) the DNA-binding domain on one of the fusion proteins.

In other embodiments, one fusion protein contains at least one domain capable of directing the fusion protein to a particular cellular location such as the cell membrane, nucleus, ER or other organelle or cellular component. Localization domains which target the cell membrane, for example, include domains such as a myristoylation site or a transmembrane region of a receptor protein or other membrane-spanning protein. Another fusion protein can contain a signaling domain capable, upon membrane localization and/or clustering, of activating a cellular signal transduction pathway. Examples of signaling domains include an intracellular domain of a growth factor or cytokine receptor, an apoptosis triggering domain such as the intracellular domain of FAS or TNF-R1, and domains derived from other intracellular signaling proteins such as SOS, Raf, Ick, ZAP-70, etc. A number of signaling proteins are disclosed in PCT/US94/01617 (see e.g. pages 23–26). In still other embodiments, each of the fusion proteins contains at least one FRB domain and at least one FKBP domain, as well as one or more heterologous domains. Such fusion proteins are capable of homodimerization and triggering signaling in the presence of the rapalog. In general, domains containing peptide sequence endogenous to the host cell are preferred in applications involving whole organisms. Thus, for human gene therapy applications, domains of human origin are of particular interest.

Recombinant nucleic acid constructs encoding the fusion proteins are also provided, as are nucleic acid constructs capable of directing their expression, and vectors containing such constructs for introducing them into cells, particularly eukaryotic cells, of which yeast and animal cells are of particular interest. In view of the constituent components of the fusion proteins, the recombinant DNA molecules which encode them are capable of selectively hybridizing (a) to a DNA molecule encoding a polypeptide comprising an FRB domain or FKBP domain and (b) to a DNA molecule encoding the heterologous domain or a protein from which the heterologous protein domain was derived. DNAs are also encompassed which would be capable of so hybridizing but for the degeneracy of the genetic code.

Using nucleic acid sequences encoding the fusion proteins, nucleic acid constructs for directing their expression in eukaryotic cells, and vectors or other means for introducing such constructs into cells, especially animal cells, one may genetically engineer cells, particularly animal cells, preferably mammlian cells, and most preferably human cells, for a number of important uses. To do so, one first provides an expression vector or nucleic acid construct for directing the expression in a eukaryotic (preferably animal) cell of the desired chimeric protein(s) and then introduces the recombinant DNA into the cells in a manner permitting DNA uptake and expression of the introduced DNA in at least a portion of the cells. One may use any of the various methods and materials for introducing DNA into cells for heterologous gene expression, a variety of which are well known and/or commercially available.

One object of this invention is thus a method for multimerizing fusion proteins, such as described herein, in cells, preferably animal cells. To recap, one of the fusion proteins is capable of binding to the improved rapalog of this invention and contains at least one FKBP domain and at least one domain heterologous thereto. The second fusion protein contains at least one FRB domain and at least one domain heterologous thereto and is capable of forming a tripartite complex with the first fusion protein and one or more molecules of the improved rapalog. In some embodiments one or more of the heterologous domains present on one of the fusion proteins are also present on the other fusion protein, i.e., the two fusion proteins have one or more common heterologous domains. In other embodiments, each fusion protein contains one or more different heterologous domains.

The method comprises contacting appropriately engineered cells with the improved rapalog by adding the rapalog to the culture medium in which the cells are located or administering the rapalog to the organism in which the cells are located. The cells are preferably eukaryotic cells, more preferably animal cells, and most preferably mammalian cells. Primate cells, especially human cells, are of particular interest. Administration of the improved rapalog to a human or non-human animal may be effected using any pharmaceutically acceptable formulation and route of administration. Oral administration of a pharmaceutically acceptable composition containing the improved rapalog together with one or more pharmaceuticaly acceptable carriers, buffers or other excipients is currently of greatest interest.

A specific object of this invention is a method, as otherwise described above, for inducing transcription of a target gene in a rapalog-dependent manner. The cells typically contain, in addition to recombinant DNAs encoding the two fusion proteins, a target gene construct which comprises a target gene operably linked to a DNA sequence which is responsive to the presence of a complex of the fusion proteins with rapamycin or a rapalog. The target gene construct may be recombinant, and the target gene and/or a regulatory nucleic acid sequence linked thereto may be heterologous with respect to the host cell. In certain embodiments the cells are responsive to contact with an improved rapalog which binds to the FKBP fusion protein and participates in a complex with a FRB fusion protein with a detectable preference over binding to endogenous FKBP and/or FRB-containing proteins of the host cell.

Another specific object of this invention is a method, as otherwise described above, for inducing cell death in a rapalog-dependent manner. In such cells, at least one of the heterologous domains on at least one fusion protein, and usually two fusion proteins, is a domain such as the intracellular domain of FAS or TNF-R1, which, upon clustering, triggers apoptosis of the cell.

Another specific object of this invention is a method, as otherwise described above, for inducing cell growth, differentiation or proliferation in a rapalog-dependent manner. In such cells, at least one of the heterologous domains of at least one of the fusion proteins is a signaling domain such as, for example, the intracellular domain of a receptor for a hormone which mediates cell growth, differentiation or proliferation, or a downstream mediator of such a receptor. Cell growth, differentiation and/or proliferation follows clustering of such signalling domains. Such clustering occurs in nature following hormone binding, and in engineered cells of this invention following contact with an improved rapalog.

Cells of human origin are preferred for human gene therapy applications, although cell types of various origins (human or other species) may be used, and may, if desired, be encapsulated within a biocompatible material for use in human subjects.

Also provided are materials and methods for producing the foregoing engineered cells. This object is met by providing recombinant nucleic acids, typically DNA molecules, encoding the fusion proteins, together with any desired ancillary recombinant nucleic acids such as a target gene construct, and introducing the recombinant nucleic acids into the host cells under conditions permitting nucleic acid uptake by cells. Such transfection may be effected ex vivo, using host cells maintained in culture. Cells that are engineered in culture may subsequently be introduced into a host organism, e.g. in ex vivo gene therapy applications. Doing so thus constitutes a method for providing a host organism, preferably a human or non-human mammal, which is responsive (as described herein) to the presence of an improved rapalog as provided herein. Alternatively transfection may be effected in vivo, using host cells present in a human or non-human host organism. In such cases, the nucleic acid molecules are introduced directly into the host organism under conditions permitting uptake of nucleic acids by one or more of the host organism's cells. This approach thus constitutes an alternative method for providing a host organism, preferably a human or non-human mammal, which is responsive (as described herein) to the presence of an improved rapalog. Various materials and methods for the introduction of DNA and RNA into cells in culture or in whole organisms are known in the art and may be adapted for use in practicing this invention.

Other objects are achieved using the engineered cells described herein. For instance, a method is provided for multimerizing fusion proteins of this invention by contacting cells engineered as described herein with an effective amount of the improved rapalog permitting the rapalog to form a complex with the fusion proteins. In embodiments in which multimerization of the fusion proteins triggers transcription of a target gene, this constitutes a method for activating the expression of the target gene. In embodiments in which the fusion proteins contain one or more signaling domains, this constitutes a method for activating a cellular signal transduction pathway. In specific embodiments in which the signaling domains are selected based on their ability following clustering to trigger cell growth, proliferation, diffeentiation or cell death, improved rapalog-mediated clustering constitutes a method for actuating cell growth, proliferation, diffeentiation or cell death, as the case may be. These methods may be carried out in cell culture or in whole organisms, including human patients. In the former case, the rapamycin or rapalog is added to the culture medium. In the latter case, the rapamycin or rapalog (which may be in the form of a pharmaceutical or veterinary composition) is administered to the whole organism, e.g., orally, parenterally, etc. Preferably, the dose of the improved rapalog administered to an animal is below the dosage level that would cause undue immunosuppression in the recipient.

Also disclosed are kits for use in the genetic engineering of cells or human or non-human animals as described herein. One such kit contains one or more recombinant nucleic acid constructs encoding fusion proteins of this invention. The recombinant nucleic acid constructs will generally be in the form of eukaryotic expression vectors suitable for introduction into animal cells and capable of directing the expression of the fusion proteins therein. Such vectors may be viral vectors as described elsewhere herein. The kit may also contain a sample of an improved rapalog of this invention capable of forming a complex with the encoded fusion proteins. The kit may further contain a multimerization antagonist such as FK506 or some other compound capable of binding to one of the fusion proteins but incapable of forming a complex with both. In certain embodiments, the recombinant nucleic acid constructs encoding the fusion proteins will contain a cloning site in place of DNA encoding one or more of the heterologous domains, thus permitting the practitioner to introduce DNA encoding a heterologous domain of choice. In some embodiments the kit may also contain a target gene construct containing a target gene or cloning site linked to a DNA sequence responsive to the presence of the complexed fusion proteins, as described in more detail elsewhere. The kit may contain a package insert identifying the enclosed nucleic acid construct(s), and/or instructions for introducing the construct(s) into host cells or organisms.

DETAILED DESCRIPTION OF THE INVENTION

Definitions

Figure 1:
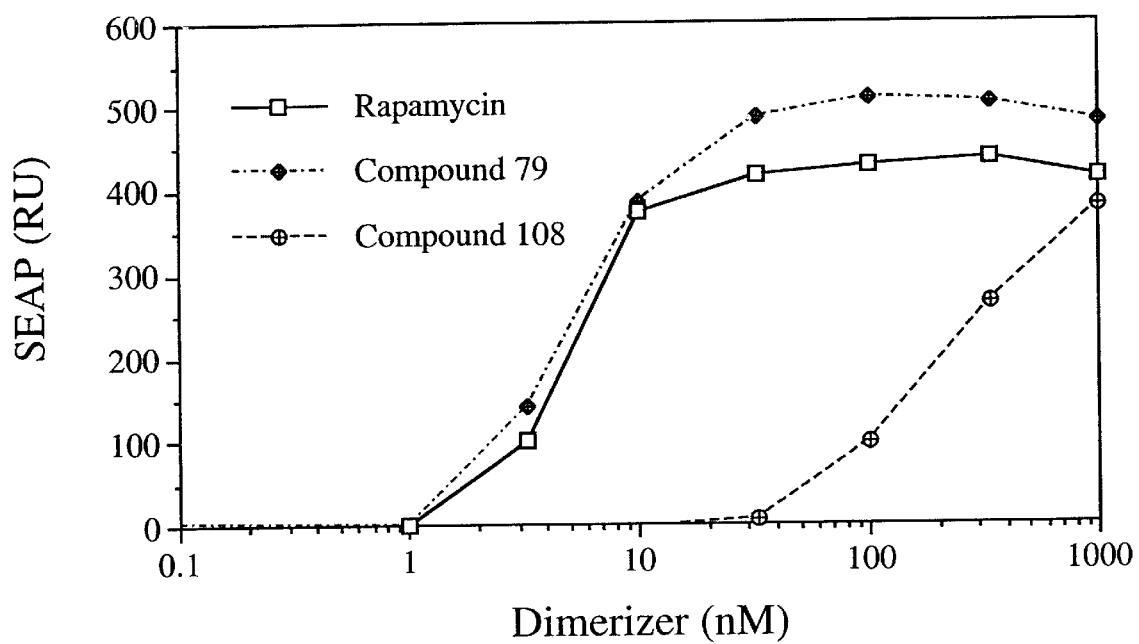
FIG. 1 demonstrates the ability of 13-F-rapalogs (compounds 79 and 108, synthesized as described in Examples 6.1 and 6.21, respectively) to stimulate expression of a DNA sequence encoding secreted alkaline phosphatase ("SEAP") in HT1080 cells engineered as described in Example 7.

The definitions and orienting information below will be helpful for a full understanding of this document.

FRB domains are polypeptide regions (protein "domains"), typically of at least about 89 amino acid residues, which are capable of forming a tripartite complex with an FKBP protein and rapamycin (or an improved rapalog of this invention). FRB domains are present in a number of naturally occurring proteins, including FRAP proteins (also referred to in the literature as "RAPT1" or "RAFT") from human and other species; yeast proteins including Tor1 and Tor2; and a Candida FRAP homolog. Information concerning the nucleotide sequences, cloning, and other aspects of these proteins is already known in the art, permitting the synthesis or cloning of DNA encoding the desired FRB peptide sequence, e.g., using well known methods and PCR primers based on published sequences.

| protein source | reference/sequence accession numbers |
| --- | --- |
| human FRAP | Brown et al, 1994, Nature 369, 756–758; GenBank accession #L34075, NCBI Seq ID 508481; Chiu et al, 1994, PNAS USA 91, 12574–12578; Chen et al, 1995, PNAS USA 92, 4947–4951 |
| murine RAPT1 | Chiu et al, supra. |
| yeast Tor1 | Helliwell et al, 1994, Mol Cell Biol 5, 105–118; EMBL Accession #X74857, NCBI Seq Id #468738 |
| yeast Tor 2 | Kunz et al, 1993, Cell 73, 585–596; EMBL Accession #X71416, NCBI Seq ID 298027 |
| Candida TOR | WO95/33052 (Berlin et al) |

FRB domains for use in this invention generally contain at least about 89–100 amino acid residues. FIG. 2 of Chiu et al, supra, displays a 160-amino acid span of human FRAP, murine FRAP, S. cerevisiae TOR1 and S. cerevisiae TOR2 encompassing the conserved FRB region. Typically the FRB sequence selected for use in fusion proteins of this invention will span at least the 89-amino acid sequence Glu-39 through Lys/Arg-127, as the sequence is numbered in that figure. For reference, using the numbering of Chen et al or Sabitini et al, the 89-amino acid sequence is numbered Glu-2025 through Lys-2113 in the case of human FRAP, Glu-1965 through Lys-2053 in the case of Tor2, and Glu-1962 through Arg-2050 in the case of Tor1. An FRB domain for use in fusion proteins of this invention will be capable of binding to a complex of an FKBP protein bound to rapamycin or an improved rapalog of this invention (as may be determined by any means, direct or indirect, for detecting such binding, including, for example, means for detecting such binding employed in the FRAP/RAFT/RAPT and Tor-related references cited herein). The peptide sequence of such an FRB domain comprises (a) a naturally occurring peptide sequence spanning at least the indicated 89-amino acid region of the proteins noted above or corresponding regions of homologous proteins; (b) a variant of a naturally occurring FRB sequence in which up to about ten (preferably 1–5, more preferably 1–3, and in some embodiments just one) amino acids of the naturally-occurring peptide sequence have been deleted, inserted, or replaced with substitute amino acids; or (c) a peptide sequence encoded by a DNA sequence capable of selectively hybridizing to a DNA molecule encoding a naturally occurring FRB domain or by a DNA sequence which would be capable, but for the degeneracy of the genetic code, of selectively hybridizing to a DNA molecule encoding a naturally occurring FRB domain.

FKBPs (FK506 binding proteins) are the cytosolic receptors for macrolides such as FK506, FK520 and rapamycin and are highly conserved across species lines. For the purpose of this disclosure, FKBPs are proteins or protein domains which are capable of binding to rapamycin or to an improved rapalog of this invention and further forming a tripartite complex with an FRB-containing protein. An FKBP domain may also be referred to as a "rapamycin binding domain". Information concerning the nucleotide sequences, cloning, and other aspects of various FKBP species is already known in the art, permitting the synthesis or cloning of DNA encoding the desired FKBP peptide sequence, e.g., using well known methods and PCR primers based on published sequences. See e.g. Staendart et al, 1990, Nature 346, 671–674 (human FKBP12); Kay, 1996, Biochem. J. 314, 361–385 (review). Homologous FKBP proteins in other mammalian species, in yeast, and in other organsims are also known in the art and may be used in the fusion proteins disclosed herein. See e.g. Kay, 1996, Biochem. J. 314, 361–385 (review). The size of FKBP domains for use in this invention varies, depending on which FKBP protein is employed. An FKBP domain of a fusion protein of this invention will be capable of binding to rapamycin or an improved rapalog of this invention and participating in a tripartite complex with an FRB-containing protein (as may be determined by any means, direct or indirect, for detecting such binding). The peptide sequence of an FKBP domain of an FKBP fusion protein of this invention comprises (a) a naturally occurring FKBP peptide sequence, preferably derived from the human FKBP12 protein (exemplified below) or a peptide sequence derived from another human FKBP, from a murine or other mammalian FKBP, or from some other animal, yeast or fungal FKBP; (b) a variant of a naturally occurring FKBP sequence in which up to about ten (preferably 1–5, more preferably 1–3, and in some embodiments just one) amino acids of the naturally-occurring peptide sequence have been deleted, inserted, or replaced with substitute amino acids; or (c) a peptide sequence encoded by a DNA sequence capable of selectively hybridizing to a DNA molecule encoding a naturally occurring FKBP or by a DNA sequence which would be capable, but for the degeneracy of the genetic code, of selectively hybridizing to a DNA molecule encoding a naturally occurring FKBP.

"Capable of selectively hybridizing" as that phrase is used herein means that two DNA molecules are susceptible to hybridization with one another, despite the presence of other DNA molecules, under hybridization conditions which can be chosen or readily determined empirically by the practitioner of ordinary skill in this art. Such treatments include conditions of high stringency such as washing extensively with buffers containing 0.2 to 6×SSC, and/or containing 0.1% to 1% SDS, at temperatures ranging from room temperature to 65–75° C. See for example F. M. Ausubel et al., Eds, Short Protocols in Molecular Biology, Units 6.3 and 6.4 (John Wiley and Sons, New York, 3d Edition, 1995).

The terms "protein", "polypeptide" and "peptide" are used interchangeably herein.

"Nucleic acid constructs", as that term is used herein, denote nucleic acids (usually DNA, but also encompassing RNA, e.g. in a retroviral delivery system) used in the practice of this invention which are generally recombinant, as that term is defined below, and which may exist in free form (i.e., not covalently linked to other nucleic acid sequence) or may be present within a larger molecule such as a DNA vector, retroviral or other viral vector or a chromosome of a genetically engineered host cell. Nucleic acid constructs of particular interest are those which encode fusion proteins of this invention or which comprise a target gene and expression control elements. The construct may further include nucleic acid portions comprising one or more of the following elements relevant to regulation of transcription, translation, and/or other processing of the coding region or gene product thereof: transcriptional promoter and/or enhancer sequences, a ribosome binding site, introns, etc.

"Recombinant", "chimeric" and "fusion", as those terms are used herein, denote materials comprising various component domains, sequences or other components which are mutually heterologous in the sense that they do not occur together in the same arrangement, in nature. More specifically, the component portions are not found in the same continuous polypeptide or nucleotide sequence or molecule in nature, at least not in the same cells or order or orientation or with the same spacing present in the chimeric protein or recombinant DNA molecule of this invention.

"Transcription control element" denotes a regulatory DNA sequence, such as initiation signals, enhancers, and promoters, which induce or control transcription of protein coding sequences with which they are operably linked. The term "enhancer" is intended to include regulatory elements capable of increasing, stimulating, or enhancing transcription from a promoter. Such transcription regulatory components can be present upstream of a coding region, or in certain cases (e.g. enhancers), in other locations as well, such as in introns, exons, coding regions, and 3' flanking sequences.

"Dimerization", "oligomerization" and "multimerization" are used interchangeably herein and refer to the association or clustering of two or more protein molecules, mediated by the binding of a drug to at least one of the proteins. In preferred embodiments, the multimerization is mediated by the binding of two or more such protein molecules to a common divalent or multivalent drug. The formation of a complex comprising two or more protein molecules, each of which containing one or more FKBP domains, together with one or more molecules of an FKBP ligand which is at least divalent (e.g. FK1012 or AP1510) is an example of such association or clustering. In cases where at least one of the proteins contains more than one drug binding domain, e.g., where at least one of the proteins contains three FKBP domains, the presence of a divalent drug leads to the clustering of more than two protein molecules. Embodiments in which the drug is more than divalent (e.g. trivalent) in its ability to bind to proteins bearing drug binding domains also can result in clustering of more than two protein molecules. The formation of a tripartite complex comprising a protein containing at least one FRB domain, a protein containing at least one FKBP domain and a molecule of rapamycin is another example of such protein clustering. In certain embodiments of this invention, fusion proteins contain multiple FRB and/or FKBP domains. Complexes of such proteins may contain more than one molecule of rapamycin or a derivative thereof or other dimerizing agent and more than one copy of one or more of the constituent proteins. Again, such multimeric complexes are still referred to herein as tripartite complexes to indicate the presence of the three types of constituent molecules, even if one or more are represented by multiple copies. The formation of complexes containing at least one divalent drug and at least two protein molecules, each of which contains at least one drug binding domain, may be referred to as "oligomerization" or "multimerization", or simply as "dimerization", "clustering" or association".

"Dimerizer" denotes an improved rapalog of this invention which brings together two or more proteins in a multimeric complex.

"Activate" as applied herein to the expression or transcription of a gene denotes a directly or indirectly observable increase in the production of a gene product.

"Genetically engineered cells" denotes cells which have been modified ("transduced") by the introduction of recombinant or heterologous nucleic acids (e.g. one or more DNA constructs or their RNA counterparts) and further includes the progeny of such cells which retain part or all of such genetic modification.

A "therapeutically effective dose" of an improved rapalog of this invention denotes a treatment- or prophylaxis-effective dose, e.g., a dose which yields detectable target gene transcription or cell growth, proliferation, differentiation, death, etc. in the genetically engineered cell, or a dose which is predicted to be treatment- or prophylaxis-effective by extrapolation from data obtained in animal or cell culture models. A therapeutically effective dose is ususally preferred for the treatment of a human or non-human mammal.

This invention involves methods and materials for multimerizing chimeric proteins in genetically engineered cells using improved rapalogs. The design and implementation of various dimerization-based biological switches has been reported, inter alia, in Spencer et al and in various international patent applications cited herein. Other accounts of successful application of this general approach have also been reported. Chimeric proteins containing an FRB domain fused to an effector domain has also been disclosed in Rivera et al, 1996, Nature Medicine 2, 1028–1032 and in WO 96/41865 (Clackson et al) and WO 95/33052 (Berlin et al). As noted previously, the fusion proteins are designed such that association of the effector domains, through ligand-mediated "dimerization" or "multimerization" of the fusion proteins which contain them, triggers a desired biological event such as transcription of a desired gene, cell death, cell proliferation, etc. For example, clustering of chimeric proteins containing an action domain derived from the intracellular portion of the T cell receptor CD3 zeta domain triggers transcription of a gene under the transcriptional control of the IL-2 promoter or promoter elements derived therefrom. In other embodiments, the action domain comprises a domain derived from the intracellular portion of a protein such as FAS or the TNF-alpha receptor (TNFalpha-R1), which are capable, upon oligomerization, of triggering apoptosis of the cell. In still other embodiments, the action domains comprise a DNA-binding domain such as GAIA or ZFHD1 and a transcription activation domain such as VP16 or p65, paired such that oligomerization of the chimeric proteins represents assembly of a transcription factor complex which triggers transcription of a gene linked to a DNA sequence recognized by (capable of specific binding interaction with) the DNA binding domain.

Chimeric proteins containing one or more ligand-binding domains and one or more action domains, e.g. for activation of transcription of a target gene, triggering cell death or other signal transduction pathway, cellular localization, etc., are disclosed in PCT/US94/01617, PCT/US94/08008 and Spencer et al, supra. The design and use of such chimeric proteins for ligand-mediated gene-knock out and for ligand-mediated blockade of gene expression or inhibition of gene product function are disclosed in PCT/US95/10591. Novel DNA binding domains and DNA sequences to which they bind which are useful in embodiments involving regulated transcription of a target gene are disclosed, e.g., in Pomeranz et al, 1995, Science 267:93–96. Those references provide substantial information, guidance and examples relating to the design, construction and use of DNA constructs encoding analogous cimeras, target gene constructs, and other aspects which may also be useful to the practitioner of the subject invention.

By appropriate choice of chimeric proteins, this invention permits one to activate the transcription of a desired gene; actuate cell growth, proliferation, differentiaion or apoptosis; or trigger other biological events in engineered cells in a rapalog-dependent manner analogous to the systems described in the patent documents and other references cited above. The engineered cells preferably animal cells, may be growing or maintained in culture or may be present within whole organisms, as in the case of human gene therapy, transgenic animals, and other such applications. The rapalog is administered to the cell culture or to the organism containing the engineered cells, as the case may be, in an amount effective to multimerize the FKBP fusion proteins and FRB fusion proteins (as may be observed indirectly by monitoring target gene transcription, apoptosis or other biological process so triggered). In the case of administration to whole organisms, the rapalog may be administered in a composition containing the rapalog and one or more acceptable verterinary or pharmaceutical diluents and/or excipients.

A compound which binds to one of the chimeric proteins but does not form tripartite complexes with both chimeric proteins may be used as a multimerization antagonist. As such it may be administered to the engineered cells, or to organisms containing them (preferably in a composition as described above in the case of administration to whole animals), in an amount effective for blocking or reversing the effect of the rapalog, i.e. for preventing, inhibiting or disrupting multimerization of the chimeras. For instance, FK506, FK520 or any of the many synthetic FKBP ligands which do not form tripartite complexes with FKBP and FRAP may be used as an antagonist.

One important aspect of this invention provides materials and methods for rapalog-dependent, direct activation of transcription of a desired gene. In one such embodiment, a set of two or more different chimeric proteins, and corresponding DNA constructs capable of directing their expression, is provided. One such chimeric protein contains as its action domain(s) one or more transcriptional activation domains. The other chimeric protein contains as its action domain(s) one or more DNA-binding domains. A rapalog of this invention is capable of binding to both chimeras to form a dimeric or multimeric complex thus containing at least one DNA binding domain and at least one transcriptional activating domain. Formation of such complexes leads to activation of transcription of a target gene linked to, and under the transcriptional control of, a DNA sequence to which the DNA-binding domain is capable of binding, as can be observed by monitoring directly or indirectly the presence or concentration of the target gene product.

Preferably the DNA binding domain, and a chimera containing it, binds to its recognized DNA sequence with sufficient selectivity so that binding to the selected DNA sequence can be observed (directly or indirectly) despite the presence of other, often numerous other, DNA sequences. Preferably, binding of the chimera comprising the DNA-binding domain to the selected DNA sequence is at least two, more preferably three and even more preferably more than four orders of magnitude greater than binding to any one alternative DNA sequence, as measured by in vitro binding studies or by measuring relative rates or levels of transcription of genes associated with the selected DNA sequence as compared with any alternative DNA sequences.

Cells which have been genetically engineered to contain such a set of constructs, together with any desired accessory constructs, may be used in applications involving ligand-mediated, regulated actuation of the desired biological event, be it regulated transcription of a desired gene, regulated triggering of a signal transduction pathway such as the triggering of apoptosis, or another event. Cells engineered for regulatable expression of a target gene, for instance, can be used for regulated production of a desired protein (or other gene product) encoded by the target gene. Such cells may be grown in culture by conventional means. Addition of the rapalog to the culture medium containing the cells leads to expression of the target gene by the cells and production of the protein encoded by that gene. Expression of the gene and production of the protein can be turned off by withholding further multimerization agent from the media, by removing residual multimerization agent from the media, or by adding to the medium a multimerization antagonist reagent.

Engineered cells of this invention can also be produced and/or used in vivo, to modify whole organisms, preferably animals, especially humans, e.g. such that the cells produce a desired protein or other result within the animal containing them. Such uses include gene therapy applications.

Embodiments involving regulatable actuation of apoptosis provide engineered cells susceptible to rapalog-inducible cell death. Such engineered cells can be eliminated from a cell culture or host organism after they have served their intended purposed (e.g. production of a desired protein or other product), if they have or develop unwanted properties, or if they are no longer useful, safe or desired. Elimination is effected by adding the rapalog to the medium or administering it to the host organism. In such cases, the action domains of the chimeras are protein domains such as the intracellular domains of FAS or TNF-R1, downstream components of their signaling pathways or other protein domains which upon oligomerization trigger apoptosis.

This invention thus provides materials and methods for achieving a biological effect in cells in response to the addition of a rapalog of this invention. The method involves providing cells engineered as described herein and exposing the cells to the rapalog.

For example, this invention provides a method for activating transcription of a target gene in cells. The method involves providing cells containing (a) DNA constructs encoding a set of chimeric proteins of this invention capable upon rapalog-mediated multimerization of initiating transcription of a target gene and (b) a target gene linked to an associated cognate DNA sequence responsive to the multimerization event (e.g. a DNA sequence recognized, i.e., capable of binding with, a DNA-binding domain of a foregoing chimeric protein. The method involves exposing the cells to a rapalog capable of binding to the chimeric proteins in an amount effective to result in expression of the target gene. In cases in which the cells are growing in culture, exposing the cells to the rapalog may be effected by adding the rapalog to the culture medium. In cases in which the cells are present within a host organism, exposing them to the rapalog is effected by administering the rapalog to the host organism. For instance, in cases in which the host organism is a human or non-human, the rapalog may be administered to the host organism by oral, bucal, sublingual, transdermal, subcutaneous, intramuscular, intravenous, intra-joint or inhalation administration in an appropriate vehicle therefor. Again, depending on the design of the constructs for the chimeric proteins and of any accessory constructs, the rapalog-mediated biological event may be activation of a cellular function such as signal transduction leading to cell growth, cell proliferation, gene transcription, or apoptosis; deletion of a gene of interest, blockade of expression of a gene of interest, or inhibition of function of a gene product of interest; direct transcription of a gene of interest; etc.

This invention further encompasses a pharmaceutical composition comprising a rapalog of this invention in admixture with a pharmaceutically acceptable carrier and optionally with one or more pharmaceutically acceptable excipients. Such pharmaceutical compositions can be used to promote multimerization of chimeras of this invention in engineered cells in whole animals, e.g. in human gene therapy applications to achieve any of the objectives disclosed herein.

Said differently, this invention provides a method for achieving any of those objectives, e.g. activation of transcription of a target gene (typically a heterologous gene for a therapeutic protein), cell growth or proliferation, cell death or some other selected biological event, in an animal, preferably a human patient, in need thereof and containing engineered cells of this invention. That method involves administering to the animal a pharmaceutical composition containing the rapalog by a route of administration and in an amount effective to cause multimerization of the chimeric proteins in at least a portion of the engineered cells. Multimerization may be detected indirectly by detecting the occurrence of target gene expression; cell growth, proliferation or death; or other objective for which the chimeras were designed and the cells genetically engineered.

This invention further encompasses a pharmaceutical composition comprising a multimerization antagonist of this invention in admixture with a pharmaceutically acceptable carrier and optionally with one or more pharmaceutically acceptable excipients for inhibiting or otherwise reducing, in whole or part, the extent of multimerization of chimeric proteins in engineered cells of this invention in a subject, and thus for de-activating the transcription of a target gene, for example, or turning off another biological result of this invention. Thus, the use of the multimerizing rapalogs and of the multimerization antagonist reagents to prepare pharmaceutical compositions and achieve their pharmacologic results is encompassed by this invention.

Also disclosed is a method for providing a host organism, preferably an animal, typically a non-human mammal or a human subject, responsive to a rapalog of this invention. The method involves introducing into the organism cells which have been engineered in accordance with this invention, i.e. containing one or more nucleic acid constructs encoding the chimeric proteins, and so forth. The engineered cells may be encapsulated using any of a variety of materials and methods before being introduced into the host organism. Alternatively, one can introduce the nucleic acid constructs of this invention into a host organism, e.g. a mammal, under conditions permitting incorporation thereof into one or more cells of the host mammal, e.g. using viral vectors, introduction of DNA by injection or via catheter, etc.

Also provided are kits for producing cells responsive to a rapalog of this invention. One such kit contains one or more nucleic acid constructs encoding and capable of directing the expression of chimeras which, upon rapalog-mediated oligomerization, trigger the desired biological response. The kit may contain a quantity of a rapalog capable of multimerizing the chimeric protein molecules encoded by the construct(s) of the kit, and may contain in addition a quantity of a multimerization antagonist. The kit may further contain a nucleic acid construct encoding a target gene (or cloning site) linked to a cognate DNA sequence which is recognized by the dimerized chimeric proteins permitting transcription of a gene linked to that cognate DNA sequence in the presence of multimerized chimeric protein molecules. The constructs may be associated with one or more selection markers for convenient selection of transfectants, as well as other conventional vector elements useful for replication in prokaryotes, for expression in euaryotes, and the like. The selection markers may be the same or different for each different construct, permitting the selection of cells which contain each such construct(s).

The accessory construct for introducing into cells a target gene in association with a cognate DNA sequence may contain a cloning site in place of a target gene. A kit containing such a construct permits the engineering of cells for regulatable expression of a gene to be provided by the practitioner.

Other kits of this invention may contain one or two (or more) nucleic acid constructs for chimeric proteins in which one or more contain a cloning site in place of the transcriptional activator or DNA binding protein, permitting the user to insert whichever such domain s/he wishes. Such a kit may optionally include other elements as described above, e.g. a nucleic construct for a target gene with or without a cognate DNA sequence for a pre-selected DNA binding domain.

Any of the kits may also contain positive control cells which were stably transformed with constructs of this invention such that they express a reporter gene (for CAT, beta-galactosidase or any conveniently detectable gene product) in response to exposure of the cells to the rapalog. Reagents for detecting and/or quantifying the expression of the reporter gene may also be provided.

For further information and guidance on the design, construction and use of such systems or components thereof which may be adapted for use in practising the subject invention, reference to the following publications is suggested: Spencer et al, 1993, supra; Rivera et al, 1996, supra; Spencer et al, 1996, Current Biology 6, 839–847; Luo et al, 1996, Nature, 383, 181–185; Ho et al, 1996, Nature 382, 822–826; Belshaw et al, 1996, Proc. Natl. Acad. Sci. USA 93, 4604–4607; Spencer, 1996, TIG 12(5), 181–187; Spencer et al, 1995, Proc., Natl. Acad. Sci. USA 92, 9805–9809; Holsinger et al, 1995, Proc. Natl. Acad. Sci. USA 92, 9810–9814; Pruschy et al, 1994, Chemistry & Biology 1(3),163–172; and published international patent applications WO 94/18317, WO 95/02684, WO 95/33052, WO 96/20951 and WO 96/41865.

A key focus of the subject invention is the use of improved rapalogs as mediators of protein—protein interactions in applications using FKBP and FRB fusion proteins such as described above and elsewhere herein. The improved rapalogs may be used in the various applications of the underlying dimerization-based technology, including triggering biological events in genetically engineered cells grown or maintained in culture or present in whole organisms, including humans and other mammals. The improved rapalogs may thus be useful as research reagents in biological experiments in vitro, in experiments conducted on animals containing the genetically engineered cells, and as prophylactic or therapeutic agents in animal and human health care in subjects containing genetically engineered cells.

Rapalogs

"Rapalogs" as that term is used herein denotes a class of compounds comprising the various analogs, homologs and derivatives of rapamycin and other compounds related structurally to rapamycin. "Rapalogs" include compounds other than rapamycin which comprise the substructure shown in Formula I, bearing any number of a variety of substituents, and optionally unsaturated at one or more carbon—carbon bonds unless specified to the contrary herein.

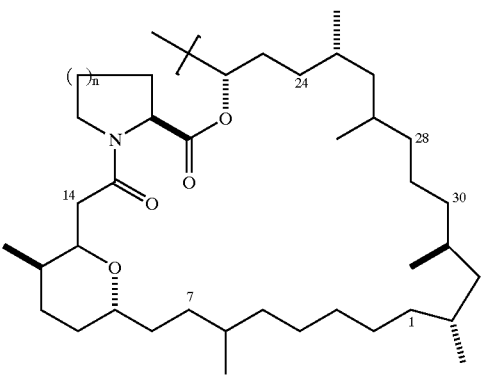

n = 1 or 2

Rapalogs include, among others, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and elimination, derivatization or replacement of one or more substituents of the cyclohexyl ring or replacement of the cyclohexyl ring with a substituted or unsubstituted cyclopentyl ring. Rapalogs, as that term is used herein, do not include rapamycin itself, and preferably do not contain an oxygen bridge between C1 and C30. Illustrative examples of rapalogs are disclosed in the documents listed in Table I. Examples of rapalogs modified at C7 are shown in Table II.

TABLE I

| | | | | |
|---|---|---|---|---|
| WO9710502 | WO9418207 | WO9304680 | US5527907 | US5225403 |
| WO9641807 | WO9410843 | WO9214737 | US5484799 | US5221625 |
| WO9635423 | WO9409010 | WO9205179 | US5457194 | US5210030 |
| WO9603430 | WO94/04540 | US5604234 | US5457182 | US5208241 |
| WO9600282 | WO9402485 | US5597715 | US5362735 | US5200411 |
| WO9516691 | WO9402137 | US5583139 | US5324644 | US5198421 |
| WO9515328 | WO9402136 | US5563172 | US5318895 | US5147877 |
| WO9507468 | WO9325533 | US5561228 | US5310903 | US5140018 |
| WO9504738 | WO9318043 | US5561137 | US5310901 | U55116756 |
| WO9504060 | WO9313663 | US5541193 | US5258389 | U55109112 |
| WO9425022 | WO9311130 | US5541189 | US5252732 | US5093338 |
| WO9421644 | WO9310122 | US5534632 | US5247076 | US5091389 |

TABLE II
Illustrative C7 rapalog structures
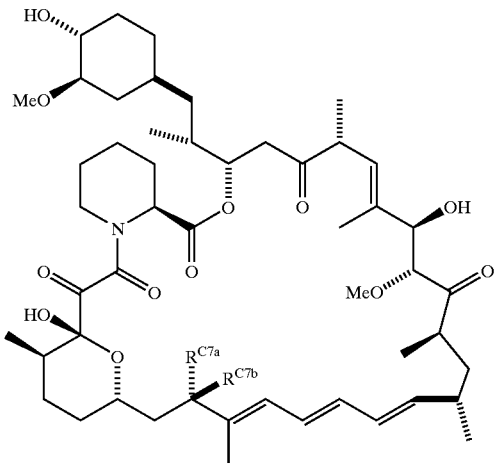
$R^{C7}$ =   ......H
             ......O-ipropyl
             ——OMe
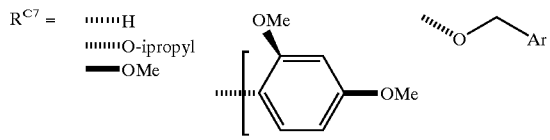
Ar = phenyl, 3-nitrophenyl, 4-chlorophenyl, 3-iodo-4-diazophenyl, 3,4-dimethoxyphenyl, or 2-methoxyphenyl
......OH
——OH
......OEt
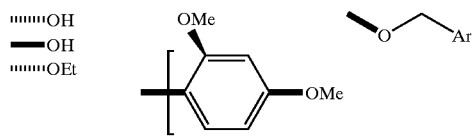
Ar = 3,4-dimethoxyphenyl
——OEt
......OCH$_2$CH$_2$OH
——OCH$_2$CH$_2$OH
—CH$_2$COPhenyl
—OCHO
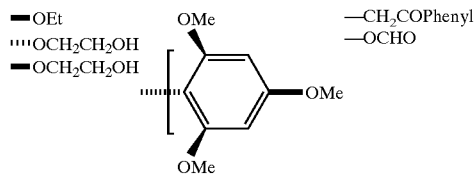
......SMe
——O-ipropyl
......SPhenyl
—CH$_2$CH$_2$OH
—CH$_2$CH(OH)CH$_2$OH
—CH$_2$CH$_2$OCH$_2$CH$_2$OCH$_2$CH$_2$OCH$_3$
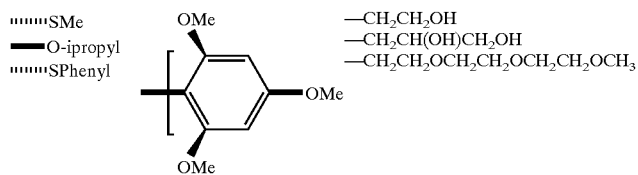

TABLE II-continued
Illustrative C7 rapalog structures
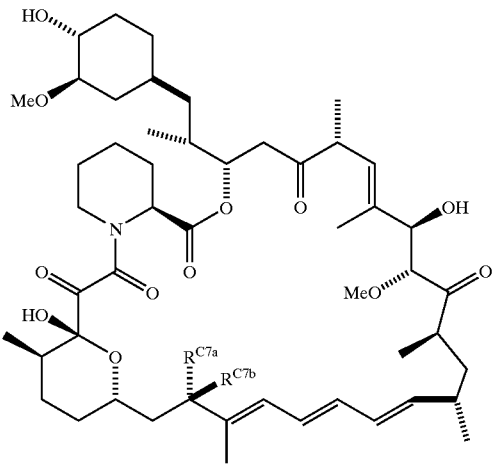
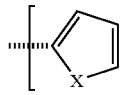 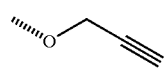
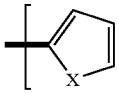 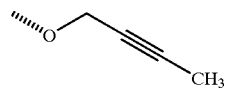
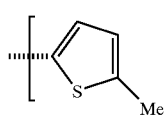 
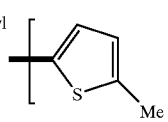 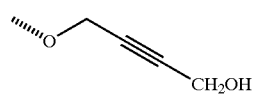
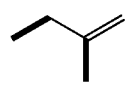 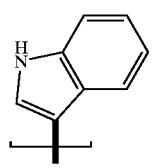 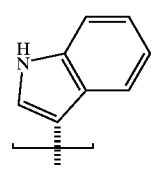

TABLE II-continued
Illustrative C7 rapalog structures
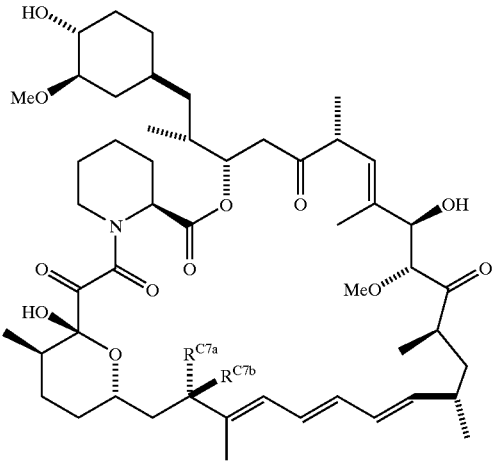
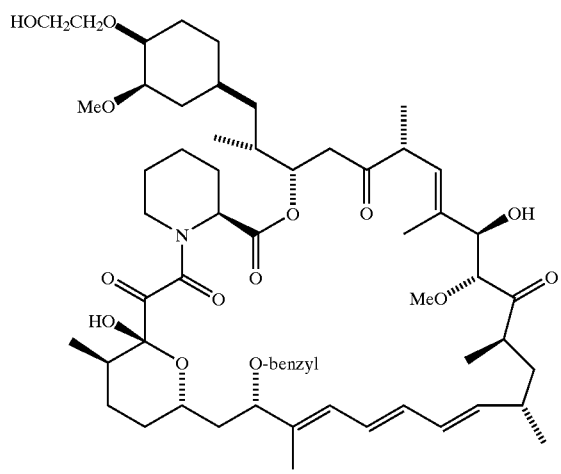
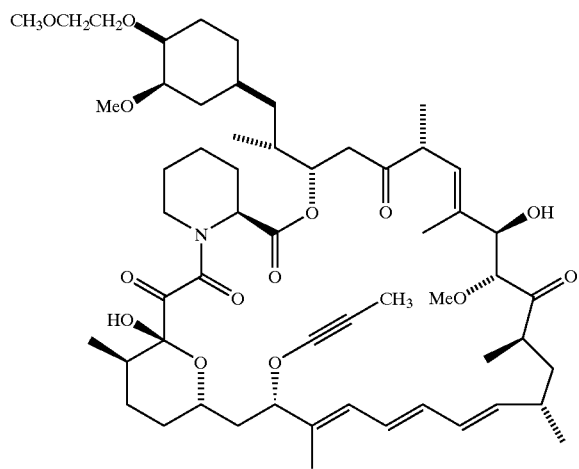

TABLE II-continued
Illustrative C7 rapalog structures
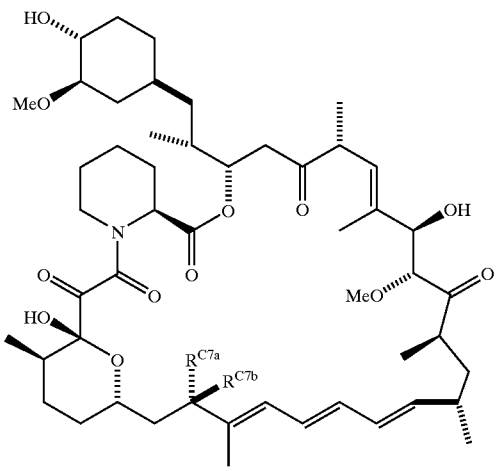
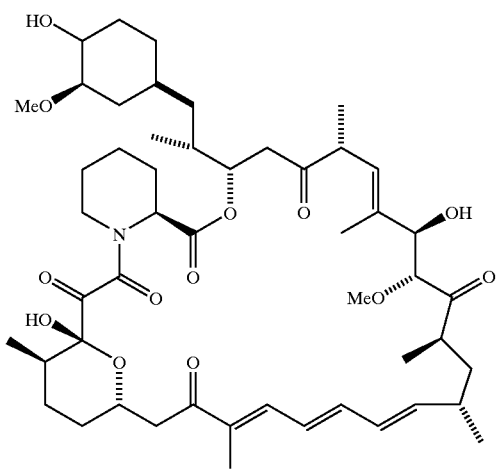
7-oxorapamycin
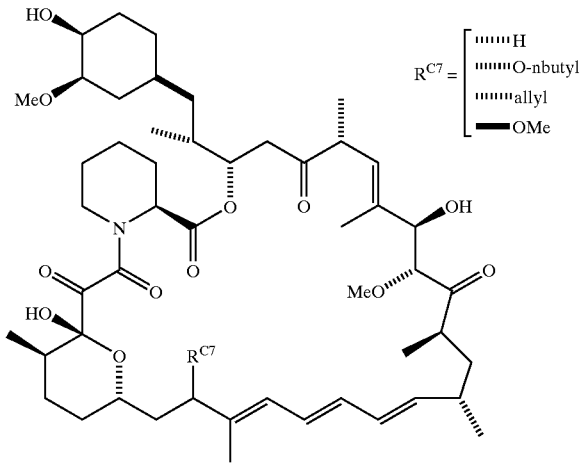
$$R^{C7} = \begin{bmatrix} \text{H} \\ \text{O-nbutyl} \\ \text{allyl} \\ \text{OMe} \end{bmatrix}$$
See e.g.,
Luengo et al, Chemistry & Biology, 1995, 2 (7):471–481; JOC, 1995, 59(22):6512–13
WO 94/02136 (SmithKline Beecham)
WO 95/16691 (Sandoz)
U.S. Pat. No. 5,583,139 (Abbott)

TABLE II-continued
Illustrative C7 rapalog structures
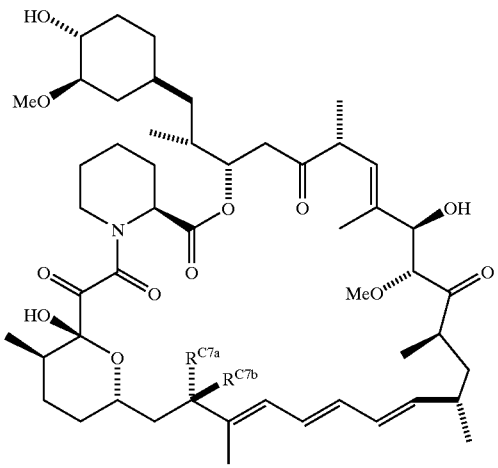
Grinfeld et al, 1994, Tett Letters 35(37):6835–6838
WO 96/41865 (ARIAD)
Other illustrative rapalogs include those depicted in Table III:
TABLE III
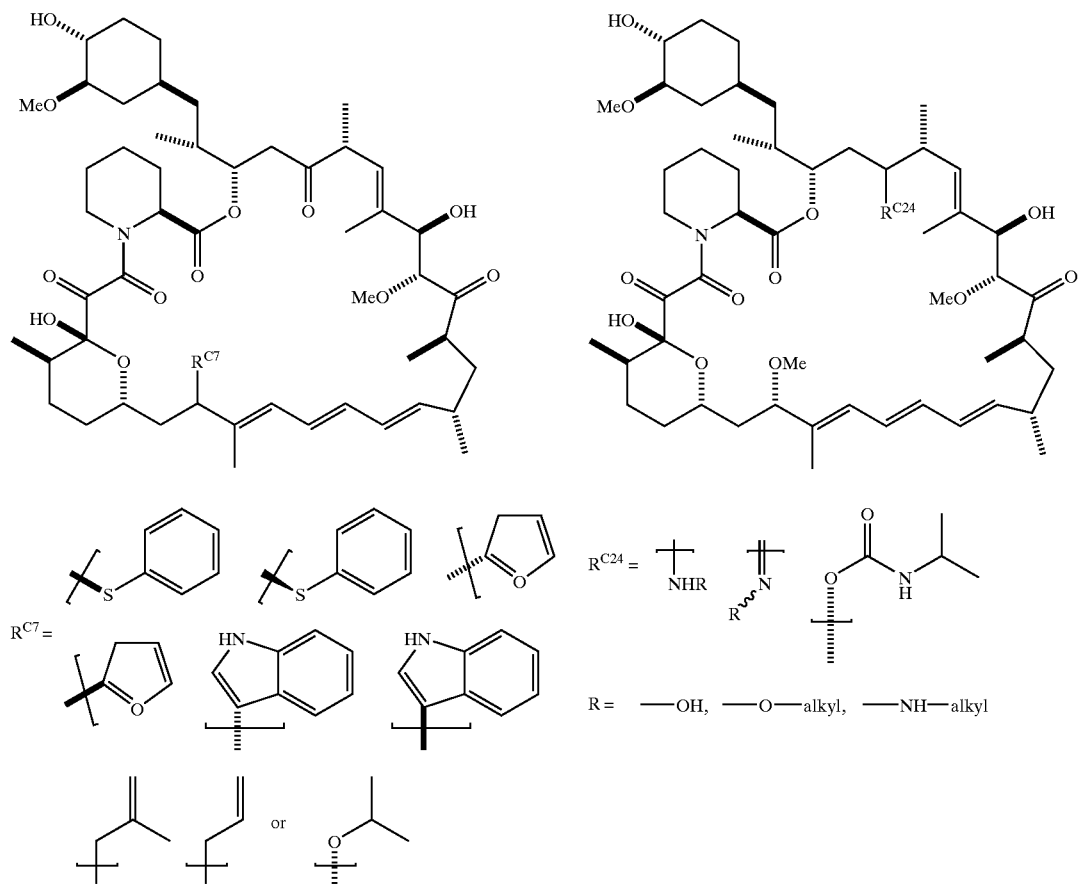

TABLE III-continued
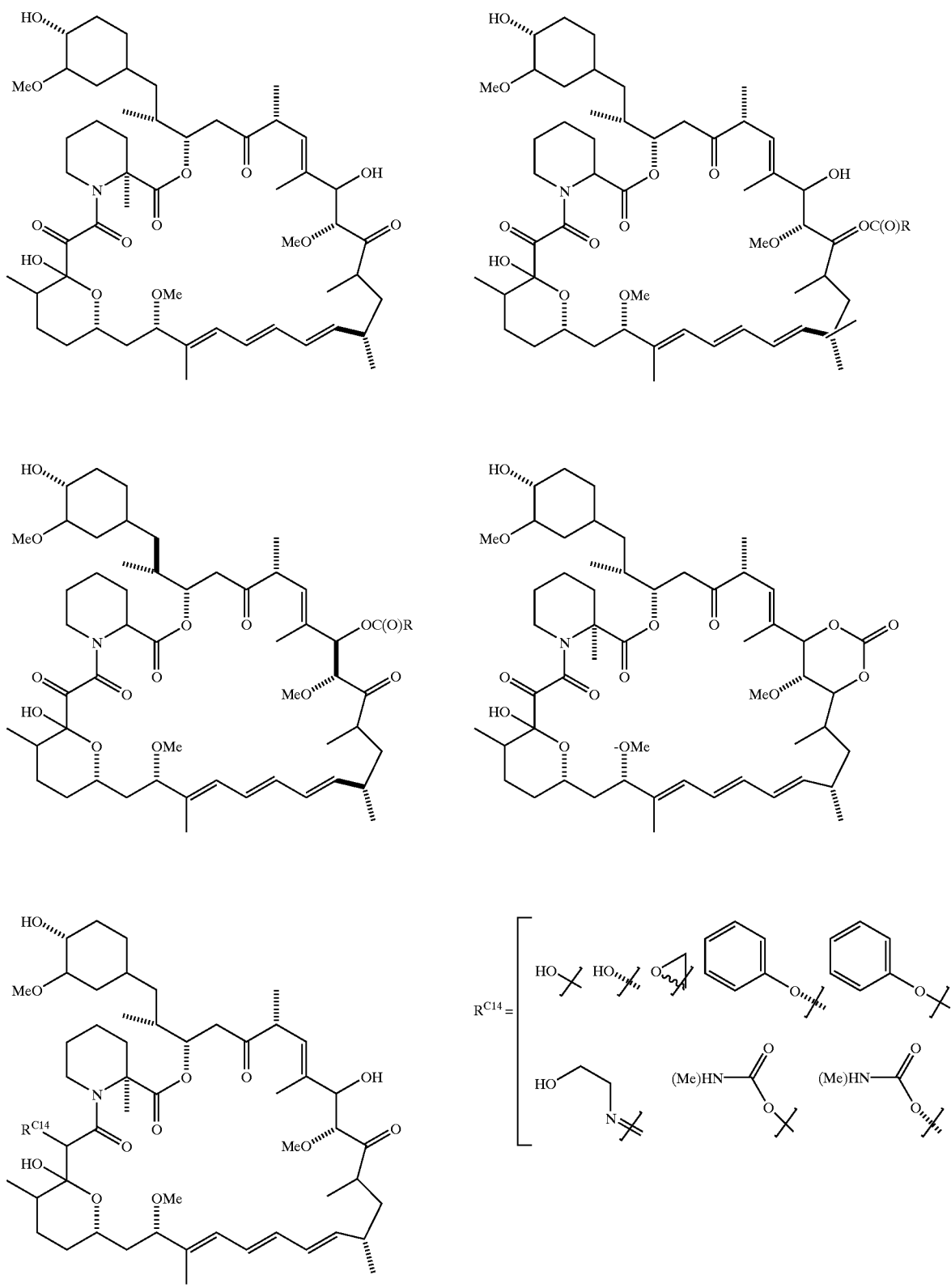

TABLE III-continued
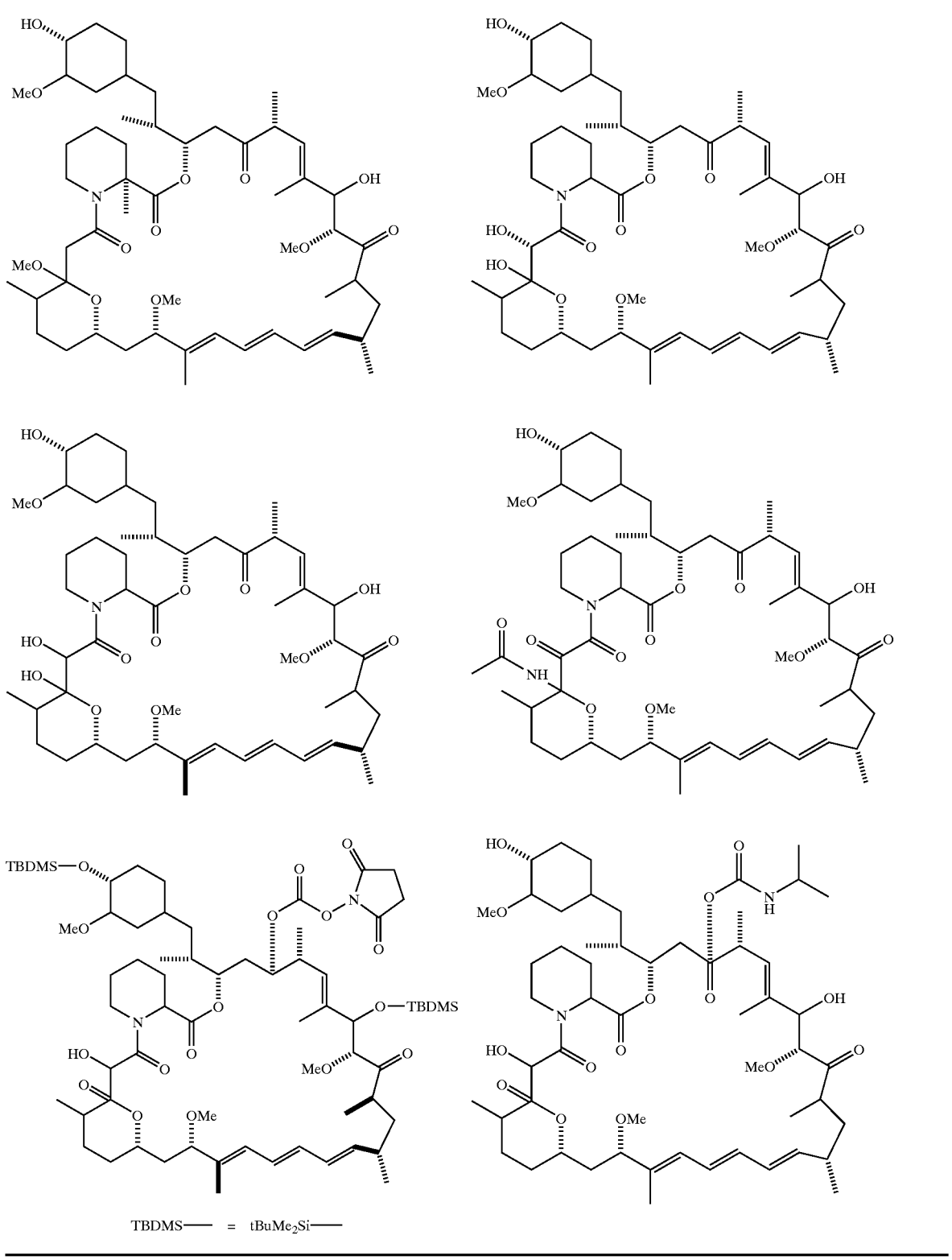
TBDMS— = tBuMe$_2$Si—

Rapalogs of particular interest for the practice of various aspects of this invention include compounds of formula II:

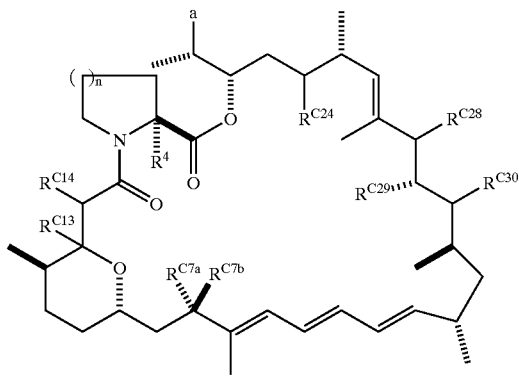

II wherein

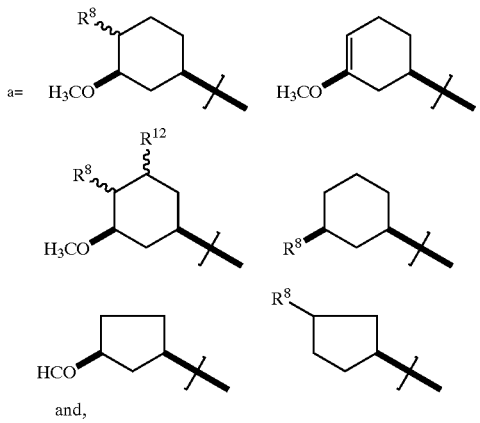

and, one of $R^{C7a}$ and $R^{C7b}$ is H and the other is —H, halo, —$R^2$, —$OR^1$, —$SR^1$, —$OC(O)R^1$, —$OC(O)NHR^1$, —$NHR^1$, —$NR^1R^2$, —$NHC(O)R^1$, or —NH—$SO_2$—$R^1$ where $R^2$=aliphatic, heteroaliphatic, aryl, heteroaryl or alkylaryl (e.g. benzyl or substituted benzyl), $R^{C30}$ is halo, —$OR^3$ or (=O), $R^{C24}$ is =O, =$NR^4$=$NOR^4$, =$NNHR^4$, —$NHOR^4$, —$NHNHR^4$, —$OR^4$, —$OC(O)R^4$ or —$OC(O)NR^4$, halo or —H, $R^{C13}$ and $R^{C28}$ are independently H, halo, —$OR^3$, —$OR^5$, —$OC(O)R^5$, —$OC(O)NHR^5$, —$SR^5$, —$SC(O)R^5$, —$SC(O)NHR^5$, —$NR^5R^{5'}$ or —$N(R^5)(CO)R^{5'}$ $R^{C14}$ is =O, —$OR^6$, —$NR^6$, —H, —$NC(O)R^6$, —$OC(O)R^6$ or —$OC(O)NR^6$ $R^3$ is H, —$R^7$, —$C(O)R^7$ or —$C(O)NHR^7$ or a cyclic moiety (e.g., carbonate) bridging C28 and C30

$R_{C29}$ is H or $OR^{11}$ (e.g., OH or OMe)

where each substituent may be present in either stereochemical orientation unless otherwise indicated, and where each occurrence of $R^1$, $R^4$, $R^5$, $R^6$, $R^7$, $R^9$, $R^{10}$ and $R^{11}$ is independently selected from H, aliphatic, heteroaliphatic, aryl and heteroaryl; and $R^8$ is H, halo, —CN, =O, —OH, —$NR^9R^{10}$, $OSO_2CF_3$, $OSO_2F$, $OSO_2R^{4'}$, $OCOR^{4'}$, $OCONR^{4'}R^{5'}$, or $OCON(OR^{4'})R^{5'}$.

Some rapalogs of Formula II differ from rapamycin only in that $R^{C13}$ is —OMe and $R^{C14}$ is H; $R^{C14}$ is —OH, —O(CO)NHMe, —O—$CH_2$— (i.e., a spiro epoxide), =$NCH_2CH_2$—OH, or —O-phenyl; $R^{C13}$ is —NHC(O)Me; $R^4$ is Me; $R^{C24}$ is =NR or —NHR, where R is —OH, O-alkyl (methyl, ethyl, isobutyl, benzyl), —NH-alkyl or an O-carboxymethyloxime or O-carboxamidomethyloxime at C24; $R^{C24}$ is —O(CO)NHCH($CH_3$)$_2$; $R^{C24}$ is —O(CO)NC(O)$CH_2CH_2C(O)$ and $R^{C28}$ O-TBDMS; $R^{C28}$ or $R^{C30}$ is —OC(O)R, or $R^{C28}$ and $R^{C30}$ together comprise —OC(O)O— linking C28 and C30 in a six-membered ring; or $R^{C7a}$ or $R^{C7b}$ is isopropoxyl, —S-phenyl, 2-thiophen-yl, 3-indol-yl or allyl or methallyl. See Table III and Liberles et al, 1997, Proc Natl Acad Sci USA 94:7825–7830. Rapalogs other than the foregoing, i.e., which contain alternative modifications or combinations of modifications relative to the structure of rapamycin, are preferred for use in practising the subject invention. Thus the improved rapalogs of this invention are rapalogs other than those depicted in Table III.

In rapamycin, $R^{C7a}$ is —OMe; $R^{C7b}$ is H; $R^{C14}$, $R^{C24}$ and $R^{C30}$ are each (=O); $R^{C13}$ and $R^{C28}$ are each —OH; $R^{C29}$ is OMe; and $R^3$ and $R^4$ are each H, all with the stereoisomerism as shown on page 1. Rapalogs useful in practicing this invention may contain substituents in any of the possible stereoisomeric orientations, and may comprise one stereoisomer substantially free of other stereoisomers (>90%, and preferably >95%, free from other stereoisomers on a molar basis) or may comprise a mixture of stereoisomers.

Also included are pharmaceutically acceptable derivatives of the foregoing compounds, where the phrase "pharmaceutically acceptable derivative" denotes any pharmaceutically acceptable salt, ester, or salt of such ester, of such compound, or any other adduct or derivative which, upon administration to a patient, is capable of providing (directly or indirectly) a rapalog as described herein, or a metabolite or residue thereof. Pharmaceutically acceptable derivatives thus include among others pro-drugs of the rapalogs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Various pro-drugs of rapamycin and of other compounds, and materials and methods for derivatizing the parent compounds to create the pro-drugs, are known and may be adapted to the present invention.

The term "aliphatic" as used herein includes both saturated and unsaturated, straight chain (i.e., unbranched), branched, cyclic, or polycyclic aliphatic hydrocarbons, which are optionally substituted with one or more functional groups. Unless otherwise specified, alkyl, other aliphatic, alkoxy and acyl groups preferably contain 1–8, and in many cases 1–6, contiguous aliphatic carbon atoms. Illustrative aliphatic groups thus include, for example, methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents.

Examples of substituents include: —OH, —$OR^{2'}$, —SH, —$SR^{2'}$, —CHO, =O, —COOH (or ester, carbamate, urea, oxime or carbonate thereof), —$NH_2$ (or substituted amine, amide, urea, carbamate or guanidino derivative therof), halo, trihaloalkyl, cyano, —$SO_2$—$CF_3$, —$OSO_2F$, —$OS(O)_2R^{11}$, —$SO_2$—$NHR^{11}$, —$NHSO_2$—$R^{11}$, sulfate, sulfonate, aryl and heteroaryl moieties. Aryl and heteroaryl substituents may themselves be substituted or unsubstituted (e.g. mono-, di- and tri-alkoxyphenyl; methylenedioxyphenyl or ethylenedioxyphenyl; halophenyl; or -phenyl-C(Me)$_2$—$CH_2$—O—CO—[C3-C6] alkyl or alkylamino).

The term "aliphatic" is thus intended to include alkyl, alkenyl, alkynyl, cycloalkyl, cycloalkenyl, and cycloalkynyl moieties.

As used herein, the term "alkyl" includes both straight, branched and cyclic alkyl groups. An analogous convention applies to other generic terms such as "alkenyl", "alkynyl" and the like. Furthermore, as used herein, the language "alkyl", "alkenyl", "alkynyl" and the like encompasses both substituted and unsubstituted groups.

The term "alkyl" refers to groups usually having one to eight, preferably one to six carbon atoms. For example, "alkyl" may refer to methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, and the like. Suitable substituted alkyls include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl and the like.

The term "alkenyl" refers to groups usually having two to eight, preferably two to six carbon atoms. For example, "alkenyl" may refer to prop-2-enyl, but-2-enyl, but-3-enyl, 2-methylprop-2-enyl, hex-2-enyl, hex-5-enyl, 2,3-dimethylbut-2-enyl, and the like. The language "alkynyl," which also refers to groups having two to eight, preferably two to six carbons, includes, but is not limited to, prop-2-ynyl, but-2-ynyl, but-3-ynyl, pent-2-ynyl, 3-methylpent-4-ynyl, hex-2-ynyl, hex-5-ynyl, and the like.

The term "cycloalkyl" as used herein refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic or heteroaliphatic or heterocyclic moieties, may optionally be substituted.

The term "heteroaliphatic" as used herein refers to aliphatic moieties which contain one or more oxygen, sulfur, nitrogen, phosphorous or silicon atoms, e.g., in place of carbon atoms. Heteroaliphatic moieties may be branched, unbranched or cyclic and include heterocycles such as morpholino, pyrrolidinyl, etc.

The term "heterocycle" as used herein refers to cyclic heteroaliphatic groups and preferably three to ten ring atoms total, includes, but is not limited to, oxetane, tetrahydrofuranyl, tetrahydropyranyl, aziridine, azetidine, pyrrolidine, piperidine, morpholine, piperazine and the like.

The terms "aryl" and "heteroaryl" as used herein refer to stable mono- or polycyclic, heterocyclic, polycyclic, and polyheterocyclic unsaturated moieties having 3–14 carbon atoms which may be substituted or unsubstituted. Substituents include any of the previously mentioned substituents. Non-limiting examples of useful aryl ring groups include phenyl, halophenyl, alkoxyphenyl, dialkoxyphenyl, trialkoxyphenyl, alkylenedioxyphenyl, naphthyl, phenanthryl, anthryl, phenanthro and the like. Examples of typical heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like (see e.g. Katritzky, Handbook of Heterocyclic Chemistry). The aryl or heteroaryl moieties may be substituted with one to five members selected from the group consisting of hydroxy, C1–C8 alkoxy, C1–C8 branched or straight-chain alkyl, acyloxy, carbamoyl, amino, N-acylamino, nitro, halo, trihalomethyl, cyano, and carboxyl. Aryl moieties thus include, e.g. phenyl; substituted phenyl bearing one or more substituents selected from groups including: halo such as chloro or fluoro, hydroxy, C1–C6 alkyl, acyl, acyloxy, C1–C6 alkoxy (such as methoxy or ethoxy, including among others dialkoxyphenyl moieties such as 2,3-, 2,4-, 2,5-, 3,4- or 3,5-dimethoxy or diethoxy phenyl or such as methylenedioxyphenyl, or 3-methoxy-5-ethoxyphenyl; or trisubstituted phenyl, such as trialkoxy (e.g., 3,4,5-trimethoxy or ethoxyphenyl), 3,5-dimethoxy-4-chloro-phenyl, etc.), amino, —$SO_2NH_2$, —$SO_2NH$(aliphatic), —$SO_2N$(aliphatic)$_2$, —O-aliphatic-COOH, and —O-aliphatic-$NH_2$ (which may contain one or two N-aliphatic or N-acyl substituents).

A "halo" substituent according to the present invention may be a fluoro, chloro, bromo or iodo substituent. Fluoro is often the preferred halogen.

Compounds of formula II, exclusive of any compounds depicted in Table III, are of special interest and constitute an important class of novel compounds. Compounds of this class may differ from rapamycin with respect to one, two, three, four, five, six or seven substituent moieties. This class includes among others rapalogs with modifications, relative to rapamycin, at C7 and C13; C7 and C14; C7 and a; C7 and C43; C7 and C24; C7 and C28; C7 and C30; C7, C13 and C14; C7, C13 and a; C7, C13 and C43; C7, C13 and C24; C7, C13 and C28; C7, C13 and C30; C7, C14 and a; C7, C14 and C43; C7, C14 and C24; C7, C14 and C28; C7, C14 and C30; C7, a and C24; C7, a and C28; C7, a and C30; C7, C24 and C30; C7, C24, C30 and a; C7, C24, C30 and C13; C7, C24, C30 and C14; C24, C30 and C13; C24, C30 and a; C24, C30 and C14; and C24, C30, C13 and a, exclusive of any compounds depicted in Table III or otherwise previously reported publicly.

One subset of improved rapalogs of special interest for practicing the methods of this invention are those compounds of formula II (or pharmaceutically acceptable derivatives thereof) in which $R^{C7a}$ is a moiety other than OMe. This subset ("C7 rapalogs") includes compounds in which one of $R^{C7a}$ and $R^{C7b}$ is H and the other is selected from substituted or unsubstituted alkenyl, aryl, heteroaryl or -Z-aliphatic, Z-aryl, -Z-heteroaryl, or Z-acyl, where Z and Z' are independently O, S or NH and acyl comprises —CHO, —(C=O)-aliphatic, —(C=O)-aryl, —(C=O)-heteroaryl, —(C=O)-Z'-aliphatic, —(C=O)-Z'-aryl, —(C=O)-Z'-heteroaryl. In certain embodiments of this subset, $R^{C7a}$ and $R^{C7b}$ are independently selected from the following groups: H; a substituted or unsubstituted two to eight carbon straightchain, branched or cyclic alkenyl, alkoxyl or alkylmercapto; and a substituted or unsubstituted aryl, heteroaryl, aryloxy or heteroaryloxy, arylmercapto or heteroarylmercapto. Compounds of this subset include among others those in which $R^{C7a}$ is H; (together with $R^{C7b}$) =O; alkoxy; alkylmercapto; amino (1°, 2° or 3°); amido; carbamate; aryl or substituted aryl; phenyl or substituted phenyl; substituted or unsubstituted heteroaryl such as substituted or unsubstituted thiophenyl, furyl, indolyl, etc.; or benzyloxy or substituted benzyloxy. Other illustrative C7 rapalogs and types of C7 rapalogs which may be used in practicing the methods of this invention include those in which one of $R^{C7a}$ and $R^{C7b}$ is H and the other is selected from -OEt, —O-propyl, —O-butyl, —$OCH_2CH_2$—OH, —O-benzyl, —O-substituted benzyl (including e.g., 3-nitro-, 4-chloro-, 3-iodo-4-diazo-, 3,4-dimethoxy-, and 2-methoxy-), —S-Me, —S-phenyl, —O(CO)Me, -allyl, —CH$_2$C(Me)=CH$_2$, —OCH$_2$—CCH, —OCH$_2$—CC-Me, —OCH$_2$—CC-Et, —OCH$_2$—CC—CH$_2$OH, or -2,4-dimethoxyphenyl, 2,4,6-trimethoxyphenyl, furanyl, thiophen-yl, methylthiophen-yl, pyrolyl and indolyl. In the foregoing types of rapalogs, the hydroxy substituent at C43 may be present in either stereochemical orientation or may be modified as described elsewhere herein. C7 rapalogs may further vary from rapamycin at one, two, three, four, five or more other positions as well. C7 rapalogs other than those depicted in Table III are novel and are encompassed by this invention as compositions of matter per se.

Another subset of improved rapalogs of special interest in the practice of the various methods of the invention are C30, C24 rapalogs of formula II, i.e., rapalogs of formula II in which $R^{C30}$ and $R^{C24}$ are both other than (=O). Of special interest are those C30, C24 rapalogs in which $R^{C7a}$ is a moiety other than OMe. In certain embodiments of this subset, $R^{C7a}$ and $R^{C7b}$ are independently selected from —H, —OR, —SR$^1$, —OC(O)R$^1$ or —OC(O)NHR$^1$, —NHR$^1$, —NHC(O)R$^1$, —NH—SO$_2$—R$^1$ and —R$^2$, where R$^2$=substituted aryl or allyl or alkylaryl (e.g. benzyl or substituted benzyl), so long as one of $R^{C7a}$ and $R^{C7b}$ is H. In certain embodiments of this subset, $R^{C30}$ and $R^{C24}$ are both —OH, e.g. in the "S" configuration. In other embodiments $R^{C30}$ and $R^{C24}$ are independently selected from OR$^3$. This subset includes among others all rapalogs in which $R^{C30}$ and $R^{C24}$ are OH and one of $R^{C7a}$ and $R^{C7b}$ comprises any of the replacement substituents at that position specified for formula II, including any of the C7 substituents identified in compounds of Tables II or III. This subset includes among others rapalogs which differ from rapamycin with respect to the moiety a. For instance, this subset includes compounds of the formula:

III

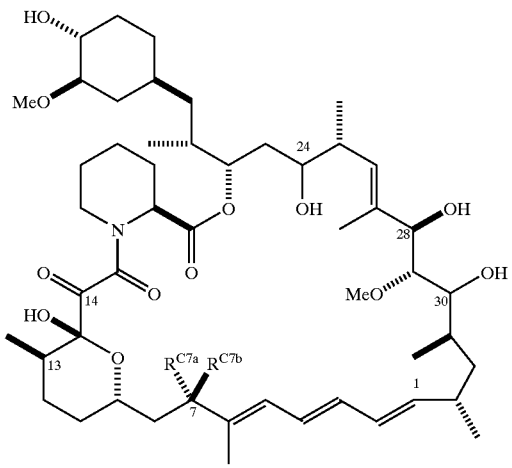

where at least one of $R^{C7a}$ and $R^{C7b}$ is other than —OMe. Alternative substituents for $R^{C7a}$ and/or $R^{C7b}$ are as disclosed elsewhere herein. Of special interest are compounds in which one of $R^{C7a}$ and $R^{C7b}$ is cyclic aliphatic, aryl, heterocyclic or heteroaryl, which may be optionally substituted. Other compounds within this subset include those in which one, two, three, four or five of the hydroxyl groups is epimerized, fluorinated, alkylated, acylated or otherwise modified via other ester, carbamate, carbonate or urea formation. An illustrative compound for example is the compound of formula III in which the hydroxyl group at C43 is epimerized and the hydroxyl groups at C28 and C30 are alkylated, acylated or linked via carbonate formation.

Another subset of improved rapalogs of special interest are those compounds of formula II in which one or both of $R^{C13}$ and $R^{C28}$ is F. In various embodiments of this subset, one, two, three, four or five other substituents in formula II differ from the substituents found in rapamycin. For instance, this subset includes C13 fluororapalogs, C28 fluororapalogs and C13, C28-difluororapalogs of the following structures, where $R^{C7a}$ and $R^{C7b}$ are as previously defined:

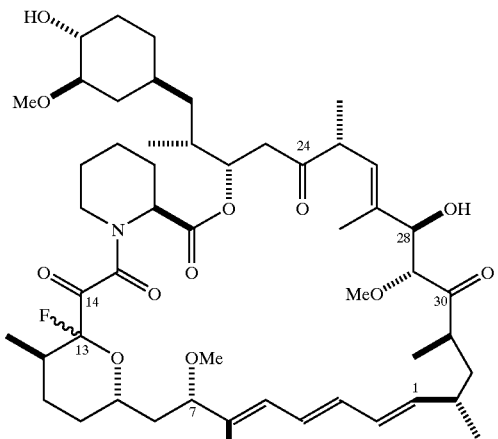

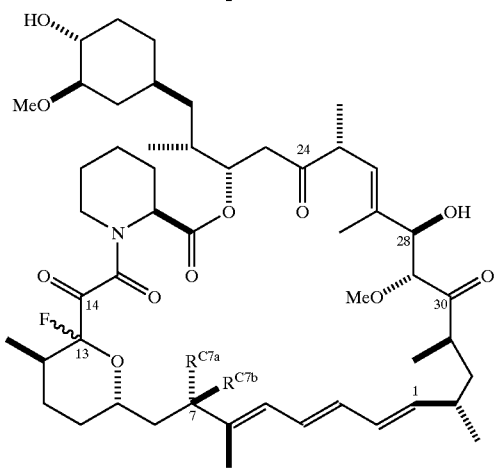

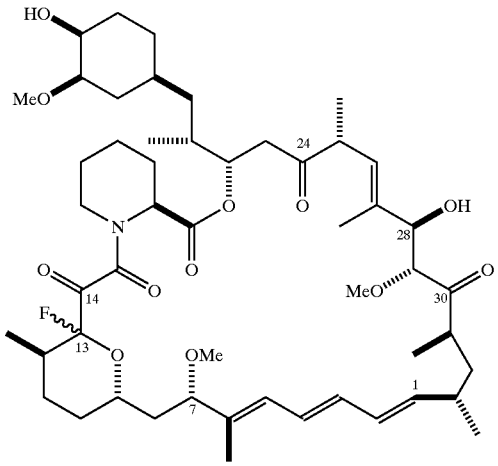

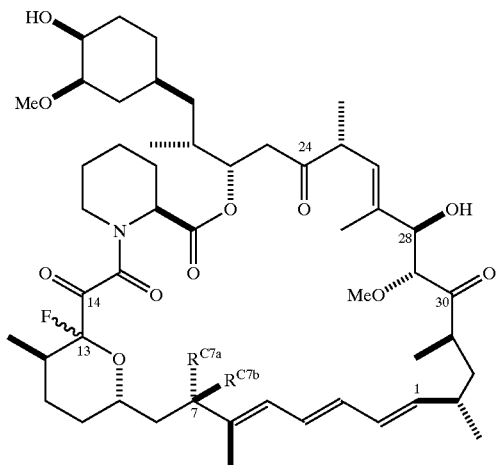
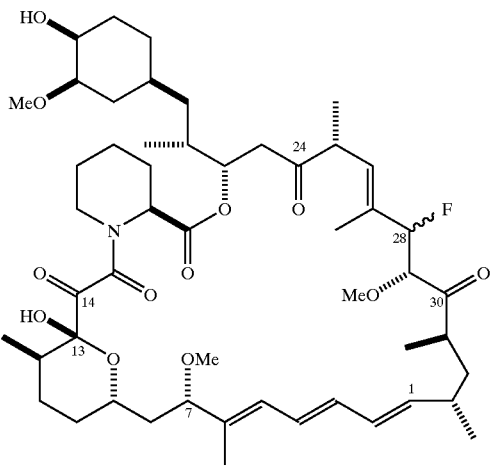
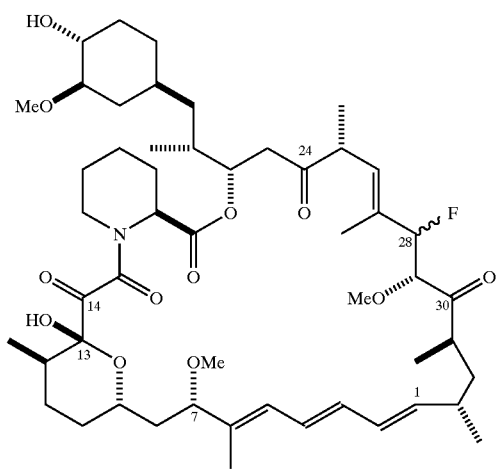
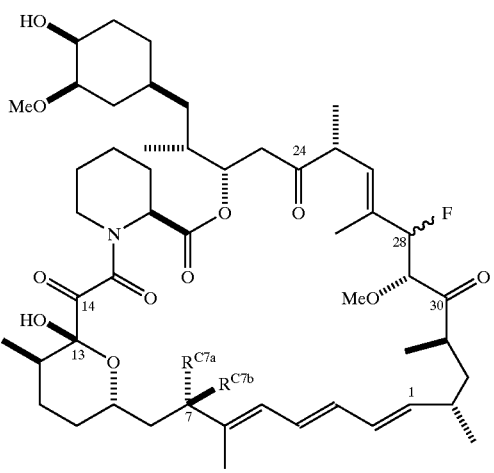
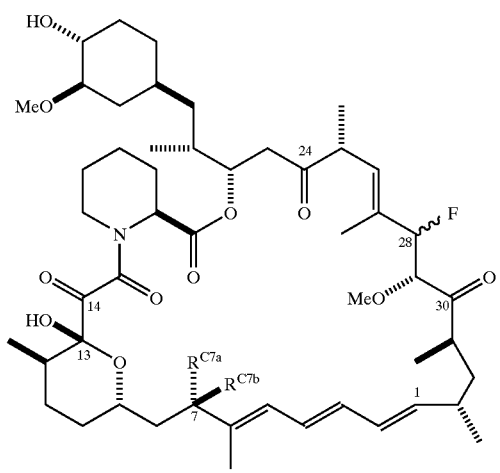
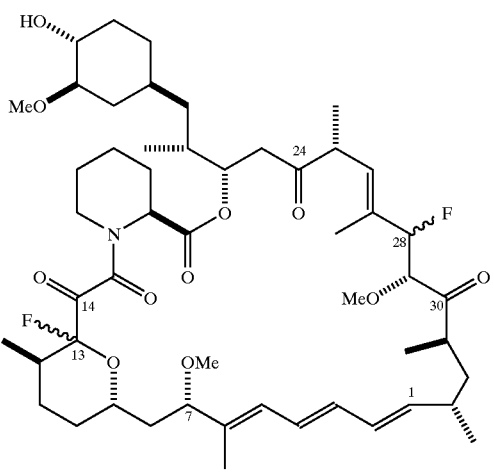

-continued

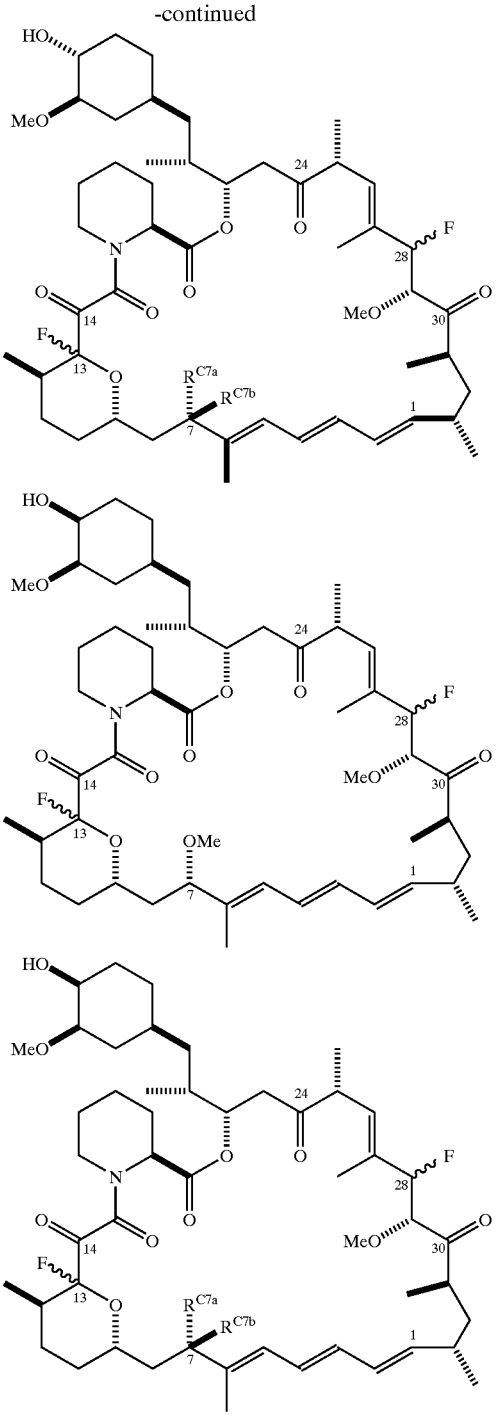

The 13-fluoro rapalogs, including in particular 13-fluoro rapamycin and analogs and derivatives thereof containing various substituents which do not abolish immunosuppressive activity in rapamycin itself, are of interest as immunosuppressants.

An interesting intersection of some of the foregoing subsets of compounds is the set of improved rapalogs comprising compounds of formula II, or pharmaceutically acceptable derivatives thereof, in which $R^{C24}$ and $R^{C30}$ are both other than (=O) and one or both of $R^{C13}$ and $R^{C28}$ is F. This set includes, inter alia, 24,30-tetrahydro-13-F rapalogs, 24,30-tetrahydro-28-F rapalogs and 24,30-tetrahydro-13,28-diF rapalogs, as well as C7 variants of any of the foregoing, in which $R^{C7a}$ is other than OMe. A portion of that set is illustrated by the following structure, where $R^{C7a}$ and $R^{C7b}$ are as previously defined:

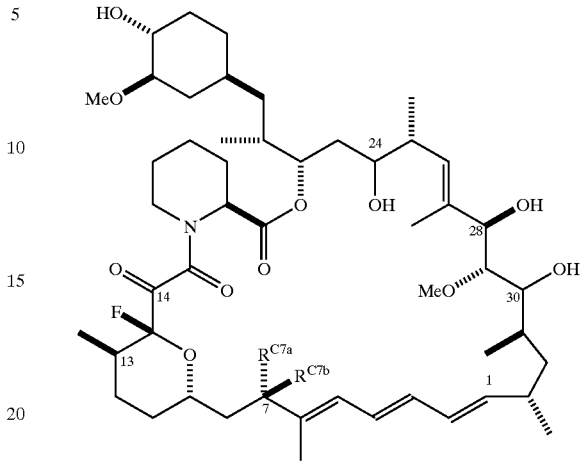

These compounds may be further derivatized, e.g., by modifications at one or both of $R^{C14}$ and $R^{C43}$ relative to the C14 and C43 substituents in rapamycin itself.

Another subset of improved rapalogs of special interest are those compounds of formula II in which $R^{C14}$ is other than O, OH or H, e.g., compounds wherein $R^{C14}$ is —$OR^6$, —$NR^6$, —$NC(O)R^6$, —$OC(O)R^6$ or —$OC(O)NR^6$, with or without one or more other modifications relative to rapamycin.

Another subset of improved rapalogs of interest are those compounds of formula II in which $R^{C13}$ is other than an alkoxyl group comprising a C1–C4 alkyl moiety, with or without one or more other modifications at other positions relative to rapamycin. For example, this subset includes rapalogs which differ in structure from rapamycin by virtue of possessing (a) in place of OH at C13, a replacement substituent $R^{C13}$ which is other than C1–C4 alkoxy, and (b) in place of MeO at C7, replacement substituents $R^{C7a}$ and $R^{C7b}$ as defined above.

Another subset of improved rapalogs of interest are those compounds of formula II in which $R^{C24}$ is other than =O, again, with or without one or more other modifications at other positions relative to rapamycin.

Another subset of improved rapalogs which is of special interest in practicing the methods of this invention include those compounds of formula II which share the stereoisomerism of rapamycin and in which $R^{C7a}$ is —OMe wherein $R^{C30}$ is not =O, $R^{C24}$ is not =O, $R^{C13}$ is not —OH, $R^{C14}$ is not =O and/or $R^3$ and/or $R^4$ are not H.

Other improved rapalogs of interest include compounds of formula II in which $R^{C14}$ is OH.

Furthermore, this invention encompasses improved rapalogs in which one or more of the carbon—carbon double bonds at the 1, 2, 3, 4 or 5, 6 positions in rapamycin are saturated, alone or in combination with a modification elsewhere in the molecule, e.g. at one or more of C7, C13, C43, C24, C28 and/or C30. It should also be appreciated that the C3, C4 double bond may be epoxidized; that the C6 methyl group may be replaced with —$CH_2OH$ or —$CH_2OMe$; that the C43 hydroxy may be converted to F, Cl or H or other substituent; and that the C42 methoxy moiety may be demethylated, in any of the compounds disclosed herein, using methods known in the art. Likewise, moiety "a" may be replaced with any of the following

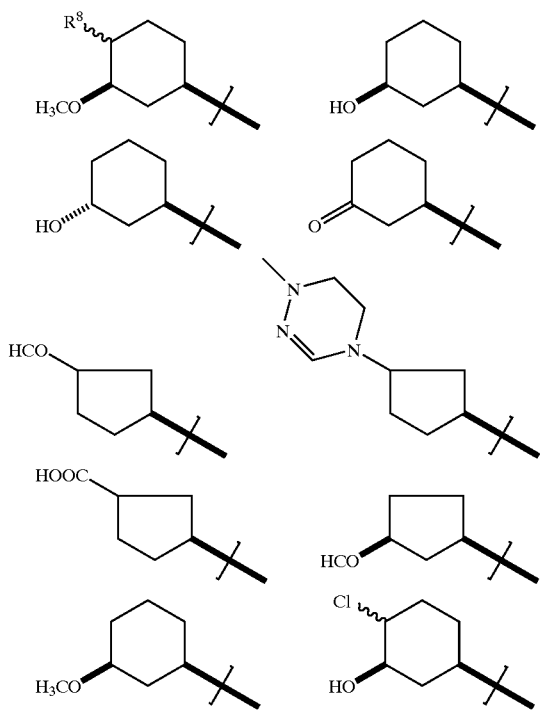

Synthetic Guidance

The production of rapamycin by fermentation and by total synthesis is known. The production of a number of rapalogs as fermentation products is also known. These include among others rapalogs bearing alternative moieties to the characteristic cyclohexyl ring or pipecolate ring of rapamycin, as well as C7-desmethyl-rapamycin, C29-desmethyl-rapamycin and C29-desmethoxyrapamycin.

Methods and materials for effecting various chemical transformations of rapamycin and structurally related macrolides are known in the art, as are methods for obtaining rapamycin and various rapalogs by fermentation. Many such chemical transformations of rapamycin and various rapalogs are disclosed in the patent documents identified in Table I, above, which serve to illustrate the level of skill and knowledge in the art of chemical synthesis and product recovery, purification and formulation which may be applied in practicing the subject invention. The following representative transformations and/or references which can be employed to produce the desired rapalogs are illustrative:

| ring position modified | literature reference |
|---|---|
| C7 | Luengo, et al. JOC 59, 6512 (1995); Chem & Biol 2(7), 471–481 (1995) |
| C-13 | C13→F: protect C28 and C43, rxn at 0° |
| C-14 | Schubert, et al. Angew Chem Int Ed Engl 23, 167 (1984). |
| C-20 | Nelson, U.S. Pat. No. 5,387,680 |
| C-24 | U.S. Pat. No. 5,373,014; 5,378,836 Lane, et al. Synthesis 1975, p136. |
| C-30 | Luengo et al. Tet. Lett. 35, 6469 (1994) |
| various positions | Or et al, U.S. Pat. Nos. 5,527,907 and 5,583,139 Luengo, WO 94/02136; Cottens et al, WO 95/16691 |

Approaches to the synthesis of the various fluoro and difluoro rapalogs are presented schematically below:

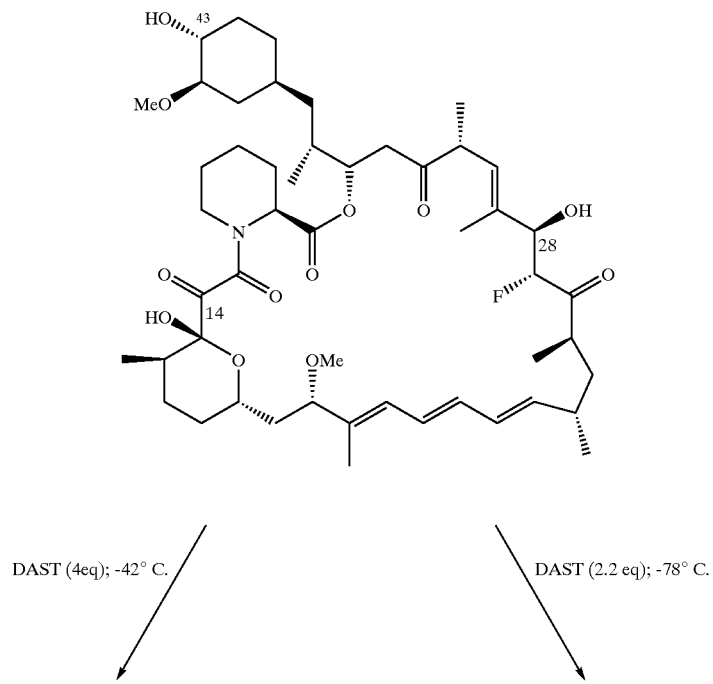

-continued
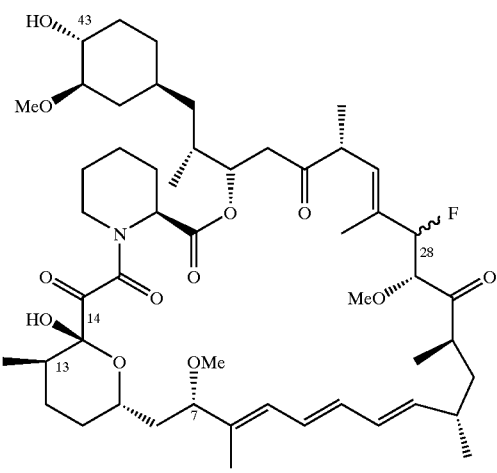
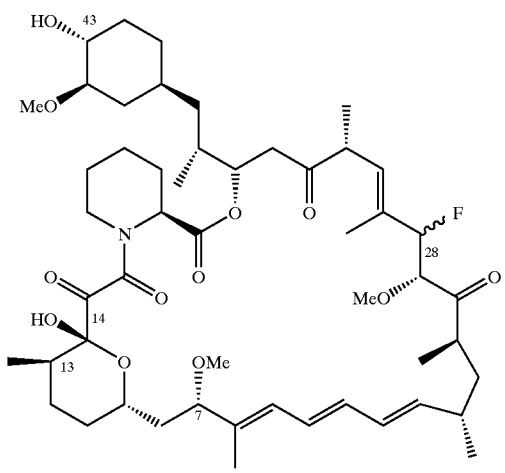
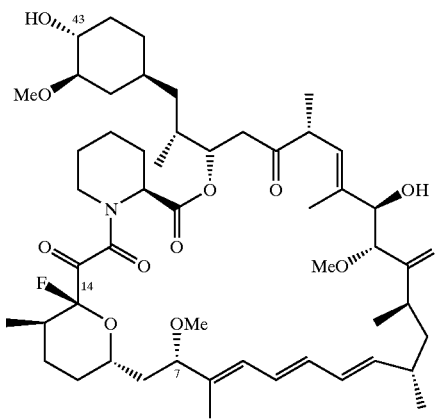
TESOTf; 2,6-lutidine
−78° C.
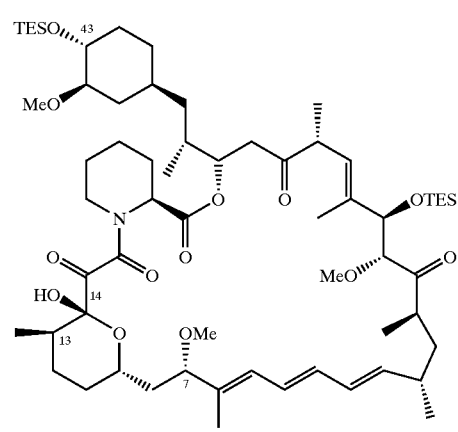
DAST (1.5 eq) / −42° C.
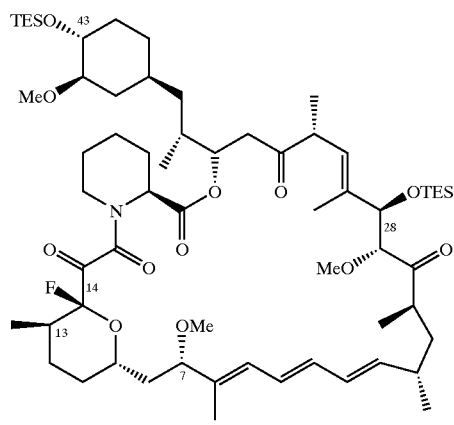
HF/Py / THF
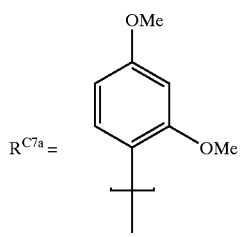

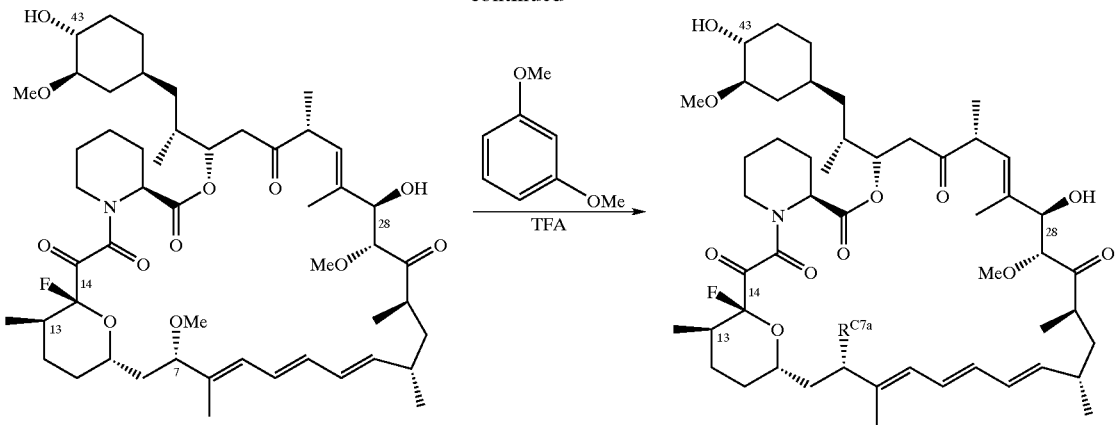
An approach to the synthesis of various 24,30-tetrahydro rapalogs is illustrated below:
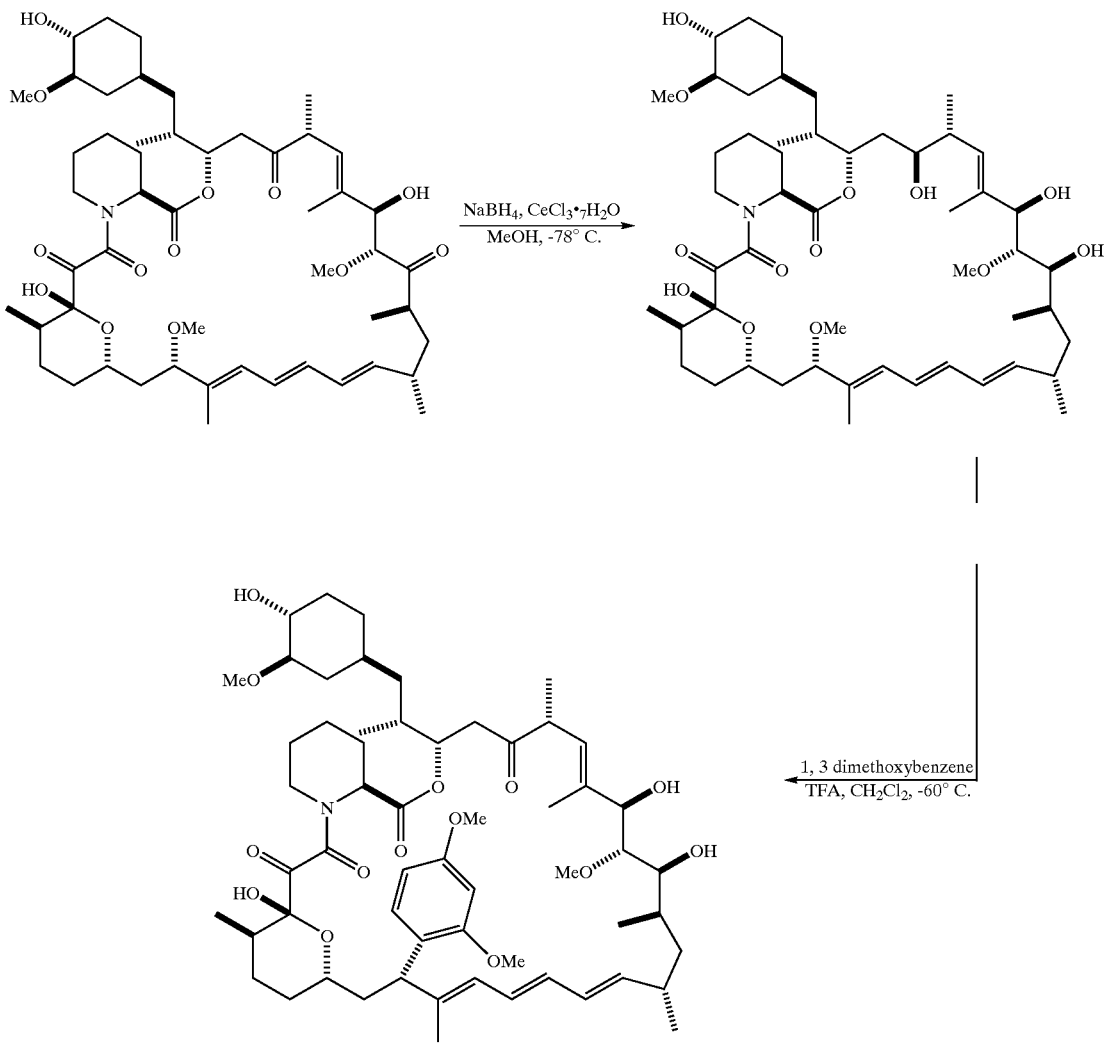

By way of further example, starting with 13-fluoro rapamycin instead of rapamycin yields the corresponding 13-fluoro-24,30-tetrahydro C7 rapalog.

One approach for the synthesis of other C13 derivatives is illustrated below:

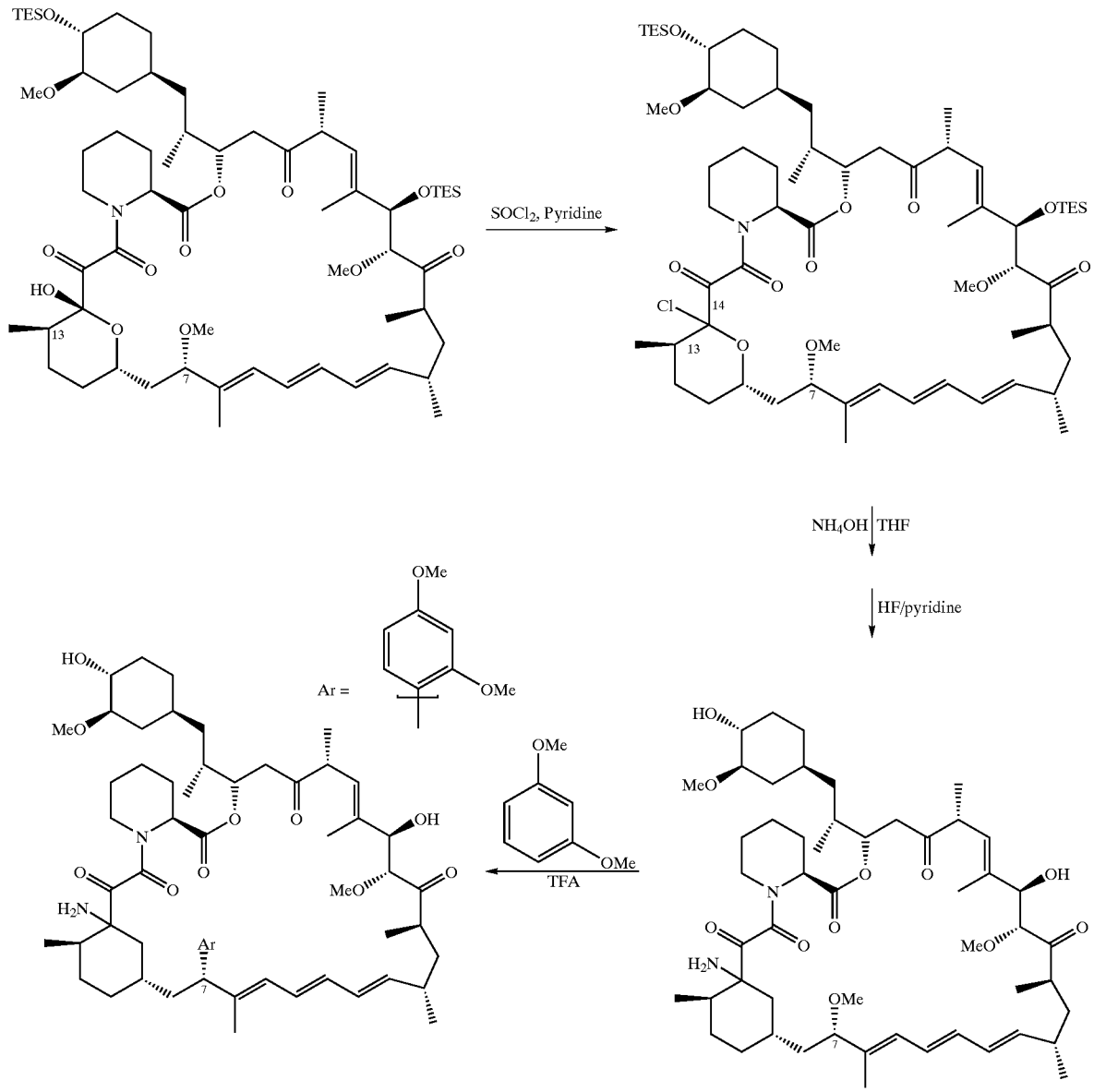

Additionally, it is contemplated that rapalogs for use in this invention as well as intermediates for the production of such rapalogs may be prepared by directed biosynthesis, e.g. as described by Katz et al, WO 93/13663 and by Cane et al, WO 9702358.

Novel rapalogs of this invention may be prepared by one of ordinary skill in this art relying upon methods and materials known in the art as guided by the disclosure presented herein. For instance, methods and materials may be adapted from known methods set forth or referenced in the documents cited above, the full contents of which are incorporated herein by reference. Additional guidance and examples are provided herein by way of illustration and further guidance to the practitioner. It should be understood that the chemist of ordinary skill in this art would be readily able to make modifications to the foregoing, e.g. to add appropriate protecting groups to sensitive moieties during synthesis, followed by removal of the protecting groups when no longer needed or desired, and would be readily capable of determining other synthetic approaches.

FKBP domains and Fusion Proteins

The FKBP fusion protein comprises at least one, FKBP domain containing all or part of the peptide sequence of an FKBP domain and at least one heterologous action domain. This chimeric protein must be capable of binding to an improved rapalog of this invention, preferably with a Kd value below about 100 nM, more preferably below about 10 nM and even more preferably below about 1 nM, as measured by direct binding measurement (e.g. fluorescence quenching), competition binding measurement (e.g. versus FK506), inhibition of FKBP enzyme activity (rotamase), or other assay methodology. Typically the chimeric protein will contain one or more protein domains comprising peptide sequence selected from that of a naturally occurring FKBP protein such as human FKBP12, e.g. as described in International Patent Application PCT/US94/01617. That peptide sequence may be modified to adjust the binding specificity, usually with replacement, insertion or deletion of 10 or fewer, preferably 5 or fewer, amino acid residues. Such modifications are elected in certain embodiments to yield one or both of the following binding profiles: (a) binding of an improved rapalog to the modified FKBP domain, or chimera containing it, preferably at least one, and more preferably at least two, and even more preferably three or four or more, orders of magnitude better (by any measure) than to FKBP12 or the FKBP endogenous to the host cells to be engineered; and (b) binding of the FKBP:rapalog complex to the FRB fusion protein, preferably at least one, and more preferably at least two, and even more preferably at least three, orders of magnitude better (by any measure) than to the FRAP or other FRB-containing protein endogenous to the host cell to be engineered.

The FKBP chimera also contains at least one heterologous action domain, i.e., a protein domain containing non-FKBP peptide sequence. The action domain may be a DNA-binding domain, transcription activation domain, cellular localization domain, intracellular signal transduction domain, etc., e.g. as described elsewhere herein or in PCT/US94/01617 or the other cited references. Generally speaking, the action domain is capable of directing the chimeric protein to a selected cellular location or of initiating a biological effect upon association or aggregation with another action domain, for instance, upon multimerization of proteins containing the same or different action domains.

A recombinant nucleic acid encoding such a fusion protein will be capable of selectively hybridizing to a DNA encoding the parent FKBP protein, e.g. human FKBP12, or would be capable of such hybridization but for the degeneracy of the genetic code. Since these chimeric proteins contain an action domain derived from another protein, e.g. Gal4, VP16, FAS, CD3 zeta chain, etc., the recombinant DNA encoding the chimeric protein will also be capable of selectively hybridizing to a DNA encoding that other protein, or would be capable of such hybridization but for the degeneracy of the genetic code.

FKBP fusion proteins of this invention, as well as FRB fusion proteins discussed in further detail below, may contain one or more copies of one or more different ligand binding domains and one or more copies of one or more action domains. The ligand binding domain(s) (i.e., FKBP and FRB domains) may be N-terminal, C-terminal, or interspersed with respect to the action domain(s). Embodiments involving multiple copies of a ligand binding domain usually have 2, 3 or 4 such copies. For example, an FKBP fusion protein may contain 2, 3 or 4 FKBP domains. The various domains of the FKBP fusion proteins (and of the FRB fusion proteins discussed below) are optionally separated by linking peptide regions which may be derived from one of the adjacent domains or may be heterologous.

Illustrative examples of FKBP fusion proteins useful in the practice of this invention include the FKBP fusion proteins disclosed in PCT/US94/01617 (Stanford & Harvard), PCT/US94/08008 (Stanford & Harvard), Spencer et al (supra), PCT/US95/10591 (ARIAD), PCT/US95/06722 (Mitotix, Inc.) and other references cited herein; the FKBP fusion proteins disclosed in the examples which follow; variants of any of the foregoing FKBP fusion proteins which contain up to 10 (preferably 1–5) amino acid insertions, deletions or substitutions in one or more of the FKBP domains and which are still capable of binding to rapamycin or to a rapalog; variants of any of the foregoing FKBP fusion proteins which contain one or more copies of an FKBP domain which is encoded by a DNA sequence capable of selectively hybridizing to a DNA sequence encoding a naturally occurring FKBP domain and which are still capable of binding to rapamycin or to a rapalog; variants of any of the foregoing in which one or more heterologous action domains are deleted, replaced or supplemented with a different heterologous action domain; variants of any of the foregoing FKBP fusion proteins which are capable of binding to rapamycin or a rapalog and which contain an FKBP domain derived from a non-human source; and variants of any of the foregoing FKBP fusion proteins which contain one or more amino acid residues corresponding to Tyr26, Phe36, Asp37, Arg42, Phe46, Phe48, Glu54, Val55, or Phe99 of human FKBP12 in which one or more of those amino acid residues is replaced by a different amino acid, the variant being capable of binding to rapamycin or a rapalog.

For instance, in a number of cases the FKBP fusion proteins comprise multiple copies of an FKBP domain containing amino acids 1–107 of human FKBP12, separated by the 2-amino acid linker Thr-Arg encoded by ACTAGA, the ligation product of DNAs digested respectively with the restriction endonucleases SpeI and XbaI. The following table provides illustrative subsets of mutant FKBP domains based on the foregoing FKBP12 sequence:

Illustrative Mutant FKBPs

| F36A | Y26V | F46A | W59A |
| F36V | Y26S | F48H | H87W |
| F36M | D37A | F48L | H87R |
| F36S | I90A | F48A | F36V/F99A |
| F99A | I91A | E54A | F36V/F99G |
| F99G | F46H | E54K | F36M/F99A |
| Y26A | F46L | V55A | F36M/F99G | note: Entries identify the native amino acid by single letter code and sequence position, followed by the replacement amino acid in the mutant. Thus, F36V designates a human FKBP12 sequence in which phenylalanine at position 36 is replaced by valine. F36V/F99A indicates a double mutation in which phenylalanine at positions 36 and 99 are replaced by valine and alanine, respectively.

FRB Domains and Fusion Proteins

The FRB fusion protein comprises at least one FRB domain (which may comprise all or part of the peptide sequence of a FRAP protein or a variant thereof, as described elsewhere) and at least one heterologous effector domain.

Generally speaking, the FRB domain, or a chimeric protein encompassing it, is encoded by a DNA molecule capable of hybridizing selectively to a DNA molecule encoding a protein comprising a naturally occurring FRB domain, e.g. a DNA molecule encoding a human or other mammalian FRAP protein or one of yeast proteins, Tor-1 or Tor-2 or the previously mentioned Candida FRB-containing protein. FRB domains of this invention include those which are capable of binding to a complex of an FKBP protein and an improved rapalog of this invention.

The FRB fusion protein must be capable of binding to the complex formed by the FKBP fusion protein with an improved rapalog of this invention. Preferably, the FRB fusion protein binds to that complex with a Kd value below 200 $\mu$M, more preferably below 10 $\mu$M, as measured by conventional methods. The FRB domain will be of sufficient length and composition to maintain high affinity for a complex of the rapalog with the FKBP fusion protein. In some embodiments the FRB domain spans fewer than about 150 amino acids in length, and in some cases fewer than about 100 amino acids. One such region comprises a 133 amino acid region of human FRAP extending from Val2012 through Tyr2144. See Chiu et al, 1994, Proc. Natl. Acad. Sci. USA 91:12574–12578. An FRB region of particular interest spans Glu2025 through Gln2114 of human FRAP and retains affinity for a FKBP12-rapamycin complex or for FKBP-rapalog complex. In some embodiments Q2214 is removed from the 90-amino acid sequence rendering this an 89-amino acid FRB domain. The FRB peptide sequence may be modified to adjust the binding specificity, usually with replacement, insertion or deletion, of 10 or fewer, preferably 5 or fewer, amino acids. Such modifications are elected in certain embodiments to achieve a preference towards formation of the complex comprising one or more molecules of the FKBP fusion protein, FRB fusion protein and an improved rapalog over formation of complexes of endogenous FKBP and FRAP proteins with the rapalog. Preferably that preference is at least one, and more preferably at least two, and even more preferably three, orders of magnitude (by any measure)

A recombinant DNA encoding such a protein will be capable of selectively hybridizing to a DNA encoding a FRAP species, or would be capable of such hybridization but for the degeneracy of the genetic code. Again, since these chimeric proteins contain an effector domain derived from another protein, e.g. Gal4, VP16, Fas, CD3 zeta chain, etc., the recombinant DNA encoding the chimeric protein will be capable of selectively hybridizing to a DNA encoding that other protein, or would be capable of such hybridization but for the degeneracy of the genetic code.

Illustrative examples of FRB chimeras useful in the practice of this invention include those disclosed in the examples which follow, variants thereof in which one or more of the heterologous domains are replaced with alternative heterologous domains or supplemented with one or more additional heterologous domains, variants in which one or more of the FRB domains is a domain of non-human peptide sequence origin (such as Tor 2 or Candida for example), and variants in which the FRB domain is modified by amino acid substitution, replacement or insertion as described herein, so long as the chimera is capable of binding to a complex formed by an FKBP protein and an improved rapalog of this invention. An illustrative FRB fusion protein contains one or more FRBs of at least 89-amino acids, containing a sequence spanning at least residues 2025–2113 of human FRAP, separated by the linker Thr-Arg formed by ligation of SpeI-XbaI sites as mentioned previously. It should be appreciated that such restriction sites or linkers in any of the fusion proteins of this invention may be deleted, replaced or extended using conventional techniques such as site-directed mutagenesis.

Mixed Chimeric Proteins

A third type of chimeric protein comprises one or more FKBP domains, one or more heterologous effector domains, and one or more FRB domains as described for the FRB fusion proteins.

Mixed chimeric protein molecules are capable of forming homodimeric or homomultimeric protein complexes in the presence of an improved rapalog to which they bind. Embodiments involving mixed chimeras have the advantage of requiring the introduction into cells of a single recombinant nucleic acid construct in place of two recombinant nucleic acid constructs otherwise required to direct the expression of both an FKBP fusion protein and a FRB fusion protein.

A recombinant DNA encoding a mixed chimeric protein will be capable of selectively hybridizing to a DNA encoding an FKBP protein, a DNA encoding FRAP, and a heterologous DNA sequence encoding the protein from which one or more effector domains is derived (e.g. Gal4, VP16, Fas, CD3 zeta chain, etc.), or would be capable of such hybridization but for the degeneracy of the genetic code.

Heterologous Domains

As mentioned above, the heterologous effector domains of the FKBP and FRB fusion proteins are protein domains which, upon mutual association of the chimeric proteins bearing them, are capable of triggering (or inhibiting) DNA-binding and/or transcription of a target gene; actuating cell growth, differentiation, proliferation or apoptosis; directing proteins to a particular cellular location; or actuating other biological events.

Embodiments involving regulatable gene transcription involve the use of target gene constructs which comprise a target gene (which encodes a polypeptide, antisense RNA, ribozyme, etc. of interest) under the transcriptional control of a DNA element responsive to the association or multimerization of the heterologous domains of the 1st and 2d chimeric proteins.

In embodiments of the invention involving direct activation of transcription, the heterologous domains of the 1st and 2d chimeric proteins comprise a DNA binding domain such as Gal4 or a chimeric DNA binding domain such as ZFHD1, discussed below, and a transcriptional activating domain such as those derived from VP16 or p65, respectively. The multimerization of a chimeric protein containing such a transcriptional activating domain to a chimeric protein containing a DNA binding domain targets the transcriptional activator to the promoter element to which the DNA binding domain binds, and thus activates the transcription of a target gene linked to that promoter element. Foregoing the transcription activation domain or substituting a repressor domain (see PCT/US94/01617) in place of a transcription activation domain provides an analogous chimera useful for inhibiting transcription of a target gene. Composite DNA binding domains and DNA sequences to which they bind are disclosed in Pomerantz et al, 1995, supra, the contents of which are incorporated herein by reference. Such composite DNA binding domains may be used as DNA binding domains in the practice of this invention, together with a target gene construct containing the cognate DNA sequences to which the composite DBD binds.

In embodiments involving indirect activation of transcription, the heterologous domains of the chimeras are effector domains of signaling proteins which upon aggregation or multimerization trigger the activation of transcription under the control of a responsive promoter. For example, the signaling domain may be the intracellular domain of the zeta subunit of the T cell receptor, which upon aggregation, triggers transcription of a gene linked to the IL-2 promoter or a derivative thereof (e.g. iterated NF-AT binding sites).

In another aspect of the invention, the heterologous domains are protein domains which upon mutual association are capable of triggering cell death. Examples of such domains are the intracellular domains of the Fas antigen or of the TNF R1. Chimeric proteins containing a Fas domain can be designed and prepared by analogy to the disclosure of PCT/US94/01617.

Engineered Receptor Domains

As noted previously, the FKBP and FRB domains may contain peptide sequence selected from the peptide sequences of naturally occurring FKBP and FRB domains. Naturally occurring sequences include those of human FKBP12 and the FRB domain of human FRAP. Alternatively, the peptide sequences may be derived from such naturally occurring peptide sequences but contain generally up to 10, and preferably 1–5, mutations in one or both such peptide sequences. As disclosed in greater detail elswhere herein, such mutations can confer a number of important features. For instance, an FKBP domain may be modified such that it is capable of binding an improved rapalog preferentially, i.e. at least one, preferably two, and even more preferably three or four or more orders of magnitude more effectively, with respect to rapalog binding by the unmodified FKBP domain. An FRB domain may be modified such that it is capable of binding a (modified or unmodified) FKBP:rapalog complex preferentially, i.e. at least one, preferably two, and even more preferably three orders of magnitude more effectively, with respect to the unmodified FRB domain. FKBP and FRB domains may be modified such that they are capable of forming a tripartite complex with an improved rapalog, preferentially, i.e. at least one, preferably two, and even more preferably three orders of magnitude more effectively, with respect to unmodified FKBP and FRB domains.

(a) FKBP

Methods for identifying FKBP mutations that confer enhanced ability to bind derivatives of FK506 containing various substituents ("bumps") were disclosed in PCT/US94/01617. Similar strategies can be used to obtain modified FKBPs that preferentially bind bumped rapamycin derivatives, i.e., rapalogs. The structure of the complex between rapamycin and FKBP12 is known (see for example Van Duyne et al., J. Am. Chem. Soc. (1991) 113, 7433–7434). Such data can be used to reveal amino acid residues that would clash with various rapalog substituents. In this approach, molecular modelling is used to identify candidate amino acid substitutions in the FKBP domain that would accommodate the rapalog substituent(s), and site-directed mutagenesis may then be used to engineer the protein mutations so identified. The mutants are expressed by standard methods and their binding affinity for the rapalogs measured, for example by inhibition of rotamase activity, or by competition for binding with a molecule such as FK506, if the mutant retains appropriate activity/affinity.

More particularly, we contemplate that certain improved rapalogs of this invention, e.g. rapalogs with modifications relative to rapamycin at C-13 or C-14 bind preferentially to FKBPs in which one or more of the residues, Tyr26, Phe36, Asp37, Tyr82 and Phe99, are substituted with amino acids that have smaller side chains (such as Gly, Ala, Val, Met and Ser). Examples of mutant FKBPs with modifications at positions 26 or 36 are noted in the "Illustrative Mutant FKBPs" table above. Similarly, we contemplate that rapalogs with modifications at C20 (i.e., rapalogs in which R4 is other than —H) bind preferentially to FKBPs in which Tyr82 and/or Ile56 are replaced by other amino acids, especially those with smaller side chains. In a further example, we contemplate that rapalogs bearing modifications at C24 (i.e., in which W is other than =O) bind preferentially to FKBPs in which one or more of Phe46, Phe48 and Val55 are replaced by other amino acids, again especially those with smaller side chains. Moreover, we envisage that rapalogs with modifications at C28 and/or C30 (i.e., in which R3 is other than H and/or V is other than =O) bind preferentially to FKBPs in which Glu54 is replaced by another amino acid, especially one with a smaller side chain. In all of the above examples, single or multiple amino acid substitutions may be made. Again, specific examples are noted in the previous table.

An alternative to iterative engineering and testing of single or multiple mutants is to co-randomize structurally-identified residues that are or would be in contact with or near one or more rapalog or rapamycin substituents. A collection of polypeptides containing FKBP domains randomized at the identified positions (such as are noted in the foregoing paragraph) is prepared e.g. using conventional synthetic or genetic methods. Such a collection represents a set of FKBP domains containing replacement amino acids at one or more of such positions. The collection is screened and FKBP variants are selected which possess the desired rapalog binding properties. In general, randomizing several residues simultaneously is expected to yield compensating mutants of higher affinity and specificity for a given bumped rapalog as it maximizes the likelihood of beneficial cooperative interactions between sidechains. Techniques for preparing libraries randomized at discrete positions are known and include primer-directed mutagenesis using degenerate oligonucleotides, PCR with degenerate oligonucleotides, and cassette mutagenesis with degenerate oligonucleotides (see for example Lowman, H. B, and Wells, J. A. Methods: Comp. Methods Enzymol. 1991. 3, 205–216; Dennis, M. S. and Lazarus, R. A. 1994. J. Biol. Chem. 269, 22129–22136; and references therein).

We further contemplate that in many cases, randomization of only the few residues in or near direct contact with a given position in rapamycin may not completely explore all the possible variations in FKBP conformation that could optimally accommodate a rapalog substituent (bump). Thus the construction is also envisaged of unbiased libraries containing random substitutions that are not based on structural considerations, to identify subtle mutations or combinations thereof that confer preferential binding to bumped rapalogs. Several suitable mutagenesis schemes have been described, including alanine-scanning mutagenesis (Cunningham and Wells (1989) Science 244, 1081–1085), PCR misincorporation mutagenesis (see eg. Cadwell and Joyce, 1992, PCR Meth. Applic. 2, 28–33), and 'DNA shuffling' (Stemmer, 1994, Nature 370, 389–391 and Crameri et al, 1996, Nature Medicine 2, 100–103). These techniques produce libraries of random mutants, or sets of single mutants, that are then searched by screening or selection approaches.

In many cases, an effective strategy to identify the best mutants for preferential binding of a given bump is a combination of structure-based and unbiased approaches. See Clackson and Wells, 1994, Trends Biotechnology 12, 173–184 (review). For example we contemplate the construction of libraries in which key contact residues are randomized by PCR with degenerate oligonucleotides, but with amplification performed using error-promoting conditions to introduce further mutations at random sites. A further example is the combination of component DNA fragments from structure-based and unbiased random libraries using DNA shuffling.

Screening of libraries for desirable mutations may be performed by use of a yeast 2-hybrid system (Fields and Song (1989) Nature 340, 245–246). For example, an FRB-VP16 fusion may be introduced into one vector, and a library of randomized FKBP sequences cloned into a separate GAL4 fusion vector. Yeast co-transformants are treated with rapalog, and those harboring complementary FKBP mutants are identified by for example beta-galactosidase or luciferase production (a screen), or survival on plates lacking an essential nutrient (a selection), as appropriate for the vectors used. The requirement for bumped rapamycin to bridge the FKBP-FRAP interaction is a useful screen to eliminate false positives.

A further strategy for isolating modified ligand-binding domains from libraries of FKBP (or FRB) mutants utilizes a genetic selection for functional dimer formation described by Hu et. al. (Hu, J. C., et al. 1990. Science. 250:1400–1403; for review see Hu, J. C. 1995. Structure. 3:431–433). This strategy utilizes the fact that the bacteriophage lambda repressor cI binds to DNA as a homodimer and that binding of such homodimers to operator DNA prevents transcription of phage genes involved in the lytic pathway of the phage life cycle. Thus, bacterial cells expressing functional lambda repressor are immune to lysis by superinfecting phage lambda. Repressor protein comprises an amino terminal DNA binding domain (amino acids 1–92), joined by a 40 amino acid flexible linker to a carboxy terminal dimerization domain. The isolated N-terminal domain binds to DNA with low affinity due to inefficient dimer formation. High affinity DNA binding can be restored with heterologous dimerization domains such as the GCN4 "leucine zipper". Hu et al have described a system in which phage immunity is used as a genetic selection to isolate GCN4 leucine zipper mutants capable of mediating lambda repressor dimer formation from a large population of sequences (Hu et al., 1990).

For example, to use the lambda repressor system to identify FRAP mutants complementary to bumped rapalogs, lambda repressor-FRAP libraries bearing mutant FRAP sequences are transformed into *E. coli* cells expressing wildtype lambda repressor-FKBP protein. Plasmids expressing FRAP mutants are isolated from those colonies that survive lysis on bacterial plates containing high titres of lambda phage and "bumped" rapamycin compounds. Alternatively, to isolate FKBP mutants, the above strategy is repeated with lambda repressor-FKBP libraries bearing mutant FKBP sequences transformed into E. coli cells expressing wildtype lambda repressor-FRAP protein.

A further alternative is to clone the randomized FKBP sequences into a vector for phage display, allowing in vitro selection of the variants that bind best to the rapalog. Affinity selection in vitro may be performed in a number of ways. For example, rapalog is mixed with the library phage pool in solution in the presence of recombinant FRAP tagged with an affinity handle (for example a hexa-histidine tag, or GST), and the resultant complexes are captured on the appropriate affinity matrix to enrich for phage displaying FKBP harboring complementary mutations. Techniques for phage display have been described, and other in vitro selection selection systems can also be contemplated (for example display on lambda phage, display on plasmids, display on baculovirus). Furthermore, selection and screening strategies can also be used to improve other properties of benefit in the application of this invention, such as enhanced stability in vivo. For a review see Clackson, T. & Wells, J. A. 1994. Trends Biotechnol. 12, 173–184.

(b) FRAP

Similar considerations apply to the generation of mutant FRB domains which bind preferentially to improved rapalogs containing modifications (i.e., are 'bumped') relative to rapamycin in the FRAP-binding portion of the macrocycle. For example, one may obtain preferential binding using rapalogs bearing substituents other than -Me at the C7 position with FRBs based on the human FRAP FRB peptide sequence but bearing amino acid substitutions for one or more of the residues Tyr2038, Phe2039, Thr2098, Gln2099, Trp2101 and Asp2102. Exemplary mutations include Y2038H, Y2038L, Y2038V, Y2038A, F2039H, F2039L, F2039A, F2039V, D2102A, T2098A, T2098N, and T2098S. Rapalogs bearing substituents other than —OH at C28 and/or substituents other than =O at C30 may be used to obtain preferential binding to FRAP proteins bearing an amino acid substitution for Glu2032. Examplary mutations include E2032A and E2032S. Proteins comprising an FRB containing one or more amino acid replacements at the foregoing positions, libraries of proteins or peptides randomized at those positions (i.e., containing various substituted amino acids at those residues), libraries randomizing the entire protein domain, or combinations of these sets of mutants are made using the-procedures described above to identify mutant FRAPs that bind preferentially to bumped rapalogs.

The affinity of candidate mutant FRBs for the complex of an FKBP protein complexed with a rapalog may be assayed by a number of techniques; for example binding of in vitro translated FRB mutants to GST-FKBP in the presence of drug (Chen et al. 1995. Proc. Natl. Acad. Sci. USA 92, 4947–4951); or ability to participate in a rapalog-dependent transcriptionally active complex with an appropriate FKBP fusion protein in a yeast two-hybrid assay.

FRB mutants with desired binding properties may be isolated from libraries displayed on phage using a variety of sorting strategies. For example, a rapalog is mixed with the library phage pool in solution in the presence of recombinant FKBP tagged with an affinity handle (for example a hexa-histidine tag, or GST), and the resultant complexes are captured on the appropriate affinity matrix to enrich for phage displaying FRAP harboring complementary mutations.

An additional feature of the FRB fusion protein that may vary in the various embodiments of this invention is the exact sequence of the FRB domain used. In some applications it may be preferred to use portions of an FRB which are larger than the minimal (89 amino acid) FRB domain. These include extensions N-terminal to residue Glu2025 (preferably extending to at least Arg2018 or Ile2021), as well as C-terminal extensions beyond position 2113, e.g. to position 2113, 2141 or 2174 or beyond), which may in some cases improve the stability of the folded FRB domain and/or the efficiency of expression. Other applications in which different FRB sequence termini may be used include those in which a long linker is desired for steric reasons on one or both sides of the FRB domain, for example to accommodate the distortions of the polypeptide chain required for FRB-mediated protein—protein association at the cell membrane or on DNA. Conversely, in other applications short linkers on one or both sides of the FRB domain may be preferred or required to present the heterologous effector domain(s) appropriately for biological function. In human gene therapy applications the use of naturally occurring human FRAP sequence for such linkers will generally be preferred to the introduction of heterologous sequences, or reduce the risk of provoking an immune response in the host organism.

Some rapalogs, especially rapalogs with modifications or substituents (relative to rapamycin) at positions believed to lie near the boundary between the FKBP binding domain and the FRAP binding domain, such as those on C28, C30, C7 and C24, possess reduced ability, relative to rapamycin, to form complexes with both mammalian FKBP and FRB domains, in particular, with those domains containing naturally occurring human peptide sequence. That reduced ability may be manifested as a reduced binding affinity as determined by any of the direct or indirect assay means mentioned herein or as reduced immunosuppressive activity as determined in an appropriate assay such as a T cell proliferation assay. In such cases, iterative procedures may be used to identify pairs of mutant FKBPs and mutant FRBs that are capable of complexing with the rapalog more effectively than the corresponding domains containing naturally occurring human peptide sequence. For example, one may first identify a complementary modified FKBP domain capable of binding to the rapalog, as discussed previously, and then using this mutant FKBP domain as an affinity matrix in complex with the rapalog, one may select a complementary modified FRB domain capable of associating with that complex. Several cycles of such mutagenesis and screening may be performed to optimize the protein pair.

For some embodiments, it will be desirable to use FRB and/or FKBP domains containing mutations that can affect the protein—protein interaction. For instance, mutant FKBP domains which when bound to a given rapalog are capable of complexing with an endogenous FRB measurably less effectively than to a mutant FRB are of particular interest. Also of interest are mutant FRB domains which are capable of associating with a complex of a mutant FKBP with a given rapalog measurable more effectively than with a complex of an endogenous FKBP with the rapalog. Similar selection and screening approaches to those delineated previously can be used (i) to identify amino acid substitutions, deletions or insertions to an FKBP domain which measurably diminish the domain's ability to form the tripartite complex with a given rapalog and the endogenous FRB; (ii) to identify amino acid substitutions, deletions or insertions to an FRB domain which measurably diminish the domain's ability to form the tripartite complex with a given rapalog and the endogenous FKBP; and (iii) to select and/or otherwise identify compensating mutation(s) in the partner protein. As examples of suitable mutant FKBPs with diminished effectiveness in tripartite complex formation, we include mammalian, preferably human FKBP in which one or both of His87 and Ile90 are replaced with amino acids such as Arg, Trp, Phe, Tyr or Lys which contain bulky side chain groups; FRB domains, preferably containing mammalian, and more preferably of human, peptide sequence may then be mutated as described above to generate complementary variants which are capable of forming a tripartite complex with the mutant FKBP and a given rapalog. Illustrative FRB mutations which may be useful with H87W or H87R hFKBP12s include human FRBs in which Y2038 is replaced by V, S, A or L; F2039 is replaced by A; and/or R2042 is replaced by L, A or S. Illustrative FRB mutations which may be useful with I90W or I90R hFKBP12s include human FRBs in which K2095 is replaced with L, S, A or T.

Additionally, in optimizing the receptor domains of this invention, it should be appreciated that immunogenicity of a polypeptide sequence is thought to require the binding of peptides by MHC proteins and the recognition of the presented peptides as foreign by endogenous T-cell receptors. It may be preferable, at least in human gene therapy applications, to tailor a given foreign peptide sequence, including junction peptide sequences, to minimize the probability of its being immunologically presented in humans. For example, peptide binding to human MHC class I molecules has strict requirements for certain residues at key 'anchor' positions in the bound peptide: eg. HLA-A2 requires leucine, methionine or isoleucine at position 2 and leucine or valine at the C-terminus (for review see Stern and Wiley (1994) Structure 2, 145–251). Thus in engineering proteins in the practice of this invention, this periodicity of these residues is preferably avoided, especially in human gene therapy applications. The foregoing applies to all protein engineering aspects of the invention, including without limitation the engineering of point mutations into receptor domains, and to the choice or design of boundaries between the various protein domains.

Other Components, Design Features and Applications

The chimeric proteins may contain as a heterologous domain a cellular localization domain such as a membrane retention domain. See e.g. PCT/US94/01617, especially pages 26–27. Briefly, a membrane retention domain can be isolated from any convenient membrane-bound protein, whether endogenous to the host cell or not. The membrane retention domain may be a transmembrane retention domain, i.e., an amino acid sequence which extends across the membrane as in the case of cell surface proteins, incluing many receptors. The transmembrane peptide sequence may be extended to span part or all of an extracellular and/or intracellular domain as well. Alternatively, the membrane retention domain may be a lipid membrane retention domain such as a myristoylation or palmitoylation site which permits association with the lipids of the cell surface membrane. Lipid membrane retention domains will usually be added at the 5' end of the coding sequence for N-terminal binding to the membrane and, proximal to the 3' end for C-terminal binding. Peptide sequences involving post-translational processing to provide for lipid membrane binding are described by Carr, et al., PNAS USA (1988) 79, 6128; Aitken, et al., FEBS Lett. (1982) 150, 314; Henderson, et al., PNAS USA (1983) 80, 319; Schulz, et al., Virology (1984), 123, 2131; Deliman, et al., Nature (1985) 314, 374; and reviewed in Ann. Rev, of Biochem. (1988) 57, 69. An amino acid sequence of interest includes the sequence M-G-S-S-K-S-K-P-K-D-P-S-Q-R (SEQ ID NO 1). Various DNA sequences can be used to encode such sequences in the various chimeric proteins of this invention. Other localization domains include organelle-targeting domains and sequences such as -K-D-E-L (SEQ ID NO 2) and -H-D-E-L (SEQ ID NO 3) which target proteins bearing them to the endoplasmic reticulum, as well as nuclear localization sequences which are particularly useful for chimeric proteins designed for (direct) transcriptional regulation. Various cellular localization sequences and signals are well known in the art.

Further details which may be used in the practice of the subject invention relating to the design, assembly and use of constructs encoding chimeric proteins containing various effector domains including cytoplasmic signal initiation domains such as the CD3 zeta chain, nuclear transcription factor domains including among others VP16 and GAL4, domains capable of triggering apoptosis including the Fas cytoplasmic domain and others are disclosed in PCT/US94/01617 and PCT/US95/10591. The latter international application further discloses additional features particularly applicable to the creation of, genetically engineered animals which may be used as disease models in biopharmaceutical research. Those features include the use of tissue specific regulatory elements in the constructs for expression of the chimeric proteins and the application of regulated transcription to the expression of Cre recombinase as the target gene leading to the elimination of a gene of interest flanked by loxP sequences. Alternatively, flp and its cognate recognition sequences may be used instead of Cre and lox. Those features may be adapted to the subject invention.

In various cases, especially in embodiments involving whole animals containing cells engineered in accordance with this invention, it will often be preferred, and in some cases required, that the various domains of the chimeric proteins be derived from proteins of the same species as the host cell. Thus, for genetic engineering of human cells, it is often preferred that the heterologous domains (as well as the FKBP and FRB domains) be of human origin, rather than of bacterial, yeast or other non-human source.

We also note that epitope tags may also be incorporated into chimeric proteins of this invention to permit convenient detection.

Tissue-Specific or Cell-Type Specific Expression

It will be preferred in certain embodiments, that the chimeric proteins be expressed in a cell-specific or tissue-specific manner. Such specificity of expression may be achieved by operably linking one ore more of the DNA sequences encoding the chimeric protein(s) to a cell-type specific transcriptional regulatory sequence (e.g. promoter/enhancer). Numerous cell-type specific transcriptional regulatory sequences are known. Others may be obtained from genes which are expressed in a cell-specific manner. See e.g. PCT/US95/10591, especially pp. 36–37.

For example, constructs for expressing the chimeric proteins may contain regulatory sequences derived from known genes for specific expression in selected tissues.

Representative examples are tabulated below:

| Tissue | Gene | Reference |
|---|---|---|
| lens | g2-crystallin | Breitman, M.L., Clapoff, S., Rossant, J., Tsui, L.C., Golde, L.M., Maxwell, I.H., Bernstin, A. (1987) Genetic Ablation: targeted expression of a toxin gene causes microphthalmia in transgenic mice. Science 238: 1563–1565 |
| | aA-crystallin | Landel, C.P., Thao, J., Bok, D., Evans, G.A. (1988) Lens-specific expression of a recombinant ricin induces developmental defects in the eyes of transgenic mice. Genes Dev. 2: 1168–1178<br>Kaur, S., key, B., Stock, J., McNeish, J.D., Akeson, R., Potter, S.S. (1989) Targeted ablation of alpha-crystallin-synthesizing cells produces lens-deficient eyes in transgenic mice. Development 105: 613–619 |
| pituitary-somatrophic cells | Growth hormone | Behringer, R.R., Mathews, L.S., Palmiter, R.D., Brinster, R.L. (1988) Dwarf mice produced by genetic ablation of growth hormone-expressing cells. Genes Dev. 2: 453461 |
| pancreas | Insulin-Elastase - acinar cell specific | Omitz, D.M., Palmiter, R.D., Hammer, R.E., Brinster, R.L., Swift, G.H., MacDonald, R.J. (1985) Specific expression of an elastase-human growth fusion in pancreatic acinar cells of trausgeneic mice. Nature 131: 600–603<br>Palmiter, R.D., Behringer, R.R., Quaife, C.J., Maxwell, F., Maxwell, I.H., Brinster, R.L. (1987) Cell lineage ablation in transgeneic mice by cell-specific expression of a toxin gene. Cell 50: 435443 |
| T cells | 1ck promoter | Chaffin, K.E., Beals, C.R., Wilkie, T.M., Forbush, K.A., Simon, M.L, Perlmutter, R.M. (1990) EMBO Journal 9: 3821–3829 |
| B cells | Immunoglobulin kappa light chain | Borelli, E., Heyman, R., Hsi, M., Evans, R.M. (1988) Targeting of an inducible toxic phenotype in animal cells. Proc. Natl. Acad. Sci. USA 85: 7572–7576<br>Heyman, R.A., Borrelli, E., Lesley, J., Anderson, D., Richmond, D.D., Baird, S.M., Hyman, R., Evans, R.M. (1989) Thymidine kinase obliteration: creation of transgenic mice with controlled immunodeficiencies. Proc. Natl. Acad. Sci. USA 86: 2698–2702 |
| Schwann cells | $P_0$ promoter | Messing, A., Behringer, R.R., Hammang, J.P. Palmiter, RD, Brinster, RL, Lemke, G. ,PO promoter directs espression of reporter and toxin genes to Schwann cells of transgenic mice. Neuron 8:507–520 1992 |
| | Myelin basic protein | Miskimins, R. Knapp, L., Dewey,MJ, Zhang, X. Cell and tissue-specific expression of a heterologous gene under control of the myelin basic protein gene promoter in trangenic mice. Brain Res Dev Brain Res 1992 Vol 65: 217–21 |
| spermatids | protamine | Breitman, M.L., Rombola, H., Maxwell, I.H., Klintworth, G.K., Bernstein, A. (1990) Genetic ablation in transgenic mice with attenuated diphtheria toxin A gene. Mol. Cell. Biol. 10: 474–479 |
| lung | Lung surfacant gene | Ornitz, D.M., Palmiter, R.D., Hammer, R.E., Brinster, R.L., Swift, G.H., MacDonald, R.J. (1985) Specific expression of an elastase-human growth fusion in pancreatic acinar cells of transgeneic mice. Nature 131: 600–603 |
| adipocyte P2 | | Ross, S.R, Braves, RA, Spiegelman, BM Targeted expression of a toxin gene to adipose tissue: transgenic mice resistant to obesity Genes and Dev 7: 1318–24 1993 |
| muscle | myosin light chain | Lee, KJ, Ross, RS, Rockman, HA, Harris, AN, (YBrien, TX, van-Bilsen, M., Shubeita, HE, Kandolf, R., Brem, C., Prices et alJ. Biol. Chem. 1992 Aug 5, 267: 15875–85 |
| | Alpha actin | Muscat, GE., Perry, S. , Prentice, H. Kedes, L. The human skeletal alpha-actin gene is regulated by a muscle-specific enhancer that binds three nuclear factors. Gene Expression 2, 111–26, 1992<br>. . . /. . . |
| neurons | neurofilament proteins | Reeben, M. Halmekyto, M. Aihonen, L. Sinervirta, R. Saarma, M. Janne,J. Tissue-specific expression of rat light neurofilament promoter-driven reporter gene in transgenic mice. BBRC 1993: 192: 465–70 |
| liver | tyrosine aminotransferase, albumin, apolipoproteins | |

Target Gene Constructs

In embodiments of the invention in which the chimeric proteins are designed such that their multimerization activates transcription of a target gene, an appropriate target gene construct is also used in the engineered cells. Appropriate target gene constructs are those containing a target gene and a cognate transcriptional control element such as a promoter and/or enhancer which is responsive to the multimerization of the chimeric proteins. In embodiments involving direct activation of transcription, that responsiveness may be achieved by the presence in the target gene construct of one or more DNA sequences recognized by the DNA-binding domain of a chimeric protein of this invention (i.e., a DNA sequence to which the chimeric protein binds). In embodiments involving indirect activation of transcription, responsiveness may be achieved by the presence in the target gene construct of a promoter and/or enhancer sequence which is activated by an intracellular signal generated by multimerization of the chimeric proteins. For example, where the chimeric proteins contain the TCR zeta chain intracellular domain, the target gene is linked to and under the expression control of the IL-2 promoter region.

This invention also provides target DNA constructs containing (a) a cognate DNA sequence, e.g. to which a DNA-binding chimeric protein of this invention is capable of binding (or which is susceptible to indirect activation as discussed above), and (b) flanking DNA sequence from the locus of a desired target gene endogenous to the host cells. These constructs permit homologous recombination of the cognate DNA sequence into a host cell in association with an endogenous target gene. In other embodiments the construct contains a desired gene and flanking DNA sequence from a target locus permitting the homologous recombination of the target gene into the desired locus. Such a target construct may also contain the cognate DNA sequence, or the cognate DNA sequence may be provided by the locus.

The target gene in any of the foregoing embodiments may encode for example a surface membrane protein (such as a receptor protein), a secreted protein, a cytoplasmic protein, a nuclear protein, a recombinase such as Cre, a ribozyme or an antisense RNA. See PCT/US94/01617 for general design and construction details and for various applications including gene therapy and see PCT/US95/10591 regarding applications to animal models of disease.

This invention encompasses a variety of configurations for the chimeric proteins. In all cases involving the activation of target gene transcription, however, the chimeric proteins share an important characteristic: cells containing constructs encoding the chimeras and a target gene construct express the target gene at least one, preferably at least two, and more preferably at least three or four or more orders of magnitude more in the presence of the multimerizing ligand than in its absence. Optimally, expression of the selected gene is not observed unless the cells are or have been exposed to a multimerizing ligand.

To recap, the chimeric proteins are capable of initiating a detectable level of transcription of target genes within the engineered cells upon exposure of the cells to the an improved rapalog, i.e., following multimerization of the chimeras. Thus, transcription of target genes is activated in genetically engineered cells of this invention following exposure of the cells to an improved rapalog capable of multimerizing the chimeric protein molecules. Said differently, genetically engineered cells of this invention contain chimeric proteins as described above and are responsive to the presence and/or concentration of an improved rapalog which is capable of multimerizing those chimeric protein molecules. That responsiveness is manifested by the activation of transcription of a target gene. Such transcriptional activity can be readily detected by any conventional assays for transcription of the target gene. In other embodiments, the biological response to ligand-mediated multimerization of the chimeras is cell death or other biological events rather than direct activation of transcription of a target gene.

Design and Assembly of the DNA Constructs

Constructs may be designed in accordance with the principles, illustrative examples and materials and methods disclosed in the patent documents and scientific literature cited herein, each of which is incorporated herein by reference, with modifications and further exemplification as described herein. Components of the constructs can be prepared in conventional ways, where the coding sequences and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc. as appropriate. In the case of DNA constructs encoding fusion proteins, DNA sequences encoding individual domains and sub-domains are joined such that they constitute a single open reading frame encoding a fusion protein capable of being translated in cells or cell lysates into a single polypeptide harboring all component domains. The DNA construct encoding the fusion protein may then be placed into a vector that directs the expression of the protein in the appropriate cell type(s). For biochemical analysis of the encoded chimera, it may be desirable to construct plasmids that direct the expression of the protein in bacteria or in reticulocyte-lysate systems. For use in the production of proteins in mammalian cells, protein-encoding sequence is introduced into an expression vector that directs expression in these cells. Expression vectors suitable for such uses are well known in the art. Various sorts of such vectors are commercially available.

Constructs encoding the chimeric proteins and target genes of this invention can be introduced into the cells as one or more DNA molecules or constructs, in many cases in association with one or more markers to allow for selection of host cells which contain the construct(s). The construct(s) once completed and demonstrated to have the appropriate sequences may then be introduced into a host cell by any convenient means. The constructs may be incorporated into vectors capable of episomal replication (e.g. BPV or EBV vectors) or into vectors designed for integration into the host cells' chromosomes. The constructs may be integrated and packaged into non-replicating, defective viral genomes like Adenovirus, Adeno-associated virus (AAV), or Herpes simplex virus (HSV) or others, including retroviral vectors, for infection or transduction into cells. Viral delivery systems are discussed in greater detail below. Alternatively, the construct may be introduced by protoplast fusion, electroporation, biolistics, calcium phosphate transfection, lipofection, microinjection of DNA or the like. The host cells will in some cases be grown and expanded in culture before introduction of the construct(s), followed by the appropriate treatment for introduction of the construct(s) and integration of the construct(s). The cells will then be expanded and screened by virtue of a marker present in the constructs. Various markers which may be used successfully include hprt, neomycin resistance, thymidine kinase, hygromycin resistance, etc., and various cell-surface markers such as Tac, CD8, CD3, Thy1 and the NGF receptor.

In some instances, one may have a target site for homologous recombination, where it is desired that a construct be integrated at a particular locus. For example, one can delete and/or replace an endogenous gene (at the same locus or elsewhere) with a recombinant target construct of this invention. For homologous recombination, one may generally use either Ω or O-vectors. See, for example, Thomas and Capecchi, Cell (1987) 51, 503–512; Mansour, et al., Nature (1988) 336, 348–352; and Joyner, et al., Nature (1989) 338, 153–156.

The constructs may be introduced as a single DNA molecule encoding all of the genes, or different DNA molecules having one or more genes. The constructs may be introduced simultaneously or consecutively, each with the same or different markers.

Vectors containing useful elements such as bacterial or yeast origins of replication, selectable and/or amplifiable markers, promoter/enhancer elements for expression in procaryotes or eucaryotes, and mammalian expression control elements, etc. which maybe used to prepare stocks of construct DNAs and for carrying out transfections are well known in the art, and many are commercially available.

Delivery of Nuceic Acid: Ex vivo and in vivo

Any means for the introduction of heterologous nucleic acids into host cells, especially eucaryotic cells, an in particular animal cells, preferably human or non-human mammalian cells, may be adapted to the practice of this invention. For the purpose of this discussion, the various nucleic acid constructs described herein may together be referred to as the transgene. Ex vivo approaches for delivery of DNA include calcium phosphate precipitation, electroporation, lipofection and infection via viral vectors. Two general in vivo gene therapy approaches include (a) the delivery of "naked", lipid-complexed or liposome-formulated or otherwise formulated DNA and (b) the delivery of the heterologous nucleic acids via viral vectors. In the former approach, prior to formulation of DNA, e.g. with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126–139, 1995). Formulation of DNA, e.g. with various lipid or liposome materials, may then be effected using known methods and materials and delivered to the recipient mammal.

While various viral vectors may be used in the practice of this invention, retroviral-, AAV- and adenovirus-based approaches are of particular interest. See, for example, Dubensky et al. (1984) Proc. Natl. Acad. Sci. USA 81, 7529–7533; Kaneda et al., (1989) Science 243,375–378; Hiebert et al. (1989) Proc. Natl. Acad. Sci. USA 86, 3594–3598; Hatzoglu et al. (1990) J. Biol. Chem. 265, 17285–17293 and Ferry, et al. (1991) Proc. Natl. Acad. Sci. USA 88, 8377–8381. The following additional guidance on the choice and use of viral vectors may be helpful to the practitioner.

Retroviral Vectors

Retroviruses are a class of RNA viruses in which the RNA genome is reversely transcribed to DNA in the infected cell. The retroviral genome can integrate into the host cell genome and requires three viral genes, gag, pol and env, as well as the viral long terminal repeats (LTRs). The LTRs also act as enhancers and promoters for the viral genes. The packaging sequence of the virus, (Ψ), allows the viral RNA to be distinguished from other RNAs in the cell (Verma et al., Nature 389:239–242, 1997). For expression of a foreign gene, the viral proteins are replaced with the gene of interest in the viral vector, which is then transfected into a packaging line containing the viral packaging components. Packaged virus is secreted from the packaging line into the culture medium, which can then be used to infect cells in culture. Since retroviruses are unable to infect non-dividing cells, they have been used primarily for ex vivo gene therapy.

AAV Vectors

Adeno-associated virus (AAV)-based vectors are of general interest as a delivery vehicle to various tissues, including muscle and lung. AAV vectors infect cells and stably integrate into the cellular genome with high frequency. AAV can infect and integrate into growth-arrested cells (such as the pulmonary epithelium), and is non-pathogenic.

The AAV-based expression vector to be used typically includes the 145 nucleotide AAV inverted terminal repeats (ITRs) flanking a restriction site that can be used for subcloning of the transgene, either directly using the restriction site available, or by excision of the transgene with restriction enzymes followed by blunting of the ends, ligation of appropriate DNA linkers, restriction digestion, and ligation into the site between the rTRs. The capacity of AAV vectors is about 4.4 kb. The following proteins have been expressed using various AAV-based vectors, and a variety of promoter/enhancers: neomycin phosphotransferase, chloramphenicol acetyl transferase, Fanconi's anemia gene, cystic fibrosis transmembrane conductance regulator, and granulocyte macrophage colony-stimulating factor (Kotin, R. M., Human Gene Therapy 5:793–801, 1994, Table I). A transgene incorporating the various DNA constructs of this invention can similarly be included in an AAV-based vector. As an alternative to inclusion of a constitutive promoter such as CMV to drive expression of the recombinant DNA encoding the fusion protein(s), an AAV promoter can be used (ITR itself or AAV p5 (Flotte, et al. J. Biol. Chem. 268:3781–3790, 1993)).

Such a vector can be packaged into AAV virions by reported methods. For example, a human cell line such as 293 can be co-transfected with the AAV-based expression vector and another plasmid containing open reading frames encoding AAV rep and cap under the control of endogenous AAV promoters or a heterologous promoter. In the absence of helper virus, the rep proteins Rep68 and Rep78 prevent accumulation of the replicative form, but upon superinfection with adenovirus or herpes virus, these proteins permit replication from the YFRs (present only in the construct containing the transgene) and expression of the viral capsid proteins. This system results in packaging of the transgene DNA into AAV virions (Carter, B. J., Current Opinion in Biotechnology 3:533–539, 1992; Kotin, R. M, Human Gene Therapy 5:793–801, 1994)). Methods to improve the titer of AAV can also be used to express the transgene in an AAV virion. Such strategies include, but are not limited to: stable expression of the ITR-flanked transgene in a cell line followed by transfection with a second plasmid to direct viral packaging; use of a cell line that expresses AAV proteins inducibly, such as temperature-sensitive inducible expression or pharmacologically inducible expression. Additionally, one may increase the efficiency of AAV transduction by treating the cells with an agent that facilitates the conversion of the single stranded form to the double stranded form, as described in Wilson et al., WO96/39530.

Concentration and purification of the virus can be achieved by reported methods such as banding in cesium chloride gradients, as was used for the initial report of AAV vector expression in vivo (Flotte, et al. J. Biol. Chem. 268:3781–3790, 1993) or chromatographic purification, as described in O'Riordan et al., WO97/08298.

For additional detailed guidance on AAV-technology which may be -useful in the practice of the subject invention, including methods and materials for the incorporation of a transgene, the propagation and purification of the recombinant AAV vector containing the transgene, and its use in transfecting cells and mammals, see e.g. Carter et al, U.S. Pat. No. 4,797,368 (Jan. 10, 1989); Muzyczka et al, U.S. Pat. No. 5,139,941 (Aug. 18, 1992); Lebkowski et al, U.S. Pat. No. 5,173,414 (Dec. 22, 1992); Srivastava, U.S. Pat. No. 5,252,479 (Oct. 12, 1993); Lebkowski et al, U.S. Pat. No. 5,354,678 (Oct. 11, 1994); Shenk et al, U.S. Pat. No. 5,436,146 (Jul. 25, 1995); Chatteree et al, U.S. Pat. No. 5,454,935 (Dec. 12, 1995), Carter et al WO 93/24641 (published Dec. 9, 1993), and Flotte et al., U.S. Pat. No. 5,658,776 (Aug. 19, 1997).

Adenovirus Vectors

Various adenovirus vectors have been shown to be of use in the transfer of genes to mammals, including humans. Replication-deficient adenovirus vectors have been used to express marker proteins and CFTR in the pulmonary epithelium. The first generation E1a deleted adenovirus vectors have been improved upon with a second generation that includes a temperature-sensitive E2a viral protein, designed to express less viral protein and thereby make the virally infected cell less of a target for the immune system (Goldman et al., Human Gene Therapy 6:839–851, 1995). More recently, a viral vector deleted of all viral open reading frames has been reported (Fisher et al., Virology 217:11–22, 1996). Moreover, it has been shown that expression of viral IL-10 inhibits the immune response to adenoviral antigen (Qin et al., Human Gene Therapy 8:1365–1374, 1997).

DNA sequences of a number of adenovirus types are available from Genbank. The adenovirus DNA sequences may be obtained from any of the 41 human adenovirus types currently identified. Various adenovirus strains are available from the American Type Culture Collection, Rockville, Md., or by request from a number of commercial and academic sources. A transgene as described herein may be incorporated into any adenoviral vector and delivery protocol, by the same methods (restriction digest, linker ligation or filling in of ends, and ligation) used to insert the CFTR or other genes into the vectors. Hybrid Adenovirus-AAV vectors represented by an adenovirus capsid containing selected portions of the adenovirus sequence, 5' and 3' AAV ITR sequences flanking the transgene and other conventional vector regulatory elements may also be used. See e.g. Wilson et al, International Patent Application Publication No. WO 96/13598. For additional detailed guidance on adenovirus and hybrid adenovirus-AAV technology which may be useful in the practice of the subject invention, including methods and materials for the incorporation of a transgene, the propagation and purification of recombinant virus containing the transgene, and its use in transfecting cells and mammals, see also Wilson et al, WO 94/28938, WO 96/13597 and WO 96/26285, and references cited therein.

Generally the DNA or viral particles are transferred to a biologically compatible solution or pharmaceutically acceptable delivery vehicle, such as sterile saline, or other aqueous or non-aqueous isotonic sterile injection solutions or suspensions, numerous examples of which are well known in the art, including Ringer's, phosphate buffered saline, or other similar vehicles.

Preferably, in gene therapy applications, the DNA or recombinant virus is administered in sufficient amounts to transfect cells at a level providing therapeutic benefit without undue adverse effects. Optimal dosages of DNA or virus depends on a variety of factors, as discussed elsewhere, and may thus vary somewhat from patient to patient. Again, therapeutically effective doses of viruses are considered to be in the range of about 20 to about 50 ml of saline solution containing concentrations of from about $1\times10^7$ to about $1\times10^{10}$ pfu of virus/ml, e.g. from $1\times10^8$ to $1\times10^9$ pfu of virus/ml.

Host Cells

This invention is particularly useful for the engineering of animal cells and in applications involving the use of such engineered animal cells. The animal cells may be insect, worm or mammalian cells. While various mammalian cells may be used, including, by way of example, equine, bovine, ovine, canine, feline, murine, and non-human primate cells, human cells are of particular interest. Among the various species, various types of cells may be used, such as hematopoietic, neural, glial, mesenchymal, cutaneous, mucosal, stromal, muscle (including smooth muscle cells), spleen, reticulo-endothelial, epithelial, endothelial, hepatic, kidney, gastrointestinal, pulmonary, fibroblast, and other cell types. Of particular interest are hematopoietic cells, which may include any of the nucleated cells which may be involved with the erythroid, lymphoid or myelomonocytic lineages, as well as myoblasts and fibroblasts. Also of interest are stem and progenitor cells, such as hematopoietic, neural, stromal, muscle, hepatic, pulmonary, gastrointestinal and mesenchymal stem cells The cells may be autologous cells, syngeneic cells, allogeneic cells and even in some cases, xenogeneic cells with respect to an intended host organism. The cells may be modified by changing the major histocompatibility complex ("MHC") profile, by inactivating $\beta$2-microglobulin to prevent the formation of functional Class I MHC molecules, inactivation of Class II molecules, providing for expression of one or more MHC molecules, enhancing or inactivating cytotoxic capabilities by enhancing or inhibiting the expression of genes associated with the cytotoxic activity, or the like.

In some instances specific clones or oligoclonal cells may be of interest, where the cells have a particular specificity, such as T cells and B cells having a specific antigen specificity or homing target site specificity.

Introduction of Constructs into Animals

Cells which have been modified ex vivo with the DNA constructs may be grown in culture under selective conditions and cells which are selected as having the desired construct(s) may then be expanded and further analyzed, using, for example, the polymerase chain reaction for determining the presence of the construct in the host cells and/or assays for the production of the desired gene product(s). Once modified host cells have been identified, they may then be used as planned, e.g. grown in culture or introduced into a host organism.

Depending upon the nature of the cells, the cells may be introduced into a host organism, e.g. a mammal, in a wide variety of ways. Hematopoietic cells may be administered by injection into the vascular system, there being usually at least about $10^4$ cells and generally not more than about $10^{10}$ cells. The number of cells which are employed will depend upon a number of circumstances, the purpose for the introduction, the lifetime of the cells, the protocol to be used, for example, the number of administrations, the ability of the cells to multiply, the stability of the therapeutic agent, the physiologic need for the therapeutic agent, and the like. Generally, for myoblasts or fibroblasts for example, the number of cells will be at least about 104 and not more than about 109 and may be applied as a dispersion, generally being injected at or near the site of interest. The cells will usually be in a physiologically-acceptable medium.

Cells engineered in accordance with this invention may also be encapsulated, e.g. using conventional biocompatible materials and methods, prior to implantation into the host organism or patient for the production of a therapeutic protein. See e.g. Hguyen et al, Tissue Implant Systems and Methods for Sustaining viable High Cell Densities within a Host, U.S. Pat. No. 5,314,471 (Baxter International, Inc.); Uludag and Sefton, 1993, J Biomed. Mater. Res. 27(10):1213–24 (HepG2 cells/hydroxyethyl methacrylate-methyl methacrylate membranes); Chang et al, 1993, Hum Gene Ther 4(4):433–40 (mouse Ltk- cells expressing hGH/immunoprotective perm-selective alginate microcapsules; Reddy et al, 1993, J Infect Dis 168(4):1082–3 (alginate); Tai and Sun, 1993, FASEB J 7(11):1061–9 (mouse fibroblasts expressing hGH/alginate-poly-L-lysine-alginate membrane); Ao et al, 1995, Transplanataion Proc. 27(6):3349, 3350 (alginate); Rajotte et al, 1995, Transplantation Proc. 27(6):3389 (alginate); Lakey et al, 1995, Transplantation Proc. 27(6):3266 (alginate); Korbutt et al, 1995, Transplantation Proc. 27(6):3212 (alginate); Dorian et al, U.S. Pat. No. 5,429,821 (alginate); Emerich et al, 1993, Exp Neurol 122(1):37–47 (polymer-encapsulated PC12 cells); Sagen et al, 1993, J Neurosci 13(6):2415–23 (bovine cnromaffin cells encapsulated in semipermeable polymer membrane and implanted into rat spinal subarachnoid space); Aebischer et al, 1994, Exp Neurol 126(2):151–8 (polymer-encapsulated rat PC12 cells implanted into monkeys; see also Aebischer, WO 92/19595); Savelkoul et al, 1994, J Immunol Methods 170(2):185–96 (encapsulated hybridomas producing antibodies; encapsulated transfected cell lines expressing various cytokines); Winn et al, 1994, PNAS USA 91(6):2324–8 (engineered BHK cells expressing human nerve growth factor encapsulated in an immunoisolation polymeric device and transplanted into rats); Emerich et al, 1994, Prog Neuropsychopharmacol Biol Psychiatry 18(5):935–46 (polymer-encapsulated PC12 cells implanted into rats); Kordower et al, 1994, PNAS USA 91(23):10898–902 (polymer-encapsulated engineered BHK cells expressing hNGF implanted into monkeys) and Butler et al WO 95/04521 (encapsulated device). The cells may then be introduced in encapsulated form into an animal host, preferably a mammal and more preferably a human subject in need thereof. Preferably the encapsulating material is semipermeable, permitting release into the host of secreted proteins produced by the encapsulated cells. In many embodiments the semipermeable encapsulation renders the encapsulated cells immunologically isolated from the host organism in which the encapsulated cells are introduced. In those embodiments the cells to be encapsulated may express one or more chimeric proteins containing component domains derived from proteins of the host species and/or from viral proteins or proteins from species other than the host species. For example in such cases the chimeras may contain elements derived from GAL4 and VP16. The cells may be derived from one or more individuals other than the recipient and may be derived from a species other than that of the recipient organism or patient.

Instead of ex vivo modification of the cells, in many situations one may wish to modify cells in vivo. For this purpose, various techniques have been developed for modification of target tissue and cells in vivo. A number of viral vectors have been developed, such as adenovirus, adeno-associated virus, and retroviruses, as discussed above, which allow for transfection and, in some cases, integration of the virus into the host. See, for example, Dubensky et al. (1984) Proc. Natl. Acad. Sci. USA 81, 7529–7533; Kaneda et al., (1989) Science 243,375–378; Hiebert et al. (1989) Proc. Natl. Acad. Sci. USA 86, 3594–3598; Hatzoglu et al. (1990) J. Biol. Chem. 265, 17285–17293 and Ferry, et al. (1991) Proc. Natl. Acad. Sci. USA 88, 8377–8381. The vector may be administered by injection, e.g. intravascularly or intramuscularly, inhalation, or other parenteral mode. Non-viral delivery methods such as administration of the DNA via complexes with liposomes or by injection, catheter or biolistics may also be used.

In accordance with in vivo genetic modification, the manner of the modification will depend on the nature of the tissue, the efficiency of cellular modification required, the number of opportunities to modify the particular cells, the accessibility of the tissue to the DNA composition to be introduced, and the like. By employing an attenuated or modified retrovirus carrying a target transcriptional initiation region, if desired, one can activate the virus using one of the subject transcription factor constructs, so that the virus may be produced and transfect adjacent cells.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

Binding Properties, Assays

Rapamycin is known to bind to the human protein, FKBP12 and to form a tripartite complex with hFKBP12 and FRAP, a human counterpart to the yeast proteins TOR1 and TOR2. Rapalogs may be characterized and compared to rapamycin with respect to their ability to bind to human FKBP12 and/or to form tripartite complexes with human FKBP12 and human FRAP (or fusion proteins or fragments containing its FRB domain). See WO 96/41865 (Clackson et al). That application discloses various materials and methods which can be used to quantify the ability of a compound to bind to human FKBP12 or to form a tripartite complex with (i.e., "heterodimerize") proteins comprising human FKBP12 and the FRB domain of human FRAP, respectively. Such assays include fluorescence polarization assays to measure binding. Also included are cell based transcription assays in which the ability of a compound to form the tripartite complex is measured indirectly by correlation with the observed level of reporter gene product produced by engineered mammalian cells in the presence of the compound. Corresponding cell-based assays may also be conducted in engineered yeast cells. See e.g. WO 95/33052 (Berlin et al).

It will often be preferred that the rapalogs of this invention be physiologically acceptable (i.e., lack undue toxicity toward the cell or organism with which it is to be used), can be taken orally by animals (i.e., is orally active in applications in whole animals, including gene therapy), and/or can cross cellular and other membranes, as necessary for a particular application.

In addition, preferred rapalogs are those which bind preferentially to mutant immunophilins (by way of non-limiting example, a human FKBP in which Phe36 is replaced with a different amino acid, preferably an amino acid with a less bulky R group such as valine or alanine) over native or naturally-ocurring immunophilins. For example, such compounds may bind preferentially to mutant FKBPs at least an order of magnitude better than they bind to human FKBP12, and in some cases may bind to mutant FKBPs greater than 2 or even 3 or more orders of magnitude better than they do to human FKBP12, as determined by any scientifically valid or art-accepted assay methodology.

Binding affinities of various rapalogs of this invention with respect to human FKBP12, variants thereof or other immunophilin proteins may be determined by adaptation of known methods used in the case of FKBP. For instance, the practitioner may measure the ability of a compound of this invention to compete with the binding of a known ligand to the protein of interest. See e.g. Sierkierka et al, 1989, Nature 341, 755–757 (test compound competes with binding of labeled FK506 derivative to FKBP).

One set of preferred rapalogs of this invention which binds, to human FKBP12, to a mutant thereof as discussed above, or to a fusion protein containing such FKBP domains, with a Kd value below about 200 nM, more preferably below about 50 nM, even more preferably below about 10 nM, and even more preferably below about 1 nM, as measured by direct binding measurement (e.g. fluorescence quenching), competition binding measurement (e.g. versus FK506), inhibition of FKBP enzyme activity (rotamase), or other assay methodology. In one subset of such compounds, the FKBP domain is one in which phenylalanine at position 36 has been replaced with an amino acid having a less bulky side chain, e.g. alanine, valine, methionine or serine.

A Competitive Binding FP Assay is described in detail in the examples which follow. That assay permits the in vitro measurement of an IC50 value for a given compound which reflects its ability to bind to an FKBP protein in competition with a labeled FKBP ligand, such as, for example, FK506.

One preferred class of compounds of this invention are those rapalogs which have an IC50 value in the Competitive Binding FP Assay better than 1000 nM, preferably better than 300 nM, more preferably better than 100 nM, and even more preferably better than 10 nM with respect to a given FKBP domain and ligand pair, e.g. human FKBP12 or a variant thereof with up to 10, preferably up to 5 amino acid replacements, with a flouresceinated FK506 standard. In one subset of that class, the FKBP domain has one of the abovementioned modifications at position 36.

The ability of the rapalogs to multimerize chimeric proteins may be measured in cell-based assays by measuring the occurrence of an event triggered by such multimerization. For instance, one may use cells containing and capable of expressing DNA encoding a first chimeric protein comprising one or more FKBP- domains and one or more effector domains as well as DNA encoding a second chimeric protein containing an FRB domain and one or more effector domains capable, upon multimerization, of actuating a biological response. We prefer to use cells which further contain a reporter gene under the transcriptional control of a regulatory element (i.e., promoter) which is responsive to the multimerization of the chimeric proteins. The design and preparation of illustrative components and their use in so engineered cells is described in WO96/41865 and the other international patent applications referred to in this and the foregoing section. The cells are grown or maintained in culture. A rapalog is added to the culture medium and after a suitable incubation period (to permit gene expression and secretion, e.g. several hours or overnight) the presence of the reporter gene product is measured. Positive results, Le., multimerization, correlates with transcription of the reporter gene as observed by the appearance of the reporter gene product. The reporter gene product may be a conveniently detectable protein (e.g. by ELISA) or may catalyze the production of a conveniently detectable product (e.g. colored). Materials and methods for producing appropriate cell lines for conducting such assays are disclosed in the international patent applications cited above in this section. Typically used target genes include by way of example SEAP, hGH, beta-galactosidase, Green Fluorescent Protein and luciferase, for which convenient assays are commercially available.

Another preferred class of compounds of this invention are those which are capable of inducing a detectable signal in a 2-hybrid transcription assay based on fusion proteins containing an FKBP domain. Preferably, the FKBP domain is an FKBP domain other than wild-type human FKBP12.

Another assay for measuring the ability of the rapalogs to multimerize chimeric proteins, like the FKBP-based transcription assay, is a cell-based assay which measures the occurrence of an event triggered by such multimerization. In this case, one uses cells which constitutively express a detectable product. The cells also contain and are capable of expressing DNAs encoding chimeric proteins comprising one or more immunophilin-derived ligand binding domains and one or more effector domains, such as the intracellular domain of FAS, capable, upon multimerization, of triggering cell death. The design and preparation of illustrative components and their use in so engineering cells is described in WO95/02684. See also WO96/41865. The cells are maintained or cultured in a culture medium permitting cell growth or continued viability. The cells or medium are assayed for the presence of the constitutive cellular product, and a base-line level of reporter is thus established. One may use cells engineered for constitutive production of hGH or any other conveniently detectable product to serve as the reporter. The compound to be tested is addded to the medium, the cells are incubated, and the cell lysate or medium is tested for the presence of reporter at one or more time points. Decrease in reporter production indicates cell death, an indirect measure of multimerization of the fusion proteins.

Another preferred class of compounds of this invention are those which are capable of inducing a detectable signal in such an FKBP/FRB-based apoptosis assay. Preferably, the FKBP domain is an FKBP domain other than wild-type human FKBP12. In some cases, the FKBP domain is modified, as discussed above. Also preferably, the FRB domain is an FRB domain other than wild-type FRB from human FRAP. In some cases, the FRB domain is modified at position 2098, as described above.

Conducting such assays permits the practitioner to select rapalogs possessing the desired IC50 values and/or binding preference for a mutant FKBP over wild-type human FKBP12. The Competitive Binding FP Assay permits one to select monomers or rapalogs which possess the desired IC50 values and/or binding preference for a mutant FKBP or wild-type FKBP relative to a control, such as FK506.

Applications

The rapalogs can be used as described in WO94/18317, WO95/02684, WO96/20951, WO95/41865, e.g. to regulatably activate the transcription of a desired gene, delete a target gene, actuate apoptosis, or trigger other biological events in engineered cells growing in culture or in whole organisms, including in gene therapy applications. The following are non-limiting examples of applications of the subject invention.

1. Regulated gene therapy. In many instances, the ability to switch a therapeutic gene on and off at will or the ability to titrate expression with precision are important for therapeutic efficacy. This invention is particularly well suited for achieving regulated expression of a therapeutic target gene in the context of human gene therapy. One example uses a pair of chimeric proteins (one containing at least one FRB domain, the other containing at least one FKBP domain), an improved rapalog of this invention capable of dimerizing the chimeras, and a target gene construct to be expressed. One of the chimeric proteins comprises a DNA-binding domain, preferably a composite DNA-binding domain as described in Pomerantz et al, supra, as the heterologous effector domain. The second chimeric protein comprises a transcriptional activating domain as the heterologous effector domain. The improved rapalog is capable of binding to both chimeras and thus of effectively cross-linking the chimeras. DNA molecules encoding and capable of directing the expression of these chimeric proteins are introduced into the cells to be engineered. Also introduced into the cells is a target gene linked to a DNA sequence to which the DNA-binding domain is capable of binding. Contacting the engineered cells or their progeny with the improved rapalog (by administering it to the animal or patient) leads to assembly of the transcription factor complex and hence to expression of the target gene. The design and use of similar components is disclosed in PCT/US93/01617 and in WO 96/41865 (Clackson et al). In practice, the level of target gene expression should be a function of the number or concentration of chimeric transcription factor complexes, which should in turn be a function of the concentration of the improved rapalog. Dose (of improved rapalog)-responsive gene expression is typically observed.

The improved rapalog may be administered to the patient as desired to activate transcription of the target gene. Depending upon the binding affinity of the improved rapalog, the response desired, the manner of administration, the biological half-life of the rapalog and/or target gene mRNA, the number of engineered cells present, various protocols may be employed. The improved rapalog may be administered by various routes, including parenterally or orally. The number of administrations will depend upon the factors described above. The improved rapalog may be taken orally as a pill, powder, or dispersion; bucally; sublingually; injected intravascularly, intraperitoneally, intramuscularly, subcutaneously; by inhalation, or the like. The improved rapalog (and monomeric antagonist compound) may be formulated using conventional methods and materials well known in the art for the various routes of administration. The precise dose and particular method of administration will depend upon the above factors and be determined by the attending physician or human or animal healthcare provider. For the most part, the manner of administration will be determined empirically.

In the event that transcriptional activation by the improved rapalog is to be reversed or terminated, a monomeric compound which can compete with the improved rapalog may be administered. Thus, in the case of an adverse reaction or the desire to terminate the therapeutic effect, an antagonist to the dimerizing agent can be administered in any convenient way, particularly intravascularly, if a rapid reversal is desired. Alternatively, one may provide for the presence of an inactivation domain (or transcriptional silencer) with a ligand binding domain. In another approach, cells may be eliminated through apoptosis via signalling through Fas or TNF receptor as described elsewhere. See International Patent Applications PCT/US94/01617 and PCT/US94/08008.

The particular dosage of the improved rapalog for any application may be determined in accordance with the procedures used for therapeutic dosage monitoring, where maintenance of a particular level of expression is desired over an extended period of times, for example, greater than about two weeks, or where there is repetitive therapy, with individual or repeated doses of improved rapalog over short periods of time, with extended intervals, for example, two weeks or more. A dose of the improved rapalog within a predetermined range would be given and monitored for response, so as to obtain a time-expression level relationship, as well as observing therapeutic response. Depending on the levels observed during the time period and the therapeutic response, one could provide a larger or smaller dose the next time, following the response. This process would be iteratively repeated until one obtained a dosage within the therapeutic range. Where the improved rapalog is chronically administered, once the maintenance dosage of the improved rapalog is determined, one could then do assays at extended intervals to be assured that the cellular system is providing the appropriate response and level of the expression product.

It should be appreciated that the system is subject to many variables, such as the cellular response to the improved rapalog, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like.

2. Production of recombinant proteins and viruses. Production of recombinant therapeutic proteins for commercial and investigational purposes is often achieved through the use of mammalian cell lines engineered to express the protein at high level. The use of mammalian cells, rather than bacteria or yeast, is indicated where the proper function of the protein requires post-translational modifications not generally performed by heterologous cells. Examples of proteins produced commercially this way include erythropoietin, tissue plasminogen activator, clotting factors such as Factor VIII:c, antibodies, etc. The cost of producing proteins in this fashion is directly related to the level of expression achieved in the engineered cells. A second limitation on the production of such proteins is toxicity to the host cell: Protein expression may prevent cells from growing to high density, sharply reducing production levels. Therefore, the ability to tightly control protein expression, as described for regulated gene therapy, permits cells to be grown to high density in the absence of protein production. Only after an optimum cell density is reached, is expression of the gene activated and the protein product subsequently harvested.

A similar problem is encountered in the construction and use of "packaging lines" for the production of recombinant viruses for commercial (e.g., gene therapy) and experimental use. These cell lines are engineered to produce viral proteins required for the assembly of infectious viral particles harboring defective recombinant genomes. Viral vectors that are dependent on such packaging lines include retrovirus, adenovirus, and adeno-associated virus. In the latter case, the titer of the virus stock obtained from a packaging line is directly related to the level of production of the viral rep and core proteins. But these proteins are highly toxic to the host cells. Therefore, it has proven difficult to generate high-titer recombinant AAV viruses. This invention provides a solution to this problem, by allowing the construction of packaging lines in which the rep and core genes are placed under the control of regulatable transcription factors of the design described here. The packaging cell line can be grown to high density, infected with helper virus, and transfected with the recombinant viral genome. Then, expression of the viral proteins encoded by the packaging cells is induced by the addition of dimerizing agent to allow the production of virus at high titer.

3. Biological research. This invention is applicable to a wide range of biological experiments in which precise control over a target gene is desired. These include: (1) expression of a protein or RNA of interest for biochemical purification; (2) regulated expression of a protein or RNA of interest in tissue culture cells (or in vivo, via engineered cells) for the purposes of evaluating its biological function; (3) regulated expression of a protein or RNA of interest in transgenic animals for the purposes of evaluating its biological function; (4) regulating the expression of a gene encoding another regulatory protein, ribozyme or antisense molecule that acts on an endogenous gene for the purposes of evaluating the biological function of that gene. Transgenic animal models and other applications in which the components of this invention may be adapted include those disclosed in PCT/US95/10591.

This invention further provides kits useful for the foregoing applications. Such kits contain DNA constructs encoding and capable of directing the expression of chimeric proteins of this invention (and may contain additional domains as discussed above) and, in embodiments involving regulated gene transcription, a target gene construct containing a target gene linked to one or more transcriptioal control elements which are activated by the multimerization of the chimeric proteins. Alternatively, the target gene construct may contain a cloning site for insertion of a desired target gene by the practitioner. Such kits may also contain a sample of a dimerizing agent capable of dimerizing the two recombinant proteins and activating transcription of the target gene.

Formulations, Dosage and Administration

By virtue of its capacity to promote protein—protein interactions, a rapalog of this invention may be used in pharmaceutical compositions and methods for promoting formation of complexes of chimeric proteins of this invention in a human or non-human mammal containing genetically engineered cells of this invention.

The preferred method of such treatment or prevention is by administering to the mammal an effective amount of the compound to promote measurable formation of such complexes in the engineered cells, or preferably, to promote measurable actuation of the desired biological event triggered by such complexation, e.g. transcription of a target gene, apoptosis of engineered cells, etc.

Therapeutic/Prophylactic Administration & Pharmaceutical Compositions

The rapalogs can exist in free form or, where appropriate, in salt form. Pharmaceutically acceptable salts of many types of compounds and their preparation are well-known to those of skill in the art. The pharmaceutically acceptable salts of compounds of this invention include the conventional non-toxic salts or the quaternary ammonium salts of such compounds which are formed, for example, from inorganic or organic acids of bases.

The compounds of the invention may form hydrates or solvates. It is known to those of skill in the art that charged compounds form hydrated species when lyophilized with water, or form solvated species when concentrated in a solution with an appropriate organic solvent.

This invention also relates to pharmaceutical compositions comprising a therapeutically (or prophylactically) effective amount of the compound, and one or more pharmaceutically acceptable carriers and/or other excipients. Carriers include e.g. saline, buffered saline, dextrose, water, glycerol, ethanol, and combinations thereof, and are discussed in greater detail below. The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Formulation may involve mixing, granulating and compressing or dissolving the ingredients as appropriate to the desired preparation.

The pharmaceutical carrier employed may be, for example, either a solid or liquid.

Illustrative solid carrier include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions, and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elix and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water -(partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The carrier or excipient may include time delay material well known to the art, such as glyceryl monostearate or glyceryl distearate along or with a wax, ethylcellulose, hydroxypropylmethylcellulose, methylmethacrylate and the like. When formulated for oral administration, 0.01% Tween 80 in PHOSAL PG-50 (phospholipid concentrate with 1,2-propylene glycol, A. Nattermann & Cie. GmbH) has been recognized as providing an acceptable oral formulation for other compounds, and may be adapted to formulations for various compounds of this invention.

A wide variety of pharmaceutical forms can be employed. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, a pharmaceutically acceptable salt of the multimerizer may be dissolved in an aqueous solution of an organic or inorganic acid, such as a 0.3M solution of succinic acid or citric acid. Alternatively, acidic derivatives can be dissolved in suitable basic solutions. If a soluble salt form is not available, the compound is dissolved in a suitable cosolvent or combinations thereof. Examples of such suitable cosolvents include, but are not limited to, alcohol, propylene glycol, polyethylene glycol 300, polysorbate 80, glycerin, polyoxyethylated fatty acids, fatty alcohols or glycerin hydroxy fatty acids esters and the like in concentrations ranging from 0–60% of the total volume.

Various delivery systems are known and can be used to administer the multimerizer, or the various formulations thereof, including tablets, capsules, injectable solutions, encapsulation in liposomes, microparticles, microcapsules, etc. Methods of introduction include but are not limited to dermal, intradermal, intramuscular, intraperitoneal, intravenous, subcutaneous, intranasal, pulmnonary, epidural, ocular and (as is usually preferred) oral routes. The compound may be administered by any convenient or otherwise appropriate route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For treatment or prophylaxis of nasal, bronchial or pulmonary conditions, preferred routes of administration are oral, nasal or via a bronchial aerosol or nebulizer.

In certain embodiments, it may be desirable to administer the compound locally to an area in need treatment; this may be achieved by, for example, and not by way of limitation, local infusion during surgery, topical application, by injection, by means of a catheter, by means of a suppository, or by means of a skin patch or implant, said implant being of a porous, non-porous, or gelatinous material, including membranes, such as sialastic membranes, or fibers.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration to an individual of an effective amount of the compound can also be accomplished topically by administering the compound(s) directly to the affected area of the skin of the individual. For this purpose, the compound is administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included.

In addition, in certain instances, it is expected that the compound may be disposed within devices placed upon, in, or under the skin. Such devices include patches, implants, and injections which release the compound into the skin, by either passive or active release mechanisms.

Materials and methods for producing the various formulations are well known in the art and may be adapted for practicing the subject invention. See e.g. U.S. Pat. Nos. 5,182,293 and 4,837,311 (tablets, capsules and other oral formulations as well as intravenous formulations) and European Patent Application Publication Nos. 0 649 659 (published Apr. 26, 1995; illustrative formulation for IV administration) and 0 648 494 (published Apr. 19, 1995; illustrative formulation for oral administration).

The effective dose of the compound will typically be in the range of about 0.01 to about 50 mg/kgs, preferably about 0.1 to about 10 mg/kg of mammalian body weight, administered in single or multiple doses. Generally, the compound may be administered to patients in need of such treatment in a daily dose range of about 1 to about 2000 mg per patient.

The amount of compound which will be effective in the treatment or prevention of a particular disorder or condition will depend in part on the characteristics of the fusion proteins to be multimerized, the characteristics and location of the genetically engineered cells, and on the nature of the disorder or condition, which can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

The invention also provides a pharmaceutical pack or kit comprising one or more containers containing one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration. The notice or package insert may contain instructions for use of an improved rapalog of this invention, consistent with the disclsoure herein.

EXAMPLES

Example 1

Synthesis of Representative C-24 modified Rapalogs 1.1. Rapamycin purification.

Rapamycin was obtained by fermentation. The rapamycin producing organism, *Streptomyces hygroscopicus* (ATCC# 29253), was cultivated on a complex media in 15 L or 30 L fed-batch fermentations. The biomass was harvested after 9–14 days by centrifugation. The supernatant was contacted for 1–2 hours with a nonionic, polymeric adsorbent resin, XAD-16 (Rohm and Haas). The adsorbent was recovered by centrifugation, combined with the biomass, and extracted repeatedly with methylene chloride. The solvent was removed in vacuo and the resulting residue extracted with acetonitrile which was then condensed in a similar manner. Chromatographic purification of the crude rapamycin was achieved by flash chromatography on silica gel (40% Acetone/Hexanes) followed by C-18 reversed-phase HPLC (70% CH3CN/H2O). Rapamycin obtained exhibited identical HPLC, spectroscopic, and biological characteristics as an authentic sample of rapamycin.

1.2. Rapamycin (E and Z)-24-(O-methyloxime) (5, 6) (general procedure)

A solution of rapamycin (60 mg 65.6 mmol) in MeOH (2 mL) was treated with NaOAc (22 mg 262 mmol, 4.0 eq) followed by methoxylamine hydrochloride (22 mg 262 mmol, 4.0 eq) and stirred at room temperature for 48 h. After this time the reaction mixture was quenched with H2O (10 mL) and extracted with EtOAc (3×10 ml). The combined organic extracts were washed with saturated NaCl solution (2×10 mL), dried over Na2 SO4, filtered, and the solution concentrated in vacuo. The resulting residue was subjected to flash chromatography on silica gel (10% MeOH/dichloromethane) to afford a mixture of isomers. The isomer mixture was separated by HPLC (35% Æ 25% H20/MeCN through a Kromasil C-18 250×20 mm column, 12 mL/min) to provide 13 mg (21%) of the faster eluting Z isomer and 7.6 mg (12%) of the E isomer. Z isomer: high-resolution mass spectrum (FAB) m/z 965.5749 [(M+Na)+, calcd for C52 H82N2O13Na 965.5710]. E isomer: high-resolution mass spectrum (FAB) m/z 965.5701 [(M+Na)+, calcd for C52 H82N2O13Na 965.5710].

1.3. Rapamycin (E and Z)-24-(O-ethyloxime) (7, 8)

Prepared in an analogous manner to Rapamycin (E and Z)-24-(O-methyloxime). The isomer mixture was separated by HPLC (30% H20/MeCN through a Kromasil C-18 250× 20 mm column, 12 mL/min) to provide 7.7 mg (25%) of the faster eluting Z isomer and 0.5 mg (2%) of the E isomer. Z isomer: high-resolution mass spectrum (FAB) m/z 979.5902 [(M+Na)+, calcd for C53 H84N2O13Na 979.5871].

1.4 Rapamycin (E and Z)-24-(O-isobutyloxime) (9, 10)

Prepared in an analogous manner to Rapamycin (E and Z)-24-(O-methyloxime). The isomer mixture was separated by HPLC (15% H20/MeCN through a Kromasil C-18 250× 20 mm column, 12 mL/min) to provide 28 mg (65%) of the faster eluting Z isomer and 3.0 mg (7%) of the E isomer. Z isomer: high-resolution mass spectrum (FAB) m/z 1007.6146 [(M+Na)+, calcd for C55 H88N2O13Na 1007.6184]. E isomer: high-resolution mass spectrum (FAB) m/z 1007.6157 [(M+Na)+, calcd for C55 H88N2O13Na 1007.6184].

1.5. apamycin (E and Z)-24-(O-benzyloxime) (11, 12)

Prepared in an analogous manner to Rapamycin (E and Z)-24-(O-methyloxime). The isomer mixture was separated by HPLC (15% H20/MeCN through a Kromasil C-18 250× 20 mm column, 12 mL/min) to provide 19.6 mg (44%) of the faster eluting Z isomer and 6.1 mg (14%) of the E isomer. Z isomer: high-resolution mass spectrum (FAB) m/z 1041.6033 [(M+Na)+, calcd for C58 H86N2O13Na 1041.6028]. E isomer: high-resolution mass spectrum (FAB) m/z 1041.5988 [(M+Na)+, calcd for C58 H86N2O13Na 1041.6028].

1.6. Rapamycin (E and Z)-24-(O-carboxymethyloxime) (13, 14))

Prepared in an analogous manner to Rapamycin (E and Z)-24-(O-methyloxime). The isomer mixture was separated by HPLC (45% H20/MeCN through a Kromasil C-18 250× 20 mm column, 12 mL/min) to provide 4.6 mg (11%) of the faster eluting Z isomer and 1.0 mg (2%) of the E isomer. Z isomer: high-resolution mass spectrum (FAB) m/z 1009.5664 [(M+Na)+, calcd for C53 H82N2O15Na 1009.5613]. E isomer: high-resolution mass spectrum (FAB) m/z 1009.5604 [(M+Na)+, calcd for C53 H82N2O15Na 1009.5613].

1.7. Rapamycin (E and Z)-24-(O-carboxamidomethyloxime) (15, 16)

Prepared in an analogous manner to Rapamycin (E and Z)-24-(Omethyloxime). The isomer mixture was separated by HPLC (35% H20/MeCN through a Kromasil C-18 250× 20 mm column, 12 mL/min) to provide 6.2 mg (10%) of the faster eluting Z isomer and 1.4 mg (2%) of the E isomer. Z isomer: high-resolution mass spectrum (FAB) m/z 1008.5790 [(M+Na)+, calcd for C53 H83N3O14Na 1008.5768]. E isomer: high-resolution mass spectrum (FAB) m/z 1008.5753 [(M+Na)+, calcd for C53 H83N3O14Na 1008.5768].

Example 2

Assay of binding of rapamycin C24 derivatives to FKBP

Affinities of rapamycin C24 analogs for FKBP were determined using a competitive assay based on fluorescence polarization (FP). A fluorescein-labelled FK506 probe (AP1491) was synthesized, and the increase in the polarization of its fluorescence used as a direct readout of % bound probe in an equilibrium binding experiment containing sub-saturating FKBP and variable amounts of rapamycin analog as competitor.

Synthesis of Fluoresceinated FK506 Probe (AP1491)
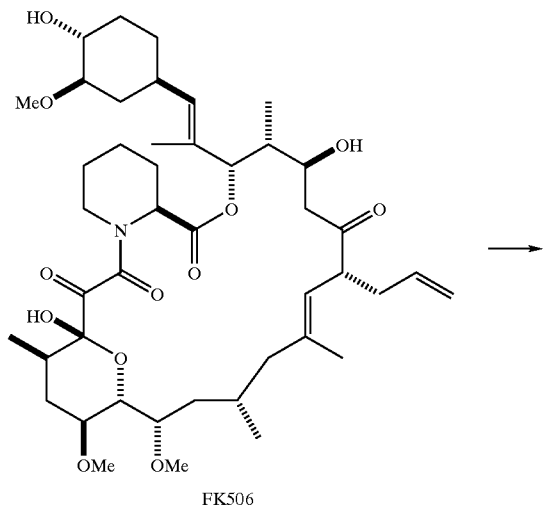
FK506
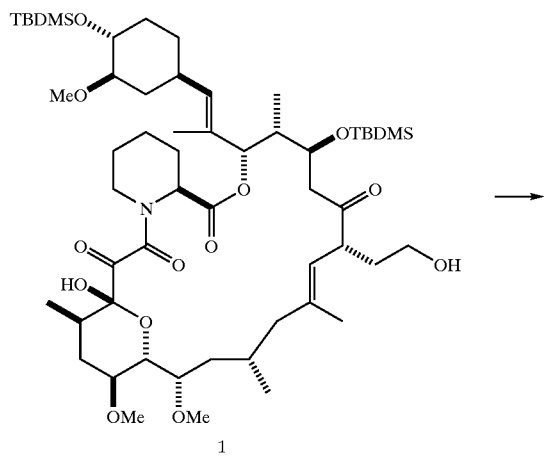
1
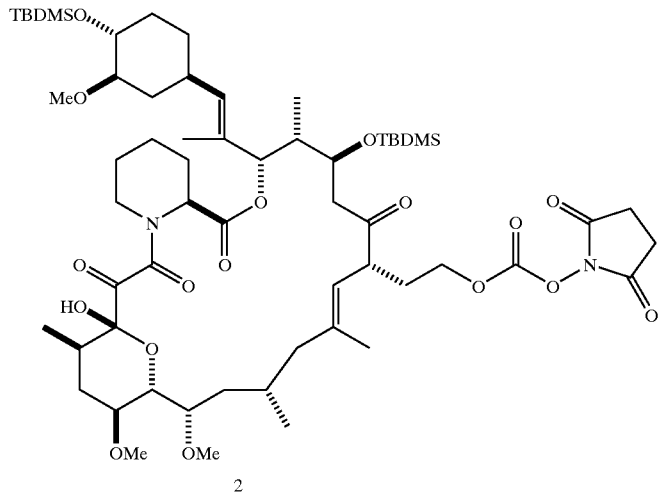
2

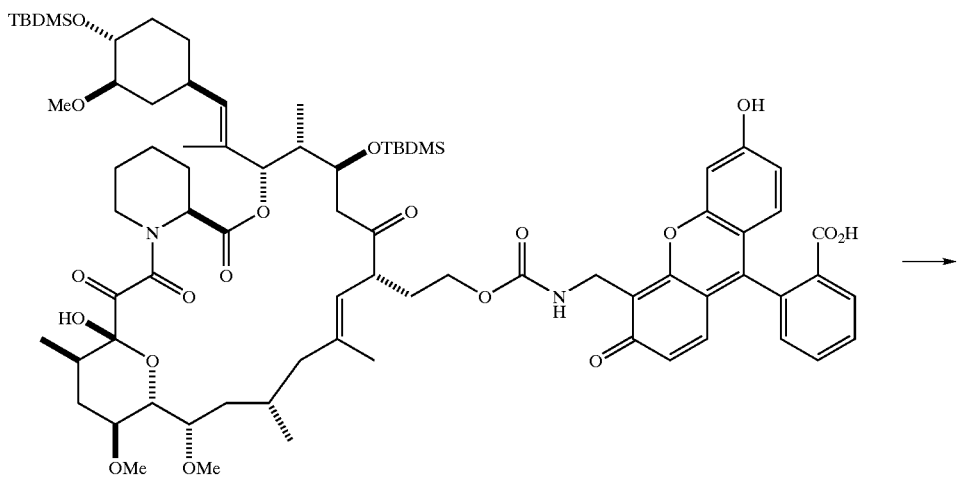

3

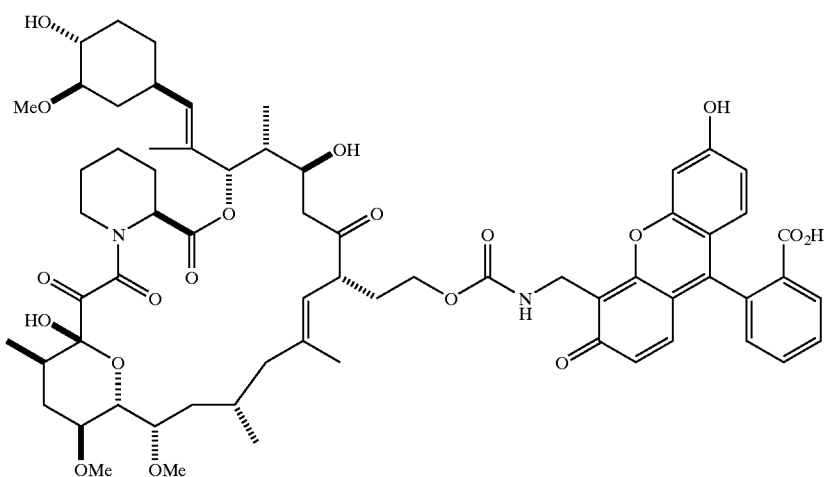

4

2.1. 24,32-Bis(tert-Butyldimethylsilyl)ether of FK506 tert-Butyldimethylsilyl trifluoromethanesulfonate (108 µL, 470 µmol) was added dropwise to a stirred solution of FK506 (103 mg, 128 µmol) and 2,6-lutidine (89.5 µL, 768 µmol) in dichloromethane (3 mL) at 0° C. The resulting solution was stirred at 0° C. for 2 h, and then treated with MeOH (0.5 mL) and ether (15 mL). The mixture was washed with 10% aqueous NaHCO3 (3 mL) and brine (3 mL). The organic layer was decanted, dried over anhydrous Na2SO4, filtered, and concentrated to a yellow oil. Column chromatography (silica-gel, hexanes-EtOAc 3:1) gave the title compound as a colorless oil (104 mg).

2.2. Intermediate 1

To a solution of 24,32-bis(tert-butyldimethylsilyl)ether of FK506 (100 mg, 97 µmol) in THF (2.5 mL) was added morpholine N-oxide (68 mg, 580 µmol), followed by water (60 µL), and a 4% aqueous solution of osmium tetroxide (123 µL, 20 µmol). The resulting mixture was stirred at room temperature for 4.5 h. It was then treated with 50% aqueous MeOH (1.5 mL) and sodium periodate (207 mg, 970 µmol), and the suspension stirred for an additional 1 h. The mixture was diluted with ether (10 mL) and washed with saturated aqueous NaHCO3 (2×4 mL). The organic layer was decanted, dried over anhydrous sodium sulfate containing a small amount of sodium sulfite, filtered, and concentrated. The residue was dissolved in anhydrous THF (2.8 mL), cooled to −78° C. under nitrogen, and treated with a 0.5 M solution of lithium tris [(3-ethyl-3-pentyl)oxy]aluminum hydride in THF (282 µL). The resulting solution was stirred at −78° C. for 1.75 h, and then quenched by addition of ether (6 mL) and saturated ammonium chloride solution (250 μL). The mixture was allowed to warm up to room temperature and treated with anhydrous sodium sulfate. Filtration and concentration under reduced pressure afforded a pale yellow oil (97 mg), which was purified by column chromatography (silica-gel, hexanes-EtOAc 3:1) to afford 1 as a colorless oil.

2.3 Intermediate 2

A solution of the above alcohol (300 mg, 290 μmol) in acetonitrile (10 mL) was treated with 2,6-lutidine (338 μL, 2.9 mmol) and N,N'-disuccinimidylcarbonate (371 mg, 1.45 mmol). The resulting suspension was stirred at room temperature for 14.5 h, and then concentrated under reduced pressure. The residue was chromatographed (silica-gel, hexanes-EtOAc 2:1 to 100% EtOAc gradient) to afford the mixed carbonate 2 as a pale yellow oil (127 mg).

2.4 Intermediate 3

A solution of the above carbonate (30 mg, 26 μmol) and triethylamine (36 μL, 260 μmol) in acetonitrile (1 mL) was treated with 4'-(aminomethyl)fluorescein (13.5 mg, 34 μmol). The resulting bright orange suspension was stirred at room temperature for 1 h, and then concentrated under reduced pressure. The residue was chromatographed (silica-gel, hexanes-EtOAc 1:1 to 100% EtOAc to EtOAc-MeOH 1:1 gradient) to give 3 (20.5 mg) as a bright yellow solid.

2.5 Compound 4

A solution of bis-silyl ether 3 (35 mg, 25 μmol) in acetonitrile (2 mL) was treated with 48% (w/w) HF in water (250 μL). The resulting mixture was stirred at room temperature for 5.5 h. It was then diluted with dichloromethane (10 mL) and washed with water (2×2 mL). The organic layer was decanted, dried over anhydrous sodium sulfate, and concentrated under reduced pressure. The residue was chromatographed (silica-gel, 100% EtOAc) to afford 4 (13 mg) as a bright yellow solid.

2.6 Determination of binding affinities (IC50s) of rapalogs using FP

Serial 10-fold dilutions of each analog were prepared in 100% ethanol in glass vials and stored on ice. All other manipulations were performed at room temperature. A stock of recombinant pure FKBP (purified by standard methods, see eg. Wiederrecht, G. et al. 1992. J. Biol. Chem. 267, 21753–21760) was diluted to approximately 3 nM in 50 mM potassium phosphate pH 7.8/150 mM NaCl/100 μg/ml bovine gamma globulin ("FP buffer": prepared using only low-fluorescence reagents from Panvera) and 98 μl aliquots transferred to wells of a Dynatech micro-fluor black 96-well fluorescence plate. 2.0 μl samples of the rapamycin analogs were then transferred in duplicate to the wells with mixing. Finally, a probe solution was prepared containing 10 nM AP1491 in 0.1% ethanol/FP buffer, and 100 μl added to each well with mixing. Duplicate control wells contained ethanol instead of rapamycin analog (for 100% probe binding) or ethanol instead of rapamycin analog and FP buffer instead of FKBP (0% binding).

The plates were stored covered in the dark for approximately 30 min to permit equilibration and then the fluorescence polarization of the sample in each well read on a Jolley FPM-2 FP plate reader (Jolley Consulting and Research, Inc., Grayslake, Ill.) in accordance with the manufacturer's recommendations. The mean polarization (mP units)

TABLE 4

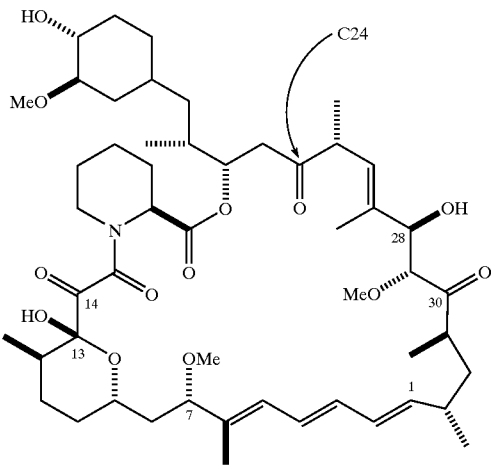

| cmpd | C24 | isomer | FKBPwt FP binding assay IC50 (nM) | fold loss in affinity (vs rapamycin) |
|---|---|---|---|---|
| rapamycin | | | 2.3 | (1) |
| C14 desoxo | | | 63.3 | 27.5 |
| 17 | | Z (major) | 618 | 269 |
| 18 | | E (minor) | 59.1 | 25.7 |
| 5 | | Z (major) | 1416 | 616 |
| 6 | | E (minor) | 438 | 190 |
| 7 | | Z (major) | 2960 | 1287 |

TABLE 4-continued

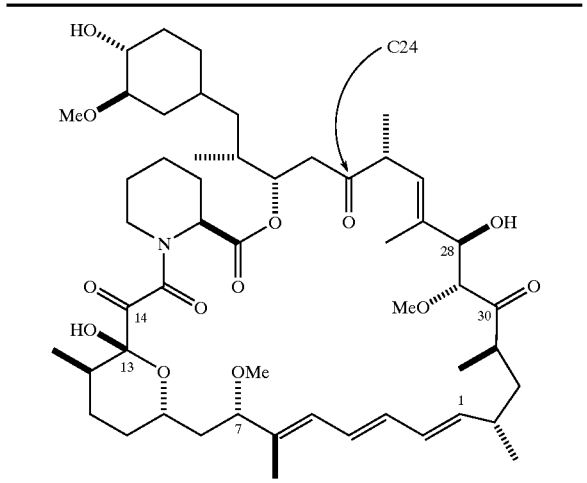

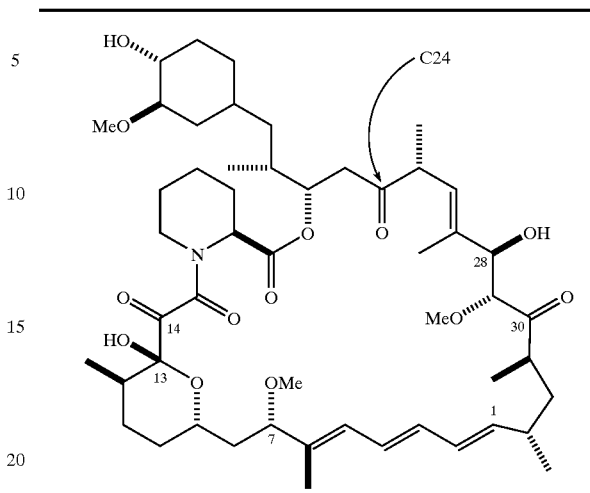

| cmpd | C24 | isomer | FKBPwt FP binding assay IC50 (nM) | fold loss in affinity (vs rapamycin) |
|---|---|---|---|---|
| 8 | (O-ethyl oxime) | E (minor) | 1664 | 723 |
| 9 | (O-isobutyl oxime) | Z (major) | >30000 | >13043 |
| 10 | (O-isobutyl oxime) | E (minor) | 2048 | 890 |
| 19 | (O-t-butyl oxime) | Z (major) | >30000 | >13043 |
| 20 | (O-t-butyl oxime) | E (minor) | 2406 | 1046 |

| cmpd | C24 | isomer | FKBPwt FP binding assay IC50 (nM) | fold loss in affinity (vs rapamycin) |
|---|---|---|---|---|
| 11 | (O-benzyl oxime) | Z (major) | 8342 | 3627 |
| 12 | (O-benzyl oxime) | E (minor) | 1416 | 616 |
| 13 | (O-carboxymethyl oxime) | Z (major) | 7960 | 3461 |
| 14 | (O-carboxymethyl oxime) | E (minor) | 2351 | 1022 |

TABLE 4-continued

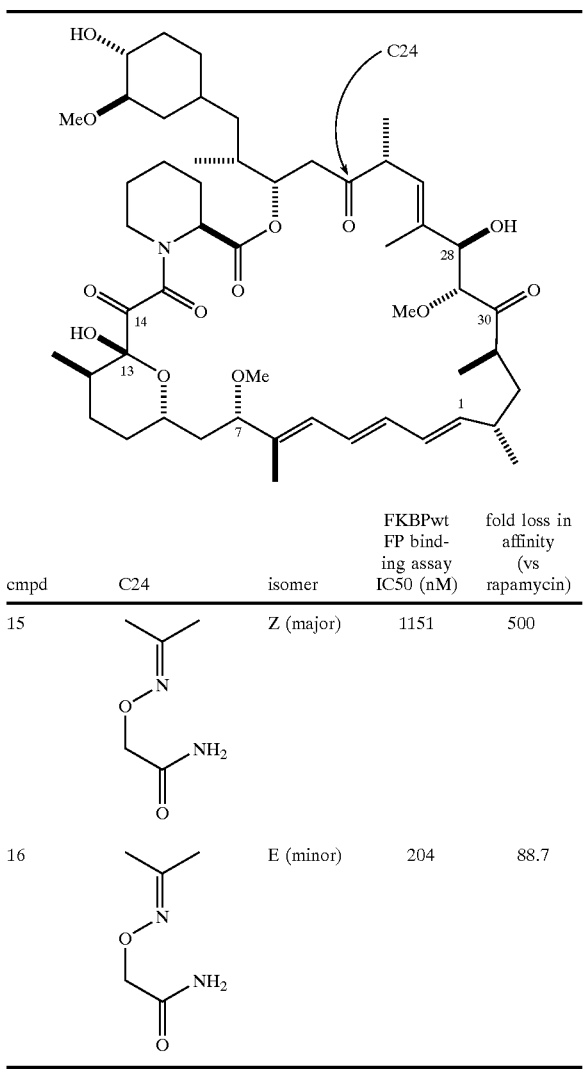

| cmpd | C24 | isomer | FKBPwt FP binding assay IC50 (nM) | fold loss in affinity (vs rapamycin) |
|---|---|---|---|---|
| 15 | (structure: oxime with -O-CH2-C(=O)-NH2) | Z (major) | 1151 | 500 |
| 16 | (structure: oxime with -O-CH2-C(=O)-NH2) | E (minor) | 204 | 88.7 | for each competitor concentration was usually converted to % total binding by reference to the control values and plotted (y) vs. log molar final concentration of competitor (x). Non-linear least square analysis was used to fit the curve and extract the IC50 using the following equation:

$$y = M1 + (M4-M1)/(1+\exp(M2*(M3-x)))$$

where M3 is the IC50. For incomplete curves the IC50 was determined by interpolation. Rapamycin and C14-desoxo-rapamycin were included as controls in each case (C14-desoxo-rapamycin was prepared as described by Luengo, J. I. et al. 1994 Tet Lett. 35, 6469–6472).

2.7 Results of binding analysis of Rapamycin C24 oximes
Affinities are reported as IC50s and as fold loss in affinity (=IC50/IC50 of rapamycin). (Comparative binding data of C24 rapalogs vs rapamycin and desoxo-rapamycin towards human FKBP12 are plotted in PCT/US86/09848.)

Example 3

Synthesis of C7 rapalogs; Assay of binding of C7 rapalog-FKBP complexes to FRAP

A series of C7 rapalogs containing various C7 substituents selected from branched and unbranched alkoxy, arylalkyloxy, —NHCO-Oalkyl, —NHSO$_2$alkyl and substituted aryl and heteroaryl moieties was synthesized using chemistry generally as described in the literature except as noetd (see e.g., Luengo et al. 1995. Chemistry and Biology 2, 471–481, and the references cited in Table II for additional background). See also the table which follows.

3.1 Compounds 27, 28—($R^{C7}$=Et) are synthesized as described in Luengo et al, Chemistry & Biology July 1995, 2:471–481.

3.2 Compound 29—($R^{C7}$=iPr) A solution of rapamycin (60 mg, 0.066 mmol) in 2-propanol (3 mL) at room-temperature was treated with para-tolueniesulfonic acid (75 mg, 0.394 mmol) and allowed to stir for 4 h. After this time the reaction was poured onto a biphasic solution of saturated aqueous NaHCO$_3$ (20 mL) and EtOAc (30 mL). The organic layer was washed with additional solution of saturated aqueous NaHCO$_3$ (2×20 mL) followed by a saturated aqueous solution of NaCl (2×10 mL) then dried over Na$_2$SO$_4$, filtered, evaporated. The resulting material was purified by HPLC on a Kromasil C-18 column (20×250 mm) at 55 C using 65% acetonitrile/water as eluant to afford AP1700 (25 mg). MS(FAB): (M+Na)$^+$ calcd: 964.5762, found: 964.5753.

3.3 Compound 30—$R^{C7}$=benzyl) is synthesized as described in Chemistry & Biology July 1995, 2:471–481.

3.4 Compounds 31 32—($R^{C7}$=—NH—CO—OMe) may be synthesized as described in Chemistry & Biology July 1995, 2:471–481.

3.5 Compound 33—($R^{C7}$=—NH—SO$_2$-Me) A solution of rapamycin (75 mg, 0.082 mmol) and methanesufonamide (312 mg, 3.282 mmol) in dichloromethane (3 mL) at −40° C. was treated dropwise with trifluoroacetic acid (126 μL, 1.636 mmol) and allowed to stir for 3 h. After this time the reaction was poured onto a biphasic solution of saturated aqueous NaHCO$_3$ (20 mL) and EtOAc (10 mL). The organic layer was washed with a saturated aqueous solution of NaCl (2×10 mL) then dried over Na$_2$SO$_4$, filtered, evaporated, and flash chromatographed on a silica gel (dichloromethane:hexane:EtOAc: MeOH, 200:50:42.5:7.5). The resulting semipurified material was purified by HPLC on a Kromasil C-18 column (20×250 mm) at 55 C using 65% acetonitrile/water as eluant to afford AP1705 (24 mg). MS(FAB): (M+Na)$^+$ calcd: 999.5246, found: 999.5246.

3.6 Compounds 34, 35—($R^{C7}$=furanyl) These compounds may be synthesized as described in Chemistry & Biology July 1995, 2:471–481.

3. Compounds 36, 37—($R^{C7}$=methylthiophene) These compounds may be synthesized as described in J. Org. Chem 1994, 59, 6512–6513.

3.8 Compounds 39, 38—($R^{C7}$=ethylthiophene) A solution of rapamycin (50 mg, 0.055 mmol) and 2-ethylthiophene (248 μL, 2.188 mmol) in dichloromethane (1.5 mL) at −40° C. was treated dropwise with trifluoroacetic acid (84 uL, 1.094 mmol) and allowed to stir for 3 h. After this time the reaction was poured onto a biphasic solution of saturated aqueous NaHCO$_3$ (15 mL) and EtOAc (10 mL). The organic layer was washed with a saturated aqueous solution of NaCl (2×10 mL) then dried over Na$_2$SO$_4$, filtered, evaporated, and flash chromatographed on a silica gel (MeOH:dichloromethane, 2:98 then 5:95). The resulting semipurified material was purified by HPLC on a Kromasil C-18 column (20×250 mm) at 55 C
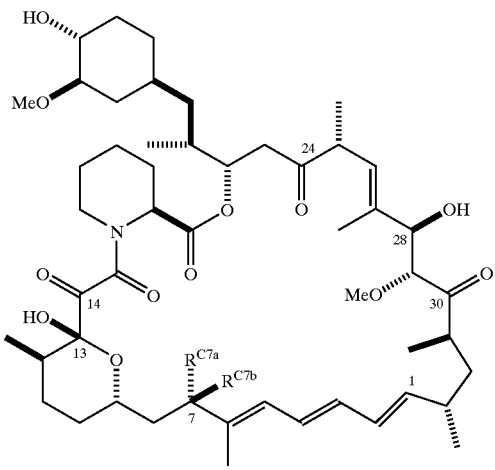
| # | $R^{C7a}$ | $R^{C7b}$ |
|---|---|---|
| rapamycin | —OMe | H |
| C14-desoxo rapamycin | —OMe | H |
| 27 | —OEt | H |
| 28 | H | —OEt |
| 29 | —O-iPr | H |
| 30 | —O-benzyl | H |
| 32 | —NH—(C=O)—OMe | H |
| 31 | H | —NH—(C=O)—OMe |
| 33 | —NH—SO$_2$Me | H |
| 34 | 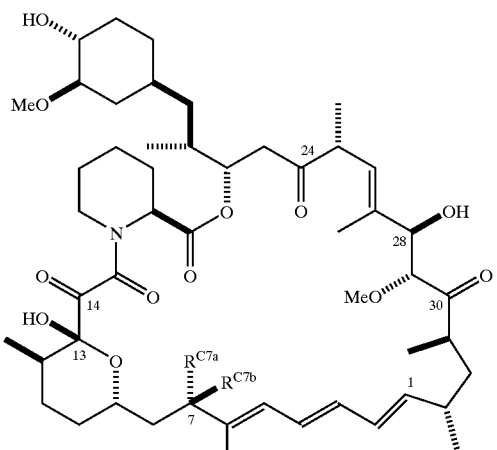 | H |
| 35 | H | 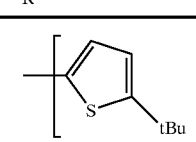 |
| 36 |  | H |
| 37 | H | 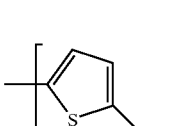 |
| 38 | 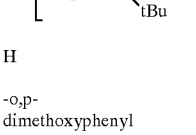 | H |
| 39 | H |  |
-continued
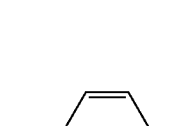
| # | $R^{C7a}$ | $R^{C7b}$ |
|---|---|---|
| 41 | 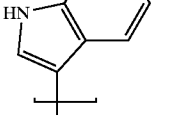 | H |
| 40 | H |  |
| 42 | -o,p-dimethoxyphenyl | H |
| 43 | H | -o,p-dimethoxyphenyl |
| 44 |  | H |
| 45 | H |  |
| 46 | -o,p-diethoxyphenyl | H |
| 47 |  | H |
| 48 |  | H |
| 49 | -2,4,6-trimethoxyphenyl | H |

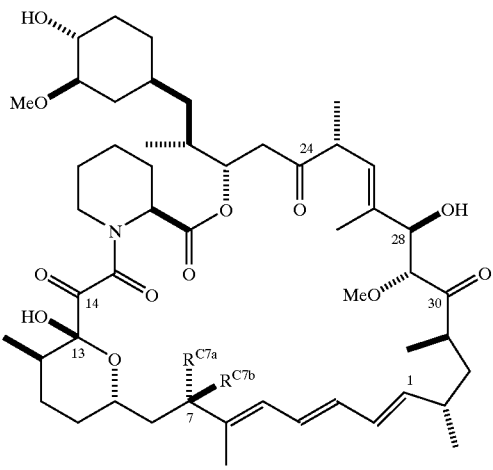

| # | R$^{C7a}$ | R$^{C7b}$ |
|---|---|---|
| 50 | H | -2,4,6-trimethoxyphenyl |
| 51 | —NH—(C=O)—OEt | H |
| 52 | H | —NH—(C=O)—OEt | using 80% acetonitrile/water as eluant to afford AP1858 (6 mg) and AP1859 (28 mg). MS(ES+): (M+NH$_4$)$^+$ 1016; MS(ES–): (M–H)$^-$ 992.

3.9 Compounds 40, 41—(R$^{C7}$=tertbutyl thiophene) A solution of rapamycin (50 mg, 0.055 mmol) and 2-tertbutylylthiophene (276 mg, 2.188 mmol) in dichloromethane (1.5 mL) at –40° C. was treated dropwise with trifluoroacetic acid (84 µL, 1.094 mmol) and allowed to stir for 3 h. After this time the reaction was poured onto a biphasic solution of saturated aqueous NaHCO$_3$ (15 mL) and EtOAc (10 mL). The organic layer was washed with a saturated aqueous solution of NaCl (2×10 mL) then dried over Na$_2$SO$_4$, filtered, evaporated, and flash chromatographed on a silica gel (MeOH:dichloro-methane, 2:98 then 5:95). The resulting semipurified material was purified by HPLC on a Kromasil C-18 column (20×250 mm) at 55 C using 80% acetonitrile/water as eluant to afford AP1856 (4 mg) and AP1857 (14 mg). MS(ES+): (M+Na)+1045; MS(ES–): (M–H)$^-$ 1021.

3.10 Compounds 43, 42—(R$^{C7}$=o,p-dimethoxyphenyl) These compounds may be found in Chemistry & Biology July 1995, 2:471–481.

3.11 Compounds 44, 45—(R$^{C7}$=indolyl) A solution of rapamycin (50 mg, 0.055 mmol) and indole (64 mg, 0.547 mmol) in dichloromethane (2.0 mL) at –40° C. was treated dropwise with trifluoroacetic acid (84 µL, 1.094 mmol) and allowed to stir for 3 h. After tis time the reaction was poured onto a biphasic solution of saturated aqueous NaHCO$_3$ (15 mL) and EtOAc (10 mL). The organic layer was washed with a saturated aqueous solution of NaCl (2×10 mL) then dried over Na$_2$SO$_4$, filtered, evaporated, and flash chromatographed on a silica gel (dichloromethane:hexane:EtOAc: MeOH, 200:50:42.5:7.5). The resulting semipurified material was purified by HPLC on a Kromasil C-18 column (20×250 mm) using 65% acetonitrile/water as eluant for AP1701 (12 mg) and AP1702 (7.6 mg). MS(FAB): (M+Na)$^+$ calcd: 1021.5765, found: 1021.5788 (AP1701) and 1021.5797 (AP1702).

3.12 Compound 46—(R$^{C7}$=o,p-diethoxyphenyl) A solution of rapamycin (108 mg, 0.118 mmol) and 1,3-diethoxybenzene (783 mg, 4.72 mmol) in dichloromethane (2.0 mL) at –40° C. was treated dropwise with trifluoroacetic acid (154 µL, 2.01 mmol) and allowed to stir for 3 h. After this time the reaction was poured onto a biphasic solution of saturated aqueous NaHCO$_3$ (15 mL) and EtOAc (15 mL). The organic layer was washed with a saturated aqueous solution of NaCl (2×10 mL) then dried over Na$_2$SO$_4$, filtered, evaporated, and flash chromatographed on a silica gel (dichloromethane:hexane:EtOAc:MeOH, 200:50:42.5:7.5). The resulting material was purified by HPLC on a Rainin silica column (20×250 mm) using (dichloromethane:hexane:EtOAc:MeOH, 210:65:65:10) as eluant for AP20808 (20 mg). MS(ES+): (M+Na)$^+$ 1065.95.

3.13 Compound 47—(R$^{C7}$=methylthiophene) A solution of rapamycin (105 mg, 0.115 mmol) and 3-methylthiophene (445 µL, 4.60 mmol) in dichloromethane (2.0 mL) at –40° C. was treated dropwise with trifluoroacetic acid (150 µL, 1.96 mmol) and allowed to stir for 3 h. After this time the reaction was poured onto a biphasic solution of saturated aqueous NaHCO$_3$ (15 mL) and EtOAc (15 mL). The organic layer was washed with a saturated aqueous solution of NaCl (2×10 mL) then dried over Na$_2$SO$_4$, filtered, evaporated, and flash chromatographed on a silica gel (dichloromethane:hexane:EtOAc:MeOH, 200:50:42.5:7.5). The resulting material was purified by HPLC on a Rainin silica column (20×250 mm) using (dichloromethane:hexane:EtOAc:MeOH, 210:65:65:10) as eluant for AP20809 (60 mg). MS(ES+): (M+Na)$^+$ 1002.96.

3.14 Compound 48—(R$^{C7}$=N-methylpyrrole) A solution of rapamycin (51 mg, 0.056 mmol) and N-methylpyrrole (198 µL 2.23 mmol) in dichloromethane (2.0 mL) at 0° C. was treated with zinc chloride (76 mg, 0.557 mmol) and allowed to warm to rt overnight. After this time the reaction was poured onto a biphasic solution of saturated aqueous NaHCO$_3$ (15 mL) and EtOAc (15 mL). The organic layer was washed with a saturated aqueous solution of NaCl (2×10 mL) then dried over Na$_2$SO$_4$, filtered, evaporated, and flash chromatographed on a silica gel (dichloromethane:hexane:EtOAc:MeOH, 100:150:150:10). The resulting material was purified by HPLC on a Rainin Si column (20×250 mm) using (dichloromethane:hexane:EtOAc:MeOH, 210–65:65:10) as eluant for AP20810 (10 mg). MS(ES+): (M+NH4)$^+$ 981.05; MS(ES–): (M–H)$^-$ 961.69.

The C7 rapalogs were characterized by exact mass spec and NMR.

3.15 Assay of FKBP binding affinity of C7 rapalogs

The affinity of a variety of the C7 rapalogs for FKBP was assayed as described for C24 rapalogs above, using competitive FP. Rapamycin and C14-desoxo-rapamycin (prepared as described by Luengo et al. 1994. Tetrahedron Lett. 35, 6469–6472) were included as controls.

Affinities are reported below as IC50s and fold loss in affinity (=IC50/IC50 of rapamycin). See "Illustrative C7 Rapalogs" Table below. These data indicate that these large C7 substituents do not necessarily cause large reductions in the affinity of the rapalogs for human FKBP.

| Compound | FKBPwt FP binding assay IC50 (nM) | fold loss in affinity (cf rapamycin) |
|---|---|---|
| rapamycin | 2.3 | (1) |
| C14 desoxorap | 34 | 15 |
| 27 | 2.6 | 1.1 |
| 28 | 3.7 | 1.6 |
| 29 | 2.2 | 1.0 |
| 30 | 12 | 5.2 |
| 32 | 4.3 | 1.9 |
| 31 | 2.6 | 1.1 |
| 33 | 2.5 | 1.1 |

-continued

| Compound | FKBPwt FP binding assay IC50 (nM) | fold loss in affinity (cf rapamycin) |
|---|---|---|
| 34 | 28 | 12 |
| 35 | 29 | 13 |
| 36 | 3.7 | 1.6 |
| 37 | 4.3 | 1.9 |
| 38 | 2.5 | 1.1 |
| 39 | 2.4 | 1.0 |
| 41 | 2.9 | 1.3 |
| 40 | 3.4 | 1.5 |
| 42 | 2.2 | 1.0 |
| 43 | 20 | 8.7 |
| 44 | 7.8 | 3.3 |
| 45 | 5.9 | 2.6 |

Example 4
Preparation of Rapalogs modified at $R^{C24}$ and $R^{C30}$: 24(S),30(S)-tetrahydrorapamycin (53)

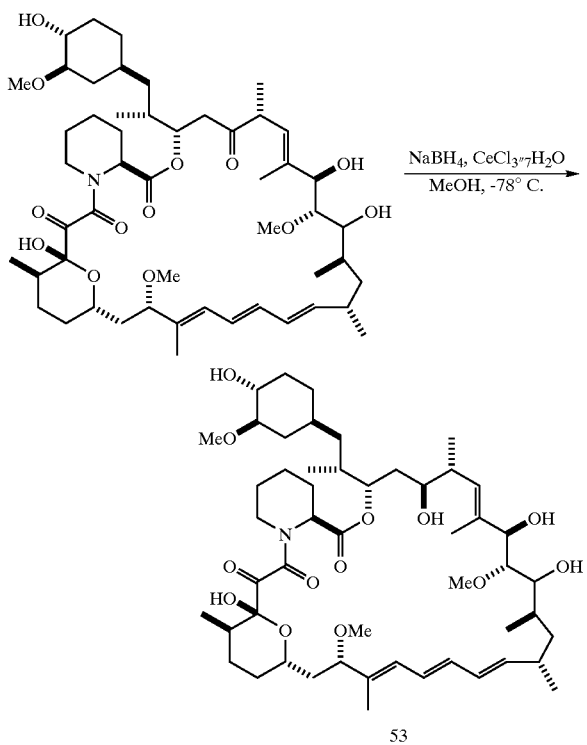

Example 5
Preparation of Rapalogs modified at C24, C30 and C7

24(S),30(S)-tetrahydrorapamycin (53), prepared as in Example 4, may be modified at C7 using approaches illustrated in the prior C7 rapalog examples. For example:

5.1 7(S)-(2',4'-dimethoxy)benzyl-7-demethoxy-24(S),30(S)-tetrahydro-rapamycin

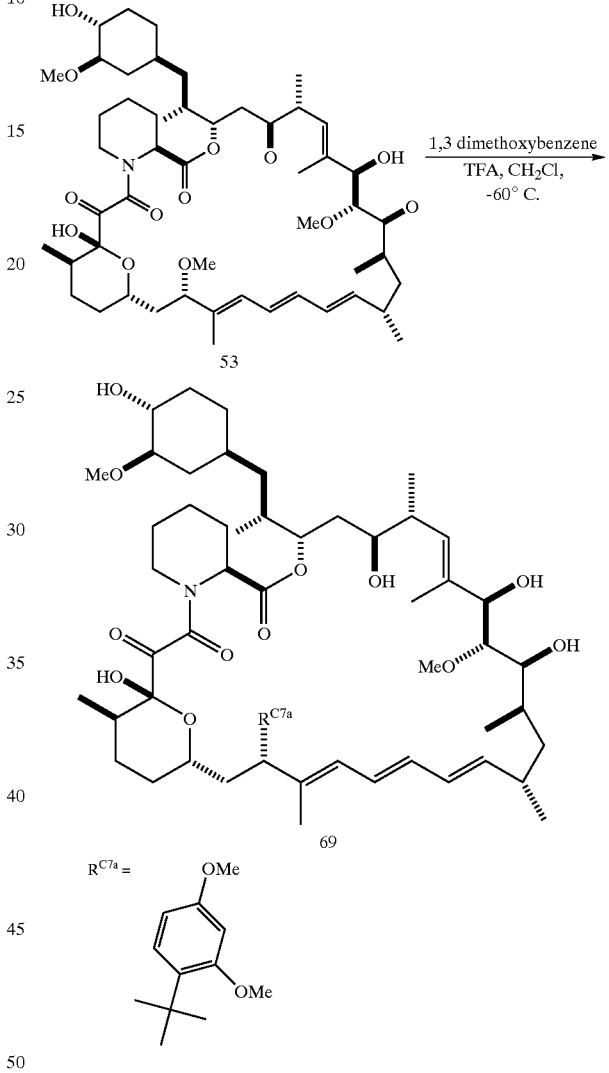

Rapamycin (46 mg, 0.050 mmol) was dissolved in 2.0 mL of methanol, cooled to −78° C., and cerium (III) chloride heptahydrate (46 mg, 0.123 mmol) was added. The solution was stirred for 0.25 h., then sodium borohydride (7.6 mg, 0.20 mmol) was added. After 0.5 h, the reaction mixture was partitioned between ethyl acetate (15 mL) and 5% aqueous hydrochloric acid (2 mL). The organic phase was washed with water (2 mL) and brine (1 mL), dried over anhydrous magnesium sulfate, filtered, and concentrated. Flash chromatography (silica gel, 15:75:50:200 methanol:ethyl acetate:hexane:dichloromehane) yielded 35 mg (76%) of the desired product as a white foam. Mass spectral data: (ES+/NaCl/NH3) m/z 942.21 (M+Na)+, 935.83 (M+NH4)+; (ES−/NaCl) m/z 963.04 (M+Cl)−, 917.34 (M−H)⁻ lit. ref. Luengo, J. I.; Rozamus, L. W.; Holt, D. A. Tetrahedron Lett. 1994, 35, 6469–6472.

24(S),30(S)-tetrahydro-rapamycin (20 mg, 0.022 mmol) was dissolved in dichloro-methane (1.0 mL). 1,3-dimethoxybenzene (0.20 mL, 1.5 mmol) was added, and the solution was cooled to −60° C. Trifluoroacetic acid (0.030 mL, 0.39 mmol) was added, and the reaction mixture was stirred for 1 h at −60° C., then partitioned between ethyl acetate (10 mL) and saturated aqueous sodium bicarbonate (1 mL). The organic phase was washed with water (2 mL) and brine (1 mL), dried over anhydrous magnesium sulfate, filtered, and concentrated. Flash chromatography (silica gel, 15:75:50:200 methanol:ethyl acetate:hexane:dichloromehane) yielded 8 mg (35%) of the desired product as a white solid. Mass spectral data: (ES+/NaCl/NH3) m/z 1046.96 (M+Na)+, 1042.15 (M+NH4)+; (ES/NaCl) m/z 1069.09 (M+Cl)− lit. ref. Luengo, J. I.; Konialian-Beck, A.; Rozamus, L. W.; Holt, D. A. J. Org. Chem. 1994, 59, 6512–6513.

By analogous means, one may produce 24(S),30(S)-tetrahydro rapamycins bearing other C7 substituents as described elsewhere herein, e.g., containing alternatively substituted aryl groups, heteroaryl, —O-aliphatic groups, thioethers, or any of the other types of moieties designated previously for $R^{C7a}$ or $R^{C7b}$. These compounds may be obtained by reduction at C24 and C30 of the appropriate C7 rapalog, or by transformation at C7 of the appropriate C24, C30-tetrahydro rapalog. Illustrative examples follow.

Rapalogs modified at C24, C30 and C7 may also be differ from rapamycin at the various positions discussed herein, e.g. with respect to one or more of $R^{C13}$ $R^{C43}$, $R^{C28}$, $R^{C29}$, $R^4$, "a", etc. By way of example, starting with 13-F- rapamycin in place of rapamycin yields the 13-fluoro analogs of compounds 53–79.

5.2 Compounds 54, 55—($R^{C7}$=Et) are synthesized as described in Example 4.1, but substituting Compounds 27 and 28. respectively, for rapamycin.

5.3 Compound 56—($R^{C7}$=iPr) is synthesized as described in Example 4.1, but substituting Compound 29 for rapamycin.

5.4 Compound 57—($R^{C7}$=benzyl) is synthesized as described in Example 4.1, but substituting Compound 30 for rapamycin.

5.5 Compounds 58, 59—($R^{C7}$=—NH—CO—OMe) are synthesized as described in Example 4.1, but substituting Compounds 32 and 31 respectively, for rapamycin.

5.6 Compound 60—($R^{C7}$=—NH—SO2-Me) is synthesized as described in Example 4.1, but substituting Compound 33 for rapamycin.

5.7 Compounds 61 and 62—($R^{C7}$=furanyl) are synthesized as described in Example 4.1, but substituting Compounds 34 and 35, respectively, for rapamycin.

5.8 Compounds 63, 64—($R^{C7}$=methylthiophene) are synthesized as described in Example 4.1, but substituting Compounds 36 and 37 respectively, for rapamycin.

5.9 Compounds 65, 66—($R^{C7}$=ethylthiophene) are synthesized as described in Example 4.1, but substituting Compounds 38 and 39 respectively, for rapamycin.

5.10 Compounds 67, 68—($R^{C7}$=tertbutyl thiophene) are synthesized as described in Example 4.1, but substituting Compounds 41 and 40, respectively, for rapamycin.

5.11 Compounds 69, 70—($R^{C7}$=o,p-dimethoxyphenyl) are synthesized as described in Example 4.1, but substituting Compounds 43 and 42 respectively, for rapamycin.

5.12 Compounds 71, 72—($R^{C7}$=indolyl) are synthesized as described in Example 4.1, but substituting Compounds 45 and 44, respectively, for rapamycin.

5.13 Compound 73—($R^{C7}$=o,p-diethoxyphenyl) is synthesized as described in Example 4.1, but substituting Compound 46 for rapamycin.

5.14 Compound 74—($R^{C7}$=methylthiophene) is synthesized as described in Example 4.1, but substituting Compound 47 for rapamycin.

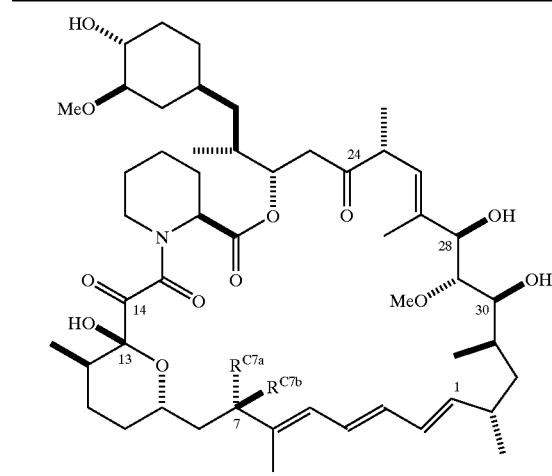

| # | $R^{C7a}$ | $R^{C7b}$ |
|---|---|---|
| 53 | —OMe | H |
| 54 | —OEt | H |
| 55 | H | —OEt |
| 56 | —O-iPr | H |
| 57 | —O-benzyl | H |
| 58 | —NH—(C=O)—OMe | H |
| 59 | H | —NH—(C=O)—OMe |
| 60 | —NH—SO$_2$Me | H |
| 61 | furanyl | H |
| 62 | H | furanyl |
| 63 | methylthiophene | H |
| 64 | H | methylthiophene |
| 65 | ethylthiophene | H |
| 66 | H | ethylthiophene |
| 67 | tBu-thiophene | H |

-continued

| # | R^{C7a} | R^{C7b} |
|---|---|---|
| 68 | H | [thiophene-tBu] |
| 69 | -o,p-(MeO)₂phenyl | H |
| 70 | H | -o,p-(MeO)₂phenyl |
| 71 | [indole] | H |
| 72 | H | [indole] |
| 73 | -o,p-diethoxyphenyl | H |
| 74 | [thiophene] | H |
| 75 | [N-methylpyrrole] | H |
| 76 | -2,4,6-(MeO)₃phenyl | H |
| 77 | H | -2,4,6-(MeO)₃phenyl |
| 78 | —NH—(C=O)—OEt | H |
| 79 | H | —NH—(C=O)—OEt |

5.15 Compound 75—($R^{C7}$=N-methylpyrrole) is synthesized as described in Example 4.1, but substituting Compound 48 for rapamycin.

5.16 Compound 75, 76—($R^{C7}$=2,4,6-trimethoxyphenyl) is synthesized as described in Example 5.1, but substituting 1,3,5-trimethoxybenzene for 1,3-dimethoxybenzene.

Example 6

Preparation of fluoro-rapalogs 6.1 C13-Fluoro-rapalogs

A new class of rapalogs, C13-Fluoro-rapalogs, may be prepared by the following route:

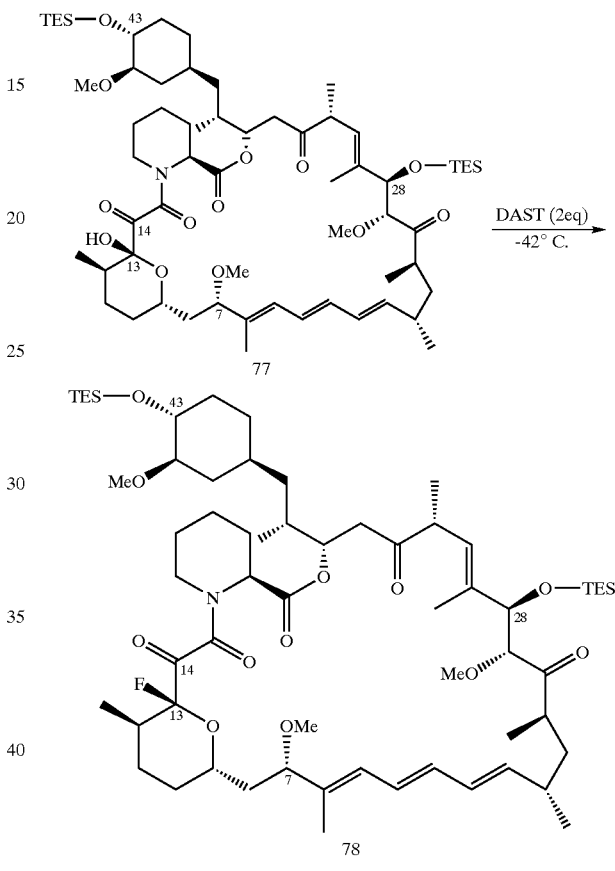

In this example, the hydroxyl moieties at positions 28 and 43 are protected prior to treatment with DAST. We have used bis-triethylsilyl (as shown above) and bis-triisopropylsilyl protecting groups. Various alternative protecting groups may be used, based on user preference or convenience and in consideration of the reaction conditions of subsequent transformations prior to or concurrent with removal of protecting groups. The protected compound is then treated with the DAST reagent to introduce the 13-fluoro substituent. The DAST reaction may be conducted, e.g., at −42° C. as shown, or at 0° C.

13-Fluoro rapamycin may then be modified at position 7 as desired to produce the family of 13-fluoro C7-rapalogs bearing any of the variety of moieties designated previously for $R^{C7a}$ or $R^{C7b}$. For instance, the 7-(o,p-dimethoxy)-13-fluoro-rapalogs (96 and 97) may be prepared (and separately recovered if desired) by transformation of 78 at C7 followed by removal of protecting groups, or, as shown below, by removal of protecting groups from 78 followed by transformation at C7.

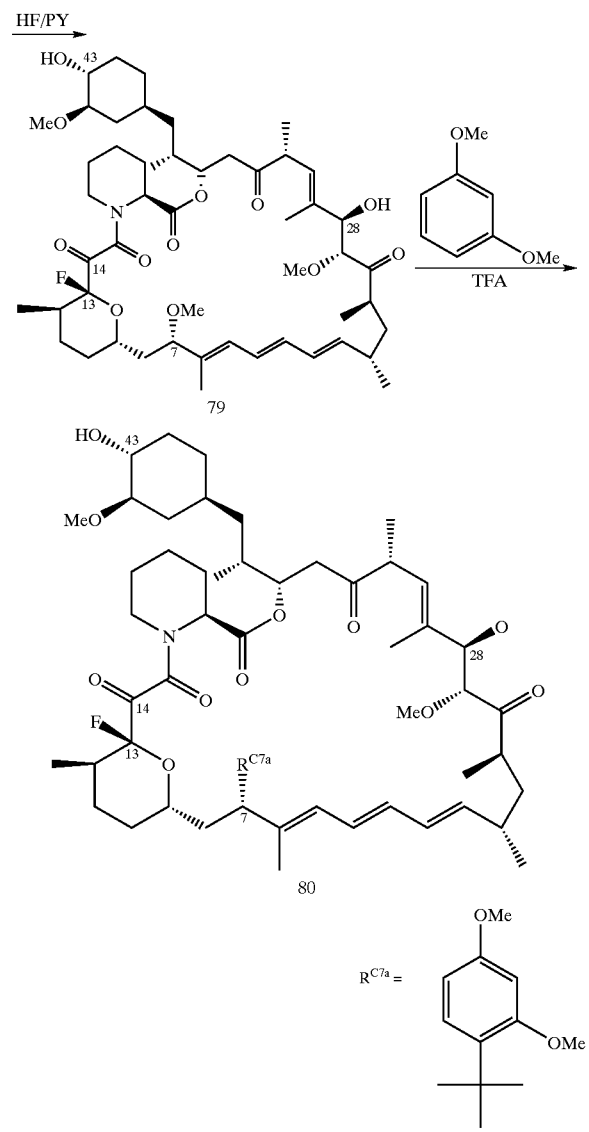

One may subject 13-F-rapamycin, instead of rapamycin, to various other chemical transformations such as are disclosed or referred to herein, including, for instance, fluorination at C28, reduction at C24 and C30, fluorination at C24 and C30, modification at C43, etc., in addition to or as an alternative to modification at C7, in order to obtain the corresponding 13-F analog.

6.2 Compounds 81, 82—($R^{C7}$=Et) are synthesized as described in Example 3.1, but substituting 13-F-rapamycin (79) for rapamycin.

6.3 Compound 83—($R^{C7}$-iPr) is synthesized as described in Example 3.2, but substituting 13-F-rapamycin (79) for rapamycin.

6.4 Compound 84—($R^{C7}$=benzyl) is synthesized as described in Example 3.3, but substituting 13-F-rapamycin (79) for rapamycin.

6.5 Compounds 85, 86—($R^{C7}$=—NH—CO—OMe) are synthesized as described in Example 3.4, but substituting 13-F-rapamycin (79) for rapamycin.

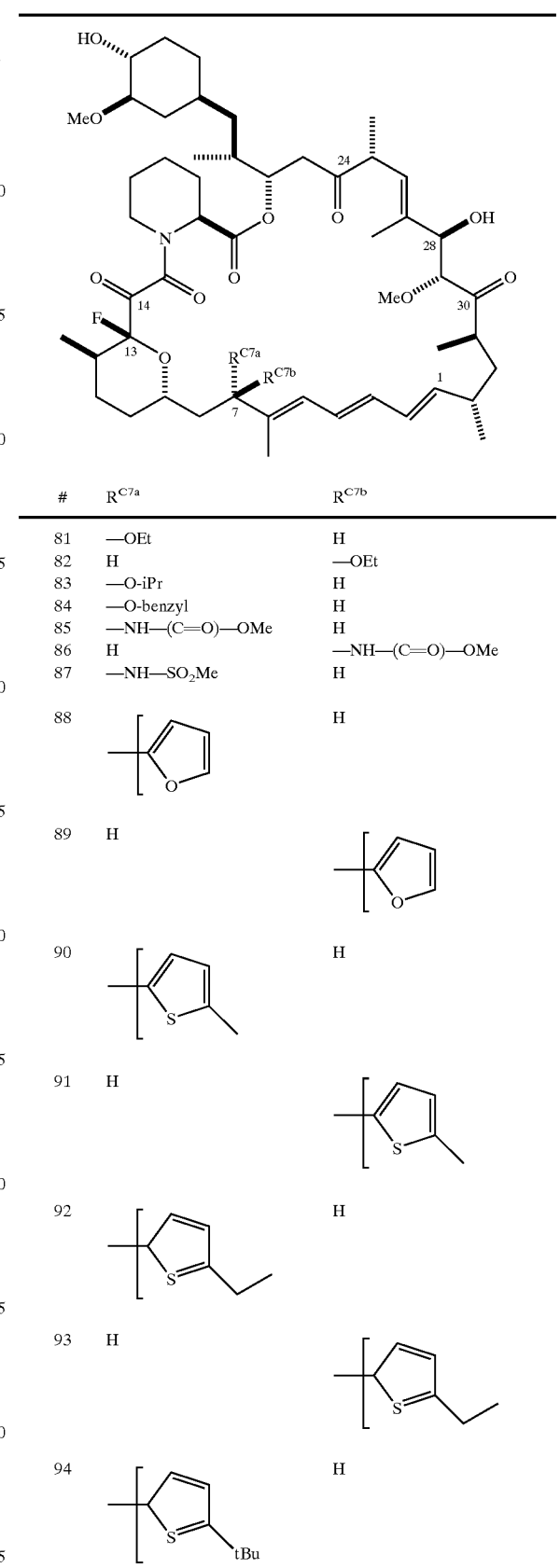

| # | $R^{C7a}$ | $R^{C7b}$ |
|---|---|---|
| 81 | —OEt | H |
| 82 | H | —OEt |
| 83 | —O-iPr | H |
| 84 | —O-benzyl | H |
| 85 | —NH—(C=O)—OMe | H |
| 86 | H | —NH—(C=O)—OMe |
| 87 | —NH—SO$_2$Me | H |
| 88 | furanyl | H |
| 89 | H | furanyl |
| 90 | methylthienyl | H |
| 91 | H | methylthienyl |
| 92 | ethylthienyl | H |
| 93 | H | ethylthienyl |
| 94 | tBu-thienyl | H |

-continued

| # | R^{C7a} | R^{C7b} |
|---|---------|---------|
| 95 | H | (thiophene-tBu) |
| 96 | -o,p-(MeO)₂phenyl | H |
| 97 | H | -o,p-(MeO)₂phenyl |
| 98 | (indolyl) | H |
| 99 | H | (indolyl) |
| 100 | -o,p-diethoxyphenyl | H |
| 101 | (thiophene) | H |
| 102 | (pyrrole) | H |
| 103 | -2,4,6-(MeO)₃phenyl | H |
| 104 | H | -2,4,6-(MeO)₃phenyl |
| 105 | —NH—(C=O)—OEt | H |
| 106 | H | —NH—(C=O)—OEt |

6.6 Compound 87—(R$^{C7}$=—NH—SO2-Me) is synthesized as described in Example 3.5, but substituting 13-F-rapamycin (79) for rapamycin.

6.7 Compounds 88 and 89—(R$^{C7}$=furanyl) are synthesized as described in Example 3.6, but substituting 13-F-rapamycin (79) for rapamycin.

6.8 Compounds 90, 91—(R$^{C7}$=methylthiophene) are synthesized as described in Example 3.7, but substituting 13-F-rapamycin (79) for rapamycin.

6.9 Compounds C, 92, 93—(R$^{C7}$=ethylthiophene) are synthesized as described in Example 3.8, but substituting 13-F-rapamycin (79) for rapamycin.

6.10 Compounds 68, 69—(R$^{C7}$=tertbutyl thiophene) are synthesized as described in Example 3.9 but substituting 13-F-rapamycin (79) for rapamycin.

6.11 Compounds 94, 95—(R$^{C7}$=o-p-dimethoxyphenyl) are synthesized as described in Example 3.10, but substituting 13-F-rapamycin (79) for rapamycin.

6.12 Compounds 96, 97—(R$^{C7}$=indolyl) are synthesized as described in Example 3.11, but substituting 13-F-rapamycin (79) for rapamycin.

6.13 Compound 98—(R$^{C7}$=o,p-diethoxyphenyl)-is synthesized as described in Example 3.12, but substituting 13-F-rapamycin (79) for rapamycin.

6.14 Compound 99—(R$^{C7}$=methylthiophene) is synthesized as described in Example 3.13, but substituting 13-F-rapamycin (79) for rapamycin.

6.15 Compound 100—(R$^{C7}$=N-methylpyrrole) is synthesized as described in Example 3.14, but substituting 13-F-rapamycin (79) for rapamycin.

6.20 Preparation of 28-F-rapamycin (107)

To a solution of rapamycin (71 mg, 0.078 mmol) in methylene chloride (1 mL) at −78° C. was added DAST (21 mL, 0.156 mmol) and reaction was allowed to stir for 2 h before MeOH was added to quench the reaction. The reaction mixture was taken to room temperature and stirred for 30 min. It was poured onto a biphasic solution of saturated aqueous NaHCO3 (20 mL) and EtOAc (30 mL). The organic layer was washed with additional solution of saturated aqueous NaHCO3 (2×20 mL) followed by a saturated aqueous solution of NaCl (2×10 mL) then dried over Na2SO4, filtered, evaporated. The resulting material was flash chromatographed on a silica gel (hexane:EtOAc, 1:1 to 1:2). MS, Fluorine NMR indicated C28 fluorinated rapamycin. Stereoisomers can be separated by reverse phase chromatography (C18 column, MeOH:H2O, 80:20) and may be used in place of rapamycin for the synthesis of various F-28 rapalogs.

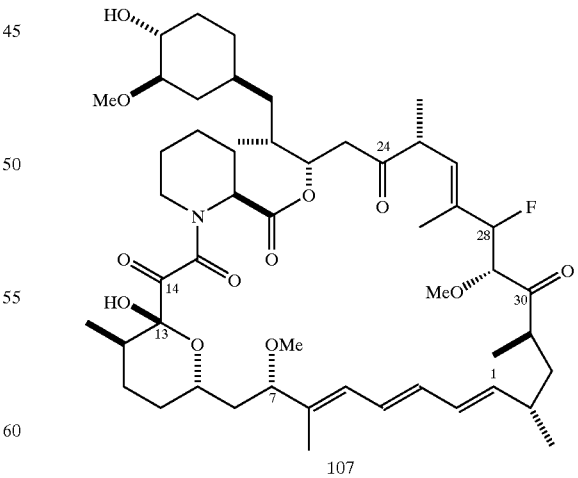

107

6.21 Compound 108-(13F, 28-F-rapamycin) is synthesized as described above for 28-F-rapamycin, but with twice the volume of DAST (41 mL) at a higher temperature (40° C.).

Example 7

Constructs Encoding Chimeric Transcription Factors

A. Unless otherwise stated, all DNA manipulations described in this and other examples were performed using standard procedures (See e.g., F. M. Ausubel et al., Eds., Current Protocols in Molecular Biology (John Wiley & Sons, New York, 1994).

B. Plasmids

Constructs encoding fusions of human FKBP12 with the yeast GAL4 DNA binding domain, the HSV VP16 activation domain, human T cell CD3 zeta chain intracellular domain or the intracellular domain of human FAS are disclosed in PCT/US94/01617.

Additional DNA vectors for directing the expression of fusion proteins relevant to this invention were derived from the mammalian expression vector pCGNN (Attar, R. M. and Gilman, M. Z. 1992. MCB 12: 2432–2443). Inserts cloned as XbaI-BamHI fragments into pCGNN are transcribed under the control of the human CMV promoter and enhancer sequences (nucleotides −522 to +72 relative to the cap site), and are expressed with an optional epitope tag (a 16 amino acid portion of the H. influenzae hemaglutinin gene that is recognized by the monoclonal antibody 12CA5) and, in the case of transcription factor domains, with an N-terminal nuclear localization sequence (NLS; from SV40 T antigen).

Except where stated, all fragments cloned into pCGNN were inserted as XbaI-BamHI fragments that included a SpeI site just upstream of the BamHI site. As XbaI and SpeI produce compatible ends, this allowed further XbaI-BamHI fragments to be inserted downstream of the initial insert and facilitated stepwise assembly of proteins comprising multiple components. A stop codon was interposed between the SpeI and BamHI sites. For initial constructs, the vector pCGNN-GAL4 was additionally used, in which codons 1–94 of the GAL4 DNA binding domain gene were cloned into the XbaI site of pCGNN such that a XbaI site is regenerated only at the 3' end of the fragment. Thus XbaI-BamHI fragments could be cloned into this vector to generate GAL4 fusions, and subsequently recovered.

(a) Constructs encoding GAL4 DNA binding domain-FRAP fusions

To obtain portions of the human FRAP gene, human thymus total RNA (Clontech #64028-1) was reverse transcribed using MMLV reverse transcriptase and random hexamer primer (Clontech 1st strand synthesis kit). This cDNA was used directly in a PCR reaction containing primers 1 and 2 and Pfu polymerase (Stratagene). The primers were designed to amplify the coding sequence for amino acids 2025–2113 inclusive of human FRAP: an 89 amino acid region essentially corresponding to the minimal 'FRB' domain identified by Chen et al. (Proc. Natl. Acad. Sci. USA (1995) 92,49474951) as necessary and sufficient for FKBP-rapamycin binding (hereafter named FRB). The appropriately-sized band was purified, digested with XbaI and SpeI, and ligated into XbaI-SpeI digested pCGNN-GAL4. This construct was confirmed by restriction analysis (to verify the correct orientation) and DNA sequencing and designated pCGNN-GAL4-1FRB.

Constructs encoding FRB multimers were obtained by isolating the FRB XbaI-BamHI fragment, and then ligating it back into pCGNN-GAL4-1FRB digested with SpeI and BamHI to generate pCGNN-GAL4-2FRB, which was confirmed by restriction analysis. This procedure was repeated analogously on the new construct to yield pCGNN-GAL4-3FRB and pCGNN-GAL4-4FRB.

Vectors were also constructed that encode larger fragments of FRAP, encompassing the minimal FRB domain (amino acids 2025–2113) but extending beyond it. PCR primers were designed that amplify various regions of FRAP flanked by 5' XbaI and 3' SpeI sites as indicated below.

| Designation | amino acid | 5' primer | 3' primer |
|---|---|---|---|
| FRAPa | 2012-2127 | 6 | 7 |
| FRAPb | 1995-2141 | 5 | 8 |
| FRAPc | 1945-2113 | 3 | 2 |
| FRAPd | 1995-2113 | 5 | 2 |
| FRAPe | 2012-2113 | 6 | 2 |
| FRAPf | 2025-2127 | 1 | 7 |
| FRAPg | 2025-2141 | 1 | 8 |
| FRAPh | 2025-2174 | 1 | 4 |
| FRAPi | 1945-2174 | 3 | 4 |

Initially, fragment FRAPi was amplified by RT-PCR as described above, digested with XbaI and SpeI, and ligated into XbaI-SpeI digested pCGNN-GAL4. This construct, pCGNN-GAL4-FRAPi, was analyzed by PCR to confirm insert orientation and verified by DNA sequencing. It was then used as a PCR substrate to amplify the other fragments using the primers listed. The new fragments were cloned as GAL4 fusions as described above to yield the constructs pCGNN-GAL4-FRAPa, pCGNN-GAL-FRAPb etc, which were confirmed by DNA sequencing.

Vectors encoding concatenates of two of the larger FRAP fragments, FRAPd and FRAPe, were generated by analogous methods to those used earlier. XbaI-BamHI fragments encoding FRAPd and FRAPe were isolated from pCGNN-GAL4-FRAPd and pCGNN-GAL4-FRAPe and ligated back into the same vectors digested with SpeI and BamHI to generate pCGNN-GAL4-2FRAPd and pCGNN-GAL4-2FRAPe. This procedure was repeated analogously on the new constructs to yield pCGNN-GAL4-3FRAPd, pCGNN-GAL4-3FRAPe, pCGNN-GAL4-4FRAPd and pCGNN-GAL4-4FRAPe. All constructs were verified by restriction analysis.

(b) Constructs encoding FRB-VP16 activation domain fusions

To generate N-terminal fusions of FRB domain(s) with the activation domain of the Herpes Simplex Virus protein VP16, the XbaI-BamHI fragments encoding 1, 2, 3 and 4 copies of FRB were recovered from the GAL4 fusion vectors and ligated into XbaI-BamHI digested pCGNN to yield pCGNN-1FRB, pCGNN-2FRB etc. These vectors were then digested with SpeI and BamHI. An XbaI-BamHI fragment encoding amino acids 414–490 of VP16 was isolated from plasmid pCG-Gal4-VP16 (Das, G., Hinkley, C. S. and Herr, W. (1995) Nature 374, 657–660) and ligated into the SpeI-BamHI digested vectors to generate pCGNN-1FRB-VP16, pCGNN-2FRB-VP16, etc. The constructs were verified by restriction analysis and/or DNA sequencing.

(c) Constructs encoding ZFHD1 DNA binding domain-FRB fusions

An expression vector for directing the expression of ZFHD1 coding sequence in mammalian cells was prepared as follows. Zif268 sequences were amplified from a cDNA clone by PCR using primers 5'Xba/Zif and 3'Zif+G. Oct1 homeodomain sequences were amplified from a cDNA clone by PCR using primers 5'Not Oct HD and Spe/Bam 3'Oct. The Zif268 PCR fragment was cut with XbaI and NotI. The OctI PCR fragment was cut with NotI and BamHI. Both fragments were ligated in a 3-way ligation between the XbaI and BamHI sites of pCGNN (Attar and Gilman, 1992) to make pCGNNZFHD1 in which the cDNA insert is under the transcriptional control of human CMV promoter and enhancer sequences and is linked to the nuclear localization sequence from SV40 T antigen. The plasmid pCGNN also contains a gene for ampicillin resistance which can serve as a selectable marker. (Derivatives, pCGNNZFHD1-FKBP×1 and pCGNNZFHD1-FKBP×3, were prepared containing one or three tandem repeats of human FKBP12 ligated as an XbaI-BamHI fragment between the SpeI and BamHI sites of pCGNNZFHD1. A sample of pCGNNZFHD1-FKBP×3 has been deposited with the American Type Culture Collection under ATCC Accession No. 97399. Sequences of primers is shown in WO 96/41865.

To generate C-terminal fusions of FRB domain(s) with the chimeric DNA binding protein ZFHD1, the XbaI-BamHI fragments encoding 1, 2, 3 and 4 copies of FRB were recovered from the GAL4 fusion vectors and ligated into Spe-BamHI digested pCGNN-ZFHD1 to yield pCGNN-ZFHD1-1FRB, pCGNN-ZFHD1-2FRB etc. Constructs were verified by restriction analysis and/or DNA sequencing.

To examine the effect of introducing additional 'linker' polypeptide between ZFHD1 and a C-terminal FRB domain, FRAP fragments encoding extra sequence N-terminal to FRB were cloned as ZFHD1 fusions. XbaI-BamHI fragments encoding FRAPa, FRAPb, FRAPc, FRAPd and FRAPe were excised from the vectors pCGNN-GAL4-FRAPa, pCGNN-GAL4-FRAPb etc and ligated into SpeI-BamHI digested pCGNN-ZFHD1 to yield the vectors pCGNN-ZFHD1-FRAPa, pCGNN-ZFHD1-FRAPb, etc. Vectors encoding fusions of ZFHD1 to 2, 3 and 4 C-terminal copies of FRAPe were also constructed by isolating XbaI-BamHI fragments encoding 2FRAPe, 3FRAPe and 4FRAPe from pCGNNGAL4-2FRAPe, pCGNN-GAL4-3FRAPe and pCGNN-GAL4-4FRAPe and ligating them into SpeI-BamHI digested pCGNN-ZFHD1 to yield the vectors pCGNN-ZFHD1-2FRAPe, pCGNN-ZFHD1-3FRAPe and pCGNN-ZFHD1-4FRAPe. All constructs were verified by restriction analysis.

Vectors were also constructed that encode N-terminal fusions of FRB domain(s) with ZFHD1. XbaI-BamHI fragments encoding 1, 2, 3 and 4 copies of FRAPe were isolated from pCGNN-GAL4-1FRAPe, pCGNN-GAL4-2FRAPe etc and ligated into XbaI-BamHI digested pCGNN to yield the plasmids pCGNN-1FRAPe, pCGNN-2FRAPe etc. These vectors were then digested with SpeI and BamHI, and an XbaI-BamHI fragment encoding ZFHD1 (isolated from pCGNN-ZFHD1) ligated in to yield the constructs pCGNN-1FRAPe-ZFHD1, pCGNN-2FRAPe-ZFHD1 etc, which were verified by restriction analysis.

(d) Constructs encoding FRB-p65 activation domain fusions

To generate fusions of FRB domain(s) with the activation domain of the human NF-kB $p^{65}$ subunit (hereafter designated p65), two fragments were amplified by PCR from the plasmid pCG-p65. Primers 9 (p65/ 5' Xba) and 11 (p65 3' Spe/Bam) amplify the coding sequence for amino acids 450-550, and primers 10 (p65/361 Xba) and 11 amplify the coding sequence for amino acids 361–550, both flanked by 5' XbaI and 3' SpeI/BamHI sites. PCR products were digested with XbaI and BamHI and cloned into XbaI-BamHI digested pCGNN to yield pCGNN-p65(450–550) and pCGNN-p65(361–550). The constructs were verified by restriction analysis and DNA sequencing.

DNA sequences encoding the 100 amino acid P65 transcription activation sequence and the more extended p65 transcription activation domain (351–550) are shown in WO 96/41865.

To generate N-terminal fusions of FRB domain(s) with portions of the p65 activation domain, plasmids pCGNN-1FRB, pCGNN-2FRB etc were digested with SpeI and BamHI. An XbaI-BamHI fragment encoding p65 (450–550) was isolated from pCGNN-p65(450–550) and ligated into the SpeI-BamHI digested vectors to yield the plasmids pCGNN-1FRB-p65(450–550), pCGNN-2FRB-p65 (450–550) etc. The construct pCGNN-1FRB-p65(361–550) was made similarly using an XbaI-BamHI fragment isolated from pCGNN-p65(361–550). These constructs were verified by restriction analysis.

To examine the effect of introducing additional 'linker' polypeptide between the p65 activation domain and an N-terminal FRB domain, FRAP fragments encoding extra sequence C-terminal to FRB were cloned as p65 fusions. XbaI-BamHI fragments encoding FRAPa, FRAPb, FRAPf, FRAPg and FRAPh were excised from the vectors pCGNN-GAL4-FRAPa, pCGNN-GAL4-FRAPb etc and ligated into XbaI-BamHI digested pCGNN to yield the vectors pCGNN-FRAPa, pCGNN-FRAPb, etc. These plasmids were then digested with SpeI and BamHI, and a XbaI-BamHI fragment encoding p65 (amino acids 450–550) ligated in to yield the five vectors pCGNN-FRAPa-p65, pCGNN-FRAPb-p65, etc, which were verified by restriction analysis.

Vectors encoding fusions of p65 to 1 and 3 N-terminal copies of FRAPe were also prepared by digesting pCGNN-1FRAPe and pCGNN-3FRAPe with SpeI and BamHI. XbaI-BamHI fragments encoding p65(450–550) and p65 (361–550) (isolated from pCGNN-p65(450–550) and pCGNN-p65(361–550)) were then ligated in to yield the vectors pCGNN-1FRAPe-p65(450–550), pCGNN-3FRAPe-p65(450–550), pCGNN-1FRAPe-p65(361–550) and pCGNN-3FRAPe-p65(361–550). All constructs were verified by restriction analysis.

Vectors were also constructed that encode C-terminal fusions of FRB domain(s) with portions of the p65 activation domain. Plasmids pCGNN-p65(450–550) and pCGNN-p65(361–550) were digested with SpeI and BamHI, and XbaI-BamHI fragments encoding 1 and 3 copies of FRAPe (isolated from pCGNN-GAL4-1FRAPe and pCGNN-GAL4-3FRAPe) and 1 copy of FRB (isolated from pCGNN-GAL4-1FRB) ligated in to yield the plasmids pCGNN-p65 (450–550)-1FRAPe, pCGNN-p65(450–550)-3FRAPe, pCGNN-p65(361–550)-1FRAPe, pCGNN-p65(361–550)-3FRAPe, pCGNN-p65(450–550)-1FRB and pCGNN-p65 (361–550)-1FRB. All constructs were verified by restriction analysis.

(e) Further constructs

Other constructs can be made analogously with the above procedures, but using alternative portions of the FRAP sequence or FRB domains containing modified peptide sequence. For example, primers 12 and 13 are used to amplify the entire coding region of FRAP. Primers 1 and 13, 6 and 13, and 5 and 13, are used to amplify three fragments encompassing the FRB domain and extending through to the C-terminal end of the protein (including the lipid kinase homology domain). These fragments differ by encoding different portions of the protein N-terminal to the FRB domain. In each case, RT-PCR is used as described above to amplify the regions from human thymus RNA, the PCR products are purified, digested with XbaI and SpeI, ligated into XbaI-SpeI digested pCGNN, and verified by restriction analysis and DNA sequencing.

(f) Primer sequences 1  5'GCATGTCTAGAGAGATGTGGCATGAAGGCCTGGAAG
   (SEQ ID NO 4)

2  5'GCATCACTAGTCTTTGAGATTCGTCGGAACACATG
   (SEQ ID NO 5)

3  5'GCACATTCTAGAATTGATACGCCCAGACCCTTG
   (SEQ ID NO 6)

4  5'CGATCAACTAGTAAGTGTCAATTTCCGGGGCCT
   (SEQ ID NO 7)

5  5'GCACTATCTAGACTGAAGAACATGTGTGAGCACAGC
   (SEQ ID NO 8)

6  5'GCACTATCTAGAGTGAGCGAGGAGCTGATCCGAGTG
   (SEQ ID NO 9)

7  5'CGATCAACTAGTGGAAACATATTGCAGCTCTAAGGA
   (SEQ ID NO 10)

8  5'CGATCAACTAGTTGGCACAGCCAATTCAAGGTCCCG
   (SEQ ID NO 11)

9  5'ATGCTCTAGACTGGGGGCCTTGCTTGGCAAC
   (SEQ ID NO 12)

10 5'ATGCTCTAGAGATGAGTTTCCCACCATGGTG
   (SEQ ID NO 13)

11 5'GCATGGATCCGCTCAACTAGTGGAGCTGATCTGACTCAG
   (SEQ ID NO 14)

12 5'ATGCTCTAGACTTGGAACCGGACCTGCCGCC
   (SEQ ID NO 15)

13 5'GCATCACTAGTCCAGAAAGGGCACCAGCCAATAT
   (SEQ ID NO 16)

BamHI fragment containing ZFHD1-3FKBP was then cloned downstream of pBS-IRES to create pBS-IRES-ZFHD1-3FKBP. The XbaI-BamHI fragment from this plasmid was next cloned into SpeI/BamHI-cut pCGNN-1FRB-p65(361–550) to create pCGNN-1FRB-p65(361–550)-IRES-ZFHD1-3FKBP.

C. Retroviral Vectors for the Expression of Chimeric Proteins

Retroviral vectors used to express transcription factor fusion proteins from stably integrated, low copy genes were derived from pSRaMSVtkNeo (Muller et al., MCB 11:1785–92, 1991) and pSRaMSV(XbaI) (Sawyers et al., J. Exp. Med. 181:307–313, 1995). Unique BamHI sites in both vectors were removed by digesting with BamHI, filling in with Klenow and religating to produce pSMTN2 and pSMTX2, respectively. pSMTN2 expresses the Neo gene from an internal thyrridine kinase promoter. A Zeocin gene (Invitrogen) is cloned as a NheI fragment into a unique XbaI site downstream of an internal thymidine kinase promoter in pSMTX2 to yield pSNTZ. This Zeocin fragment was generated by mutagenizing pZeo/SV (Invitrogen) using the following primers to introduce NheI sites flanking the zeocin coding sequence.

Primer1 5'-GCCATGGTGGCTAGCCTATAGTGAG (SEQ ID NO 17)

Primer2 5'-GGCGGTGTTGGCTAGCGTCGGTCAG (SEQ ID NO 18)

pSMTN2 contains unique EcoRI and HindIII sites downstream of the LTR. To facilitate cloning of transcription factor fusion proteins synthesized as XbaI-BamHI fragments the following sequence was inserted between the EcoRI and HindIII sites to create pSMTN3:

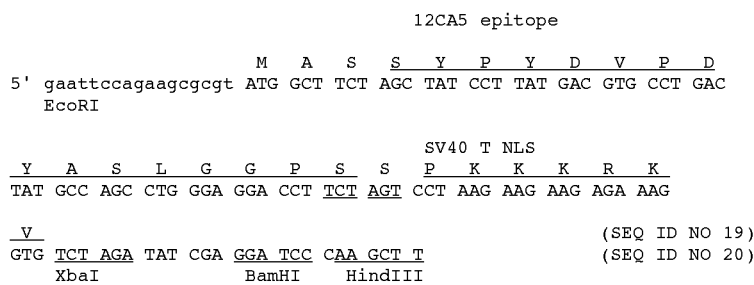

Restriction sites are XbaI=TCTAGA, SpeI=ACGAGT, BamHI=GGATCC.

(g) DNA sequence of representative final construct: pCGNN-ZFHD1-1FRB encoding a 12CA5 epitope-SV40 NLS-ZFHD1-FRB fusion is shown in WO 96/41865.

(h) Bicistronic constructs

The internal ribosome entry sequence (IRES) from the encephalomyocarditis virus was amplified by PCR from pWZL-Bleo. The resulting fragment, which was cloned into pBS-SK+ (Stratagene), contains an XbaI site and a stop codon upstream of the IRES sequence and downstream of it, an NcoI site encompassing the ATG followed by SpeI and BamHI sites. To facilitate cloning, the sequence around the initiating ATG of pCGNN-ZFHD1-3FKBP was mutated to an NcoI site and the XbaI site was mutated to a NheI site using oligonucleotides shown in WO 96/41865. An NcoI- The equivalent fragment is inserted into a unique EcoRI site of pSMTZ to create pSMTZ3 with the only difference being that the 3' HindIII site is replaced by an EcoRI site.

pSMTN3 and pSMTZ3 permit chimeric transcription factors to be cloned downstream of the 5' viral LTR as XbaI-BamHI fragments and allow selection for stable integrants by virtue of their ability to confer resistance to the antibiotics G418 or Zeocin respectively.

To generate the retroviral vector SMTN-ZFHD1-3FKBP, pCGNN-ZFHD1-3FKBP was first mutated to add an EcoRI site upstream of the first amino acid of the fusion protein. An EcoRI-BamHI(blunted) fragment was then cloned into EcoRI-HindIII(blunted) pSRaMSVtkNeo so that ZFHD1-3FKBP was expressed from the retroviral LTR.

Example 8

Rapamycin-dependent Transcriptional Activation

In preliminary experiments, three copies of FKBP fused either to a Gal4 DNA binding domain or a transcription activation domain activated both the stably integrated or transiently transfected reporter gene more strongly than corresponding fusion proteins containing only one or two FKBP domains. To evaluate this parameter with FRB fusion proteins, effector plasmids containing Gal4 DNA binding domain fused to one or more copies of an FRB domain were co-transfected with a plasmid encoding three FKBP domains and a p65 activation domain (3×FKBP-p65) by transient transfection. It was found that in this system, four copies of the FRB domain fused to the Gal4 DNA binding domain activated the stably integrated reporter gene more strongly than other corresponding fusion proteins with fewer FRB domains.

Method: HT1080 B cells were grown in MEM supplemented with 10% Bovine Calf Serum. Approximately 4×105 cells/well in a 6 well plate (Falcon) were transiently transfected by Lipofection procedure as recommended by the supplier (GIBCO, BRL). The DNA: Lipofectamine ratio used in this experiment correspond to 1:6. Cells in each well recieved 500 ng of pCGNN F3-p65, 1.9 ug of PUC 118 plasmid as carrier and 100 ng of one of the following plasmids: pCGNN Gal4-1FRB, pCGNN Gal4-2FRB, pCGNN Gal4-3FRB or pCGNN Gal4-4FRB. Following transfection, 2 ml fresh media was added and supplemented with Rapamycin to the indicated concentration. After 24 hrs, 100 ul of the media was assayed for SEAP activity as described (Spencer et al, 1993).

To test whether multiple FRB domains fused to a p65 activation domain results in increased transcriptional activation of the reporter gene, we co-transfected HT1080 B cells with plasmids expressing Gal4-3×FKBP and 1, 2, 3 or 4 copies of FRB fused to p65 activation domain. Surprisingly, unlike the DNA binding domain-FRB fusions, a single copy of FRB fused to p65 activation domain activated the reporter gene significantly more strongly than corresponding fusion proteins containing 2 or more copies of FRB.

Method: HT1080 B cells were grown in MEM supplemented with 10% Bovine Calf Serum. Approximately 4×105 cells/well in a 6 well plate were transiently transfected by Lipofection procedure as recommended by GIBCO, BRL. The DNA: Lipofectamine ratio used correspond to 1:6. Cells in each well recieved 1.9 ug of PUC 118 plasmid as carrier, 100 ng of pCGNNGal4F3 and 500 ng one of the following plasmids :pCGNN1, 2, 3 or 4 FRB-p65. Following transfection, 2 ml fresh media was added and supplemented with Rapamycin to the indicated concentration. After 24 hrs, 100 ul of the media was assayed for SEAP activity as described (Spencer et al, 1993).

Similar experiments were also conducted using another stable cell line (HT1080 B14) containing the 5×Gal4-IL2-SEAP reporter gene and DNA sequences encoding a fusion protein containing a Gal4 DNA binding domain and 3 copies of FKBP stably integrated. These cells were transiently transfected with effector plasmids expressing p65 activation domain fused to 1 or more copies of an FRB domain. Similar to our observations with HT1080 B cells, in these experiments effector plasmids expressing a single copy of FRB-p65 activation domain fusion protein activated the reporter gene more strongly than others with 2 or more copies of FRB.

Example 9

A. RAPAMYCIN-Dependent Transcriptional Activation in Transiently Transfected cells: ZFHD1 and p65 fusions Human fibrosarcoma cells transiently transfected with a SEAP target gene and plasmids encoding representative ZFHD-FKBP- and FRB-p65-containing fusion proteins exhibited rapamycin-dependent and dose-responsive secretion of SEAP into the cell culture medium. See WO 96/41865, FIG. 4A. SEAP production was not detected in cells in which one or both of the transcription factor fusion plasmids was omitted, nor was it detected in the absence of added rapamycin WO 96/418651, (FIG. 4B). When all components were present, however, SEAP secretion was detectable at rapamycin concentrations as low as 0.5 nM WO 96/41865, (FIG. 4A). Peak SEAP secretion was observed at 5 nM. Similar results have been obtained when the same transcription factors were used to drive rapamycin-dependent activation of an hGH reporter gene or a stably integrated version of the SEAP reporter gene made by infection with a retroviral vector. It is difficult to determine the fold activation in response to rapamycin since levels of SEAP secretion in the absence of drug are undetectable, but it is clear that in this system there is at least a 1000-fold enhancement over background levels in the absence of rapamycin. Thus, this system exhibits undetectable background activity and high dynamic range.

Several different configurations for transcription factor fusion proteins were explored (See See WO 96/41865, FIG. 5). When FKBP domains were fused to ZFHD1 and FRBs to p65, optimal levels of rapamycin-induced activation ocurred when there were multiple FKBPs fused to ZAMD1 and fewer FRBs fused to p65. The preference for multiple drug-binding domains on the DNA-binding protein may reflect the capacity of these proteins to recruit multiple activation domains and therefore to elicit higher levels of promoter activity. The presence of only 1 drug-binding domain on the activation domain should allow each FKBP on ZFHD to recruit one p65. Any increase in the number of FRBs on $p^{65}$ would increase the chance that fewer activation domains would be recruited to ZFHD, each one linked my multiple FRB-FKBP interactions.

Methods:

HT1080 cells (ATCC CCL-121), derived from a human fibrosarcoma, were grown in MEM supplemented with non-essential amino acids and 10% Fetal Bovine Serum. Cells plated in 24-well dishes (Falcon, 6×104 cells/well) were transfected using Lipofectamine under conditions recommended by the manufacturer (GIBCO/BRL). A total of 300 ng of the following DNA was transfected into each well: 100 ng ZFHD×12-CMV-SEAP reporter gene, 2.5 ng pCGNN-ZFHD1-3FKBP or other DNA binding domain fusion, 5 ng pCGNN-1FRB-p65(361–550) or other activation domain fusion and 192.5 ng pUC118. In cases where the DNA binding domain or activation domain were omitted an equivalent amount of empty pCGNN expression vector was substituted. Following lipofection (for 5 hours) 500 $\mu$l medium containing the indicated amounts of rapamycin was added to each well. After 24 hours, medium was removed and assayed for SEAP activity as described (Spencer et al, Science 262:1019–24, 1993) using a Luminescence Spectrometer (Perkin Elmer) at 350 nm excitation and 450 nm emission. Background SEAP activity, measured from mock-transfected cells, was subtracted from each value.

To prepare transiently transfected HT1080 cells for injection into mice (See below), cells in 100 mm dishes (2×106 cells/dish) were transfected by calcium phosphate precipitation for 16 hours (Gatz, C., Kaiser, A. & Wendenburg, R., 1991, Mol. Gen. Genet. 227, 229–237) with the following DNAs: 10 mg of ZHWTx12-CMV-hGH, 1 mg pCGNN-ZFHD1-3FKBP, 2 mg pCGNN-1FRB-p65(361–550) and 7 mg pUC118. Transfected cells were rinsed 2 times with phosphate buffered saline (PBS) and given fresh medium for 5 hours. To harvest for injection, cells were removed from the dish in Hepes Buffered Saline Solution containing 10 mM EDTA, washed with PBS/0.1% BSA/0.1% glucose and resuspended in the same at a concentration of 2×107 cells/ml.

Plasmids: Construction of the transcription factor fusion plasmids is described above.

pZHWTx12-CMV-SEAP

This reporter gene, containing 12 tandem copies of a ZFHD1 binding site (Pomerantz et al., 1995) and a basal promoter from the immediate early gene of human cytomegalovirus (Boshart et. al., 1985) driving expression of a gene encoding secreted alkaline phosphatase (SEAP), was prepared by replacing the NheI-HindIII fragment of pSEAP Promoter (Clontech) with an NheI-XbaI fragment containing 12 ZFHD binding sites shown in WO 96/41865 and an XbaI-HindIII fragment containing a minimal CMV promoter (−54 to +45), also shown in WO 96/41865.

pZHWTx12-CMV-hGH

Activation of this reporter gene leads to the production of hGH. It was constructed by replacing the HindIII-BamHI (blunted) fragment of pZHWTx12CMV-SEAP (containing the SEAP coding sequence) with a HindIII (blunted) -EcoRI fragment from pOGH (containing an hGH genomic clone; Selden et al., MCB 6:3171–3179, 1986; the BamHI and EcoRI sites were blunted together).

pZHWTx12-IL2-SEAP

This reporter gene is identical to pZHWTx12-CMV-SEAP except the XbaI-HindIII fragment containing the minimal CMV promoter was replaced with the following XbaI-HindIII fragment containing a minimal IL2 gene promoter (−72 to +45 with respect to the start site; Siebenlist et al., MCB 6:3042–3049, 1986) (see WO 96/41865)

pLH

To facilitate the stable integration of a single, or few, copies of reporter gene the following retroviral vector was constructed. pLH (LTR-hph), which contains the hygromycin B resistance gene driven by the Moloney murine leukemia virus LTR and a unique internal ClaI site, was constructed as follows: The hph gene was cloned as a HindIII-ClaI fragment from pBabe Hygro (Morganstern and Land, NAR 18:3587–96, 1990) into BamHI-ClaI cut pBabe Bleo (resulting in the loss of the bleo gene; the BamHI and HindIII sites were blunted together).

pLH-ZHWTx12-IL2-SEAP

To clone a copy of the reporter gene containing 12 tandem copies of the ZFHD1 binding site and a basal promoter from the IL2 gene driving expression of the SEAP gene into the pLH retroviral vector, the MluI-ClaI fragment from pZHWTx12-IL2-SEAP (with ClaI linkers added) was cloned into the ClaI site of pLH. It was oriented such that the directions of transcription from the viral LTR and the internal ZFHD-IL2 promoters were the same.

pLH-G5-IL2-SEAP

To construct a retroviral vector containing 5 Gal4 sites embedded in a minimal IL2 promoter driving expression of the SEAP gene, a ClaI-BstBI fragment consisting of the following was inserted into the ClaI site of pLH such that the directions of transcription from the viral LTR and the internal Gal4-IL2 promoters were the same: A ClaI-HindIII fragment containing 5 Gal4 sites and regions −324 to −294 and −72 to +45 of the 112 gene (shown in WO 96/41865) and a HindIII-BstBI fragment containing the SEAP gene coding sequence (Berger et al., Gene 66:1–10, 1988) mutagenized to add a BstBI site immediately after the stop codon (shown in WO 96/471865).

B. Rapamycin-Dependent Transcriptional Activation in Stably Transfected Cells

The following experiments confirmed that this system exhibits similar properties in stably transfected cells. We generated stable cell lines by sequential transfection of a SEAP target gene and expression vectors for ZFHD1-3FKBP and 1FRB-p65, respectively. A pool of several dozen stable clones resulting from the final transfection exhibited rapamycin-dependent SEAP production. From this pool, we characterized several individual clones, many of which produced high levels of SEAP in response to rapamycin. Results from one such clone are shown in FIG. 4C of WO 96/41865. This clone produced SEAP at levels approximately forty times higher than the pool and significantly higher than transiently transfected cells. In an attempt to rigorously quantitate background SEAP production and induction ratio in this clone, we performed a second set of assays in which the length of the SEAP assay was increased by a factor of approximately 50 to detect any SEAP activity in untreated cells. Under these conditions, mock transfected cells produced 47 arbitrary fluorescence units, while the transfected clone produced 54 units in the absence of rapamycin and over 90,000 units at 100 nM rapamycin. Thus, in this stable cell line, background gene expression was negligible and the induction ratio (7 units to 90,000 units) was greater than four orders of magnitude.

To simplify the task of stable transfection, we used a bicistronic expression vector that directs the production of both ZFHD1-3FKBP and 1FRB-p65 through the use of an internal ribosome entry sequence (IRES). This expression plasmid was cotransfected, together with a zeocin-resistance marker plasmid, into a cell line carrying a retrovirally-transduced SEAP reporter gene, and a pool of approximately fifty drug-resistant clones was selected and expanded. This pool of clones also exhibited rapamycin-dependent SEAP production with no detectable background and a very similar dose-response curve to that observed in transiently transfected cells. This pool would be expected to contain individual clones with performance similar to the clone studied in FIG. 4C of WO 96/41865. Thus, rapamycin-responsive gene expression can be readily obtained in both transiently and stably transfected cells. In both cases, regulation is characterized by very low background and high induction ratios.

Stable cell lines. Helper-free retroviruses containing the reporter gene or DNA binding domain fusion were generated by transient co-transfection of 293T cells (Pear, W. S., Nolan, G. P., Scott, M. L. & Baltimore D., 1993, Production of high-titer helper-free retroviruses by transient transfection. Proc. Natl. Acad. Sci. USA 90, 8392–8396) with a Psi(−) amphotropic packaging vectorand the retroviral vectors pLH-ZHWTx12-IL2-SEAP or SMTN-ZFHD1-3FKBP, respectively. To generate a clonal cell line containing the reporter gene stably integrated, HT1080 cells infected with retroviral stock were diluted and selected in the presence of 300 mg/ml Hygromycin B. Individual clones from this and other cell lines described below were screened by transient transfection of the missing components followed by the addition of rapamycin as described above. All 12 clones analyzed were inducible and had little or no basal activity. The most responsive clone, HT1080L, was selected for further study.

HT20-6 cells, which contain the pLH-ZHWTx12-IL2-SEAP reporter gene, ZFHD1-3FKBP DNA binding domain and 1FRB-p65(361–550) activation domain stably integrated, were generated by first infecting HT1080L cells with SMTN-ZFHD1-3FKBP-packaged retrovirus and selecting in medium containing 500 mg/ml G418. A strongly responsive clone, HT1080L3, was then transfected with linearized pCGNN-1FRB-p65(361–550) and pZeoSV (Invitrogen) and selected in medium containing 250 mg/ml Zeocin. Individual clones were first tested for the presence of 1FRB-p65(361–550) by western. Eight positive clones were analyzed by addition of rapamycin. All eight had low basal activity and in six of them, gene expression was induced by at least two orders of magnitude. The clone that gave the strongest response, HT20-6, was selected for further analysis.

HT23 cells were generated by co-transfecting HT1080L cells with linearized pCGNN-1FRB-p65(361–550)-IRES-ZFHD1-3FKBP and pZeoSV and selecting in medium containing 250 mg/ml Zeocin. Approximately 50 clones were pooled for analysis.

For analysis, cells were plated in 96-well dishes (1.5×104 cells/well) and 200 μl medium containing the indicated amounts of rapamycin (or vehicle) was added to each well. After 18 hours, medium was removed and assayed for SEAP activity. In some cases, medium was diluted before analysis and relative SEAP units obtained multiplied by the fold-dilution. Background SEAP activity, measured from untransfected HT1080 cells, was subtracted from each value.

Example 10

Rapamycin-dependent Production of hGH in Mice

In Vivo Methods: Animals, husbandry, and general procedures. Male nu/nu mice were obtained from Charles River Laboratories (Wilmington, Mass.) and allowed to acclimate for five days prior to experimentation. They were housed under sterile conditions, were allowed free access to sterile food and sterile water throughout the entire experiment, and were handled with sterile techniques throughout. No immunocompromised animal demonstrated outward infection or appeared ill as a result of housing, husbandry techniques, or experimental techniques.

To transplant transiently transfected cells into mice, 2×106 transfected HT1080 cells, were suspended in 100 ml PBS/0.1% BSA/0.1% glucose buffer, and administered into four intramuscular sites (approximately 25 ml per site) on the haunches and flanks of the animals. Control mice received equivalent volume injections of buffer alone.

Rapamycin was formulated for in vivo administration by dissolution in equal parts of N,N-dimethylacetamide and a 9:1 (v:v) mixture of polyethylene glycol (average molecular weight of 400) and polyoxyethylene sorbitan monooleate. Concentrations of rapamycin, in the completed formulation, were sufficient to allow for in vivo administration of the appropriate dose in a 2.0 ml/kg injection volume. The accuracy of the dosing solutions was confirmed by HPLC analysis prior to intravenous administration into the tail veins. Some control mice, bearing no transfected HT1080 cells, received 10.0 mg/kg rapamycin. In addition, other control mice, bearing transfected cells, received only the rapamycin vehicle.

Blood was collected by either anesthetizing or sacrificing mice via CO2 inhalation. Anesthetized mice were used to collect 100 ml of blood by cardiac puncture. The mice were revived and allowed to recover for subsequent blood collections. Sacrificed mice were immediately exsanguinated. Blood samples were allowed to clot for 24 hours, at 4° C., and sera were collected following centrifugation at 1000×g for 15 minutes. Serum hGH was measured by the Boehringer Mannheim non-isotopic sandwich ELISA (Cat No. 1 585 878). The assay had a lower detection limit of 0.0125 ng/ml and a dynamic range that extended to 0.4 ng/ml. Recommended assay instructions were followed. Absorbance was read at 405 nm with a 490 nm reference wavelength on a Molecular Devices microtiter plate reader. The antibody reagents in the ELISA demonstrate no cross reactivity with endogenous, murine hGH in diluent sera or native samples.

hGH expression In Vivo. For the assessment of dose-dependent rapamycin-induced stimulation of hGH expression, rapamycin was administered to mice approximately one hour following injection of HT1080 cells. Rapamycin doses were either 0.01, 0.03, 0.1, 0.3, 1.0, 3.0, or 10.0 mg/kg. Seventeen hours following rapamycin administration, the mice were sacrificed for blood collection.

To address the time course of in vivo hGH expression, mice received 10.0 mg/kg of rapamycin one hour following injection of the cells. Mice were sacrificed at 4(8, 17, 24, and 42 hours following rapamycin administration.

The ability of rapamycin to induce sustained expression of hGH from transplanted HT1080 cells was tested by repeatedly administering rapamycin. Mice were administered transfected HT1080 cells as described above. Approximately one hour following injection of the cells, mice received the first of five intravenous 10.0 mg/kg doses of rapamycin. The four remaining doses were given under anesthesia, immediately subsequent to blood collection, at 16, 32, 48, and 64 hours. Additional blood collections were also performed at 72, 80, 88, and 96 hours following the first rapamycin dose. Control mice were administered cells, but received only vehicle at the various times of administration of rapamycin. Experimental animals and their control counterparts were each assigned to one of two groups. Each of the two experimental groups and two control groups received identical drug or vehicle treatments, respectively. The groups differed in that blood collection times were alternated between the two groups to reduce the frequency of blood collection for each animal.

Results

Rapamycin elicited dose-responsive production of hGH in these animals (FIG. 6 of WO 96/41865). hGH concentrations in the rapamycin-treated animals compared favorably with normal circulating levels in humans (0.2–0.3 ng/ml). No plateau in hGH production was observed in these experiments, suggesting that the maximal capacity of the transfected cells for hGH production was not reached. Control animals—those that received transfected cells but no rapamycin and those that received rapamycin but no cells—exhibited no detectable serum hGH. Thus, the production of hGH in these animals was absolutely dependent upon the presence of both engineered cells and rapamycin.

The presence of significant levels of hGH in the serum 17 hours after rapamycin administration was noteworthy, because hGH is cleared from the circulation with a half-life of less than four minutes in these animals. This observation suggested that the engineered cells continued to secrete hGH for many hours following rapamycin treatment. To examine the kinetics of rapamycin control of hGH production, we treated animals with a single dose of rapamycin and then measured hGH levels at different times thereafter. Serum hGH was observed within four hours of rapamycin treatment, peaked at eight hours (at over one hundred times the sensitivity limit of the hGH ELISA), and remained detectable 42 hours after treatment. hGH concentration decayed from its peak with a half-life of approximately 11 hours. This half-life is several hundredfold longer than the half-life of hGH itself and approximately twice the half-life of rapamycin (4.6 hr) in these animals. The slower decay of serum hGH relative to rapamycin could reflect the presence of higher tissue concentrations of rapamycin in the vicinity of the implanted cells. Alternatively, persistence of hGH production from the engineered cells may be enhanced by the stability of hGH mRNA.

Interestingly, administration of a second dose of rapamycin to these animals at 42 hr resulted in a second peak of serum hGH, which decayed with similar kinetics indicating that the engineered cells retained the ability to respond to rapamycin for at least two days. Therefore, to ascertain the ability of this system to elevate and maintain circulating hGH concentrations, we performed an experiment in which animals received multiple doses of rapamycin at 16-hour intervals. This interval corresponds to the time required for hGH levels to peak and then decline approximately halfway. According to this regimen, rapamycin concentration is predicted to approach a steady-state trough concentration of 1.7 µg/ml after two doses (shown as dotted line in FIG. 8 of WO 96/41865). hGH levels should also approach a steady state trough concentration following the second dose. Treated animals indeed held relatively stable levels of circulating hGH in response to repeated doses of rapamycin. After the final dose, hGH levels remained constant for 16 hours and then declined with a similar half-life as rapamycin (6.8 hours for hGH versus 4.6 hours for rapamycin). These data suggest that upon multiple dosing, circulating rapamycin imparts tight control over the secretion of hGH from transfected cells in vivo. In particular, it is apparent that protein production is rapidly terminated upon withdrawal of drug.

Discussion

These experiments demonstrate the feasibility of controlling the production of a secreted therapeutic protein from genetically engineered cells using a small-molecule drug. This system has many of the features required for use in human gene and cell therapy. It is characterized by very low background activity and high induction ratio. It functions independently of host physiology or any cell-type-specific factors. It is composed completely of human proteins. The controlling drug is well behaved in vivo and orally bioavailable.

With a system of this general design, it should be possible to provide stable and precisely titrated doses of secreted therapeutic proteins from engineered cells in vivo. Intermittent and pulsatile dosing should also be feasible. A considerable advantage of protein delivery from engineered cells under small-molecule control is that the rate of protein production at any given time is a function of the circulating concentration of the small-molecule drug. Therefore, the apparent pharmacokinetics of a therapeutic protein such as hGH can be dramatically altered. In our experiments, for example, the kinetics of circulating hGH delivered from engineered cells following a single administration of rapamycin are markedly different from those observed following a single administration of recombinant protein. hGH administered to mice intravenously is cleared with a half-time of a few minutes, whereas hGH levels from engineered cells induced with rapamycin decayed with a half-time of approximately eleven hours. Even in humans, where the half-time for hGH clearance is approximately twenty minutes, injections must be given every other day, and serum hGH levels fluctuate dramatically. It is likely that protein delivery from engineered cells under precise pharmacologic control will lead to more effective therapy, particularly for proteins with poor pharmacokinetics or low therapeutic index.

The use of a small-molecule drug to link a DNA-binding domain and activation domain is an effective strategy for regulating gene expression in vivo. One especially attractive feature is that the system is entirely modular, allowing each component to be optimized and engineered independently. In contrast to bacterial repressors, which rely on relatively subtle allosteric intramolecular interactions to control DNA-binding activity, the dimerization strategy can be adapted to virtually any DNA-binding and activation domain. We have used here a DNA-binding domain of defined structure which readily supports rational engineering of DNA-binding affinity and new recognition specificities. Similarly, activation domains can be engineered for maximal potency and other suitable properties. Indeed, the engineered transcription factors used in these experiments elicit very high levels of gene expression relative to conventional promoter/enhancer systems, and further enhancements in either domain can be readily incorporated. The ability to introduce engineered transcription factors dedicated to the transcription of a single target gene provides opportunities to achieve lower backgrounds and substantially higher levels of gene expression in vivo than conventional expression vectors.

We have also chosen to construct our regulated transcription factors from human proteins to minimize the potential for recognition by the immune system. It has been reported that autologous T cells expressing a fusion protein composed of bacterial hygromycin phosphotransferase and herpes virus thymidine kinase were effectively recognized and eliminated by host cytotoxic T cells, even in AIDS patients with debilitated immune systems (Riddell, S. R., et al. T-cell mediated rejection of gene-modified HIV-specific cytotoxic T lymphocytes in HIV-infected patients. Nature Med. 2, 216–223 (1996)). This observation suggests that the risk of immune recognition of heterologous proteins in engineered cells is a real one and that, therefore, the use of human proteins for performing regulatory functions in human cells is prudent. Although each individual component of our transcription factor fusion proteins is human in sequence, each protein contains junction peptides which could potentially be recognized as foreign. These junctions may be designed or selected, however, to minimize their presentation to the immune system, as discussed previously.

The principal limitation of rapamycin-based systems is the native biological activity of rapamycin, which, through inhibition of FRAP activity blocks cell-cycle progression leading to immunosuppression in vivo. However, the ability to introduce substituents or otherwise modify the structure of rapamycin to substantially reduce or abolish binding to FKBP and/or FRAP provides access to rapalogs devoid of undue immunosuppressive activity. Use of such rapalogs, especially improved rapalogs of this invention, together with correspondingly engineered FKBP and/or FRB domains should prove widely useful for the regulation of engineered protein production as well as the regulation of a wide variety of other biological processes in experimental animals and human gene therapy.

Example 11

FP Assay for rapalog binding to FKBP

Affinities of rapalogs for FKBP proteins may be determined using a competitive assay based on fluorescence polarization (FP). A fluorescein-labelled FK506 probe (AP1491) was synthesized as described in WO 96/41865 (See Example 6 therein), and the increase in the polarization of its fluorescence used as a direct readout of % bound probe in an equilibrium binding experiment containing sub-saturating FKBP and variable amounts of rapamycin analog as competitor.

Determination of Binding Affinities (IC50s) of Rapalogs Using FP

Serial 10-fold dilutions of each analog are prepared in 100% ethanol in glass vials and stored on ice. All other manipulations are performed at room temperature. A stock of recombinant pure FKBP (purified by standard methods, see eg. Wiederrecht, G. et al. 1992. J. Biol. Chem. 267, 21753–21760) is diluted to 11.25 nM in 50 mM potassium phosphate pH 7.8/150 mM NaCl/100 $\mu$g/ml bovine gamma globulin ("FP buffer": prepared using only low-fluorescence reagents from Panvera) and 98 $\mu$l aliquots transferred to wells of a Dynatech micro-fluor black 96-well fluorescence plate. 2.0 $\mu$l samples of the rapalogs are then transferred in duplicate to the wells with mixing. Finally, a probe solution is prepared containing 10 nM AP1491 in 0.1% ethanol/FP buffer, and 100 $\mu$l added to each well with mixing. Duplicate control wells contain ethanol instead of rapalog (for 100% probe binding) or ethanol instead of rapalog and FP buffer instead of FKBP (0% binding).

The plates are stored covered in the dark for approximately 30 min to permit equilibration and then the fluorescence polarization of the sample in each well is read on a Jolley FPM-2 FP plate reader (Jolley Consulting and Research, Inc., Grayslake, Ill.) in accordance with the manufacturer's recommendations. The mean polarization (mP units) for each competitor concentration is usually converted to % total binding by reference to the control values and plotted (y) vs. log molar final concentration of competitor (x). Non-linear least square analysis was used to fit the curve and extract the IC50 using the following equation:

$$y=M1+(M4-M1)/(1+\exp(M2*(M3-x)))$$

where M3 is the IC50. For incomplete curves the IC50 is determined by interpolation.

Rapamycin and C14desoxorapamycin may be included as controls in each case (C14-desoxo-rapamycin was prepared as described by Luengo, J. I. et al. 1994 Tetrahedron Lett. 35, 6469–6472).

Example 12

Rapalog-dependent Transcriptional Activation in Transiently Transfected Cells

Rapalogs may be assayed for their ability to dimerize FKBP and FRB fusion proteins using a transcription read out as follows. Constructs encoding rapalog-dependent transcription factor fusion proteins are introduced into cells which contain, or are engineered to contain, a reporter gene linked to transcriptional regulatory DNA permitting reporter gene expression following rapalog-dependent dimerization of the transcription factor fusion proteins. The transcription factor fusion proteins include (a) an FKBP fusion protein containing, as a heterologous effector domain, a DNA binding domain (DBD) and (b) an FRB fusion protein containing, as a heterologous effector domain, a transcription activator domain. The FKBP and/or FRB domains may contain naturally occurring or non-naturally occurring peptide sequence. The presence of a rapalog which is capable of mediating dimerization of the two fusion proteins leads to expression of the reporter gene. The level of reporter observed is indicative of the activity of the rapalog as a dimerizer. Use of a target gene of interest in place of a reporter gene renders this a regulated gene expression system for use in cells grown in culture or in whole organisms.

We have made use of such as system as follows: HT1080 cells (ATCC CCL-121), derived from a human fibrosarcoma, were grown in MEM supplemented with non-essential amino acids and 10% Fetal Bovine Serum. Cells plated in 24-well dishes (Falcon, $6\times10^4$ cells/well) were transfected using Lipofectamine under conditions recommended by the manufacturer (GIBCO/BRL). A total of 300 ng of the following DNA was transfected into each well:

(a) 100 ng ZFHD×12-CMV-SEAP. reporter gene (reporter gene linked to 12 recognition sites for the ZFHD1 DNA-binding domain), (b) 2.5 ng pCGNN-ZFHD1-3FKBP or other DNA binding domain fusion (fusion protein comprising 3 FKBP domains and one ZFHD1 domain), (c) 5 ng pCGNN-1FRB-p65(361–550) (fusion protein comprising an FRB domain and and a p65 transcription activation domain) and (d) 192.5 ng pUC118.

Figure 2A:
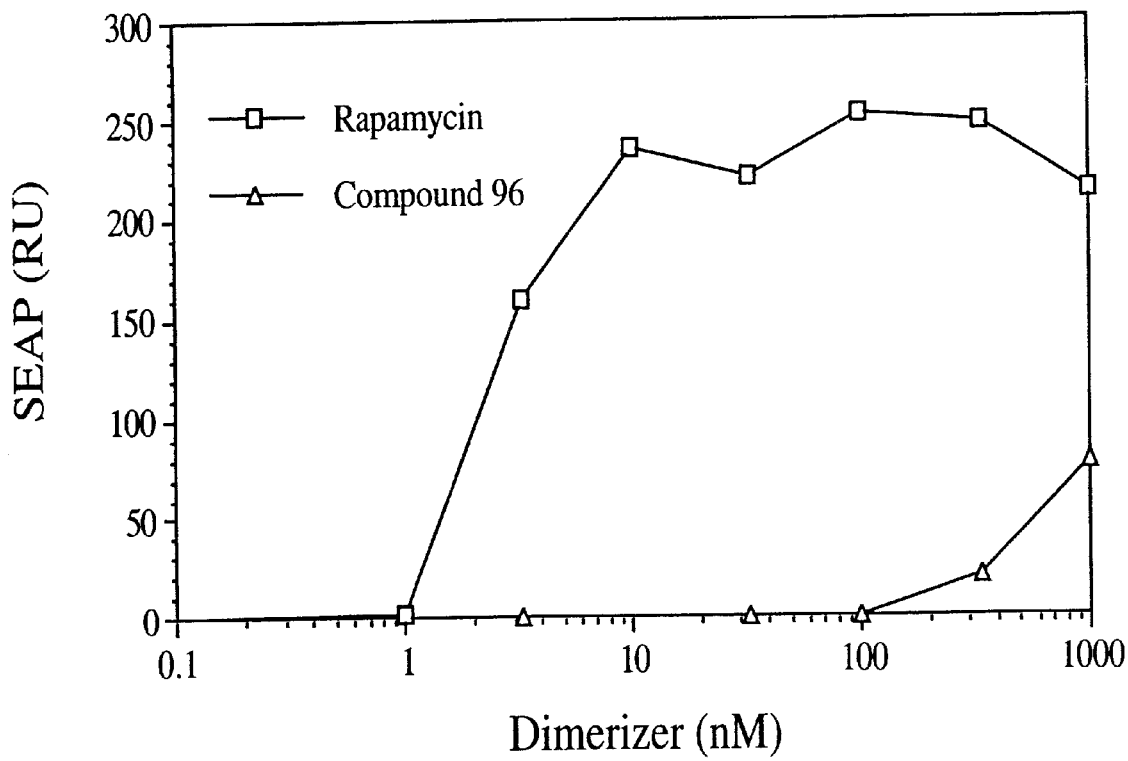
FIG. 2A depicts results of transcription assays using rapalog 96, synthesized as described herein, as the dimerizer. The rapalog was tested in cells expressing wild-type FRB. A rapamycin control is shown.
Figure 2B:
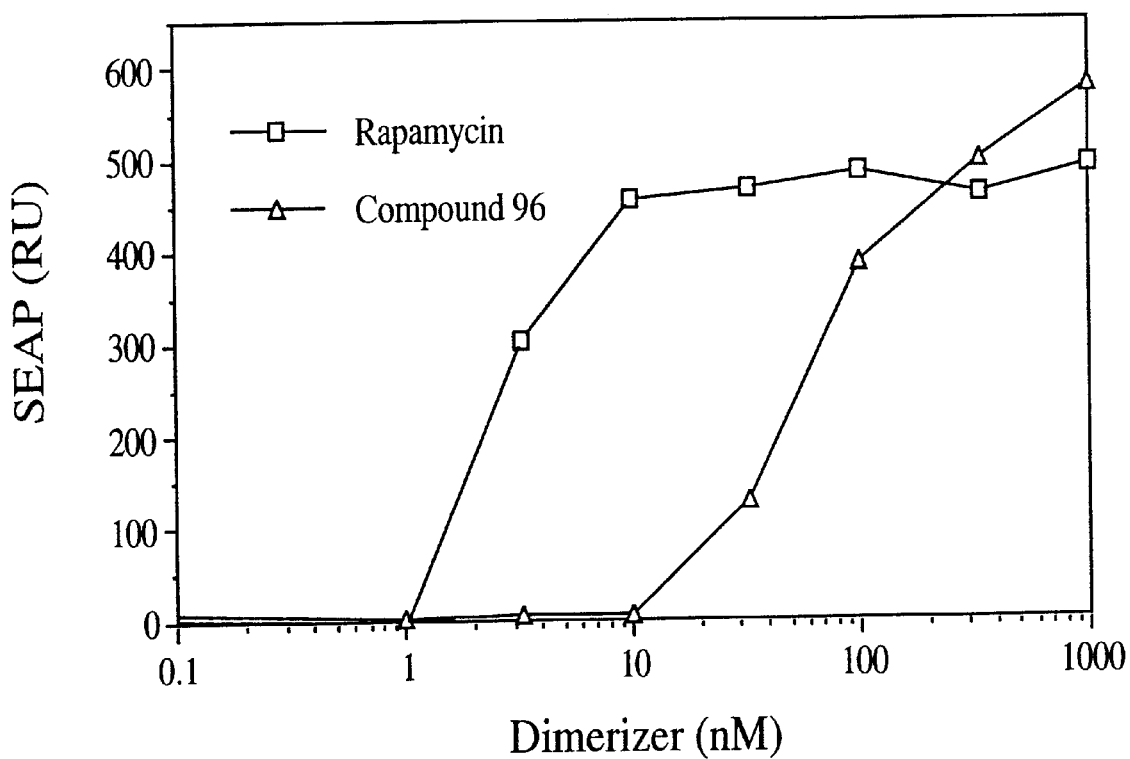
FIG. 2B depicts results of transcription assays using rapalog 96, synthesized as described herein, as the dimerizer. The rapalog was tested in cells expressing a mutant FRB in which Thr 2098 was replaced by Leu. A rapamycin control is shown.
Figure 2C:
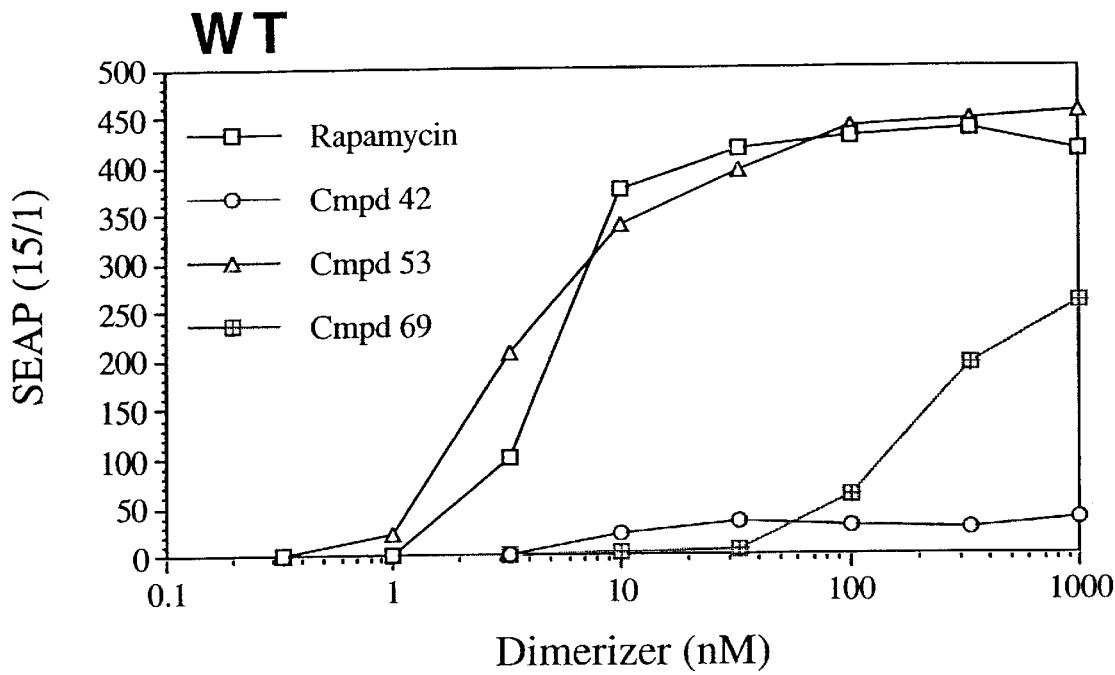
FIG. 2C depicts results of transcription assays using rapalogs 42, 53 and 69, synthesized as described herein, as the dimerizers. The rapalogs were tested in cells expressing wild-type FRB. A rapamycin control is shown.
Figure 2D:
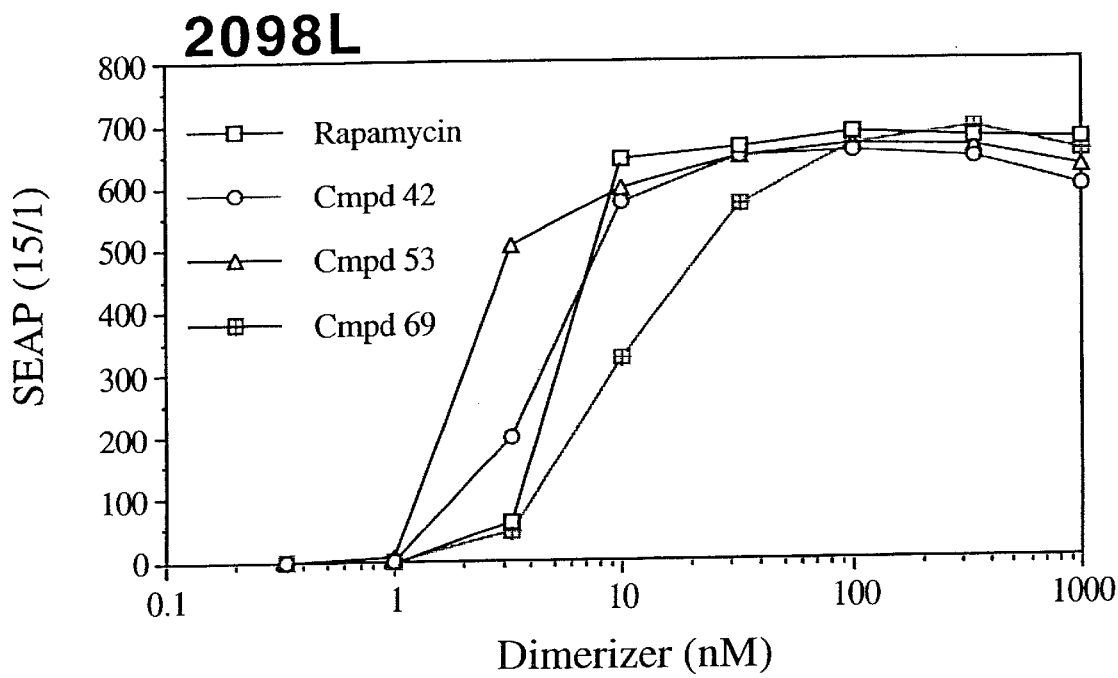
FIG. 2D depicts results of transcription assays using rapalogs 42, 53 and 69, synthesized as described herein, as the dimerizers. The rapalogs were tested in cells expressing a mutant FRB in which Thr 2098 was replaced by Leu. A rapamycin control is shown.
Figure 2E:
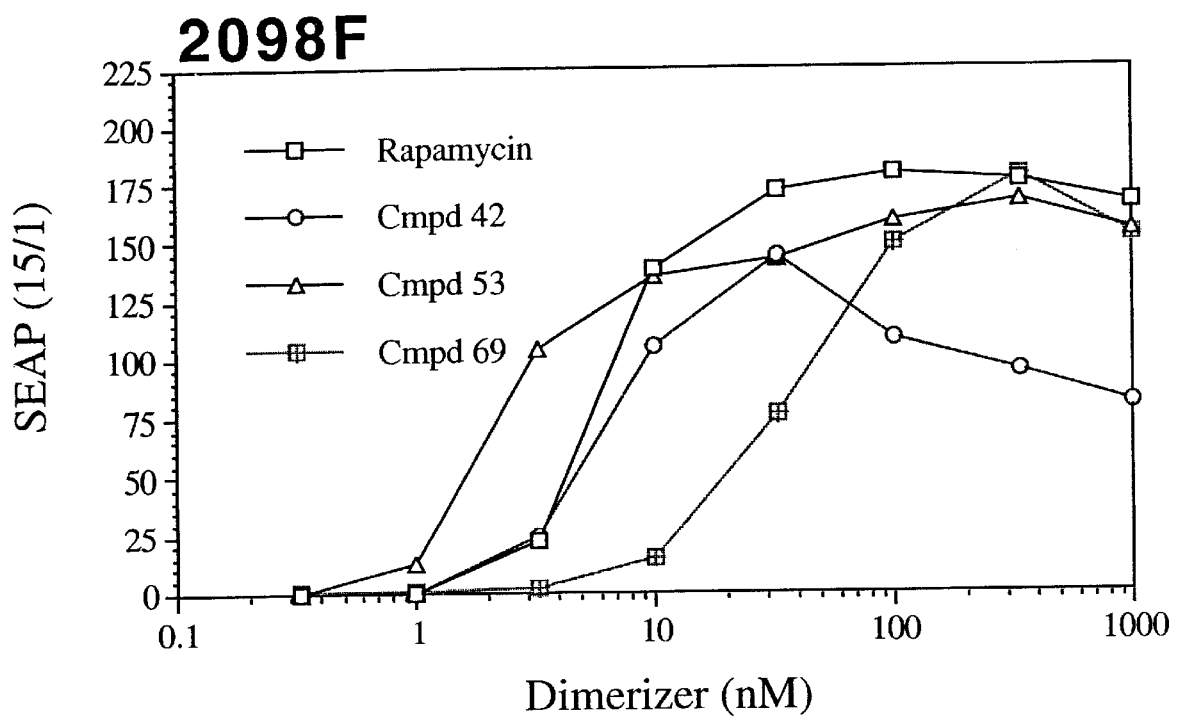
FIG. 2E depicts results of transcription assays using rapalogs 42, 53 and 69, synthesized as described herein, as the dimerizers. The rapalogs were tested in cells expressing a mutant FRB in which Thr 2098 was replaced by Phe. A rapamycin control is shown.

In some experiments, pCGNN-1FRB(T2098L)-p65 (361–550) was used in place of pCGNN-1FRB-p65 (361–550) to generate an FRB fusion protein containing an engineered FRB domain. In control experiments where the DNA binding domain or activation domain were omitted, an equivalent amount of empty pCGNN expression vector was substituted. For detailed information on the assembly and use of constructs including those mentioned herein, see WO 96/41865 (Clackson et al), especially the Examples therein (which are specifically incorporated by reference herein). Following lipofection (for 5 hours) 500 ul medium containing the indicated amounts of rapalog was added to each well. After 24 hours, medium was removed and assayed for SEAP activity as described (Spencer et al, Science 262:1019–24, 1993). Human fibrosarcoma cells transiently transfected with a SEAP target gene and plasmids encoding representative ZFHD-FKBP- and FRB-p65-containing fusion proteins exhibited rapalog-dependent and dose-responsive secretion of SEAP into the cell culture medium. SEAP production was not detected in cells in which one or both of the transcription factor fusion plasmids was omitted, nor was it detected in the absence of added rapalog. As shown in FIG. 1, cells transfected with wild-type FKBP and FRB constructs exhibited SEAP production at dimerizer concentrations as low as 1 nM. FIG. 2 illustrates preferential stimulation of SEAP production in cells expressing a mutant FRB (T2098L, FIGS. 2B and 2D; 12098F, FIG. 2E) as compared to wild-type (FIGS. 2A and 2C). Similar results have been obtained when the same transcription factors were used to drive rapalog-dependent activation of an hGH target gene or a stably integrated version of the SEAP reporter gene made by infection with a retroviral vector.

Example 13

Mutagenesis and Phage Display to Generate Modified Ligand-Binding Domains Complementary to Various Rapalogs

A. Engineered FKBP and FRB Domains

We have designed and prepared recombinant DNA constructs encoding the fusion proteins tabulated below which bear illustrative modified ligand-binding domains. Except a otherwise stated, mutants were generated using oligonucleotide-mediated site-directed mutagenesis according to standard methods (Kunkel, T. A., Bebenek, K. and McClary, J. 1991. Meth Enzymol. 204, 235–139), and confirmed by dideoxy sequencing.

Fusion Proteins containing modified FKBP domains (F36V hFKBP12)---p65
(F36V hFKBP12)---(F36V hFKBP12)---p65
(F36V hFKBP12)---(F36V hFKBP12)---(F36V hFKBP12)---p65
(F36M hFKBP12)---p65
(F36M hFKBP12)---(F36M hFKBP12)---p65
(F36M hFKBP12)---(F36M hFKBP12)---(F36M hFKBP12)---p65
(F36V hFKBP12)---ZFHD1
(F36V hFKBP12)---(F36V hFKBP12)---ZFHD1
(F36V hFKBP12)---(F36V hFKBP12)---(F36V hFKBP12)---ZFHD1
(F36M hFKBP12)---ZFHD1
(F36M hFKBP12)---(F36M hFKBPI2)---ZFHD1
(F36M hFKBP12)---(F36M hFKBP12)---(F36M hFKBP12)---ZFHD1
myr-(F36V hFKBP12)---(F36V hFKBPI2)---Fas
myr-(F36M hFKBP12)---(F36M hFKBP12)---Fas
myr-(F36A hFKBP12)---(F36A hFKBP12)---Fas
myr-(F36S/F99A hFKBP12)---(F36S/F99A hFKBP12)---Fas notes:
1. "hFKBP12" indicates amino acids 1–107 of human FKBP12 referred to previously
2. "p65" indicates residues 361–550 of p65
3. "Fas" indicates residues 175–304 of human Fas
4. "ZFHD1" is as described elsewhere
5. "myr" indicates the src myristoylation sequence
6. mutations are indicated using the previously described convention We have also prepared constructs encoding the following FRB fusion proteins:

Fusion Proteins containing modified (hFRAP) FRB domains (T2098A FRB)---p65
(T2098N FRB)---p65
(D2102A FRB)---p65
(Y2038H FRB)---p65
(Y2038L FRB)---p65
(Y2038A FRB)---p65
(F2039H FRB)---p65
(F2039L FRB)---p65
(F2039A FRB)---p65

(K2095S/D2096N/T2098N FRB)---p65
(TOR2 FRB)---p65 notes:
1. "p65" indicates p65 residues 361–550, as above
2. "FRB" indicates the 89 amino acid FRB of human FRAP
3. "TOR2 FRB" indicates amino acids 1961–2052 of S. cerevisiac TOR2

Yeast and Candida FRBs, modified by analogy to the modified hFRAP FRB domains discussed herein, may also be prepared by substitution of a codon for a different amino acid in place of one or more of the two conserved Phe residues and the conserved Asp and Asn residues within each of their FRB domains. Illustrative modified FRB domains derived from TOR 1 and TOR2, include the following:

| Modified TOR1 and TOR2 FRB Domains | |
|---|---|
| TOR1 | TOR2 |
| F1975H | F1978H |
| F1975L | F1978L |
| F1975A | F1978A |
| F1975S | F1978S |
| F1975V | F1978V |
| F1976H | F1979H |
| F1976L | F1979L |
| F1976A | F1979A |
| F1976S | F1979S |
| F1976V | F1979V |
| D2039A | D2042A |
| N2035A | N2038A |
| N2035S | N2038S |

These modified TOR1 and TOR2 FRBs are designed for use with rapalogs containing C7 substituents

B. Testing Rationally Designed FKBP Mutants for Binding to Rapalogs

An expression vector based on pET20b (Novageni) was constructed using standard procedures that expresses FKBP preceded by a hexahistidine tag and a portion of the H. influenza hemaglutinin protein that is an epitope for the monoclonal antibody 12CA5. The sequence of the protein encoded by this vector is as follows:

```
His6  HA tag       FKBP->
MHHHHHHYPYDVPDYAAMAHMGVQVETISPGDGRTFPKRGQTCVVHYTGMLEDGKKFDSSR
DRNKPFKFMLGKQEVIRGWEEGVAQMSVGQRAKLTISPDYAYGATGHPGIIPPHATLVFDV
ELLKLE                                              (SEQ ID NO 21)
```

To generate expression vectors for FKBPs mutated at rapamycin contact residues, oligonucleotide-mediated site-directed mutagenesis was performed on the single-stranded form of the vector prepared from E. coli CJ236, as described (Kunkel, T. A., Bebenek, K. and McClary, J. 1991. Meth Enzymol. 204, 235–139). Mutants were confirmed by dideoxy sequencing. Mutant proteins were expressed in E. coli BL21(DE3) (Novagen) as described (Wiederrecht, G. et al. 1992. J. Biol. Chem. 267,21753–21760), and purified to homogeneity as described (Cardenas, M. E. et al. 1994. EMBO J. 13, 5944–5957).

Using this protocol the following mutant human FKBP12 proteins were generated, using the indicated oligonucleotide primers (mutated bases in upper case; 5'->3'):

Mutants designed for binding to C24 rapalogs:

| | | |
|---|---|---|
| Phe46His | agcataaacttaTGgggcttgtttctg (SEQ ID NO 22) | (1) |
| Phe46Leu | agcataaactTaagggcttgtttctg (SEQ ID NO 23) | (2) |
| Phe46Ala | agcataaacttaGCgggcttgtttctg (SEQ ID NO 24) | (3) |
| Phe48His | ttgcctagcataTGcttaaagggcttg (SEQ ID NO 25) | (4) |
| Phe48Leu | ttgcctagcatTaacttaaagggcttg (SEQ ID NO 26) | (5) |
| Phe48Ala | ttgcctagcataGCcttaaagggcttg (SEQ ID NO 27) | (6) |
| Glu54Ala | cctcggatcaccGCctgcttgcctag (SEQ ID NO 28) | (7) |
| Val55Ala | cagcctcggatcGCctcctgcttgcc (SEQ ID NO 29) | (8) |

Mutants designed for binding to C13/C14 rapalogs:

| | | |
|---|---|---|
| Phe36Ala | ccgggaggaatcGGCtttctttccatcttc (SEQ ID NO 30) | (9) |
| Phe36Val | ccgggaggaatcGACtttctttccatcttc (SEQ ID NO 31) | (10) |
| Phe36Ser | ccgggaggaatcAGAtttctttccatcttc (SEQ ID NO 32) | (11) |
| Phe36Met | ccgggaggaatcCATtttctttccatcttc (SEQ ID NO 33) | (12) |
| (Phe36Met + Phe99Ala) | aagctccacatcGGCgacgagagtggc (SEQ ID NO 34) + primer 12 | (13) |
| (Phe36Met + Phe99Gly) | aagctccacatcGCCgacgagagtggc (SEQ ID NO 35) + primer 12 | (14) |
| (Phe36Ala + Phe99ALa) | primer 9 + primer 13 | |
| (Phe36Ala + Phe99Gly) | primer 9 + primer 14 | |
| Tyr26Ala | caagcatcccggtgGCgtgcaccacgcag (SEQ ID NO 36) | (15) |
| Asp37AIa | tcccgggaggaaGCaaatttctttccatc (SEQ ID NO 37) | (16) |

Mutant designed for binding to C28/C30 rapalogs:

| | | |
|---|---|---|
| Glu54Ala | cctcggatcaccGCctgcttgcctag (SEQ ID NO 38) | (17) |

To assay the relative binding affinity of rapamycin and rapalogs to FKBP mutants, a competitive fluorescence polarization (FP) assay is used that relies on the retention of FK506 (and hence probe) binding affinity by the mutants. The procedure is identical to that described in Example 12 except that a direct binding assay is first performed to determine the dilution (concentration) of mutant FKBP to use in the competition reactions in order to obtain sub-saturation. Serial dilutions of mutant FKBP are made in FP buffer (Example 12) in 100 µl volumes in Dynatech microfluor plates, and then 100 µl of 10 nM AP1491 (probe) in [FP buffer+2% ethanol] added to each well. Equilibration and plate reading are as in Example 12. A plot of mP units vs concentration of FKBP mutant is fit to following equation:

$$y=M3+(((x+M1+M2)-SQRT(((x+M1+M2)^2)-(4*x*M1)))/(2*(M1)))*(M4-M3)$$

and the final mutant concentration/dilution at which 90% of probe is specifically bound is determined by interpolation. This final concentration is then used in a competition FP assay carried out as in Example 12, with 2× the final concentration of mutant replacing 11.25 nM FKBP in the protocol. Instead of 90% saturation, 75% can be selected to impart greater sensitivity to the competition assay. Serial dilutions of rapamycin analogs are used as competitor and the results are expressed as IC50 for each rapalog binding to each mutant.

C. Testing Rationally Designed FRB Mutants for Binding to FKBP-Rapalog Complexes A NcoI-BamHI fragment encoding residues 2021–2113 (inclusive) of human FRAP was generated by PCR with primers 28 and 29 (below), and cloned into a derivative of pET20b(+) (Novagen) in which the NdeI site is mutated to NcoI, to create pET-FRAP(2021–2113). Single-stranded DNA of this vector was used as a template in site-directed mutagenesis procedures, as described above, to generate vectors encoding FRAPs mutated at rapamycin contact residues. Mutants were confirmed by dideoxy sequencing. Mutants were then amplified by PCR using primers (30 and 31) that append XbaI and SpeI sites, and cloned into XbaI-SpeI digested pCGNN-FRB-p65(361–550) (Example 7) to generate a series of constructs directing mammalian expression of chimeric proteins of the form E-N-mutant FRAP(2021–2113)-p65(361–550), where E indicates HA epitope tag and N indicates nuclear localization sequence. Constructs were verified by restriction digestion and dideoxy sequencing.

Using this procedure the following constructs encoding candidate mutant FRAPs for binding to C7 rapalogs, each fused to the p6$^5$(361–550) activation domain, were generated using the indicated oligonucleotide primers (mutated bases in upper case; 5'->3'):

| | | |
|---|---|---|
| Tyr2038His | cctttccccaaagtGcaaacgagatgc (SEQ ID NO 39) | (18) |
| Tyr2038Leu | cctttccccaaagAGcaaacgagatgc (SEQ ID NO 40) | (19) |

```
Tyr2038Ala              cctttccccaaagGCcaaacgagatgc              (20)
                        (SEQ ID NO 41)

Phe2038His              gttcctttccccAtGgtacaaacgagatg            (21)
                        (SEQ ID NO 42)

Phe2038Leu              gttcctttccccTaagtacaaacgagatg            (22)
                        (SEQ ID NO 43)

Phe2038Ala              gttcctttccccaGCgtacaaacgagatg            (23)
                        (SEQ ID NO 44)

Thr2098Ala              gtcccaggcttggGCgaggtccttgac              (24)
                        (SEQ ID NO 45)

(Lys2095Ser + Asp2096Asn + Thr2098Asn) gtcccaggcttggTTgaggrrccAgacattccctgatttc  (25)
                        (SEQ ID NO 46)

Thr2098Asn              gtcccaggcttggltgaggtccttgac              (26)
                        (SEQ ID NO 47)

Asp2102Ala              catgataatagaggGCccaggdtgggtg             (27)
                        (SEQ ID NO 48)
```

To assay the relative binding affinity of these mutants for complexes of FKBP with rapamycin and various rapalogs, each construct is transiently co-transfected into human HT1080B14 cells, as described in Example 8. Following transfection, serial dilutions of rapamycin or rapalog are added to the culture medium. After 24 hours, SEAP activity is measured as described in Example 8; the potency of SEAP activation at various rapalog concentrations is proportional to the affinity of the FRAP mutant for the complex between FKBP and the rapalog.

PCR primers (restriction sites upper case; 5'->3'):

```
gcatcCCATGGcaatcctctggcatgagatgtggCatgaaggCCtggaag    (28)
(SEQ ID NO 49)

cgtgaGGATCCtactttgagattcgtcggaacac                    (29)
(SEQ ID NO 50)

gcatcTCTAGAatcctctggcatgagatgtggcatgaaggcctggaag      (30)
(SEQ ID NO 51)

ggtctGGATCCctaataACTAGTctttgagattcgtcggaaCaCatg       (31)
(SEQ ID NO 52)
```

D. Functional Display of FKBP and FRB Domains on Filamentous Bacteriophage: one Approach to Selection as an Alternative to Rational Design of Modified Domains A phage display system for the display and selection of mutant FKBP and FRB domains is disclosed in detail in WO 96/41865 (Clackson et al), including vector construction, preparation of His6-flag-FKBP, pCANTAB-AP-FKBP, Binding enrichments, Primers, the Sequence of pCANTAB-AP-FRAP(2015–2114) and pCANTAB-AP-FKBP, the synthesis of biotinylated FK506 for affinity enrichment studies, functional FKBP display by competitive ELISA using biotinylated FK506, generation of a library of mutant FKBPs on phage targetted to the C13 and C14 positions of rapamycin andliibrary sorting.

Example 14

Rapamycin-Dependent Activation of Signal Transduction

Many cellular receptors can be activated by aggregation, either by their physiological ligand or by anti-receptor antibodies. Additionally, the aggregation of two different proteins can often trigger an intracellular signal. Rapamycin and its analogs may be used to trigger activation of a receptor effector domain by oligomerizing chimeric proteins, one of which contains one or more FKBPs and an effector domain and the other of which contains one or more FRAP domains and an effector domain. This scheme is illustrated in FIG. T1(a). While both proteins are shown anchored to the membrane, a single one could be membrane anchored, and addition of rapamycin or analog would recruit the second protein to the membrane via dimerization. Membrane anchoring may be effected through a transmembrane protein anchor or through lipid modification of the protein (s), such as myristoylation. The same effector domain may be present on both proteins, or different protein domains that interact functionally may be used, such as a protein kinase and a protein kinase substrate. Alternatively, a second effector may serve to inhibit the activity of the first effector.

We note that in some embodiments, the chimeric proteins are mixed chimeras, discussed previously, and contain FKBP and FRAP domains together with the heterologous efector domain. Oligomerization of a single mixed chimera may also be used to activate signal transduction, as shown in FIG. T1(b). Here rapamycin is shown to dimerize two identical copies of the protein. Reiteration of the FKBP and FRAP domains permits higher multiples to occur, subject to geometric constraints.

Two examples of the use of rapamycin in signal transduction are to trigger receptor tyrosine kinase activation and to trigger apoptosis via Fas activation, both of which are discussed below. Unless otherwise mentioned all DNA manipulations were performed following standard procedures (F. M. Ausubel et al., Eds., Current Protocols in Molecular Biology, John Wiley & Sons, New York, 1994) and all protein protocols were performed following standard procedures (Harlow, E. and Lane, D. 1988. Antibodies, a Laboratory Manual. Cold Spring Harbor Laboratory, Cold Spring Harbor.). All PCR products used to make constructs were confirmed by sequencing.

A. Rapamycin-inducible receptor tyrosine kinase activation.

1. Construction of pCM, an expression vector containing a myristylation signal.

A XbaI-Myr-BamHI cassette, obtained by annealing oligonucleotides 1 and 2, was digested with XbaI/BamHI and cloned into the XbaI/BamHI site of the pCG expression vector (Tanaka, M. and Herr, W. 1990. Cell 60: 375–386) to create pCGM. (For oligonucleotide sequences, see (7) below). This oligonucleotide cassette consists of an inframe XbaI site followed by sequence encoding for the first 15 amino acids residues of c-Src tyrosine kinase that has been shown to allow myristoylation and target protein to the plasma membrane (Cross et al., 1984. MCB. 4:1834–1842). The myristoylation domain is followed by an inframe SpeI site and stop codons. The XbaI site in the pCG vector is placed such that it adds two amino acids between the initiating Met and the sequence cloned. Since the spacing between the initiating Met and the myristylated Gly is crucial for membrane localization of c-Src (Pellman et al. 1985. PNAS. 82: 1623–1627) the XbaI site following the ATG in pCGM was deleted by site directed mutagenesis following manufacturers protocol (Muta-Gene, BioRad). To facilitate future cloning steps the SpeI site in the myristylation cassette was mutated to a XbaI site. Single stranded uracil-DNA of pCGM was prepared and the mutagenesis was carried out using both oligonucleotide 3 (to delete the XbaI site following ATG and add an EcoRI site 5' to ATG) and oligonucleotide 4 (to change the SpeI site following the myristylation domain to a XbaI site). The resulting sequence surrounding the ATG of the pCM vector was confirmed by sequencing using oligonucleotide 5 (see sequence 1, (8) below).

2. Addition of FKBPs and an epitope tag to pCM generates pCMF1/2/3.HA.

A SpeI-HA-BamHI cassette was prepared by annealing complementary oligonucleotides (oligonucleotides 6 and 7). This cassette has an inframe SpeI site followed by nine amino acids of H. influenzae hemaglutinin gene that is recognized by the monoclonal antibody 12CA5, stop codons and a BamHI site. The SpeI-HA-BamHI cassette was sub cloned into the SpeI/BamHI site of pCGNNF1, pCGNNF2 and pCGNNF3. Subsequently, the 1/2/3 copies of FKBP fused with HA epitope was sub cloned as an XbaI/BamHI fragment into pCM. The resulting plasmid (pCMF1/2/3.HA) has the following features: myristylation domain; an inframe XbaI site; one/two/three copies of FKBP; an inframe SpeI site; a HA epitope tag; and stop codons.

3. Addition of FRBs and an epitope tag to pCM generates pCMFR1/2/3.Flag.

A SpeI-Flag-BamHI cassette can be prepared by annealing complementary oligonucleotides (oligonucleotides 8 and 9). This cassette has the same features as the SpeI-HA-BamHI cassette described above with the exception that the inframe SpeI site is followed by sequence that codes for eight amino acids (DYKDDDDY, SEQ ID NO 53) (Hopp et al., 1988. Biotech. 6: 1205–1210) that is recognized by a monoclonal antibody anti-FLAG.M2 (Kodak Scientific Imaging Systems). The SpeI-Flag-BamHI cassette is sub cloned into the SpeI/BamHI site in pCGNN-1FRB, pCGNN-2FRB and, pCGNN-3FRB. Subsequently 1/2/3 copies of FRB domain-Flag epitope fusions are sub cloned as a XbaI/BamHI fragment into pCM. The resulting plasmid (pCMFR1/2/3.Flag) has the following features: myristylation domain; an inframe XbaI site; one/two/three copies of FRB; an inframe SpeI site; a Flag epitope tag; and stop codons.

4. Fusion of FKBP and FRB constructs to receptor tyrosine kinase cytoplasmic domain The cytoplasmic domain of receptor tyrosine kinase of choice (e.g., EGFR, erbB-2, PDGFR, KDR/Flk-1, Flt-1) is PCR amplified with inframe 5'XbaI and 3' SpeI sites. The PCR product may be subcloned either into the inframe XbaI site such that the XbaI site is restored, or into the inframe SpeI site such that the SpeI site is restored in pCMFR series or pCMFseries vectors (see above). As a result, the FKBP/FRB domain(s) can be placed either C-terminal or NH2-terminal to the cytoplasmic domain of the receptor tyrosine kinase. The vectors are constructed such that (i) the cytoplasmic domain of a given receptor is fused to both FKBP and FRB (for e.g., EGFR cytoplasmic domain fused to either FKBP or FRB) or (ii) can be constructed such that cytoplasmic domains of two different receptors are fused to FKBP and FRB (for e.g., EGFR cytoplasmic domain fused to FKBP and erbB-2 cytoplasmic domain fused to FRB). In the former case (i) addition of the drug, rapamycin, will induce the formation of homodimers (e.g., EGFR/EGFR) while, in the latter (ii) addition of the drug will induce heterodimer (e.g., EGFR/erbB-2) and result in activation of the signal transduction cascade.

5. Testing the constructs

To test the ability of rapamycin or analog to induce dimerization of FKBP- and FRB-receptor cytoplasmic domain fusions, the constructs of choice (e.g., pCMEGFR-FR1 and pCMEGFR-F1) are cotransfected into Cos-1 cells by lipofection (Gibco BRL). Three days after transfection the cells are induced with rapamycin and lysed in lysis buffer (1% Triton X-100; 50 mM Tris.cl pH8.0; 150 mM NaCl; 5 mM NaF; 1 mM sodium ortho vanadate; 10 ug/ml aprotinin; 10 ug/ml leupeptin). The fusion proteins from rapamycin-treated and untreated cell lysates are immunoprecipitated with anti-Flag and 12CA5 antibodies and immunoblotted with anti-phosphotyrosine antibody. The choice of cell type; the amount of DNA transfected; the concentration of rapamycin used and the duration of drug treatment are varied to achieve optimal results.

6. Rapamycin-inducible cell growth

A selected mammalian cell line (e.g., NIH3T3) is cotransfected with constructs encoding for FRB and FKBP fusion proteins (e.g., pCMEGFR-FR1 and pCMEGFR-F1) and stable cell lines expressing the fusion proteins are established. -To determine whether rapamycin-inducible activation of receptor cytoplasmic domain will induce cell proliferation, stable cell lines expressing the fusion proteins are grown either in the presence or absence of rapamycin and the changes in cell growth rate are determined by routine procedures (e.g., by monitoring cell number; by determining the 3H thymidine incorporation rate, etc.). The choice of receptor tyrosine kinase; the type of receptor activation (homodimer vs. heterodimer) may be chosen to obtain optimal results.

7. Oligonucleotide sequences

```
                                            (SEQ ID NO 54)
1: CATGTCTAGAGGGAGTAGCAAGAGCAAGCCTAAG GACCCCAGCCAG

CGCACTAGTTAAGAATTCTGATGAT CAGCGGATCCTAGC (SEQ ID NO 55)
2: GCTAGGATCCGCTGATCATCAGAATTCTTAACTAGTG

CGCTGGCTGGGGTCCTTAGGCTTGCTCTTGCTACTCC

CTCTAGACATG (SEQ ID NO 56)
3: CGCCTTGTAGAATTCGCGCGTATGGGAGTAGCAAGA (SEQ ID NO 57)
4: CCCAGCCAGCGCTCTAGATAAGAATTCTGA (SEQ ID NO 58)
5: AAGGGTCCCCAAACTCAC (SEQ ID NO 59)
6: GCATGACTAGTTATCCGTACGACGTACCAGACT

ACGCATAAGAAAAGTGAGGATCCTACGG (SEQ ID NO 60)
7: CCGTAGGATCCTCACTTTTATGCGTAGTCTGGT

ACGTCGTACGGATAACTAGTCATGC (SEQ ID NO 61)
8: CCGTAGGATCCTCACTTTTCTTAATAATCGTCATCG

TCTTTGTAGTCACTAGTCATGC (SEQ ID NO 62)
9: GCATGACTAGTGACTACAAAGACGATGACGATTA

TTAAGAAAAGTGAGGATCCTACGG
```

8. Sequence 1:

```
                   M   G   S   S   K   S   K   P   K
CGC CTT GTA GAA ttc GCG CGT ATG ggg agt agc aag agc aag cct aag D   P   S   Q   R   S   R   stop            stop
gac ccc agc cag cgc tct aga taa gaa ttc tga tga tca gcG GAT CCT

GAG AAC T (SEQ ID NO 64)
```

The modified sequences are in lowercase bold and the intitiating ATG is underlined. Sequences in uppercase are from the parental pCG backbone.

B. Rapamycin-Inducible Apoptosis

The ability to control Fas activation and trigger apoptosis via a small molecule has applications both in gene therapy, where it may be used to selectively eliminate engineered cells, and in experimental systems. The proteins described here are anchored to the membrane via the low affinity NGF receptor, also called p75. It should be appreciated, however, that another protein anchor could be readily substituted. p75 is useful experimentally because of the availability of antibodies to its extracellular domain, and its lack of high affinity interaction with any identified ligand (Bothwell, M. 1995. Annu. Rev. Neurosci. 18:223–253).

1. 2-Protein Rapamycin-Regulated Fas Activation
(a) Construction of the p75 vector Vectors to direct the expression of FRAP-Fas fusion proteins containing the extracellular and transmembrane domain of the low affinity NGF receptor (also known as p75) were derived from the mammalian expression vector pJ7W (Morgenstern, J. P. and Land, H. 1990. Nucleic Acids Res. 18:1068), modified by substitution of a pUC backbone for the original pBR backbone using standard methods. We call this vector pA7W. Inserts cloned into the polylinker sites of this plasmid are transcribed under the control of the simian CMV promoter and enhancer sequences. The polylinker follows the CMV sequence with HindIII-SalI-XbaI-BamHI-SmaI-SstI-EcoRI-ClaI-KpnI-BglII. Any mammalian expression vector with suitable cloning sites and promoter could be substituted.

A restriction fragment encoding a fragment of p75 flanked by HindIII and XbaI sites was generated by PCR using primers J1 (5') and J2 (3'), based on the sequence of p75 Johnson, D., Lanahan, A., Buck, C. R., Shegal, A., Morgan, C., Mercer, E., Bothwell, M., Chao, M. 1986. Cell 47:545–554). The original source of the PCR template was a clone derived from a human brain library, using primers similar to J1 and J2 but with different restriction sites. The 5' end of the resulting fragment contains a HindIII site followed by an EcoRI site, a Kozak sequence and the initiation of p75 coding sequence (amino acid 1). The 3' end generated encodes the receptor sequence up to and including amino acid 274, 2 amino acids past the predicted membrane spanning sequence, followed by an XbaI site. Analogous portions of other transmembrane receptors can be substituted for this fragment. The PCR product was subcloned as a HindIII-XbaI fragment into HindIII-XbaI cut pA7W, generating pA7Wp75. The construct was verified by restriction analysis and DNA sequencing.

(b) Addition of Fas to pA7Wp75

XbaI-SpeI fragments encoding Fas amino acids 206–304 (FasS) and Fas amino acids 206–319 (FasL) were made by PCR and subcloned into pA7Wp75 cut with the same enzymes. The primers used were J3 (5') and J4 or J5 (3'). J5 generates a fragment of Fas that ends beyond its termination codon; when cut with SpeI, the nucleotides encoding the terminal 15 aa of Fas are removed to give a truncated form of intracellular Fas we call FasS. Removal of these 15 aa increases the activity of Fas in some cell types (Itoh, N., and Nagata, S. 1993. J. Biol. Chem 268:10932). Primer J4 replaces the natural termination codon of Fas with a SpeI site, and also mutates the original SpeI site contained in Fas, generating FasL. The plasmids generated from subcloning these fragments are pA7Wp75-FasS and pA7Wp75-FasL, respectively. These construct were verified by restriction analysis and DNA sequencing. To attach an epitope tag to these inserts, the XbaI-SpeI Fas fragments were isolated and ligated into the XbaI-SpeI cut backbone of pCMF1/2/3.HA, plasmids described above which encode an epitope tag of 9 amino acids from the H. influenza haemagglutinin protein (E) 3' to the SpeI site, followed by a BamHI site. Cutting the resultant plasmid with XbaI and BamHI generated fragments encoding Fas followed by the epitope tag (designated E for these constructs).

(c). p75-FRAP-Fas-epitope fusion proteins: addition of FRAP-containing fragments to pA7Wp75-FasSE and pA7Wp75-FasLE to generate p75-FRAPx-FasSorLE and p75-FasSorL-FRAPxE The XbaI-SpeI fragments containing a portion of FRAP are described previously in this document. These XbaI-SpeI fragments were inserted into either the XbaI site directly after the p75 coding sequence to generate p75-FRAPx-FasSorLE or into the SpeI site directly after the Fas fragment to generate p75-FasSorL-FRAPxE. Alternatively, more than one FRAP fragment is subcloned in, either as a FRAPn fragment, or by sequential subcloning of XbaI-SpeI fragments into the Spe I site available after subcloning the first FRAP into either XbaI or SpeI. Thus the final series of vectors encodes (from the N to the C terminus) p75 extracellular and transmembrane sequence, one or more FRAP-derived domains fused N- or C-terminally to one or more Fas intracellular domains, and an epitope tag.

(d) p75-FKBP-Fas fusion proteins: addition of FKBP-containing fragments to pA7Wp75-FasSE and pA7Wp75-FasLE to generate p75-FKBPn-FasSorL or p75-FasSorL-FKBPn The XbaI-SpeI fragments containing one or more FKBPs have been described elsewhere in this document. These fragments were inserted into either the XbaI site directly after the p75 coding sequence to generate p75-FKBPn-FasSorL or into the SpeI site directly after the Fas fragment to generate p75-FasSorL-FKBPn. Thus the final series of vectors encodes (from the N- to the C-terminus) p75 extracellular and transmembrane sequence, one or more FKBPs fused N- or C-terminally to one or more Fas intracellular domains, and an epitope tag.

(e) Assay of Rapamycin-Mediated Fas Activation

The ability of expression of a protein containing Fas and FRAP domains and a protein containing Fas and FKBP domains to activate Fas and trigger cell death upon addition of rapamycin can be tested in either transiently or stably transfected cells.

For transient transfections, the two plasmids to be tested are cotransfected into a cell line such as HT1080 by a standard method such as lipofection, calcium phosphate precipitation or electroporation. One or more days after transfection, cells are treated with no addition or one or more concentrations of rapamycin or one or more concentrations of a dimerizing agent such as FK1012. The FK1012 serves as a positive control that the FKBP-Fas construct is functional. Several hours to 1 day later, the cells are monitored for response by one of several methods. Cell lysates were prepared by conventional means and used to generate Western blots that are probed with antibody directed against HA or against the extracellular domain of p75. Alternatively, cells can be assayed by collection in isotonic solution plus 10 mM EDTA, stained with anti-p75 monoclonal antibody and labeled secondary antibody, and the positive cells measured by FACS. A decrease in either Western blot signal or FACS signal upon treatment indicates sucessful induction of cell death (or decrease in protein expression). In addition, commercially available kits can be used to monitor apoptosis.

To stably transfect cells, a vector encoding a selectable marker such as neomycin resistance is cotransfected along with the plasmids described. Two to three days after transfection, cells are plated into G418 and the resistant population or clones are isolated by standard means. These populations can then be monitored directly for induction of apoptosis by treatment with dimerizer followed by cell counting or other measure of cell viability.

An alternative means of generating stable cell lines expressing the constructs of interest is to subclone the inserts into a retroviral vector. The inserts are excisable with Eco RI to facilitate this subcloning. The vector is then used to make transducing supernatants by a packaging cell using conventional methods.

2. Single Protein Rapamycin-Regulated Fas Activation (a). Construction of FKBP-FRAP chimeric fragments FKBP-FRAP fusion constructs for rapamycin-dependent homodimerization of Fas intracellular domain i. Structure-Assisted Design In order to design molecules containing both FRAP and FKBP domains that are capable of rapamycin-dependent homodimerization, the three dimensional structure of the ternary complex between human FKBP12, rapamycin, and a portion of human FRAP encompassing the minimal FRB domain may be considered. Requirements for homodimerization of two molecules of fusion proteins containing FRAP, FKBP and Fas moieties include (i) sufficient length and flexibility of the polypeptide to accomodate the distortions necessary for the FRAP-FKBP interaction to occur between molecules tethered at the membrane, while preserving the ability of aggregated Fas to transduce a signal; and (ii) prevention or minimization of intramolecular dimerization by rapamycin, an event expected to be highly entropically favored due to the chelate effect, and therefore to prevent the desired intermolecular molecular dimerization.

Structural considerations led us to the following design preferences for the fusion constructs:

(i) FRB and FKBP should be joined with a polypeptide linker sufficiently short that intramolecular dimerization is sterically prevented. The currently preferred configuration is FRAP-FKBP as the C-terminus of FRAP and the N-terminus of FKBP are distant, allowing a long linker (>ten amino acids) that should still prevent intramolecular dimerization yet afford flexibility.

(ii) This FRAP-FKBP 'cassette' can be present membrane-proximally (i.e. with Fas domain(s) added to the C-terminus), or membrane distal (with the Fas domain membrane-proximal and the FRAP-FKBP cassette appended C-terminally).

(iii) A long linker should be present N-terminal to the FRAP-FKBP domains, to allow for the structural distortions implied by dimerization at the membrane or if the domains are added C-terminally. Again a N-terminal location of FRAP is preferred as this long linker can then comprise natural FRAP sequence from the region N-terminal to the FRB domain, minimizing the immunogenicity of the chimeric protein.

(iv) Optimal linker lengths and fusion positions for a given protein should be confirmed empirically.

A series of 12 fusions of FKBP and FRAP, designated T1-T12, was designed. Nine were N-FRAP-FKBP-C fusions including between 13, 23 or 33 amino acids N-terminal to Arg2018 (the N-terminal linker), and 4, 7 or 10 residues separating the two proteins. The remaining three were N-FKBP-FRAP-C fusions interposing 3, 0 or -4 residues of FRAP sequence between FKBP Glu107 and FRAP Arg2018.

(ii) Construction

The twelve fusions were made as XbaI-BamHI cassettes that could be cloned directly as a single fragment, using the three-primer PCR splicing method (Yon, J. and Fried, M. 1989. Nucleic Acids Res. 17,4895). Cloning in this way avoided the introduction of restriction sites between the genes that would encode foreign sequence and alter the length of the linker. A mixture of 1 ng each of pCGNN-1FRAPi and pCANTAB-AP-FKBP was amplified using Pfu polymerase with 1 µM each of two outer primers (A and C), in the presence of 0.01 µM of a single 'splice' oligo (B) complementary to both genes that directs the desired fusion. The primers used are tabulated below:

| # | construct | oligos A | oligos B | N-term* C | N-term* (aa) | linker† (aa) |
|---|---|---|---|---|---|---|
| T1 | FRAP(1985-2116)-FKBP | 100 | 102 | 105 | 33 | 4 |
| T2 | FRAP(1995-2116)-FKBP | 93 | 102 | 105 | 23 | 4 |
| T3 | FRAP(2005-2116)-FKBP | 101 | 102 | 105 | 13 | 4 |
| T4 | FRAP(1985-2119)-FKBP | 100 | 103 | 105 | 33 | 7 |
| T5 | FRAP(1995-2119)-FKBP | 93 | 103 | 105 | 23 | 7 |
| T6 | FRAP(2005-2119)-FKBP | 101 | 103 | 105 | 13 | 7 |
| T7 | FRAP(1985-2122)-FKBP | 100 | 104 | 105 | 33 | 10 |
| T8 | FRAP(1995-2122)-FKBP | 93 | 104 | 105 | 23 | 10 |
| T9 | FRAP(2005-2122)-FKBP | 101 | 104 | 105 | 13 | 10 |
| T10 | FKBP-FRAP(2014-2114) | 106 | 107 | 110 | — | 3 |
| T11 | FKBP-FRAP(2018-2114) | 106 | 108 | 110 | — | 0 |
| T12 | FKBP-FRAP(2021-2114) | 106 | 109 | 110 | — | -4 |

*Number of amino acids between the Arg encoded by the 5' XbaI site and FRAP Arg2018 (for fusions T1–T9)
†Number of amino acids between FRAP Ser2112 and FKBP Gly1 (for fusions T1–T9); or between FKBP Glu107 and FRAP Arg 2018 (for fusions T10–T12)

PCR products were purified, digested with XbaI and BamHI, and ligated into XbaI-BamHI digested pCM. The constructs were verified by restriction analysis and DNA sequencing.

Primer sequences and the sequence of a representative FRB-FKBP construct: fusion T6 of FRAP (2005->)-FKBP are disclosed in WO 96/41865 (p. 109).

(b) Addition of FRAP-FKBP chimeric inserts to pA7Wp75-FasSE and pA7Wp75-FasLE

Subcloning of T1 through T12 as XbaI-SpeI fragments into pA7Wp75-FasSE and pA7Wp75-FasLE linearized with XbaI generates p75TFasSorLE. Subcloning into pA7Wp75-FasLE linearized with SpeI generated p75FasSorLT-E. These constructs are listed in Table 1 ((d) below).

(c) Alternative FRAP-Fas-FKBP constructs

Instead of the format of the chimeric fragments T1–T12, the single chain strategy could require a different orientation of domains for optimal activity. To this end, another series of constructs was made in which FKBP and FRB are separated by a Fas fragment. The starting points for these constructs are pCMF1HA, pCMF2HA, and PCMF3HA. Similar to the strategy described above for the construction of chimeric transcription factors, FKBP and FRB fragments (described elsewhere in this document) were cloned into the pCM backbones as XbaI-BamHI fragments that included a SpeI site just upstream of the BamHI site. As XbaI and SpeI produce compatible ends, this allowed further XbaI-BamHI fragments to be inserted downstream of the initial insert. Additionally, cloning of an XbaI-SpeI fragment results in the addition of the fragment at the 5' end of the construct. The final p75-anchored construct was made by subcloning the XbaI-SpeI fragments shown in Table 1 ((d) below) into pA7Wp75-FasSE. A similar series is made by subcloning into pA7Wp75-FasLE. Insertion into vector cut with XbaI resulted in addition of the insert 3' to the p75 fragment. Insertion into this vector cut with SpeI resulted in addition of the insert 3' to the Fas fragment. Insertion into this vector cut with XbaI and SpeI resulted in addition 3' to the p75 fragment, and elimination of the Fas fragment originally in the vector. By using these three subcloning strategies, the following series of constructs was generated. Numerical subscripts define the number of times the domain is reiterated.

TABLE 1

(d)
Code: N = p75 NGF receptor aa 1-274
Fass = Fas aa 206-304
FasL = Fas aa 206-319
K = FKBP aa 2-108
R = FRAP 2012-2113, but other boundaries can be substituted
E = HA epitope followed by termination codons as described in pCMF1/2/3.HA

| NAME | Xba 1-Spe I FRAGMENT SUBCLONED | VECTOR SITE(S) USED TO SUBCLONE INSERT INTO pA7Wp75-FasSE | CONSTRUCT |
|---|---|---|---|
| A1 | K2FasL | Spe I + Xba I | NK2FasLE |
| A2 | R | Spe I | NFasSRE |
| A3 | R | Xba I | NRFasSE |
| A4 | R2 | Spe I | NFasSR2E |
| A5 | R2 | Xba I | NR2FasSE |
| A6 | K2FasSR | Spe I | NFasSK2FasSRE |
| A7 | KFasSR | Spe I | NFasSKFasSRE |
| A8 | K2FasSR2 | Spe I | NFasSK2FasSR2E |
| A9 | KFasSR2 | Spe I | NFasSKFasSR2E |
| A10 | T1 | SpeI | NFasST1E |
| A11 | T2 | Spe I | NFasST2E |
| A12 | T3 | Spe I | NFasST3E |
| A13 | T4 | Spe I | NFasST4E |
| A14 | T5 | Spe I | NFasST5E |
| A15 | T6 | Spe I | NFasST6E |
| A16 | T7 | Spe I | NFasST7E |
| A17 | T8 | Spe I | NFasST8E |
| A18 | T9 | Spe I | NFasST9E |
| A19 | T10 | Spe I | NFasST10E |
| A20 | T11 | Spe I | NFasST11E |
| A21 | T12 | Spe I | NFasST12E |
| A22 | K2FasSR | Xba I | NK2FasSRFasSE |
| A23 | KFasSR | Xba I | NKFasSRFasSE |
| A24 | K2FasSR2 | Xba I | NK2FasSR2FasSE |
| A25 | KFasSR2 | Xba I | NKFasSR2FasSE |
| A26 | T1 | Xba I | NT1FasSE |
| A27 | T2 | Xba I | NT2FasSE |
| A28 | T3 | Xba I | NT3FasSE |
| A29 | T4 | Xba I | NT4FasSE |
| A30 | T5 | Xba I | NT5FasSE |
| A31 | T6 | Xba I | NT6FasSE |
| A32 | 17 | Xba I | NT7FasSE |
| A33 | T8 | Xba I | NT8FasSE |
| A34 | T9 | Xba I | NT9FasSE |
| A35 | T10 | Xba I | NT10FasSE |
| A36 | T11 | Xba I | NT11FasSE |
| A37 | T12 | Xba I | NT12FasSE |
| A38 | K2FasSR | Spe I + Xba I | NK2FasSRE |
| A39 | KFasSR | Spe I + Xba I | NKFasSRE |
| A40 | K2FasSR2 | Spe I + Xba I | NK2FasSR2E |
| A41 | KFasSR2 | Spe I + Xba I | NKFasSR2E |

(e) Termini/junction sequences of fragments, oligos and other details for construction of the inserts which were cloned in 3' to the myristoylation signal sequence as XbaI-BamHI or XbaI-SpeI fragments are disclosed in detail in WO 96/41865.

(f) Rapamycin-regulated apoptosis of stable transsfected human HT1080 cells in culture XbaI-BamHI fragments from constructs A30 and A31 (d, table 1) were cloned into pCM to generate M30 and M31, constructs that direct the expression of MT5FasSE and MT6FasSE, where M denotes a myristoylation domain (see this example sections A.1. and A.8.) and other abbreviations are as described in d, table 1. EcoRI-BamHI fragments containing these expression cassettes were then cloned into the retroviral vector pSMN3 (Example 7). Helper-free retroviruses containing this DNA were generated by transient co-transfection of 293T cells (Pear, W. S. et al. 1993. Proc. Natl. Acad. Sci. USA, 90, 8392–8396) with the constructs and a Psi(−) amphotropic packaging vector. HT1080 cells were infected with viral stock and selected with G418.

To assay apoptosis of the stably transfected pools of cells in response to rapamycin, cells were plated in a 96-well culture plates at 10000 cells/well. After an overnight incubation, serial dilutions of rapamycin were added, together with 50 ng/ml (final) actinomycin D, and incubation continued at 37° C. and 5% CO2 for approximately 20 hours. The media was removed and replaced with 100 μl of media containing 10% alamar blue dye. Plates were incubated as before, and the extent of cell viability assessed periodically by spectrophotometric determination of OD at 570 nm and 600 nm on a microtiter plate reader. Typically reading was continued until control (untreated) wells are at OD 0.2–0.4 after subtraction of blank.

Survival of cells stably transfected with (a) M30 and (b) M31-expressing constructs is potently reduced in the presence of rapamycin, in a dose-dependent manner. The extent of cell death is comparable to that of cells expressing a myristoylated (FKBPx2)-Fas construct (as disclosed in PCT/US94/08008) treated with a synthetic FKBP homodimerizer AP1428. This system may be adapted for use with improved rapalogs of this invention, preferably with one or more mutations in the FKBP and/or FRB domains used.

The full disclosure of each of the patent documents and scientific papers cited herein is hereby incorporated by reference. Those documents serve to illustrate the state of the art in various aspects of this invention. Numerous modifications and variations of the present invention should be apparent to one of skill in the art. Such modifications and variations, including design choices in selecting a heterologous action domain, improved rapalog, fusion protein design, DNA formulation, viral vector or other DNA delivery means, manner and route of transgene administration, etc. are intended to be encompassed by the scope of the invention and of the appended claims.

What is claimed is:

1. A method for multimerizing chimeric proteins in cells which comprises:
   (a) providing cells which contain:
      (i) a first recombinant nucleic acid encoding a first chimeric protein which binds to rapamycin or an analog thereof and which comprises at least one FK506-binding protein (FKBP) domain and at least one protein domain heterologous thereto, wherein the FKBP domain comprises a naturally occurring FKBP or a variant thereof in which up to 10 amino acid residues have been deleted, inserted, or replaced with substitute amino acids;
      (ii) a second recombinant nucleic acid encoding a second chimeric protein which forms a complex with both (a) rapamycin or a rapamycin analog and (b) the first chimeric protein, and which comprises at least one FKBP:rapamycin binding (FRB) domain and at least one domain heterologous thereto, wherein the FRB domain comprises a peptide sequence selected from a naturally occurring FRB domain, or a variant thereof in which up to 10 amino acid residues have been deleted, inserted, or replaced with substitute amino acids; and,
   (b) contacting the cells with a rapalog which forms a complex containing itself and at least one molecule of each of the first and second chimeric proteins, where the rapalog has an immunosup-pressive effect less than 0.01 times that of rapamycin and comprises the substructure of formula I:

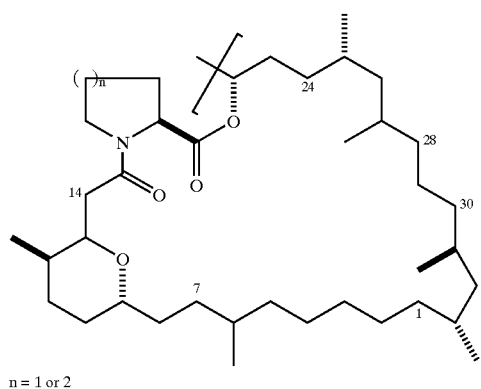

bearing one or more optional substituents, optionally unsaturated at one or more carbon—carbon bonds spanning carbons 1 through 8, as a substantially pure stereoisomer or mixture of stereoisomers, or a pharmaceutically acceptable derivative thereof.

2. A method for multimerizing chimeric proteins in cells which comprises:
   (a) providing cells which contain:
      (i) a first recombinant nucleic acid encoding a first chimeric protein which binds to rapamycin or an analog thereof and which comprises at least one FKBP domain and at least one protein domain heterologous thereto, wherein the FKBP domain comprises a naturally occurring FKBP or a variant thereof in which up to 10 amino acid residues have been deleted, inserted, or replaced with substitute amino acids;
      (ii) a second recombinant nucleic acid encoding a second chimeric protein which forms a complex with both (a) rapamycin or a rapamycin analog and (b) the first chimeric protein, and which comprises at least one FRB domain and at least one domain heterologous thereto, wherein the FRB domain comprises a naturally occurring FRB domain or a variant thereof in which up to 10 amino acid residues have been deleted, inserted, or replaced with substitute amino acids; and
   (b) contacting the cells with a rapalog which forms a complex containing itself and at least one molecule of each of the first and second chimeric proteins, where the rapalog is of the formula:

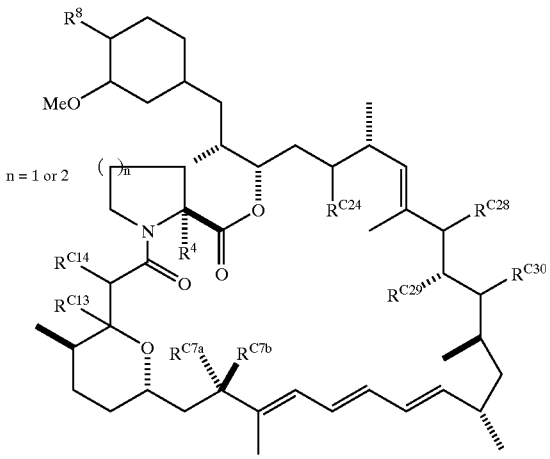

wherein
one of $R^{C7a}$ and $R^{C7b}$ is H and the other is —H, halo, —$R^2$, —$OR^1$, —$SR^1$, —$OC(O)R^1$, —$OC(O)NHR^1$, —$NHR^1$, —$NHR^1R^2$, —$NHC(O)R^1$, or —NH—$SO_2$—$R^1$, where $R^2$=aliphatic, heteroaliphatic, aryl, heteroaryl or alkylaryl, $R^{C30}$ is halo, —$OR^3$ or (=O), $R^{C24}$ is =O, =$NR^4$, =$NOR^4$, =$NNHR^4$, —$NHOR^4$, —$NHNHR^4$, —$OR^4$, —$OC(O)R^4$, —$OC(O)NR^4$, halo or —H, $R^{C14}$ is =O, —$OR^6$, —$NR^6$, —H, —$NC(O)R^6$, —$OC(O)R^6$ or —$OC(O)NR^6$ $R^3$ is H, —$R^7$, —$C(O)R^7$ or —$C(O)NHR^7$ or a cyclic moiety bridging C28 and C30

$R^{C28}$ is halo or —$OR^3$ $R^{C29}$ is H, OH or OMe where each substituent is present in either stereochemical orientation unless otherwise indicated, and where $R^1$, $R^4$, $R^5$, $R^6$, $R^7$, $R^9$, and $R^{10}$ are independently selected from H, aliphatic, heteroaliphatic, aryl or heteroaryl; $R^8$ is H, halo, —CN, =O, —OH, —NR$^9$R$^{10}$, OSO$_2$CF$_3$, OSO$_2$F, OSO$_2$R$^{4'}$, OCOR$^{4'}$, OCONR$^{4'}$R$^{5'}$, or OCON (OR4')R$^{5'}$;
in which one or both of $R^{C13}$ and $R^{C28}$ is a halo substituent; both $R^{C24}$ and $R^{C30}$ are other than =O; one of $R^{C7a}$ and $R^{C7b}$ is H and the other is phenyl, di- or tri-substituted phenyl or a mono- or di-substituted heterocyclic moiety; n is 1; and/or moiety

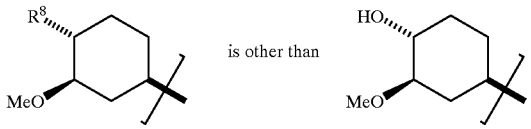

as a substantially pure stereoisomer or mixture of stereoisomers, or a pharmaceutically acceptable derivative thereof.

3. The method of claim 2, wherein both $R^{C24}$ and $R^{C30}$ are moieties other than (=O).

4. The method of claim 3 wherein one or both of $R^{C24}$ and $R^{C30}$ are —OH, —OR1 or halo.

5. The method of any of claims 1–4 wherein at least one of $R^{C7a}$ and $R^{C7b}$ is a moiety other than —OMe.

6. The method of any of claims 1–4 wherein the chimeric protein encoded by the first recombinant nucleic acid comprises at least one FKBP domain whose peptide sequence contains up to three amino acid replacements relative to a naturally occurring FKBP peptide sequence.

7. The method of any of claims 1–4 wherein the chimeric protein encoded by the first recombinant nucleic acid comprises at least one FKBP domain whose peptide sequence contains one amino acid replacement relative to a naturally occurring FKBP peptide sequence.

8. The method of any of claims 1–4 wherein the chimeric protein encoded by the first recombinant nucleic acid comprises at least one FKBP domain whose peptide sequence contains a replacement amino acid for Phenylalanine-36 of a naturally occurring FKBP peptide sequence.

9. The method of any of claims 1–4 wherein the chimeric protein encoded by the second recombinant nucleic acid comprises at least one FRB whose peptide sequence contains up to three amino acid replacements relative to a naturally occurring FRB peptide sequence.

10. The method of any of claims 1–4 wherein the chimeric protein encoded by the second recombinant nucleic acid comprises at least one FRB whose peptide sequence contains one amino acid replacement relative to a naturally occurring FRB peptide sequence.

11. The method of any of claims 1–4 wherein the chimeric protein encoded by the second recombinant nucleic acid comprises at least one FRB whose peptide sequence contains a replacement amino acid for one or more of Tyr2038, Phe2039, Thr2098, Gln2099, Trp2101 or Asp2102 in a naturally occurring FRB peptide sequence.

12. The method of any of claims 1–4 wherein at least one of the chimeric proteins comprises a heterologous domain which is a DNA-binding domain, transcription activation domain or a cellular signaling domain for triggering growth, proliferation, differentiation or apoptosis upon dimerization with another protein containing at least one such signaling domain.

13. The method of any of claims 1–4 wherein the cells are grown in a culture medium and the contacting with a rapalog is effected by adding the rapalog to the culture medium.

14. The method of any of claims 1–4 wherein the cells are present in a whole organism and the contacting with a rapalog is effected by administering the rapalog to the organism.

15. The method of any of claims 2–4 wherein the rapalog has an immunosuppressive effect less than 0.01 times that of rapamycin.

16. The method of claim 15 wherein the cells are present in a whole organism and the contacting with a rapalog is effected by administering the rapalog to the organism.

17. The method of claim 16 wherein the cells are mammalian and the organism is a mammal.

18. The method claim 17 wherein the cells are of primate origin and the organism is a primate.

19. The method of claim 17 wherein the rapalog is administered orally.

20. The method of claim 5 wherein one of $R^{C7a}$ and $R^{C7b}$ is H and the other is phenyl, di- or tri-substituted phenyl or a mono- or di-substituted heterocyclic moiety.

21. The method of claim 5 wherein one of $R^{C7a}$ and $R^{C7b}$ is H and the other is o,p-dialkoxyphenyl or trialkoxyphenyl.

22. The method of claim 5 wherein one of $R^{C7a}$ and $R^{C7b}$ is H and the other is o,p-dimethoxyphenyl, o-methoxy-p-ethoxyphenyl, o-ethoxy-p-methoxyphenyl, o,p-diethoxyphenyl, trimethoxyphenyl or triethoxyphenyl.

23. The method of claim 5 wherein the chimeric protein encoded by the first recombinant nucleic acid comprises at least one FKBP domain whose peptide sequence contains a replacement amino acid for Phenylalanine-36 of a naturally occurring FKBP peptide sequence.

24. The method of claim 5 wherein the cells are present in a whole organism and the contacting with a rapalog is effected by administering the rapalog to the organism.

25. The method of claim 6 wherein the chimeric protein encoded by the second recombinant nucleic acid comprises at least one FRB whose peptide sequence contains up to three amino acid replacements relative to a naturally occurring FRB peptide sequence.

26. The method of claim 6 wherein the chimeric protein encoded by the second recombinant nucleic acid comprises at least one FRB whose peptide sequence contains a replacement amino acid for one or more of Tyr2038, Phe2039, Thr2098, Gln2099, Trp2101 or Asp2102 in a naturally occurring FRB peptide sequence.

27. The method of claim 6 wherein at least one of the chimeric proteins comprises a heterologous domain which is a DNA-binding domain, transcription activation domain or a cellular signaling domain for triggering growth, proliferation, differentiation or apoptosis upon dimerization with another protein containing at least one such signaling domain.

28. The method of claim 6 wherein the cells are present in a whole organism and the contacting with a rapalog is effected by administering the rapalog to the organism.

29. The method of claim 25 wherein at least one of the chimeric proteins comprises a heterologous domain which is a DNA-binding domain, transcription activation domain or a cellular signaling domain for triggering growth, proliferation, differentiation or apoptosis upon dimerization with another protein containing at least one such signaling domain.

30. The method of claim 25 wherein the cells are present in a whole organism and the contacting with a rapalog is effected by administering the rapalog to the organism.

31. The method of claim 30 wherein the cells are of primate origin and the organism is a primate.

32. The method of claim 31 wherein the primate is a human.

33. The method of claim 9 wherein at least one of the chimeric proteins comprises a heterologous domain which is a DNA-binding domain, transcription activation domain or a cellular signaling domain for triggering growth, proliferation, differentiation or apoptosis upon dimerization with another protein containing at least one such signaling domain.

34. The method of claim 9 wherein the cells are present in a whole organism and the contacting with a rapalog is effected by administering the rapalog to the organism.

35. The method of claim 14 wherein the cells are mammalian and the organism is a mammal.

36. The method of claim 35 wherein the rapalog is administered orally.

* * * * *

SEQUENCE LISTING

```
<160> NUMBER OF SEQ ID NOS: 64

<210> SEQ ID NO 1
<211> LENGTH: 14
<212> TYPE: PRT
<213> ORGANISM: Artificial Sequence
<220> FEATURE:
<223> OTHER INFORMATION: membrane binding domain
<221> NAME/KEY: DOMAIN
<222> LOCATION: (1)..(14)
<223> OTHER INFORMATION: membrane binding domain

<400> SEQUENCE: 1

Met Gly Ser Ser Lys Ser Lys Pro Lys Asp Pro Ser Gln Arg
1               5                   10

<210> SEQ ID NO 2
<211> LENGTH: 4
<212> TYPE: PRT
<213> ORGANISM: Artificial Sequence
<220> FEATURE:
<223> OTHER INFORMATION: organelle binding domain
<221> NAME/KEY: DOMAIN
<222> LOCATION: (1)..(4)
<223> OTHER INFORMATION: organelle binding domain

<400> SEQUENCE: 2

Lys Asp Glu Leu
1

<210> SEQ ID NO 3
<211> LENGTH: 4
<212> TYPE: PRT
<213> ORGANISM: Artificial Sequence
<220> FEATURE:
<223> OTHER INFORMATION: organelle binding domain
<221> NAME/KEY: DOMAIN
<222> LOCATION: (1)..(4)
<223> OTHER INFORMATION: organelle binding domain

<400> SEQUENCE: 3

His Asp Glu Leu
1

<210> SEQ ID NO 4
```

```
<211> LENGTH: 36
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(36)
<223> OTHER INFORMATION: primer

<400> SEQUENCE: 4
gcatgtctag agagatgtgg catgaaggcc tggaag                            36

<210> SEQ ID NO 5
<211> LENGTH: 35
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(35)
<223> OTHER INFORMATION: primer

<400> SEQUENCE: 5
gcatcactag tctttgagat tcgtcggaac acatg                             35

<210> SEQ ID NO 6
<211> LENGTH: 33
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(36)
<223> OTHER INFORMATION: primer

<400> SEQUENCE: 6
gcacattcta gaattgatac gcccagaccc ttg                               33

<210> SEQ ID NO 7
<211> LENGTH: 33
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(33)
<223> OTHER INFORMATION: primer

<400> SEQUENCE: 7
cgatcaacta gtaagtgtca atttccgggg cct                               33

<210> SEQ ID NO 8
<211> LENGTH: 36
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(36)
<223> OTHER INFORMATION: primer

<400> SEQUENCE: 8
gcactatcta gactgaagaa catgtgtgag cacagc                            36

<210> SEQ ID NO 9
<211> LENGTH: 36
<212> TYPE: DNA
<213> ORGANISM: Artificial Sequence
<220> FEATURE:
```

```
<223> OTHER INFORMATION: primer
<221> NAME/KEY: misc_feature
<222> LOCATION: (1)..(36)
<223> OTHER INFORMATION: primer

<400> SEQUENCE: 9
gcactatcta gagtgagcga ggagctgatc cgagtg                                    36

<210> SEQ ID NO 10
<211> LENGTH: 36
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(36)
<223> OTHER INFORMATION: primer

<400> SEQUENCE: 10
cgatcaacta gtggaaacat attgcagctc taagga                                    36

<210> SEQ ID NO 11
<211> LENGTH: 36
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(36)
<223> OTHER INFORMATION: primer

<400> SEQUENCE: 11
cgatcaacta gttggcacag ccaattcaag gtcccg                                    36

<210> SEQ ID NO 12
<211> LENGTH: 31
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(31)
<223> OTHER INFORMATION: primer

<400> SEQUENCE: 12
atgctctaga ctgggggcct tgcttggcaa c                                         31

<210> SEQ ID NO 13
<211> LENGTH: 31
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(31)
<223> OTHER INFORMATION: primer

<400> SEQUENCE: 13
atgctctaga gatgagtttc ccaccatggt g                                         31

<210> SEQ ID NO 14
<211> LENGTH: 39
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(39)
<223> OTHER INFORMATION: primer
```

-continued

<400> SEQUENCE: 14
gcatggatcc gctcaactag tggagctgat ctgactcag                    39

<210> SEQ ID NO 15
<211> LENGTH: 31
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(31)
<223> OTHER INFORMATION: primer

<400> SEQUENCE: 15
atgctctaga cttggaaccg gacctgccgc c                            31

<210> SEQ ID NO 16
<211> LENGTH: 34
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(34)
<223> OTHER INFORMATION: primer

<400> SEQUENCE: 16
gcatcactag tccagaaagg gcaccagcca atat                         34

<210> SEQ ID NO 17
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(25)
<223> OTHER INFORMATION: primer

<400> SEQUENCE: 17
gccatggtgg ctagcctata gtgag                                   25

<210> SEQ ID NO 18
<211> LENGTH: 25
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(25)
<223> OTHER INFORMATION: primer

<400> SEQUENCE: 18
ggcggtgttg gctagcgtcg gtcag                                   25

<210> SEQ ID NO 19
<211> LENGTH: 27
<212> TYPE: PRT
<213> ORGANISM: Artificial Sequence
<220> FEATURE:
<223> OTHER INFORMATION: pSMTN3 construct
<221> NAME/KEY: DOMAIN
<222> LOCATION: (1)..(27)
<223> OTHER INFORMATION: pSMTN3+12CA5+SV40T NLS

<400> SEQUENCE: 19

Met Ala Ser Ser Tyr Pro Tyr Asp Val Pro Asp Tyr Ala Ser Leu Gly

```
1               5               10              15
Gly Pro Ser Ser Pro Lys Lys Arg Lys Val
                20              25
```

<210> SEQ ID NO 20
<211> LENGTH: 123
<212> TYPE: DNA
<213> ORGANISM: Artificial Sequence
<220> FEATURE:
<223> OTHER INFORMATION: pSMTN3 construct coding sequence
<221> NAME/KEY: misc_feature
<222> LOCATION: (1)..(123)
<223> OTHER INFORMATION: pSMTN3+12CA5+SV40T NLS

<400> SEQUENCE: 20

```
gaattccaga agcgcgtatg gcttctagct atccttatga cgtgcctgac tatgccagcc    60
tgggaggacc ttctagtcct aagaagaaga gaaaggtgtc tagatatcga ggatcccaag   120
ctt                                                                 123
```

<210> SEQ ID NO 21
<211> LENGTH: 128
<212> TYPE: PRT
<213> ORGANISM: Artificial Sequence
<220> FEATURE:
<223> OTHER INFORMATION: FKBP+His+HA epitopes
<221> NAME/KEY: DOMAIN
<222> LOCATION: (1)..(128)
<223> OTHER INFORMATION: FKBP+His+HA tags

<400> SEQUENCE: 21

```
Met His His His His His His Tyr Pro Tyr Asp Val Pro Asp Tyr Ala
1               5                   10                  15

Ala Met Ala His Met Gly Val Gln Val Glu Thr Ile Ser Pro Gly Asp
            20                  25                  30

Gly Arg Thr Phe Pro Lys Arg Gly Gln Thr Cys Val Val His Tyr Thr
        35                  40                  45

Gly Met Leu Glu Asp Gly Lys Lys Phe Asp Ser Ser Arg Asp Arg Asn
    50                  55                  60

Lys Pro Phe Lys Phe Met Leu Gly Lys Gln Glu Val Ile Arg Gly Trp
65                  70                  75                  80

Glu Glu Gly Val Ala Gln Met Ser Val Gly Gln Arg Ala Lys Leu Thr
                85                  90                  95

Ile Ser Pro Asp Tyr Ala Tyr Gly Ala Thr Gly His Pro Gly Ile Ile
            100                 105                 110

Pro Pro His Ala Thr Leu Val Phe Asp Val Glu Leu Leu Lys Leu Glu
        115                 120                 125
```

<210> SEQ ID NO 22
<211> LENGTH: 27
<212> TYPE: DNA
<213> ORGANISM: Artificial Sequence
<220> FEATURE:
<223> OTHER INFORMATION: FKBP12 C24 mutant primer
<221> NAME/KEY: misc_feature
<222> LOCATION: (1)..(27)
<223> OTHER INFORMATION: FBBP12 variant

<400> SEQUENCE: 22

```
agcataaact tatggggctt gtttctg                                        27
```

<210> SEQ ID NO 23
<211> LENGTH: 27

<212> TYPE: DNA
<213> ORGANISM: Artificial Sequence
<220> FEATURE:
<223> OTHER INFORMATION: FKBP12 C24 mutant primer
<221> NAME/KEY: misc_feature
<222> LOCATION: (1)..(27)
<223> OTHER INFORMATION: FKBP12 variant

<400> SEQUENCE: 23
agcataaact ttaagggctt gtttctg                                27

<210> SEQ ID NO 24
<211> LENGTH: 27
<212> TYPE: DNA
<213> ORGANISM: Artificial Sequence
<220> FEATURE:
<223> OTHER INFORMATION: FKBP12 C24 mutant primer
<221> NAME/KEY: misc_feature
<222> LOCATION: (1)..(27)
<223> OTHER INFORMATION: FKBP12 variant

<400> SEQUENCE: 24
agcataaact tagcgggctt gtttctg                                27

<210> SEQ ID NO 25
<211> LENGTH: 27
<212> TYPE: DNA
<213> ORGANISM: Artificial Sequence
<220> FEATURE:
<223> OTHER INFORMATION: FKBP12 C24 Mutant primer
<221> NAME/KEY: misc_feature
<222> LOCATION: (1)..(27)
<223> OTHER INFORMATION: FKBP12 variant

<400> SEQUENCE: 25
ttgcctagca tatgcttaaa gggcttg                                27

<210> SEQ ID NO 26
<211> LENGTH: 27
<212> TYPE: DNA
<213> ORGANISM: Artificial Sequence
<220> FEATURE:
<223> OTHER INFORMATION: FKBP12 C24 mutant primer
<221> NAME/KEY: misc_feature
<222> LOCATION: (1)..(27)
<223> OTHER INFORMATION: FKBP variant

<400> SEQUENCE: 26
ttgcctagca ttaacttaaa gggcttg                                27

<210> SEQ ID NO 27
<211> LENGTH: 27
<212> TYPE: DNA
<213> ORGANISM: Artificial Sequence
<220> FEATURE:
<223> OTHER INFORMATION: FKBP12 C24 mutant primer
<221> NAME/KEY: misc_feature
<222> LOCATION: (1)..(27)
<223> OTHER INFORMATION: FKBP12 variant

<400> SEQUENCE: 27
ttgcctagca tagccttaaa gggcttg                                27

<210> SEQ ID NO 28
<211> LENGTH: 26
<212> TYPE: DNA
<213> ORGANISM: Artificial Sequence
<220> FEATURE:
<223> OTHER INFORMATION: FKBP12 C24 mutant primer

```
<221> NAME/KEY: misc_feature
<222> LOCATION: (1)..(26)
<223> OTHER INFORMATION: FKBP12 variant

<400> SEQUENCE: 28
cctcggatca ccgcctgctt gcctag                                          26

<210> SEQ ID NO 29
<211> LENGTH: 26
<212> TYPE: DNA
<213> ORGANISM: Artificial Sequence
<220> FEATURE:
<223> OTHER INFORMATION: FKBP12 C24 mutant primer
<221> NAME/KEY: misc_feature
<222> LOCATION: (1)..(26)
<223> OTHER INFORMATION: FKBP12 variant

<400> SEQUENCE: 29
cagcctcgga tcgcctcctg cttgcc                                          26

<210> SEQ ID NO 30
<211> LENGTH: 30
<212> TYPE: DNA
<213> ORGANISM: Artificial Sequence
<220> FEATURE:
<223> OTHER INFORMATION: FKBP12 C13/C14 mutant primer
<221> NAME/KEY: misc_feature
<222> LOCATION: (1)..(30)
<223> OTHER INFORMATION: FKBP12 variant

<400> SEQUENCE: 30
ccgggaggaa tcggctttct ttccatcttc                                      30

<210> SEQ ID NO 31
<211> LENGTH: 30
<212> TYPE: DNA
<213> ORGANISM: Artificial Sequence
<220> FEATURE:
<223> OTHER INFORMATION: FKBP12 C13/C14 mutant primer
<221> NAME/KEY: misc_feature
<222> LOCATION: (1)..(30)
<223> OTHER INFORMATION: FKBP12 variant

<400> SEQUENCE: 31
ccgggaggaa tcgactttct ttccatcttc                                      30

<210> SEQ ID NO 32
<211> LENGTH: 30
<212> TYPE: DNA
<213> ORGANISM: Artificial Sequence
<220> FEATURE:
<223> OTHER INFORMATION: FKBP12 C13/C14 mutant primer
<221> NAME/KEY: misc_feature
<222> LOCATION: (1)..(30)
<223> OTHER INFORMATION: FKBP12 Variant

<400> SEQUENCE: 32
ccgggaggaa tcagatttct ttccatcttc                                      30

<210> SEQ ID NO 33
<211> LENGTH: 30
<212> TYPE: DNA
<213> ORGANISM: Artificial Sequence
<220> FEATURE:
<223> OTHER INFORMATION: FKBP12 C13/C14 mutant primer
<221> NAME/KEY: misc_feature
<222> LOCATION: (1)..(30)
<223> OTHER INFORMATION: FKBP12 variant
```

-continued

<400> SEQUENCE: 33
ccgggaggaa tccattttct ttccatcttc                                    30

<210> SEQ ID NO 34
<211> LENGTH: 27
<212> TYPE: DNA
<213> ORGANISM: Artificial Sequence
<220> FEATURE:
<223> OTHER INFORMATION: FKBP12 C13/C14 mutant primer
<221> NAME/KEY: misc_feature
<222> LOCATION: (1)..(27)
<223> OTHER INFORMATION: FKBP12 variant

<400> SEQUENCE: 34
aagctccaca tcggcgacga gagtggc                                       27

<210> SEQ ID NO 35
<211> LENGTH: 27
<212> TYPE: DNA
<213> ORGANISM: Artificial Sequence
<220> FEATURE:
<223> OTHER INFORMATION: FKBP12 C13/C14 mutant primer
<221> NAME/KEY: misc_feature
<222> LOCATION: (1)..(27)
<223> OTHER INFORMATION: FKBP variant

<400> SEQUENCE: 35
aagctccaca tcgccgacga gagtggc                                       27

<210> SEQ ID NO 36
<211> LENGTH: 29
<212> TYPE: DNA
<213> ORGANISM: Artificial Sequence
<220> FEATURE:
<223> OTHER INFORMATION: FKBP12 C13/C14 mutant primer
<221> NAME/KEY: misc_feature
<222> LOCATION: (1)..(29)
<223> OTHER INFORMATION: FKBP12 variant

<400> SEQUENCE: 36
caagcatccc ggtggcgtgc accacgcag                                     29

<210> SEQ ID NO 37
<211> LENGTH: 29
<212> TYPE: DNA
<213> ORGANISM: Artificial Sequence
<220> FEATURE:
<223> OTHER INFORMATION: FKBP12 C13/C14 mutant primer
<221> NAME/KEY: misc_feature
<222> LOCATION: (1)..(29)
<223> OTHER INFORMATION: FKBP12 variant

<400> SEQUENCE: 37
tcccgggagg aagcaaattt ctttccatc                                     29

<210> SEQ ID NO 38
<211> LENGTH: 26
<212> TYPE: DNA
<213> ORGANISM: Artificial Sequence
<220> FEATURE:
<223> OTHER INFORMATION: FKBP12 C28/C30 mutant primer
<221> NAME/KEY: misc_feature
<222> LOCATION: (1)..(38)
<223> OTHER INFORMATION: FKBP12 variant

<400> SEQUENCE: 38
cctcggatca ccgcctgctt gcctag                                        26

<210> SEQ ID NO 39
<211> LENGTH: 27
<212> TYPE: DNA
<213> ORGANISM: Artificial Sequence
<220> FEATURE:
<223> OTHER INFORMATION: FRAP C7 mutant primer
<221> NAME/KEY: misc_feature
<222> LOCATION: (1)..(27)
<223> OTHER INFORMATION: FRAP variant

<400> SEQUENCE: 39
cctttcccca aagtgcaaac gagatgc                                    27

<210> SEQ ID NO 40
<211> LENGTH: 27
<212> TYPE: DNA
<213> ORGANISM: Artificial Sequence
<220> FEATURE:
<223> OTHER INFORMATION: FRAP C7 mutant primer
<221> NAME/KEY: misc_feature
<222> LOCATION: (1)..(27)
<223> OTHER INFORMATION: FRAP variant

<400> SEQUENCE: 40
cctttcccca aagagcaaac gagatgc                                    27

<210> SEQ ID NO 41
<211> LENGTH: 27
<212> TYPE: DNA
<213> ORGANISM: Artificial Sequence
<220> FEATURE:
<223> OTHER INFORMATION: FRAP C7 mutant primer
<221> NAME/KEY: misc_feature
<222> LOCATION: (1)..(27)
<223> OTHER INFORMATION: FRAP variant

<400> SEQUENCE: 41
cctttcccca aaggccaaac gagatgc                                    27

<210> SEQ ID NO 42
<211> LENGTH: 29
<212> TYPE: DNA
<213> ORGANISM: Artificial Sequence
<220> FEATURE:
<223> OTHER INFORMATION: FRAp C7 mutant primer
<221> NAME/KEY: misc_feature
<222> LOCATION: (1)..(29)
<223> OTHER INFORMATION: FRAP variant

<400> SEQUENCE: 42
gttcctttcc ccatggtaca aacgagatg                                  29

<210> SEQ ID NO 43
<211> LENGTH: 29
<212> TYPE: DNA
<213> ORGANISM: Artificial Sequence
<220> FEATURE:
<223> OTHER INFORMATION: FRAP C7 mutant primer
<221> NAME/KEY: misc_feature
<222> LOCATION: (1)..(29)
<223> OTHER INFORMATION: FRAP variant

<400> SEQUENCE: 43
gttcctttcc cctaagtaca aacgagatg                                  29

<210> SEQ ID NO 44
<211> LENGTH: 29
<212> TYPE: DNA

```
<213> ORGANISM: Artificial Sequence
<220> FEATURE:
<223> OTHER INFORMATION: FRAP C7 muatnt primer
<221> NAME/KEY: misc_feature
<222> LOCATION: (1)..(29)
<223> OTHER INFORMATION: FRAP variant

<400> SEQUENCE: 44
gttcctttcc ccagcgtaca aacgagatg                                    29

<210> SEQ ID NO 45
<211> LENGTH: 27
<212> TYPE: DNA
<213> ORGANISM: Artificial Sequence
<220> FEATURE:
<223> OTHER INFORMATION: FRAP C7 mutant primer
<221> NAME/KEY: misc_feature
<222> LOCATION: (1)..(27)
<223> OTHER INFORMATION: FRAP variant

<400> SEQUENCE: 45
gtcccaggct tgggcgaggt ccttgac                                      27

<210> SEQ ID NO 46
<211> LENGTH: 40
<212> TYPE: DNA
<213> ORGANISM: Artificial Sequence
<220> FEATURE:
<223> OTHER INFORMATION: FRAP C7 mutant primer
<221> NAME/KEY: misc_feature
<222> LOCATION: (1)..(40)
<223> OTHER INFORMATION: FRAP variant

<400> SEQUENCE: 46
gtcccaggct tggttgaggt tcgagacatt ccctgatttc                        40

<210> SEQ ID NO 47
<211> LENGTH: 27
<212> TYPE: DNA
<213> ORGANISM: Artificial Sequence
<220> FEATURE:
<223> OTHER INFORMATION: FRAP C7 mutant primer
<221> NAME/KEY: misc_feature
<222> LOCATION: (1)..(27)
<223> OTHER INFORMATION: FRAP variant

<400> SEQUENCE: 47
gtcccaggct tggttgaggt ccttgac                                      27

<210> SEQ ID NO 48
<211> LENGTH: 29
<212> TYPE: DNA
<213> ORGANISM: Artificial Sequence
<220> FEATURE:
<223> OTHER INFORMATION: FRAP C7 mutant primer
<221> NAME/KEY: misc_feature
<222> LOCATION: (1)..(29)
<223> OTHER INFORMATION: FRAP variant

<400> SEQUENCE: 48
catgataata gagggcccag gcttgggtg                                    29

<210> SEQ ID NO 49
<211> LENGTH: 50
<212> TYPE: DNA
<213> ORGANISM: Artificial Sequence
<220> FEATURE:
<223> OTHER INFORMATION: primer
<221> NAME/KEY: misc_feature
```

<222> LOCATION: (1)..(50)
<223> OTHER INFORMATION: primer

<400> SEQUENCE: 49
gcatcccatg gcaatcctct ggcatgagat gtggcatgaa ggcctggaag        50

<210> SEQ ID NO 50
<211> LENGTH: 34
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(34)
<223> OTHER INFORMATION: primer

<400> SEQUENCE: 50
cgtgaggatc ctactttgag attcgtcgga acac        34

<210> SEQ ID NO 51
<211> LENGTH: 48
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(48)
<223> OTHER INFORMATION: primer

<400> SEQUENCE: 51
gcatctctag aatcctctgg catgagatgt ggcatgaagg cctggaag        48

<210> SEQ ID NO 52
<211> LENGTH: 47
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(47)
<223> OTHER INFORMATION: primer

<400> SEQUENCE: 52
ggtctggatc cctaataact agtctttgag attcgtcgga acacatg        47

<210> SEQ ID NO 53
<211> LENGTH: 8
<212> TYPE: PRT
<213> ORGANISM: Artificial Sequence
<220> FEATURE:
<223> OTHER INFORMATION: FLAG epitope
<221> NAME/KEY: DOMAIN
<222> LOCATION: (1)..(8)
<223> OTHER INFORMATION: FLAG epitope

<400> SEQUENCE: 53

Asp Tyr Lys Asp Asp Asp Asp Tyr
1               5

<210> SEQ ID NO 54
<211> LENGTH: 85
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (1)..(85)
<223> OTHER INFORMATION: oligonucleotide

<400> SEQUENCE: 54
catgtctaga gggagtagca agagcaagcc taaggacccc agccagcgca ctagttaaga    60
attctgatga tcagcggatc ctagc                                         85

<210> SEQ ID NO 55
<211> LENGTH: 85
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (1)..(85)
<223> OTHER INFORMATION: oligonucleotide

<400> SEQUENCE: 55
gctaggatcc gctgatcatc agaattctta actagtgcgc tggctggggt ccttaggctt    60
gctcttgcta ctccctctag acatg                                         85

<210> SEQ ID NO 56
<211> LENGTH: 37
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (1)..(37)
<223> OTHER INFORMATION: oligonucleotide

<400> SEQUENCE: 56
cgccttgtag aattcgcgcg tatggggagt agcaaga                             37

<210> SEQ ID NO 57
<211> LENGTH: 30
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (1)..(30)
<223> OTHER INFORMATION: oligonucleotide

<400> SEQUENCE: 57
cccagccagc gctctagata agaattctga                                     30

<210> SEQ ID NO 58
<211> LENGTH: 18
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (1)..(18)
<223> OTHER INFORMATION: oligonucleotide

<400> SEQUENCE: 58
aagggtcccc aaactcac                                                  18

<210> SEQ ID NO 59
<211> LENGTH: 61
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (1)..(61)
<223> OTHER INFORMATION: oligonucleotide

<400> SEQUENCE: 59
gcatgactag ttatccgtac gacgtaccag actacgcata agaaaagtga ggatcctacg    60
g    61

<210> SEQ ID NO 60
<211> LENGTH: 61
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (1)..(61)
<223> OTHER INFORMATION: oligonucleotide

<400> SEQUENCE: 60
ccgtaggatc ctcactttc ttatgcgtag tctggtacgt cgtacggata actagtcatg    60
c    61

<210> SEQ ID NO 61
<211> LENGTH: 58
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (1)..(58)
<223> OTHER INFORMATION: oligonucleotide

<400> SEQUENCE: 61
ccgtaggatc ctcactttc ttaataatcg tcatcgtctt tgtagtcact agtcatgc    58

<210> SEQ ID NO 62
<211> LENGTH: 58
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (1)..(58)
<223> OTHER INFORMATION: oligonucleotide

<400> SEQUENCE: 62
gcatgactag tgactacaaa gacgatgacg attattaaga aaagtgagga tcctacgg    58

<210> SEQ ID NO 63
<211> LENGTH: 16
<212> TYPE: PRT
<213> ORGANISM: Artificial Sequence
<220> FEATURE:
<223> OTHER INFORMATION: membrane binding domain
<221> NAME/KEY: DOMAIN
<222> LOCATION: (1)..(16)
<223> OTHER INFORMATION: membrane binding domain

<400> SEQUENCE: 63

Met Gly Ser Ser Lys Ser Lys Pro Lys Asp Pro Ser Gln Arg Ser Arg
 1               5                  10                  15

<210> SEQ ID NO 64
<211> LENGTH: 103
<212> TYPE: DNA
<213> ORGANISM: Artificial Sequence
<220> FEATURE:
<223> OTHER INFORMATION: construct containing membrane binding domain
      sequences
<221> NAME/KEY: misc_feature
<222> LOCATION: (1)..(103)

```
-continued

<223> OTHER INFORMATION: construct containing membrane binding domain

<400> SEQUENCE: 64
cgccttgtag aattcgcgcg tatggggagt agcaagagca agcctaagga ccccagccag      60
cgctctagat aagaattctg atgatcagcg gatcctgaga act                       103
```